(12) United States Patent
Schreiber et al.

(10) Patent No.: US 7,244,853 B2
(45) Date of Patent: Jul. 17, 2007

(54) DIOXANES AND USES THEREOF

(75) Inventors: Stuart L. Schreiber, Boston, MA (US); Scott M. Sternson, New York, NY (US); Jason C. Wong, Cambridge, MA (US); Christina M. Grozinger, Urbana, IL (US); Stephen J. Haggarty, Somerville, MA (US); Kathryn M. Koeller, Seattle, WA (US)

(73) Assignee: President and Fellows of Harvard College, Cambridge, MA (US)

( * ) Notice: Subject to any disclaimer, the term of this patent is extended or adjusted under 35 U.S.C. 154(b) by 320 days.

(21) Appl. No.: 10/621,276

(22) Filed: Jul. 17, 2003

(65) Prior Publication Data

US 2004/0072849 A1    Apr. 15, 2004

Related U.S. Application Data

(63) Continuation-in-part of application No. 10/144,316, filed on May 9, 2002, now abandoned.

(60) Provisional application No. 60/289,850, filed on May 9, 2001.

(51) Int. Cl.
*C07D 309/00* (2006.01)
*A01N 43/02* (2006.01)

(52) U.S. Cl. .................. 549/356; 549/200; 549/357; 514/449; 514/451; 514/452

(58) Field of Classification Search ............... 549/200, 549/356, 357; 514/449, 451, 452
See application file for complete search history.

(56) References Cited

U.S. PATENT DOCUMENTS 4,639,462 A   1/1987 Krämer et al. ............ 514/383

(Continued)

FOREIGN PATENT DOCUMENTS

DE         3242252      5/1984

(Continued)

OTHER PUBLICATIONS

Sternson et al., "Synthesis of 7200 Small Molecules . . . ", Organc Letters, vol. 3, No. 26, 2001, pp. 4239-4242.*

(Continued)

*Primary Examiner*—James O. Wilson
*Assistant Examiner*—Paul V. Ward
(74) *Attorney, Agent, or Firm*—Choate, Hall & Stewart LLP; C. Hunter Baker

(57) ABSTRACT

In recognition of the need to develop novel therapeutic agents and efficient methods for the synthesis thereof, the present invention provides novel compounds of general formula (I):

(I)

$$\begin{array}{c}R^3\\\diagup\\O\quad O\\Y\diagdown\quad\diagup(CH_2)_n-X-R^2\\R^1\end{array}$$

and pharmaceutically acceptable derivatives thereof, wherein $R^1$, $R^2$, $R^3$, n, X and Y are as defined herein. The present invention also provides pharmaceutical compositions comprising a compound of formula (I) and a pharmaceutically acceptable carrier. The present invention further provides compounds capable of inhibiting histone deacetylatase activity and methods for treating disorders regulated by histone deacetylase activity (e.g., cancer and protozoal infections) comprising administering a therapeutically effective amount of a compound of formula (I) to a subject in need thereof. The present invention additionally provides methods for modulating the glucose-sensitive subset of genes downstream of Ure2p. The present invention also provides methods for preparing compounds of the invention.

54 Claims, 78 Drawing Sheets

U.S. PATENT DOCUMENTS

| | | | | |
|---|---|---|---|---|
| 5,059,698 | A | 10/1991 | Schulthess et al. | 549/375 |
| 5,238,781 | A | 8/1993 | Schädeli | 430/270 |
| 5,393,741 | A | 2/1995 | Pettersen et al. | 514/23 |

FOREIGN PATENT DOCUMENTS

| | | |
|---|---|---|
| EP | 0 322 335 | 6/1989 |
| JP | 8-311321 | 11/1996 |
| JP | 9-124918 | 5/1997 |
| WO | WO 97/35990 | 10/1997 |
| WO | WO 98/16830 | 4/1998 |
| WO | WO98/16830 * | 4/1998 |
| WO | WO 00/20415 | 4/2000 |
| WO | WO 00/35911 | 6/2000 |

OTHER PUBLICATIONS

Kuruvilla et al., "Dissecting glucose signalling with diversity . . . ", Nature, vol. 416, 2002, pp. 653-657.*

Sternson et al., "Split-Pool Synthesis of 1,3-Dioxanes . . . ", J. Am. Chem. Soc. 001, 123, 1740-1747.*

Aggarwal, et al., "Trifluoromethanesulfonic Acid, an Efficient Catalyst for the Hetero Diels-Alder Reaction and an Improved Synthesis of Mefrosol", Tetrahecron Letters, 38(14):2569-2572, 1997.

Antonjuk, et al., "Asymmetric Induction in the Additions of Anions of Allylic Sulfoxides to Benzaldehyde", Aust. J. Chem., 33:2635-2651, 1980.

Blackwell, et al., "A One-Bead, One-Stock Solution Approach to Chemical Genetics: Part 1", Chemistry & Biology, 8:1167-1182, 2001.

Clemons, et al., "A One-Bead, One-Stock Solution Approach to Chemical Genetics: Part 2", Chemistry & Biology, 8:1183-1195, 2001.

Grozinger, et al., "Deacetylase Enzymes: Biological Functions and the Use of Small-Molecule Inhibitors", Chemistry & Biology, 9:3-16, 2002.

Haggarty, et al., "Domain-selective small-molecular inhibitor of histone deacetylase 6 (HDAC6)-mediated tubulin deacetylation", Proc. Natl. Acad. Sci, 100(8):4389-4394, 2003.

Haggarty, et al; "Multidimensional Chemical Genetic Analysis of Diversity-Oriented Synthesis-Derived Deacetylase Inhibitors Using Cell-Based Assays", Chemistry & Biology, 10:383-396, 2003.

Hunter, et al., "An Enantioselective Synthesis of Benzylidene-Protected syn-3, 5-Dihydroxy Carboxylate Esters via Osmium, Palladium, and Base Catalysis", Org Letter, 3(7):1049-1052, 2001.

Imamoto, et al., "Preparation and Synthetic Use of Trimethylsilyl Polyphosphate. A New Stereoselective Aldol-Type Reaction in the Presence of Trimethylsily Polyphosphate", J. Org. Chem. 49:1105-1110, 1984.

Imamoto, et al., "The Reaction of Aryl Methyl Ketones with Aromatic Aldehydes in Trimethylsilyl Polyphosphate (PPSE), Formation of MESO-2,4,6-Trisubstituted-5-Acyl-1,3-Dioxe", Tetrahedron Letters, 23(14):1467-1470, 1982.

Johnstone, R. "Histone-Deacetylase Inhibitors: Novel Drugs for the Treatment of Cancer", Nature, 1:287-299, 2002.

Koeller, et al., "Chemical Genetic Modifier Screens: Small Molecule Trichostatin Suppressors as Probes of Intracelluler Histone and Tubulin Acetylation", Chemistry & Biology, 10:397-410, 2003.

Kuruvilla, et al., "Dissecting Glucose Signalling with Diversity-Oriented Synthesis and Small-Molecule Microarrays", Nature, 416:653-657, 2002.

Lin, et al., "Generation And Aldol Reaction of Enolate Anion Adjacent A $\eta^3$-Allyl-Mo(CO)$_2$ Cp Moiety. A New Approach to the Stereoselective Synthesis of 1,3,5-Triol and 2-Vinyl-3 Hydroxyl-Tetrahydrofuran", Tetrahedron Letters, 31(52):7645-7648, 1990.

Lin, et al., "Role of the Histone Deacetylase Complex in Acute Promyelocytic Leukaemia", Nature, 391:811-814, 1998.

Magnaghi-Jaulin, et al., "Retinoblastoma Protein Represses Transcription by Recruiting a Histone Deacetylase", Nature, 391:601-604, 1998.

Marks, et al., "Histone Deacetylases and Cancer: Causes and Therapies", Nature Reviews/Cancer, 1:194-202, 2001.

Pyne, et al., "Reactions of Lithiated N-Tosyl S-Phenyl S-2-Propenyl Sulfoximine with Aldehydes", Sulfur Letters, 20(6):255-260, 1997.

Schreiber, et al., "Chemical Genetics Resulting from a Passion for Synthetic Organic Chemistry", Bioorganic & Medicinal Chemistry, 6:1127-1152, 1998.

Schreiber, et al., "Target-Oriented and Diversity-Oriented Organic Synthesis in Drug Discovery", Science, 287:1964-1969, 2000.

Sternson, et al., "Synthesis of 7200 Small Molecules Based on a Substructural Analysis of the Histone Deacetylase Inhibitors Trichostatin and Trapoxin", Organic Letters, 3(26):4239-4242, 2001.

Sternson, et al., "Split-Pool Synthesis of 1,3-Dioxanes Leading to Arrayed Stock Solutions of Single Compounds Sufficient for Multiple Phenotypic and Protein-Binding Assays", J. Am. Chem. Soc. 123:1740-1747, 2001.

Tallarico, et al., "An Alkylsily-Tethered, High-Capacity Solid Support Amenable to Diversity-Oriented Synthesis for One-Bead, One-Stock Solution Chemical Genetics", J. Comb. Chem. 3:312-318, 2001.

Taunton, et al., "Synthesis of Natural and Modified Trapoxins, Useful Reagents for Exploring Histone Deacetylase Function", J. Am. Chem. Soc. 118:10412-10422, 1996.

Uong, et al., "Stereocontrolled Functionlization of Acyclic Molybdenum-$\eta^{3-}$ Allyl Complexes: A New Approach to the Stereoselective Synthesis of 1,3-Diols", J. Chem. Soc. Chem. Commun., 1285-1287, 1990.

Vong, et al., "Regio- and Stereocontrolled Functionalization of Acyclic Molybdenum -$\eta^3$ - Allyl Complexes", J. Am. Chem. Soc. 113:573-582, 1991

Wong, et al., "Structural Biasing Elements for In-Cell Histone Deacetylase Paralog Selectivity", J. Am. Chem. Soc., 125:5586-5587, 2003.

* cited by examiner

FIG. 1

|  | P22 | | Y91 | | | | | L265 | |
|---|---|---|---|---|---|---|---|---|---|
| HDLP | P | L | G | G | Y | E | N | P | Y | L |
| HDAC1 | P | M | G | - | E | D | C | P | R | L |
| HDAC2 | P | M | G | - | E | D | C | P | R | L |
| HDAC3 | P | M | G | - | D | D | C | P | R | L |
| HDAC8 | A | K | G | - | Y | D | C | P | P | M |
| HDAC4 | P | E | G | V | D | S | D | T | P | L |
| HDAC5 | P | E | G | V | D | S | D | T | P | L |
| HDAC6(a) | P | E | - | - | - | - | D | S | P | K |
| HDAC6(b) | P | E | - | - | - | - | D | S | P | L |
| HDAC7 | P | E | G | G | D | T | D | T | P | L |

Class I: HDAC1, HDAC2, HDAC3, HDAC8
Class II: HDAC4, HDAC5, HDAC6(a), HDAC6(b), HDAC7

| Compound | HDAC1 | HDAC6 |
|----------|-------|-------|
| 8 | 1.2 ± 0.5 | 0.9 ± 0.2 |
| 9 | 1.7 ± 1.2 | 1.1 ± 0.1 |
| 10 | 1.5 ± 0.2 | 0.38 ± 0.04 |

Dimethylsulfoxide (0.1%)

JCWII144 (200 nM)

trichostatin (100 nM)

Dimethylsulfoxide (0.1%)

JCWII144 (2 µM)

trichostatin (1 µM)

Acetylated
Tubulin

Acetylated
Histone H3

Notes:
TSA treatment at 300nM
JCWII114 treatment at 2 µM

FIG. 15

| DMSO | TSA (200 nM) |
| --- | --- |
| JCWII114 (2 µM) | JCWII153 (2 µM) |
| JCWII169 (2 µM) | JCWII169 (20 µM) |

To FIG. 21B

Final building block — Mass contributed 115 — Mass of amine precursor 678-115 +1=564 → To FIG. 21C

FIG. 21C

| acetal fragment 103 | 3-epoxy alcohols | | | acetal fragment 117 | 3-epoxy alcohols | | |
|---|---|---|---|---|---|---|---|
| | 194 | 208 | 270 | | 194 | 208 | 270 |
| 71 | 368 | 382 | 444 | 71 | 382 | 396 | 458 |
| 78 | 375 | 389 | 451 | 78 | 389 | 403 | 465 |
| 87 | 384 | 398 | 460 | 87 | 398 | 412 | 474 |
| 101 | 398 | 412 | 474 | 101 | 412 | 426 | 488 |
| 101 | 398 | 412 | 474 | 101 | 412 | 426 | 488 |
| 111 | 408 | 422 | 484 | 111 | 422 | 436 | 498 |
| 113 | 410 | 424 | 486 | 113 | 424 | 438 | 500 |
| 116 | 413 | 427 | 489 | 116 | 427 | 441 | 503 |
| 118 | 415 | 429 | 491 | 118 | 429 | 443 | 505 |
| 125 | 422 | 436 | 498 | 125 | 436 | 450 | 512 |
| 126 | 423 | 437 | 499 | 126 | 437 | 451 | 513 |
| 127 | 424 | 438 | 500 | 127 | 438 | 452 | 514 |
| 132 | 429 | 443 | 505 | 132 | 443 | 457 | 519 |
| 136 | 433 | 447 | 509 | 136 | 447 | 461 | 523 |
| 136 | 433 | 447 | 509 | 136 | 447 | 461 | 523 |
| 143 | 440 | 454 | 516 | 143 | 454 | 468 | 530 |
| 154 | 451 | 465 | 527 | 154 | 465 | 479 | 541 |
| 155 | 452 | 466 | 528 | 155 | 466 | 480 | 542 |
| 164 | 461 | 475 | 537 | 164 | 475 | 489 | 551 |
| 165 | 462 | 476 | 538 | 165 | 476 | 490 | 552 |
| 167 | 464 | 478 | 540 | 167 | 478 | 492 | 554 |
| 167 | 464 | 478 | 540 | 167 | 478 | 492 | 554 |
| 193 | 490 | 504 | 566 | 193 | 504 | 518 | 580 |
| 194 | 491 | 505 | 567 | 194 | 505 | 519 | 581 |
| 211 | 508 | 522 | 584 | 211 | 522 | 536 | 598 |
| 217 | 514 | 528 | 590 | 217 | 528 | 542 | 604 |
| 221 | 518 | 532 | 594 | 221 | 532 | 546 | 608 |
| 231 | 528 | 542 | 604 | 231 | 542 | 556 | 618 |
| 253 | 550 | 564 | 626 | 253 | 564 | 578 | 640 |
| 263 | 560 | 574 | 636 | 263 | 574 | 588 | 650 |

30 nucleophiles

↓ To FIG. 21D

FIG. 21D possible structures
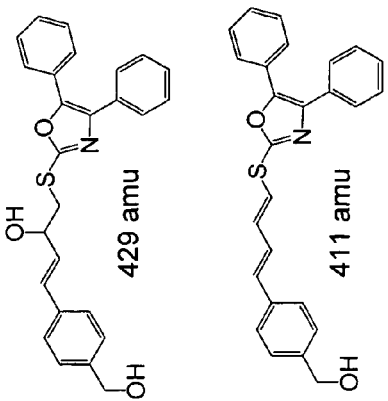
fragments
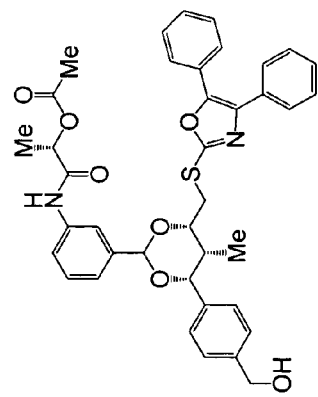
FIG. 21E
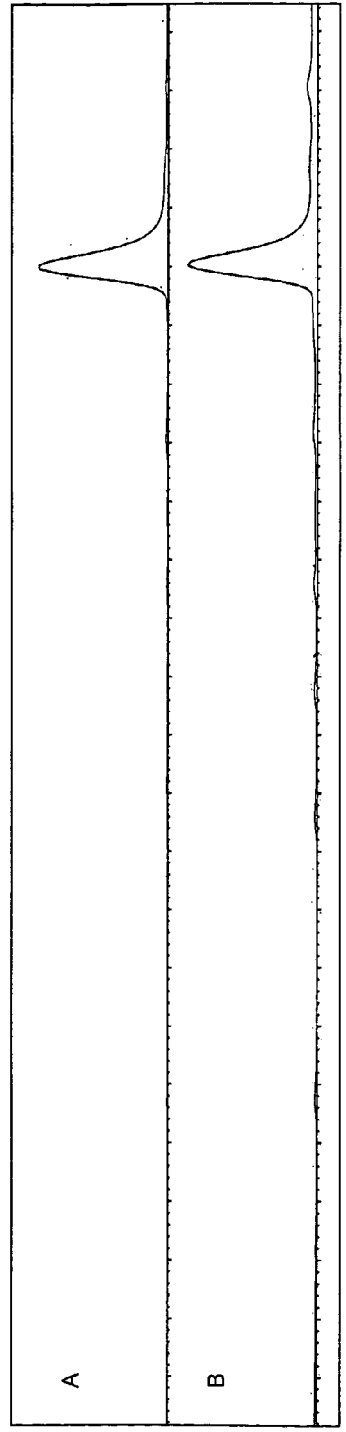

No compound      60 μM 24h (±)
13

14

One stereoisomer shown

| Uretupamine | R⁰ | R¹ | R² | R² | Activity |
|---|---|---|---|---|---|
| A | HOCH$_2$-4-Ph | Ph | 2-MDPO | CH$_2$NH$_2$ | 56 |
| B | HOCH$_2$-4-Ph | H | 2-MDPO | CH$_2$NH$_2$ | 105 |
| C | HOCH$_2$-4-Ph | (β)-CH$_3$ | 2-MDPO | CH$_2$NH$_2$ | 41* |
| D | HOCH$_2$-4-Ph | H | Ph | CH$_2$NH$_2$ | 7 |
| E | HOCH$_2$-4-Ph | H | 2-MBO | CH$_2$NH$_2$ | 10 |
| F | HOCH$_2$-4-Ph | H | 2-MDPO | H | 14 |
| G | HOCH$_2$-4-Ph | H | 2-MDPO | CH$_2$NHAc | 16 |
| H | H | H | 2-MDPO | CH$_2$NH$_2$ | 13 |

100 µM uretupamine (30 min)

| | w.t. | Ure2 Δ |
|---|---|---|
| PUT1 | +4.0 | +1.1 |
| PUT2 | +2.3 | +1.1 |
| UGA1 | +2.2 | +1.2 |
| NIL1 | +3.8 | +1.1 |
| PRB1 | +4.0 | +1.7 |

| Gene sets | w.t. | gln3Δ | nil1Δ | ure2Δ |
|---|---|---|---|---|
| GAP1, MEP2, DAL5, BAT2, AGP1 | +1.1 | +1.1 | -1.0 | -1.0 |
| PUT1, PUT2, UGA1, NIL1, PRB1 | +2.3 | +2.5 | +1.6 | +1.2 |

| Gene sets | w.t. | gln3Δ | nil1Δ | ure2Δ |
|---|---|---|---|---|
| Whole genome | 100% | 89% | 56% | 52% |
| URE2-dependent genes | 100% | 115% | 51% | 59% |

FIG. 26A

FIG. 26B

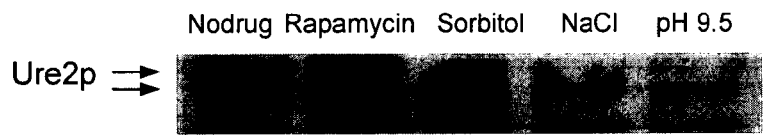

FIG. 26C

- Whole genome
- Storage carbohydrates
- Hexose transporters
- DNA replication
- Purine biosynthesis
- Proteasome
- ▶ Ure2p-dependent
- Glycolysis
- TCA cycle
- Oxidative phosphorylation
- Ubiquinone synthesis
- ATP synthesis
- RNA Pd I
- RNA Pd II
- RNA Pd III
- tRNA processing
- tRNA synthesases
- mito tRNA synthesases
- r-proteins
- mito r-proteins
- Ribosomal biogenesis
- rRNA processing
- Translation initiation
- Translation elongation
- mRNA export
- mRNA decay

Correlated    Uncorrelated    Anticorrelated

|       | Ethanol | Acetate |
|-------|---------|---------|
| PUT1  | +11.5   | > +10.0 |
| PUT2  | +2.8    | +1.6    |
| UGA1  | +4.7    | +3.3    |
| NIL1  | +2.6    | +2.5    |
| PRB1  | +2.3    | +1.4    |
| GAP1  | +3.3    | -9.0    |
| DAL1  | +1.7    | -4.8    |
| DAL2  | +3.1    | -1.5    |
| DAL3  | +2.1    | < -10.0 |
| CAR1  | +2.6    | -1.4    |

FIG. 27C

| | Assay | Abbreviation | Compounds screened in duplicate |
|---|---|---|---|
| 1. | Acetylated tubulin | AcTubulin | 7,392 |
| 2. | Acetylated tubulin + ITSA1 (chemical genetic modifier) | ITSA1+AcTubulin | 2,464 hydroxamic acids |
| 3. | Acetylated lysine | AcLysine | 7,392 |
| 4. | Acetylated histone H3 | AcHistH3 | 2,464 hydroxamic acids |
| 5. | Acetylated histone H4 | AcHistH4 | 2,464 hydroxamic acids |

Table 1. Summary of chemical genetic screens

Std. relative tubulin acetylation

Top 200 ranked compounds

Top 10 selective AcTubulin

- ● = (A) AcTubulin assay node
- ● = (B) AcLysine assay node
- ○ = (C) ITSA1+ AcTubulin assay node

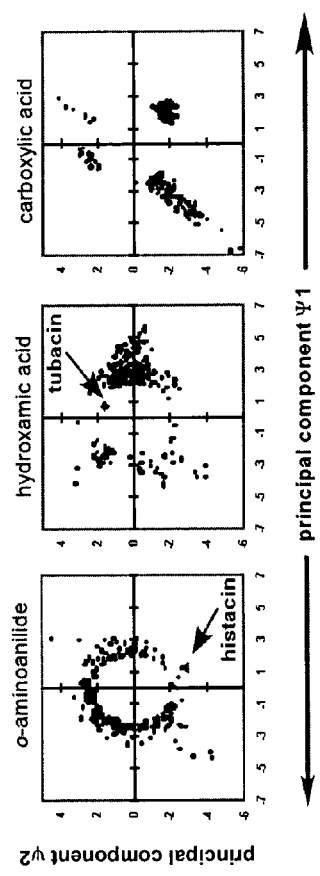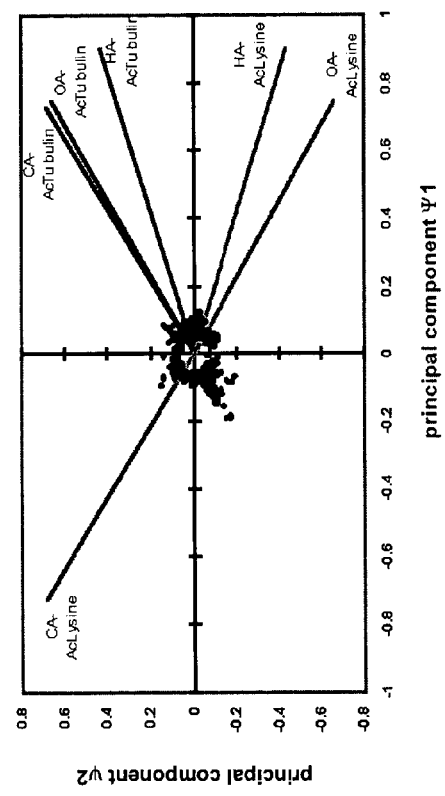
FIG. 33B
FIG. 33C tubacin (15)

histacin (16)

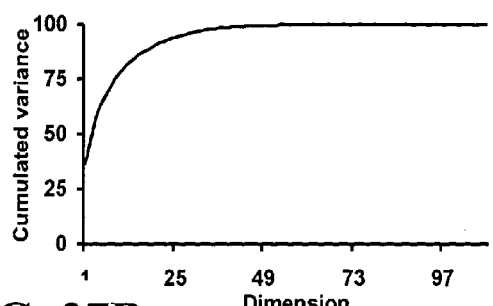
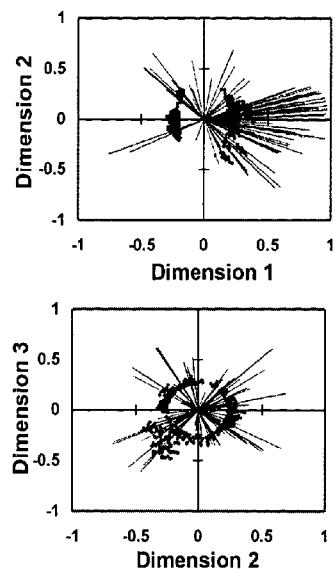
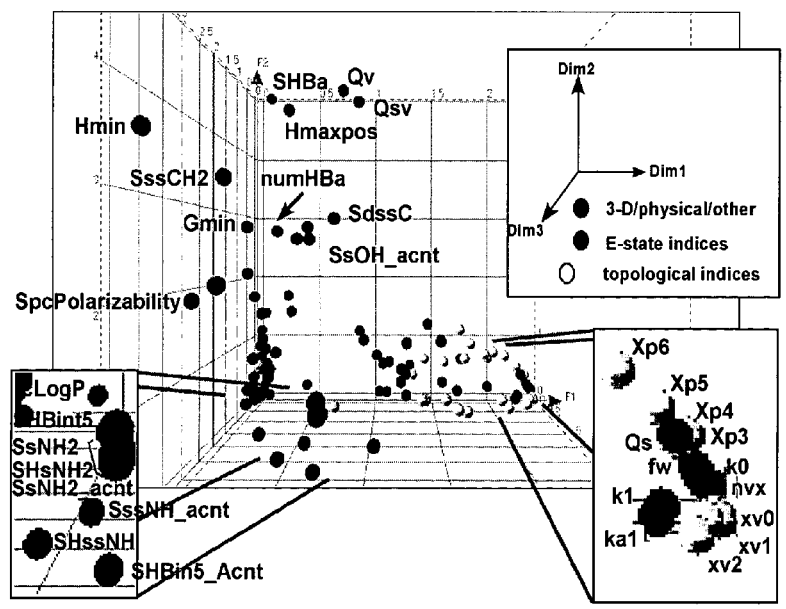
FIG. 37A
FIG. 37B
FIG. 37C
FIG. 37D

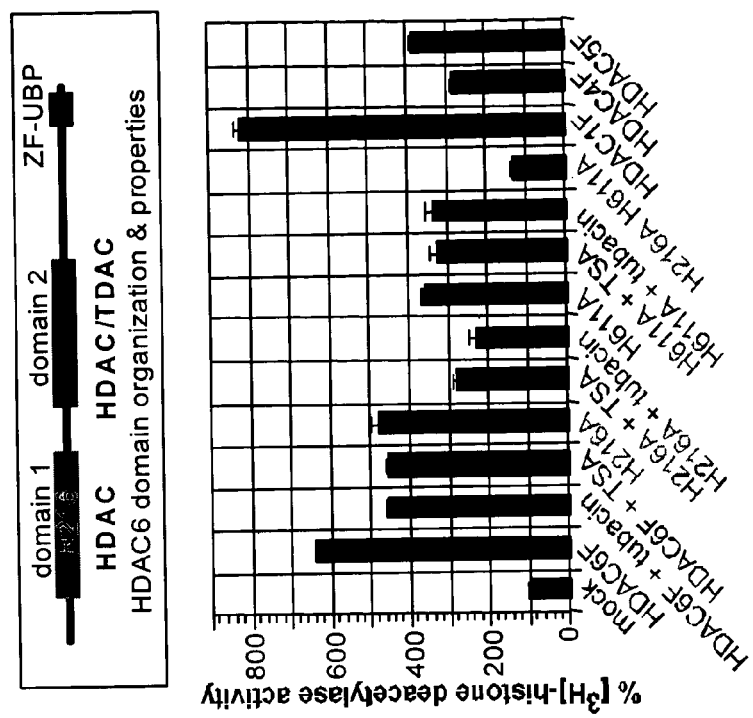
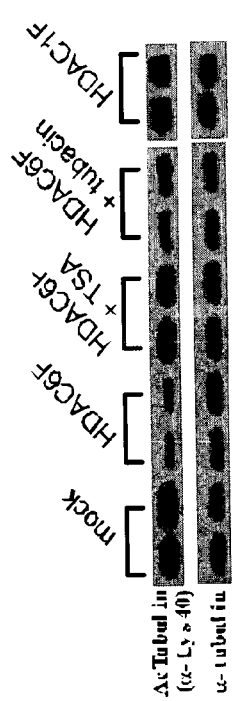
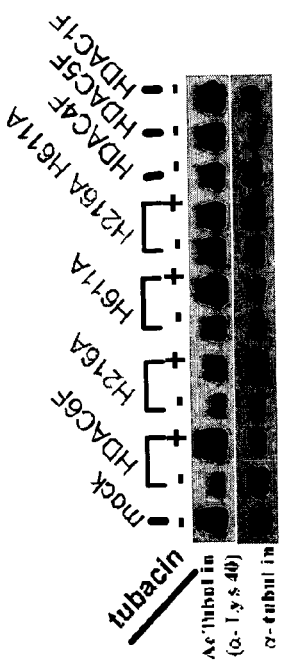
FIG. 43B
FIG. 43A
FIG. 43C

DMSO pre-treatment      tubacin (2 µM) pre-treatment

Biasing elements in diversity-oriented synthesis

| Treatment | Mean α-tubulin acetylation |
|---|---|
| DMSO | 92 |
| ITSA1 | 82 |
| TSA | 322 |
| TSA + ITSA1 | 104 |
| tubacin | 183 |
| tubacin + ITSA1 | 110 |

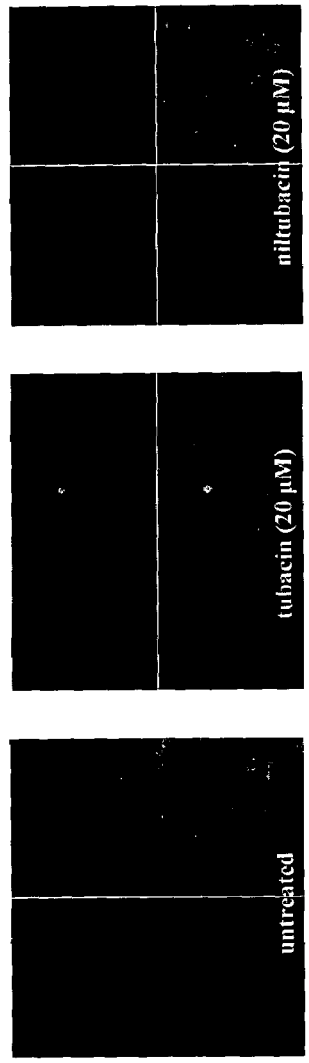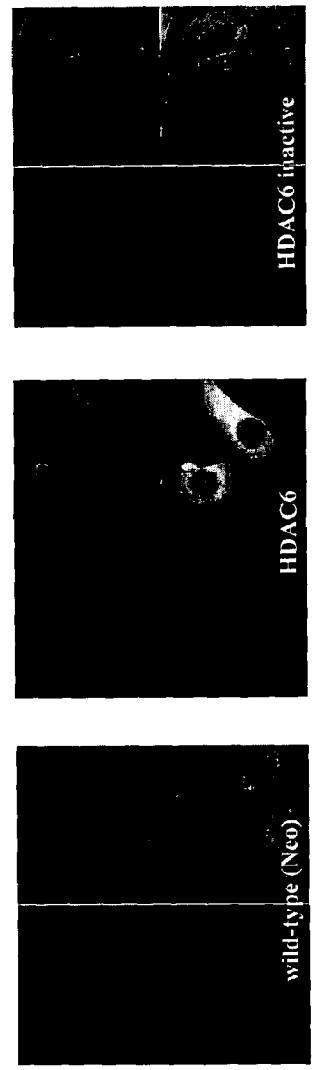
FIG. 49B
FIG. 49C

DIOXANES AND USES THEREOF

PRIORITY INFORMATION

The present application is a Continuation-In-Part of U.S. patent application Ser. No. 10/144,316; filed May 9, 2002 now abandoned, which claims priority under 35 U.S.C. § 119(e) to provisional application No. 60/289,850, filed May 9, 2001, entitled "HDAC Inhibitors", the entire contents of each of these applications are hereby incorporated by reference.

GOVERNMENT SUPPORT

The invention was supported in part by Grant No.: GM38627 from the National Institutes of Health, a grant from the Damon Runyon Cancer Research Foundation (grant No.: DRG-1650) and Predoctoral Fellowships for Jason C. Wong and Christina M. Grozinger (National Science Foundation). The U.S. government may have certain rights in this invention.

BACKGROUND OF THE INVENTION

The identification of small organic molecules that affect specific biological functions is an endeavor that impacts both biology and medicine. Such molecules are useful as therapeutic agents and as probes of biological function. In but one example from the emerging field of chemical genetics, in which small molecules can be used to alter the function of biological molecules to which they bind, these molecules have been useful at elucidating signal transduction pathways by acting as chemical protein knockouts, thereby causing a loss of protein function. (Schreiber et al., *J. Am. Chem. Soc.,* 1990, 112, 5583; Mitchison, *Chem. and Biol.,* 1994, 1, 3) Additionally, due to the interaction of these small molecules with particular biological targets and their ability to affect specific biological function, they may also serve as candidates for the development of therapeutics. One important class of small molecules, natural products, which are small molecules obtained from nature, clearly have played an important role in the development of biology and medicine, serving as pharmaceutical leads, drugs (Newman et al., *Nat. Prod. Rep.* 2000, 17, 215–234), and powerful reagents for studying cell biology (Schreiber, S. L. *Chem. and Eng. News* 1992 Oct. 26, 22–32).

Because it is difficult to predict which small molecules will interact with a biological target, and it is oftent difficult to obtain and synthesize efficiently small molecules found in nature, intense efforts have been directed towards the generation of large numbers, or libraries, of small organic compounds, often "natural product-like" libraries. These libraries can then be linked to sensitive screens for a particular biological target of interest to identify the active molecules.

One biological target of recent interest is histone deacetylase (see, for example, a discussion of the use of inhibitors of histone deacetylases for the treatment of cancer: Marks et al. *Nature Reviews Cancer* 2001, 1, 194; Johnstone et al. *Nature Reviews Drug Discovery* 2002, 1, 287). Post-translational modification of proteins through acetylation and deacetylation of lysine residues has a critical role in regulating their cellular functions. HDACs are zinc hydrolases that modulate gene expression through deacetylation of the N-acetyl-lysine residues of histone proteins and other transcriptional regulators (Hassig et al. *Curr. Opin. Chem. Biol.* 1997, 1, 300–308). HDACs participate in cellular pathways that control cell shape and differentiation, and an HDAC inhibitor has been shown effective in treating an otherwise recalcitrant cancer (Warrell et al. *J. Natl. Cancer Inst.* 1998, 90, 1621–1625). Nine human HDACs have been characterized ((a) Taunton et al. *Science* 1996, 272, 408–411; (b) Yang et al. *J. Biol. Chem.* 1997, 272, 28001–28007. (c) Grozinger et al. *Proc. Natl. Acad. Sci. U.S.A.* 1999, 96, 4868–4873. (d) Kao et al. *Genes Dev.* 2000, 14, 55–66. (e) Hu et al. *J. Biol. Chem.* 2000, 275, 15254–15264. (f) Zhou et al. *Proc. Natl. Acad. Sci. U.S.A.* 2001, 98, 10572–10577) and two inferred (Venter et al. *Science* 2001, 291, 1304–1351) these members fall into two related classes (class I and II). To date, no small molecules are known that selectively target either the two classes or individual members of this family ((for example ortholog-selective HDAC inhibitors have been reported: (a) Meinke et al. *J. Med. Chem.* 2000, 14, 4919–4922; (b) Meinke, et al. *Curr. Med. Chem.* 2001, 8, 211–235).

Clearly, it would be desirable to develop compounds capable of selectively targeting either of the two classes or individual members of this family. Additionally, it would be desirable to identify novel compounds capable of acting as probes of biological function.

SUMMARY OF THE INVENTION

As discussed above, there remains a need for the development of novel therapeutic agents and agents capable of elucidating biological functions. The present invention provides novel compounds of general formula (I),

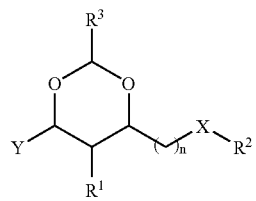

(I)

and pharmaceutical compositions thereof, as described generally and in subclasses herein, which compounds are useful as inhibitors of histone deacetylases, and thus are useful for the treatment of proliferative diseases and as antiprotozoal agents. The inventive compounds are additionally useful as tools to probe biological function.

In yet another aspect, the present invention provides methods for inhibiting histone deacetylase activity in a patient or a biological sample, comprising administering to said patient, or contacting said biological sample with an effective inhibitory amount of a compound of the invention. In still another aspect, the present invention provides methods for treating any disorder involving histone deacetylase activity, comprising administering to a subject in need thereof a therapeutically effective amount of a compound of the invention.

In yet another aspect, the present invention provides methods for preparing compounds of the invention and intermediates thereof. In another aspect of the invention, a method for the synthesis of the core structure (III$^4$) is provided, one method comprising steps of:
providing an epoxy alcohol having the structure:

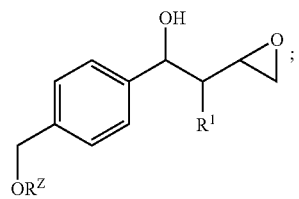

reacting the epoxy alcohol with a reagent having the structure R$^2$XH under suitable conditions to generate a diol having the core structure:

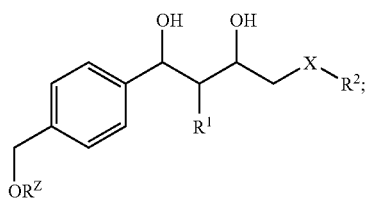

reacting the diol with a reagent having the structure R₃CH(OMe)₂ under suitable conditions to generate a scaffold having the core structure:

(III^A)

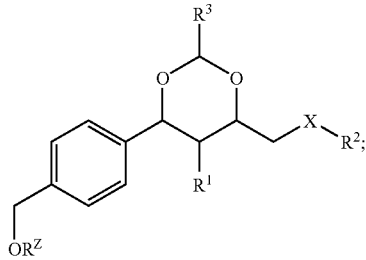

wherein R¹ is hydrogen, or an aliphatic, alicyclic, heteroaliphatic, heterocyclic, aromatic or heteroaromatic moiety;

R² is hydrogen, a protecting group, or an aliphatic, alicyclic, heteroaliphatic, heterocyclic, aromatic or heteroaromatic moiety;

X is —O—, —C(R^{2A})₂—, —S—, or —NR^{2A}—, wherein R^{2A} is hydrogen, a protecting group, or an aliphatic, alicyclic, heteroaliphatic, heterocyclic, aromatic or heteroaromatic moiety;

or wherein two or more occurrences of R² and R^{2A}, taken together, form an alicyclic or heterocyclic moiety, or an aryl or heteroaryl moiety;

R³ is an aliphatic, alicyclic, heteroaliphatic, heterocyclic, aromatic or heteroaromatic moiety; and R^Z is an aliphatic, alicyclic, heteroaliphatic, heterocyclic, aromatic or heteroaromatic moiety and is attached to a solid support.

In certain embodiments, R³ has the following structure:

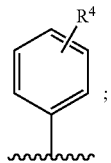

and the method described above generates the structure:

(VIII^A)

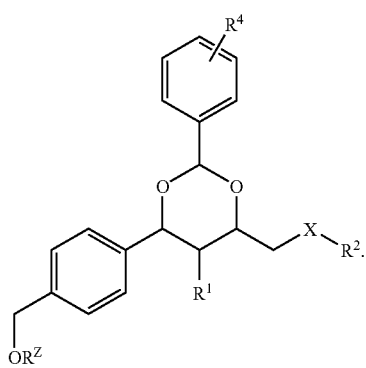

In another aspect of the invention, a method for the synthesis of the core structure (IX) is provided, one method comprising steps of:

providing an epoxy alcohol having the structure:

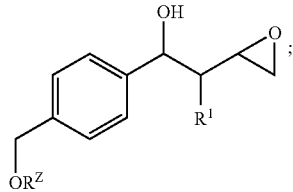

reacting the epoxy alcohol with a reagent having the structure R²XH under suitable conditions to generate a diol having the core structure:

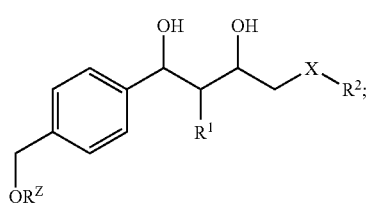

subjecting the diol with a reagent having the structure:

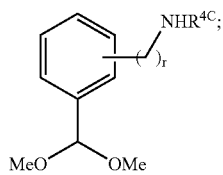

wherein R^{4C} is a nitrogen protecting group;

to suitable conditions to generate an amine having the structure:

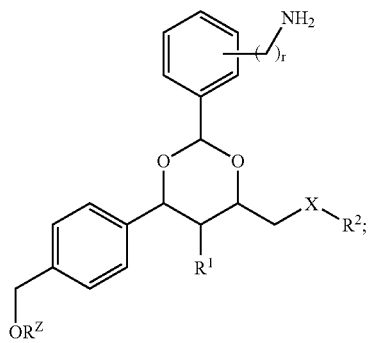

reacting the amine with a reagent having the structure:

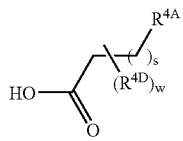

under suitable conditions to generate a scaffold having the core structure:

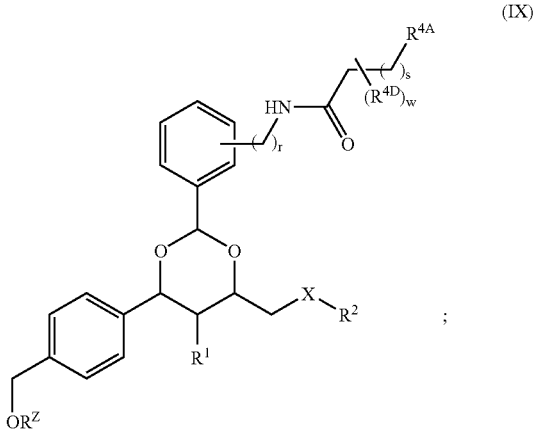

wherein R¹ is hydrogen, or an aliphatic, alicyclic, heteroaliphatic, heterocyclic, aromatic or heteroaromatic moiety;

R² is hydrogen, a protecting group, or an aliphatic, alicyclic, heteroaliphatic, heterocyclic, aromatic or heteroaromatic moiety;

X is —O—, —C(R$^{2A}$)$_2$—, —S—, or —NR$^{2A}$—, wherein R$^{2A}$ is hydrogen, a protecting group, or an aliphatic, alicyclic, heteroaliphatic, heterocyclic, aromatic or heteroaromatic moiety;

or wherein two or more occurrences of R² and R$^{2A}$, taken together, form an alicyclic or heterocyclic moiety, or an aryl or heteroaryl moiety;

r is 0 or 1;

s is an integer from 2–5;

w is an integer from 0–4;

R$^{4A}$ comprises a metal chelator;

each occurrence of R$^{4D}$ is independently hydrogen, alkyl, heteroalkyl, cycloalkyl, heterocyclic, alkenyl, alkynyl, aryl, heteroaryl, halogen, CN, NO$_2$, or WR$^{W1}$ wherein W is O, S, NR$^{W2}$, —C(=O), —S(=O), —SO$_2$, —C(=O)O—, —OC(=O), —C(=O)NR$^{W2}$, —NR$^{W2}$C(=O); wherein each occurrence of R$^{W1}$ and R$^{W2}$ is independently hydrogen, a protecting group, a prodrug moiety or an alkyl, cycloalkyl, heteroalkyl, heterocyclic, aryl or heteroaryl moiety, or, when W is NR$^{W2}$, R$^{W1}$ and R$^{W2}$, taken together with the nitrogen atom to which they are attached, form a heterocyclic or heteroaryl moiety; or any two adjacent occurrences of R$^{2B}$, taken together with the atoms to which they are attached, form a substituted or unsubstituted, saturated or unsaturated alicyclic or heterocyclic moiety, or a substituted or unsubstituted aryl or heteroaryl moiety; and R$^Z$ is an aliphatic, alicyclic, heteroaliphatic, heterocyclic, aromatic or heteroaromatic moiety and is attached to a solid support.

DEFINITIONS

Certain compounds of the present invention, and definitions of specific functional groups are also described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference. Furthermore, it will be appreciated by one of ordinary skill in the art that the synthetic methods, as described herein, utilize a variety of protecting groups. By the term "protecting group", has used herein, it is meant that a particular functional moiety, e.g., C, O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably nontoxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen and carbon protecting groups may be utilized. Exemplary protecting groups are detailed herein, however, it will be appreciated that the present invention is not intended to be limited to these protecting groups; rather, a variety of additional equivalent protecting groups can be readily identified using the above criteria and utilized in the method of the present invention. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference. Furthermore, a variety of carbon protecting groups are described in Myers, A.; Kung, D. W.; Zhong, B.; Movassaghi, M.; Kwon, S. *J. Am. Chem. Soc.* 1999, 121, 8401–8402, the entire contents of which are hereby incorporated by reference.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example of proliferative disorders, including, but not limited to cancer. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "acyl", as used herein, refers to a carbonyl-containing functionality, e.g., —C(=O)R', wherein R' is an aliphatic, alycyclic, heteroaliphatic, heterocyclic, aryl, heteroaryl, (aliphatic)aryl, (heteroaliphatic)aryl, heteroaliphatic(aryl) or heteroaliphatic(heteroaryl) moiety, whereby each of the aliphatic, heteroaliphatic, aryl, or heteroaryl moieties is substituted or unsubstituted, or is a substituted (e.g., hydrogen or aliphatic, heteroaliphatic, aryl, or heteroaryl moieties) oxygen or nitrogen containing functionality (e.g., forming a carboxylic acid, ester, or amide functionality).

The term "aliphatic", as used herein, includes both saturated and unsaturated, straight chain (i.e., unbranched) or branched aliphatic hydrocarbons, which are optionally substituted with one or more functional groups. As will be appreciated by one of ordinary skill in the art, "aliphatic" is intended herein to include, but is not limited to, alkyl, alkenyl, alkynyl moieties. Thus, as used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (substituted, unsubstituted, branched or unbranched) having 1–6 carbon atoms.

In certain embodiments, the alkyl, alkenyl and alkynyl groups employed in the invention contain 1–20 aliphatic carbon atoms. In certain other embodiments, the alkyl, alkenyl, and alkynyl groups employed in the invention contain 1–10 aliphatic carbon atoms. In yet other embodiments, the alkyl, alkenyl, and alkynyl groups employed in the invention contain 1–8 aliphatic carbon atoms. In still other embodiments, the alkyl, alkenyl, and alkynyl groups employed in the invention contain 1–6 aliphatic carbon atoms. In yet other embodiments, the alkyl, alkenyl, and alkynyl groups employed in the invention contain 1–4 carbon atoms. Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargy 1), 1-propynyl and the like.

The term "alicyclic", as used herein, refers to compounds which combine the properties of aliphatic and cyclic compounds and include but are not limited to cyclic, or polycyclic aliphatic hydrocarbons and bridged cycloalkyl compounds, which are optionally substituted with one or more functional groups. As will be appreciated by one of ordinary skill in the art, "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —CH$_2$-cyclopropyl, cyclobutyl, —CH$_2$-cyclobutyl, cyclopentyl, —CH$_2$-cyclopentyl-n, cyclohexyl, —CH$_2$-cyclohexyl, cyclohexenylethyl, cyclohexanylethyl, norborbyl moieties and the like, which again, may bear one or more substituents.

The term "alkoxy" (or "alkyloxy"), or "thioalkyl" as used herein refers to an alkyl group, as previously defined, attached to the parent molecular moiety through an oxygen atom or through a sulfur atom. In certain embodiments, the alkyl group contains 1–20 aliphatic carbon atoms. In certain other embodiments, the alkyl group contains 1–10 aliphatic carbon atoms. In yet other embodiments, the alkyl, alkenyl, and alkynyl groups employed in the invention contain 1–8 aliphatic carbon atoms. In still other embodiments, the alkyl group contains 1–6 aliphatic carbon atoms. In yet other embodiments, the alkyl group contains 1–4 aliphatic carbon atoms. Examples of alkoxy, include but are not limited to, methoxy, ethoxy, propoxy, isopropoxy, n-butoxy, tert-butoxy, neopentoxy and n-hexoxy. Examples of thioalkyl include, but are not limited to, methylthio, ethylthio, propylthio, isopropylthio, n-butylthio, and the like.

The term "alkylamino" refers to a group having the structure —NHR' wherein R' is alkyl, as defined herein. The term "aminoalkyl" refers to a group having the structure NH$_2$R'—, wherein R' is alkyl, as defined herein. In certain embodiments, the alkyl group contains 1–20 aliphatic carbon atoms. In certain other embodiments, the alkyl group contains 1–10 aliphatic carbon atoms. In yet other embodiments, the alkyl, alkenyl, and alkynyl groups employed in the invention contain 1–8 aliphatic carbon atoms. In still other embodiments, the alkyl group contains 1–6 aliphatic carbon atoms. In yet other embodiments, the alkyl group contains 1–4 aliphatic carbon atoms. Examples of alkylamino include, but are not limited to, methylamino, ethylamino, iso-propylamino and the like.

Some examples of substituents of the above-described aliphatic (and other) moieties of compounds of the invention include, but are not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alycyclic, heteroaliphatic, heterocyclic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

In general, the term "aromatic moiety", as used herein, refers to a stable mono- or polycyclic, unsaturated moiety having preferably 3–14 carbon atoms, each of which may be substituted or unsubstituted. In certain embodiments, the term "aromatic moiety" refers to a planar ring having p-orbitals perpendicular to the plane of the ring at each ring atom and satisfying the Huckel rule where the number of pi electrons in the ring is (4n+2) wherein n is an integer. A mono- or polycyclic, unsaturated moiety that does not satisfy one or all of these criteria for aromaticity is defined herein as "non-aromatic", and is encompassed by the term "alicyclic".

In general, the term "heteroaromatic moiety", as used herein, refers to a stable mono- or polycyclic, unsaturated moiety having preferably 3–14 carbon atoms, each of which may be substituted or unsubstituted; and comprising at least one heteroatom selected from O, S and N within the ring (i.e., in place of a ring carbon atom). In certain embodiments, the term "heteroaromatic moiety" refers to a planar ring comprising at least on eheteroatom, having porbitals perpendicular to the plane of the ring at each ring atom, and satisfying the Huckel rule where the number of pi electrons in the ring is (4n+2) wherein n is an integer.

It will also be appreciated that aromatic and heteroaromatic moieties, as defined herein may be attached via an alkyl or heteroalkyl moiety and thus also include -(alkyl) aromatic, -(heteroalkyl)aromatic, -(heteroalkyl)heteroaromatic, and -(heteroalkyl)heteroaromatic moieties. Thus, as used herein, the phrases "aromatic or heteroaromatic moieties" and "aromatic, heteroaromatic, -(alkyl)aromatic, -(heteroalkyl)aromatic, -(heteroalkyl)heteroaromatic, and -(heteroalkyl)heteroaromatic" are interchangeable. Substituents include, but are not limited to, any of the previously mentioned substituents, i.e., the substituents recited for aliphatic moieties, or for other moieties as disclosed herein, resulting in the formation of a stable compound.

The term "aryl", as used herein, does not differ significantly from the common meaning of the term in the art, and refers to an unsaturated cyclic moiety comprising at least one aromatic ring. In certain embodiments, "aryl" refers to a mono- or bicyclic carbocyclic ring system having one or two aromatic rings including, but not limited to, phenyl, naphthyl, tetrahydronaphthyl, indanyl, indenyl and the like.

The term "heteroaryl", as used herein, does not differ significantly from the common meaning of the term in the art, and refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups (including bicyclic aryl groups) can be unsubstituted or substituted, wherein substitution includes replacement of one or more of the hydrogen atoms thereon independently with any one or more of the following moieties including, but not limited to: aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)R$_x$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl, heteroaryl, -(alkyl)aryl or -(alkyl)heteroaryl substituents described above and herein may be substituted or unsubstituted. Additionally, it will be appreciated, that any two adjacent groups taken together may represent a 4, 5, 6, or 7-membered substituted or unsubstituted alicyclic or heterocyclic moiety. Additional examples of generally applicable substituents are illustrated by the specific embodiments shown in the Examples that are described herein.

The term "cycloalkyl", as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of aliphatic, alicyclic, heteroaliphatic or heterocyclic moieties, may optionally be substituted with substituents including, but not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described above and herein may be substituted or unsubstituted. Additional examples of generally applicable substituents are illustrated by the specific embodiments shown in the Examples that are described herein.

The term "heteroaliphatic", as used herein, refers to aliphatic moieties in which one or more carbon atoms in the main chain have been substituted with a heteroatom. Thus, a heteroaliphatic group refers to an aliphatic chain which contains one or more oxygen, sulfur, nitrogen, phosphorus or silicon atoms, e.g., in place of carbon atoms. Heteroaliphatic moieties may be linear or branched, and saturated or unsaturated. In certain embodiments, heteroaliphatic moieties are substituted by independent replacement of one or more of the hydrogen atoms thereon with one or more moieties including, but not limited to aliphatic; alicyclic; heteroaliphatic; heterocyclic; aromatic; heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described above and herein may be substituted or unsubstituted. Additional examples of generally applicable substituents are illustrated by the specific embodiments shown in the Examples that are described herein.

The term "heterocycloalkyl", "heterocycle" or "heterocyclic", as used herein, refers to compounds which combine the properties of heteroaliphatic and cyclic compounds and include, but are not limited to, saturated and unsaturated mono- or polycyclic cyclic ring systems having 5–16 atoms wherein at least one ring atom is a heteroatom selected from O, S and N (wherein the nitrogen and sulfur heteroatoms may be optionally be oxidized), wherein the ring systems are optionally substituted with one or more functional groups, as defined herein. In certain embodiments, the term "heterocycloalkyl", "heterocycle" or "heterocyclic" refers to a non-aromatic 5-, 6- or 7-membered ring or a polycyclic group wherein at least one ring atom is a heteroatom selected from O, S and N (wherein the nitrogen and sulfur heteroatoms may be optionally be oxidized), including, but not limited to, a bi- or tri-cyclic group, comprising fused six-membered rings having between one and three heteroatoms independently selected from oxygen, sulfur and nitrogen, wherein (i) each 5-membered ring has 0 to 2 double bonds, each 6-membered ring has 0 to 2 double bonds and each 7-membered ring has 0 to 3 double bonds, (ii) the nitrogen and sulfur heteroatoms may be optionally be oxidized, (iii) the nitrogen heteroatom may optionally be quaternized, and (iv) any of the above heterocyclic rings may be fused to an aryl or heteroaryl ring. Representative heterocycles include, but are not limited to, heterocycles such as furanyl, thiofuranyl, pyranyl, pyrrolyl, thienyl, pyrrolidinyl, pyrazolinyl, pyrazolidinyl, imidazolinyl, imidazolidinyl, piperidinyl, piperazinyl, oxazolyl, oxazolidinyl, isooxazolyl, isoxazolidinyl, dioxazolyl, thiadiazolyl, oxadiazolyl, tetrazolyl, triazolyl, thiatriazolyl, oxatriazolyl, thiadiazolyl, oxadiazolyl, morpholinyl, thiazolyl, thiazolidinyl, isothiazolyl, isothiazolidinyl, dithiazolyl, dithiazolidinyl, tetrahydrofuryl, and benzofused derivatives thereof. In certain embodiments, a "substituted heterocycle, or heterocycloalkyl or heterocyclic" group is utilized and as used herein, refers to a heterocycle, or heterocycloalkyl or heterocyclic group, as defined above, substituted by the independent replacement of one, two or three of the hydrogen atoms thereon with but are not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substitutents described above and herein may be substituted or unsubstituted. Additional examples or generally applicable substituents are illustrated by the specific embodiments shown in the Examples, which are described herein.

Additionally, it will be appreciated that any of the alicyclic or heterocyclic moieties described above and herein may comprise an aryl or heteroaryl moiety fused thereto. Additional examples of generally applicable substituents are illustrated by the specific embodiments shown in the Examples that are described herein. The terms "halo" and "halogen" as used herein refer to an atom selected from fluorine, chlorine, bromine and iodine.

The terms "halo" and "halogen" as used herein refer to an atom selected from fluorine, chlorine, bromine and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "amino", as used herein, refers to a primary (—NH$_2$), secondary (—NHR$_x$), tertiary (—NR$_x$R$_y$) or quaternary (—N$^+$R$_x$R$_y$R$_z$) amine, where R$_x$, R$_y$ and R$_z$ are independently an aliphatic, alicyclic, heteroaliphatic, heterocyclic, aromatic or heteroaromatic moiety, as defined herein. Examples of amino groups include, but are not limited to, methylamino, dimethylamino, ethylamino, diethylamino, diethylaminocarbonyl, methylethylamino, iso-propylamino, piperidino, trimethylamino, and propylamino.

The term "C$_{1-6}$alkylene", as used herein, refers to a substituted or unsubstituted, linear or branched saturated divalent radical consisting solely of carbon and hydrogen atoms, having from one to six carbon atoms, having a free valence "-" at both ends of the radical.

The term "C$_{2-6}$alkenylene", as used herein, refers to a substituted or unsubstituted, linear or branched unsaturated divalent radical consisting solely of carbon and hydrogen atoms, having from two to six carbon atoms, having a free valence "-" at both ends of the radical, and wherein the unsaturation is present only as double bonds and wherein a double bond can exist between the first carbon of the chain and the rest of the molecule.

Unless otherwise indicated, as used herein, the terms "alkyl", "alkenyl", "alkynyl", "heteroalkyl", "heteroalkenyl", "heteroalkynyl", "alkylidene", alkenylidene", -(alkyl) aryl, -(heteroalkyl)aryl, -(heteroalkyl)aryl, -(heteroalkyl) heteroaryl, and the like encompass substituted and unsubstituted, and linear and branched groups. Similarly, the terms "aliphatic", "heteroaliphatic", and the like encompass substituted and unsubstituted, saturated and unsaturated, and linear and branched groups. Similarly, the terms "cycloalkyl", "heterocycle", "heterocyclic", and the like encompass substituted and unsubstituted, and saturated and unsaturated groups. Additionally, the terms "cycloalkenyl", "cycloalkynyl", "heterocycloalkenyl", "heterocycloalkynyl", "aromatic", "heteroaromatic", "aryl", "heteroaryl" and the like encompass both substituted and unsubstituted groups.

The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others pro-drugs. A pro-drug is a derivative of a compound, usually with significantly reduced pharmacological activity, which contains an additional moiety, which is susceptible to removal in vivo yielding the parent molecule as the pharmacologically active species. An example of a pro-drug is an ester, which is cleaved in vivo to yield a compound of interest. Pro-drugs of a variety of compounds, and materials and methods for derivatizing the parent compounds to create the pro-drugs, are known and may be adapted to the present invention. Certain exemplary pharmaceutical compositions and pharmaceutically acceptable derivatives will be discussed in more detail herein below.

By the term "protecting group", has used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably nontoxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen and carbon protecting groups may be utilized. For example, in certain embodiments, as detailed herein, certain exemplary oxygen protecting groups are utilized. These oxygen protecting groups include, but are not limited to methyl ethers, substituted methyl ethers (e.g., MOM (methoxymethyl ether), MTM (methylthiomethyl ether), BOM (benzyloxymethyl ether), PMBM or MPM (p-methoxybenzyloxymethyl ether), to name a few), substituted ethyl ethers, substituted benzyl ethers, silyl ethers (e.g., TMS (trimethylsilyl ether), TES (triethylsilylether), TIPS (triisopropylsilyl ether), TBDMS (t-butyldimethylsilyl ether), tribenzyl silyl ether, TBDPS (t-butyldiphenyl silyl ether), to name a few), esters (e.g., formate, acetate, benzoate (Bz), trifluoroacetate, dichloroacetate, to name a few), carbonates, cyclic acetals and ketals. In certain other exemplary embodiments, nitrogen protecting groups are utilized. These nitrogen protecting groups include, but are not limited to, carbamates (including methyl, ethyl and substituted ethyl carbamates (e.g., Troc), to name a few) amides, cyclic imide derivatives, N-Alkyl and N-Aryl amines, imine derivatives, and enamine derivatives, to name a few. Certain other exemplary protecting groups are detailed herein, however, it will be appreciated that the present invention is not intended to be limited to these protecting groups; rather, a variety of additional equivalent protecting groups can be readily identified using the above criteria and utilized in the present invention. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference.

The term "solid support", as used herein, refers to a material having a rigid or semi-rigid surface. Such materials will preferably take the form of small beads, pellets, disks, chips, dishes, multi-well plates, glass slides, wafers, or the like, although other forms may be used. In some embodiments, at least one surface of the substrate will be substantially flat. The term "surface" refers to any generally two-dimensional structure on a solid substrate and may have steps, ridges, kinks, terraces, and the like without ceasing to be a surface.

The term "polymeric support", as used herein, refers to a soluble or insoluble polymer to which an amino acid or other chemical moiety can be covalently bonded by reaction with a functional group of the polymeric support. Many suitable polymeric supports are known, and include soluble polymers such as polyethylene glycols or polyvinyl alcohols, as well as insoluble polymers such as polystyrene resins. A suitable polymeric support includes functional groups such as those described below. A polymeric support is termed "soluble" if a polymer, or a polymer-supported compound, is soluble under the conditions employed. However, in general, a soluble polymer can be rendered insoluble under defined conditions. Accordingly, a polymeric support can be soluble under certain conditions and insoluble under other conditions.

The term "linker", as used herein, refers to a chemical moiety utilized to attach a compound of interest to a solid support to facilitate synthesis of inventive compounds. Exemplary linkers are described herein. It will be appreciated that other linkers (including silicon-based linkers and other linkers) that are known in the art can also be employed for the synthesis of the compounds of the invention.

The term "solid support unit" as used herein, refers to a composition comprising a solid support and a linker, as defined above and exemplified herein.

Unless indicated otherwise, the terms defined below have the following meanings:

"Compound": The term "compound" or "chemical compound" as used herein can include organometallic compounds, organic compounds, metals, transitional metal complexes, and small molecules. In certain preferred embodiments, polynucleotides are excluded from the definition of compounds. In other preferred embodiments, polynucleotides and peptides are excluded from the definition of compounds. In a particularly preferred embodiment, the term compounds refers to small molecules (e.g., preferably, non-peptidic and non-oligomeric) and excludes peptides, polynucleotides, transition metal complexes, metals, and organometallic compounds.

"Small Molecule": As used herein, the term "small molecule" refers to a non-peptidic, non-oligomeric organic compound either synthesized in the laboratory or found in nature. Small molecules, as used herein, can refer to compounds that are "natural product-like", however, the term "small molecule" is not limited to "natural product-like" compounds. Rather, a small molecule is typically characterized in that it contains several carbon-carbon bonds, and has a molecular weight of less than 1500, although this characterization is not intended to be limiting for the purposes of the present invention. Examples of "small molecules" that occur in nature include, but are not limited to, taxol, dynemicin, and rapamycin. Examples of "small molecules" that are synthesized in the laboratory include, but are not limited to, compounds described in Tan et al., ("Stereoselective Synthesis of over Two Million Compounds Having Structural Features Both Reminiscent of Natural Products and Compatible with Miniaturized Cell-Based Assays" *J. Am. Chem. Soc.* 120:8565, 1998; incorporated herein by reference). In certain other preferred embodiments, natural-product-like small molecules are utilized.

"Natural Product-Like Compound": As used herein, the term "natural product-like compound" refers to compounds that are similar to complex natural products which nature has selected through evolution. Typically, these compounds contain one or more stereocenters, a high density and diversity of functionality, and a diverse selection of atoms within one structure. In this context, diversity of functionality can be defined as varying the topology, charge, size, hydrophilicity, hydrophobicity, and reactivity to name a few, of the functional groups present in the compounds. The term, "high density of functionality", as used herein, can preferably be used to define any molecule that contains preferably three or more latent or active diversifiable functional moieties. These structural characteristics may additionally render the inventive compounds functionally reminiscent of complex natural products, in that they may interact specifically with a particular biological receptor, and thus may also be functionally natural product-like.

"Metal chelator": As used herein, the term "metal chelator" refers to any molecule or moiety that is is capable of forming a complex (i.e., "chelates") with a metal ion. In certain exemplary embodiments, a metal chelator refers to to any molecule or moiety that "binds" to a metal ion, in solution, making it unavailable for use in chemical/enzymatic reactions. In certain embodiments, the solution comprises aqueous environments under physiological conditions. Examples of metal ions include, but are not limited to, Ca2+, Fe3+, Zn2+, Na+, etc. In certain embodiments, molecules of moieties that precipitate metal ions are not considered to be metal chelators.

As used herein the term "biological sample" includes, without limitation, cell cultures or extracts thereof; biopsied material obtained from an animal (e.g., mammal) or extracts thereof; and blood, saliva, urine, feces, semen, tears, or other body fluids or extracts thereof. For example, the term "biological sample" refers to any solid or fluid sample obtained from, excreted by or secreted by any living organism, including single-celled micro-organisms (such as bacteria and yeasts) and multicellular organisms (such as plants and animals, for instance a vertebrate or a mammal, and in particular a healthy or apparently healthy human subject or a human patient affected by a condition or disease to be diagnosed or investigated). The biological sample can be in any form, including a solid material such as a tissue, cells, a cell pellet, a cell extract, cell homogenates, or cell fractions; or a biopsy, or a biological fluid. The biological fluid may be obtained from any site (e.g. blood, saliva (or a mouth wash containing buccal cells), tears, plasma, serum, urine, bile, cerebrospinal fluid, amniotic fluid, peritoneal fluid, and pleural fluid, or cells therefrom, aqueous or vitreous humor, or any bodily secretion), a transudate, an exudate (e.g fluid obtained from an abscess or any other site of infection or inflammation), or fluid obtained from a joint (e.g a normal joint or a joint affected by disease such as rheumatoid arthritis, osteoarthritis, gout or septic arthritis). The biological sample can be obtained from any organ or tissue (including a biopsy or autopsy specimen) or may comprise cells (whether primary cells or cultured cells) or medium conditioned by any cell, tissue or organ. Biological samples may also include sections of tissues such as frozen sections taken for histological purposes. Biological samples also include mixtures of biological molecules including proteins, lipids, carbohydrates and nucleic acids generated by partial or complete fractionation of cell or tissue homogenates. Although the sample is preferably taken from a human subject, biological samples may be from any animal, plant, bacteria, virus, yeast, etc. The term animal, as used herein, refers to humans as well as non-human animals, at any stage of development, including, for example, mammals, birds, reptiles, amphibians, fish, worms and single cells. Cell cultures and live tissue samples are considered to be pluralities of animals. In certain exemplary embodiments, the non-human animal is a mammal (e.g., a rodent, a mouse, a rat, a rabbit, a monkey, a dog, a cat, a sheep, cattle, a primate, or a pig). An animal may be a transgenic animal or a human clone. If desired, the biological sample may be subjected to preliminary processing, including preliminary separation techniques.

BRIEF DESCRIPTION OF THE DRAWING

FIG. 1 depicts sequence comparison of residues on the rim of the N-acetyl lysine binding channel. Amino acids in HDLP that contact TSA are boxed in gray. The numbering is based on the HDLP sequence.

FIG. 15 depicts the effect of inventive compound JCWII114 analogs on acetylated tubulin levels in A549 cells (18 h treatment).

FIG. 37 depicts chemical space derived from principal component analysis (PCA) of the molecular descriptors from the 7,200 1,3-dioxanes. Molecular descriptors were computed using QSARIS and PCA performed using XLSTAT-PRO (v5.2) using a standardized Euclidean distance metric. (A) Variance accounted for by each dimension. (B) Eigenvalues and variance of the first five principal component axes. (C) Two-dimensional plots showing a subset of the small molecules (blue balls) and relationship of descriptors (red lines). Angle between vectors is a proportional to their correlation. (D) 3-dimensional plot of descriptors (colored balls) on the first three PCA axes showing clustering of related descriptors.

DETAILED DESCRIPTION OF THE CERTAIN EXEMPLARY EMBODIMENTS OF THE INVENTION

Figure 2:
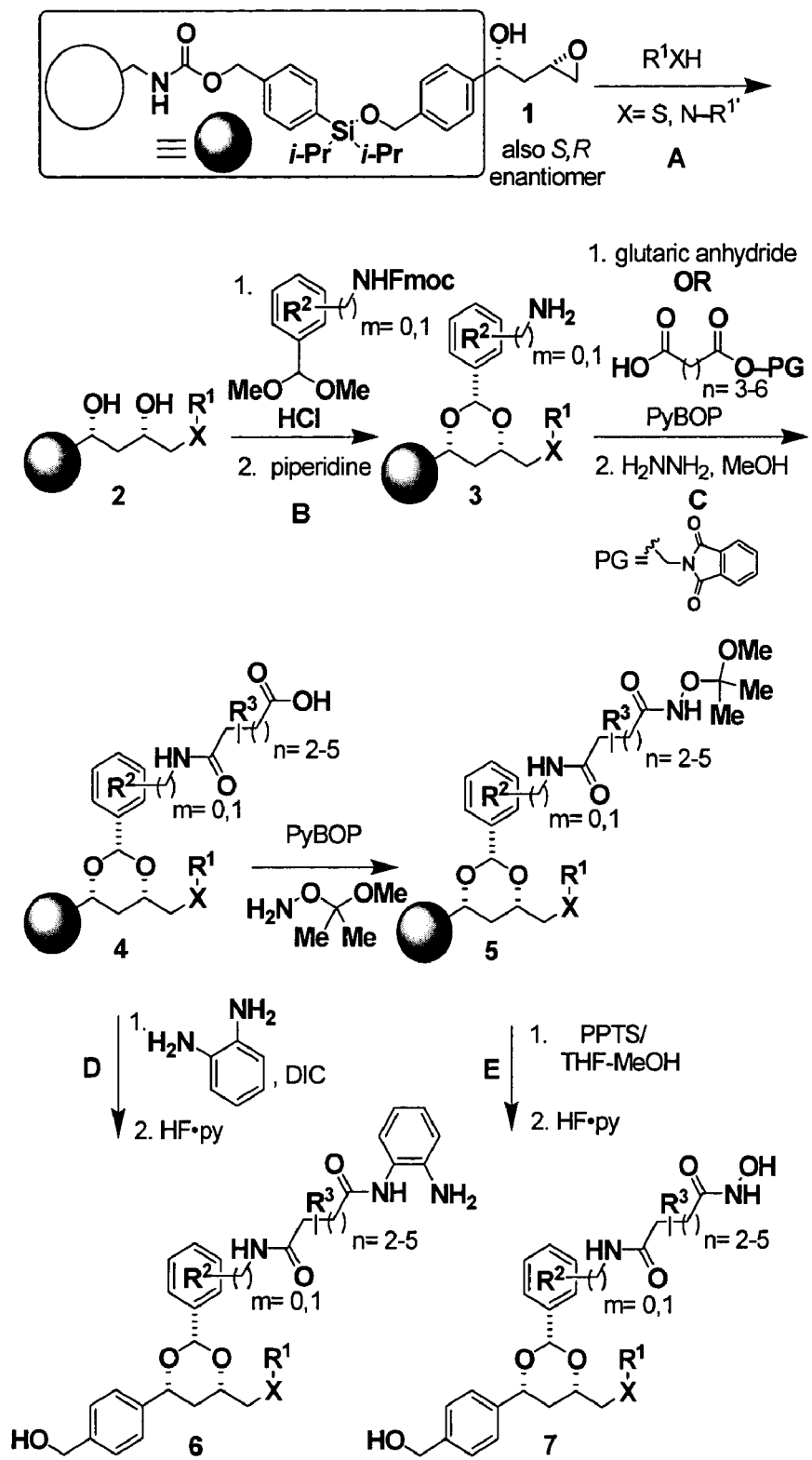
FIG. 2 depicts a scheme for synthesis of compounds of the invention.
Figure 3:
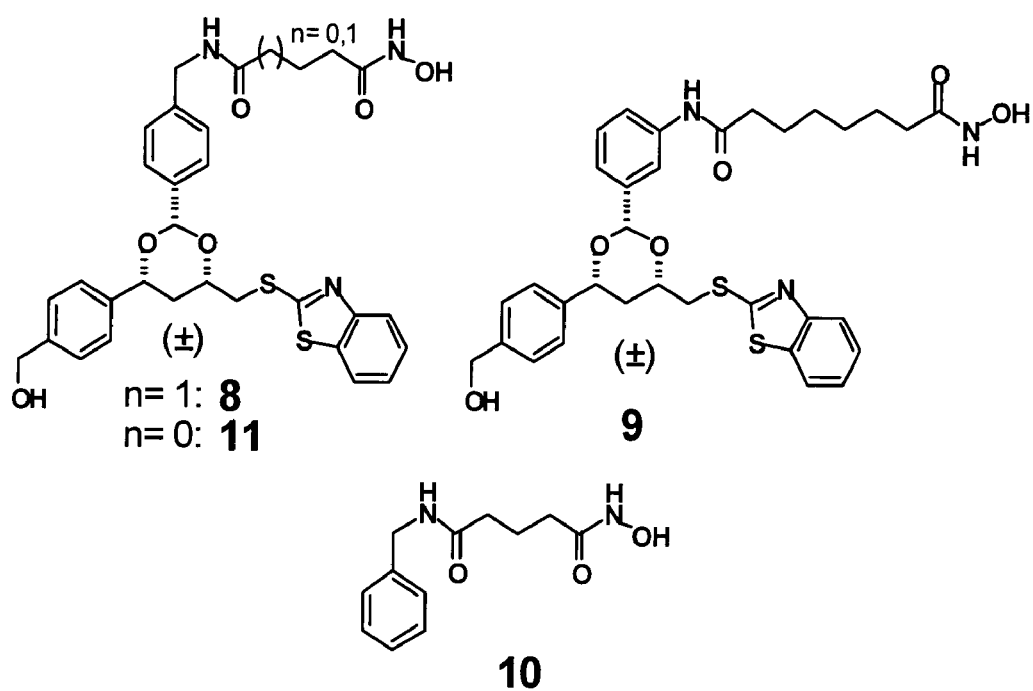
FIG. 3 depicts exemplary inhbitors of HDAC 1 and HDAC6.

As discussed above, there remains a need for the development of novel therapeutic agents and agents capable of elucidating biological functions. The present invention provides novel compounds of general formula (I), and methods for the synthesis thereof, which compounds are useful as inhibitors of histone deacetylases, and thus are useful for the treatment of proliferative diseases and as antiprotozoal agents. The inventive compounds are additionally useful as tools to probe biological function.

1) General Description of Compounds of the Invention

As discussed above, the present invention provides a novel class of compounds useful for the treatment of cancer and other proliferative conditions related thereto. In certain embodiments, the compounds of the present invention are useful as inhibitors of histone deacetylases and thus are useful as anticancer agents, and thus may be useful in the treatment of cancer, by effecting tumor cell death or inhibiting the growth of tumor cells. In certain exemplary embodiments, the inventive anticancer agents are useful in the treatment of cancers and other proliferative disorders, including, but not limited to breast cancer, cervical cancer, colon and rectal cancer, leukemia, lung cancer, melanoma, multiple myeloma, non-Hodgkin's lymphoma, ovarian cancer, pancreatic cancer, prostate cancer, and gastric cancer, to name a few. In certain embodiments, the inventive anticancer agents are active against leukemia cells and melanoma cells, and thus are useful for the treatment of leukemias (e.g., myeloid, lymphocytic, myelocytic and lymphoblastic leukemias) and malignant melanomas. Additionally, as described above and in the exemplification, the inventive compounds may also be useful in the treatment of protozoal infections. In certain exemplary embodiments, the compounds of the invention are useful for disorders resulting from histone deacetylation activity.

Compounds of this invention comprise those, as set forth above and described herein, and are illustrated in part by the various classes, subgenera and species disclosed elsewhere herein.

In general, the present invention provides compounds having the general structure (I):

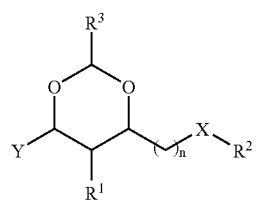

(I)

and pharmaceutically acceptable derivatives thereof;

wherein $R^1$ is hydrogen, or an aliphatic, alicyclic, heteroaliphatic, heterocyclic, aromatic or heteroaromatic moiety;

n is 1–5;

$R^2$ is hydrogen, a protecting group, or an aliphatic, alicyclic, heteroaliphatic, heterocyclic, aromatic or heteroaromatic moiety;

X is —O—, —C($R^{2A}$)$_2$—, —S—, or —N$R^{2A}$—, wherein $R^{2A}$ is hydrogen, a protecting group, or an aliphatic, alicyclic, heteroaliphatic, heterocyclic, aromatic or heteroaromatic moiety;

or wherein two or more occurrences of $R^2$ and $R^{2A}$, taken together, form an alicyclic or heterocyclic moiety, or an aryl or heteroaryl moiety;

$R^3$ is an aliphatic, alicyclic, heteroaliphatic, heterocyclic, aromatic or heteroaromatic moiety; and Y is hydrogen or an aliphatic, alicyclic, heteroaliphatic, heterocyclic, aromatic or heteroaromatic moiety.

In certain embodiments of the invention, $R^1$ is hydrogen, or an aliphatic, alicyclic, heteroaliphatic, heterocyclic, aryl, heteroaryl, -(aliphatic)aryl, -(aliphatic)heteroaryl, -(heteroaliphatic)aryl, or -(heteroaliphatic)heteroaryl moiety;

$R^2$ is hydrogen, a protecting group, or an aliphatic, alicyclic, heteroaliphatic, heterocyclic, aryl, heteroaryl, -(aliphatic)aryl, -(aliphatic)heteroaryl, -(heteroaliphatic)aryl, or -(heteroaliphatic)heteroaryl moiety;

X is —O—, —C($R^{2A}$)$_2$—, —S—, or —N$R^{2A}$—, wherein $R^{2A}$ is hydrogen, a protecting group, or an aliphatic, alicyclic, heteroaliphatic, heterocyclic, aryl, heteroaryl, -(aliphatic)aryl, -(aliphatic)heteroaryl, -(heteroaliphatic)aryl, or -(heteroaliphatic)heteroaryl moiety;

or wherein two or more occurrences of $R^2$ and $R^{2A}$, taken together, form an alicyclic or heterocyclic moiety, or an aryl or heteroaryl moiety;

$R^3$ is an aliphatic, alicyclic, heteroaliphatic, heterocyclic, aryl, heteroaryl, -(aliphatic)aryl, -(aliphatic)heteroaryl, -(heteroaliphatic)aryl, or -(heteroaliphatic)heteroaryl moiety; and Y is hydrogen or an aliphatic, alicyclic, heteroaliphatic, heterocyclic, aryl, heteroaryl, -(aliphatic)aryl, -(aliphatic)heteroaryl, -(heteroaliphatic)aryl, or -(heteroaliphatic)heteroaryl moiety.

In certain embodiments of the invention, compounds of formula (I) have the following stereochemistry and structure as shown in formula (Ia):

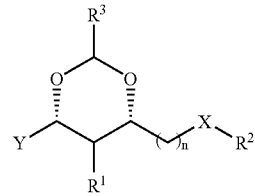

(Ia)

In certain embodiments of the invention, compounds of formula (I) have the following stereochemistry and structure as shown in formula (Ib):

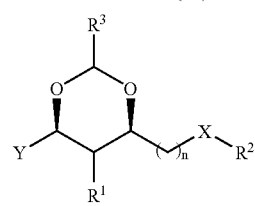

(Ib)

In certain embodiments of the invention, compounds of formula (I) have the following stereochemistry and structure as shown in formula (Ic):

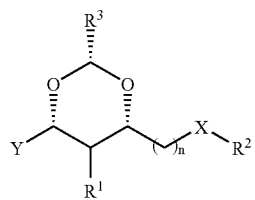

(Ic)

In certain embodiments of the invention, compounds of formula (I) have the following stereochemistry and structure as shown in formula (Id):

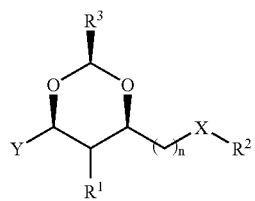

(Id)

It will be appreciated that, in certain embodiments of the compounds as described generally above and in classes and subclasses herein certain classes of compounds are excluded:

compounds where X is $NR^{2A}$ and Y is a phenyl group substituted with —C(=O)$NH_2$ or —C(=O)NH(solid support).

In certain embodiments, when $R^3$ represents a phenyl group substituted with a moiety having the structure —P-Q, the following groups do not occur simultaneously as defined:

P is selected from the group consisting of substituted or unsubstituted $C_4$–$C_8$ alkylene, $C_4$–$C_8$ alkenylene, $C_4$–$C_8$ alkynylene, and —R-T-U—, wherein R and U are independently absent or represent a $C_2$–$C_7$ alkylene, a $C_2$–$C_7$ alkenylene, or a $C_2$–$C_7$ alkynylene, and T represents O, S or $NR^T$, wherein $R^T$ represents hydrogen, lower alkyl, lower alkenyl, lower alkynyl, aralkyl, aryl or heterocyclyl; and Q is selected from the group consisting of:

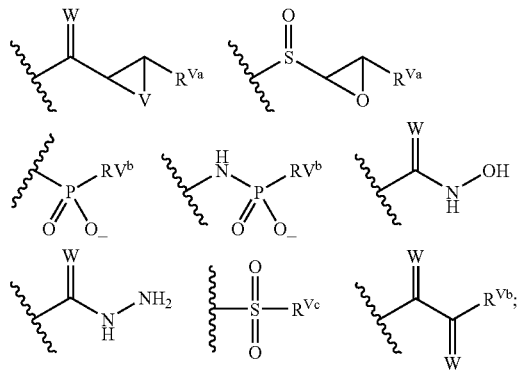

and a boronic acid moiety; wherein W is O or S; V is O, S or —$NR^{Vd}$, wherein $R^{Vd}$ is hydrogen, alkyl, alkoxycarbonyl, aryloxycarbonyl, alkylsulfonyl, arylsulfonyl, or aryl; $R^{Va}$ is hydrogen, alkyl, alkenyl, alkynyl, or aryl; $R^{Vb}$ is hydrogen, alkyl, aryl, alkoxy, aryloxy, amino, hydroxylamino, alkoxylamino or halogen; and $R^{Vc}$ is hydrogen, alkyl, aryl, hydroxyl, alkoxy, aryloxy or amino.

In certain embodiments, when $R^3$ represents a phenyl group substituted with a moiety having the structure —P-Q, the following groups do not occur simultaneously as defined:

P is selected from the group consisting of

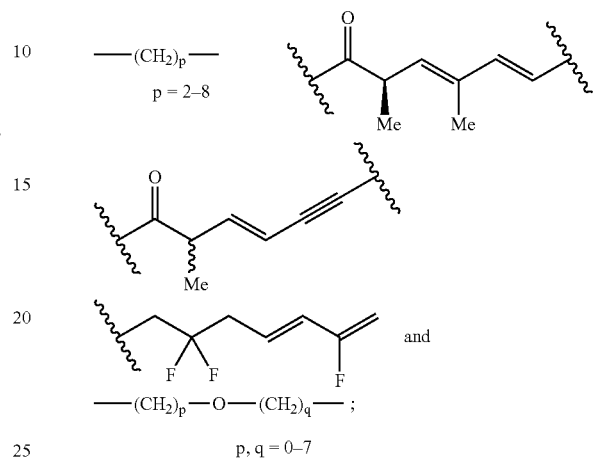

and Q is selected from the group consisting of:

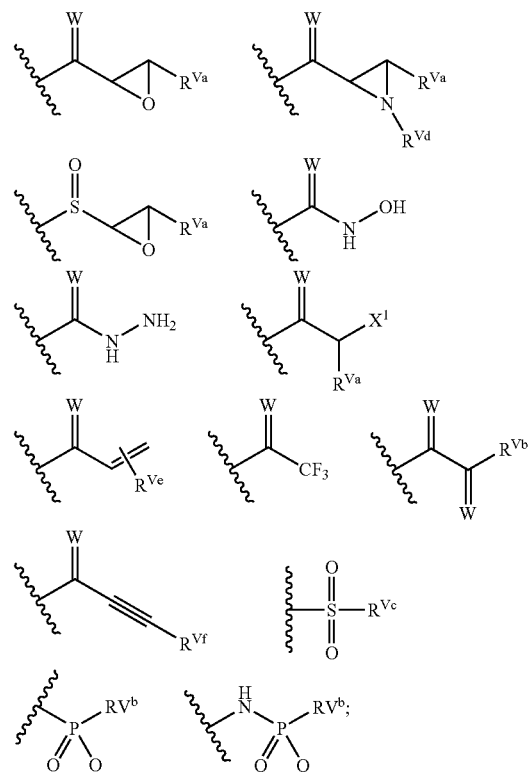

wherein W and $R^{Va-d}$ are as defined above; $X^1$ is a good leaving group (e.g., diazo, halogen, a sulfate or sulfonate ester such as a tosylate or mesylate); $R^{Ve}$ is hydrogen, alkyl, aryl, alkoxy, aryloxy, halogen; and $R^{Vf}$ is hydrogen, alkyl or halogen.

2) Featured Classes of Compounds

In certain embodiments, the present invention defines particular classes of compounds which are of special interest. For example, one class of compounds of special interest includes those compounds of the invention as described above and in certain subclasses herein, in which Y is an aryl or heteroaryl moiety substituted with Z, wherein Z is hydrogen, —(CH$_2$)$_q$OR$^Z$, —(CH$_2$)$_q$SR$^Z$, —(CH$_2$)$_q$N(R$^Z$)$_2$, —C(=O)R$^Z$, —C(=O)N(R$^Z$)$_2$, or an aliphatic, alycyclic, heteroaliphatic, heterocyclic, aryl, heteroaryl, -(aliphatic)aryl, -(aliphatic)heteroaryl, -(heteroaliphatic)aryl, or -(heteroaliphatic)heteroaryl moiety, wherein q is 0–4, and wherein each occurrence of R$^Z$ is independently hydrogen, a protecting group, a solid support unit, or an aliphatic, alycyclic, heteroaliphatic, heterocyclic, aryl, heteroaryl, -(aliphatic)aryl, -(aliphatic)heteroaryl, -(heteroaliphatic)aryl, or -(heteroaliphatic)heteroaryl moiety.

Another class of compounds of special interest includes those compounds of the invention as described above and in certain subclasses herein, wherein Y is a substituted phenyl moiety and the compounds have the general structure (II):

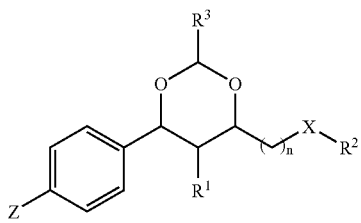

wherein Z is hydrogen, —(CH$_2$)$_q$OR$^Z$, —(CH$_2$)$_q$SR$^Z$, —(CH$_2$)$_q$N(R$^Z$)$_2$, —C(=O)R$^Z$, —C(=O)N(R$^Z$)$_2$, or an alkyl, heteroalkyl, aryl, heteroaryl, -(alkyl)aryl, -(alkyl)heteroaryl, -(heteroalkyl)aryl, or -(heteroalkyl)heteroaryl moiety, wherein q is 0–4, and wherein each occurrence of R$^Z$ is independently hydrogen, a protecting group, a solid support unit, or an alkyl, cycloalkyl, heteroalkyl, heterocyclic, aryl, heteroaryl, -(alkyl)aryl, -(alkyl)heteroaryl, -(heteroalkyl)aryl, or -(heteroalkyl)heteroaryl moiety.

Another class of compounds of special interest includes those compounds of formula (II), wherein Z is —CH$_2$OR$^Z$, and the compounds have the general structure (III):

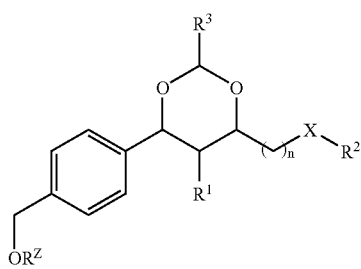

wherein R$^Z$ is as defined generally above and in classes and subclasses herein.

Yet another class of compounds of special interest includes those compounds of formula (III), wherein X is S and the compounds have the general structure (IV):

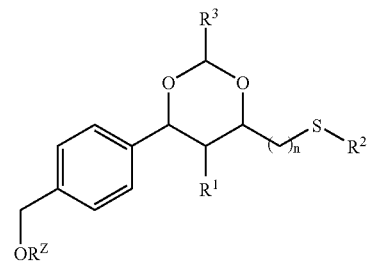

wherein R$^Z$ is as defined generally above and in classes and subclasses herein.

Yet another class of compounds of special interest includes those compounds of formula (III), wherein X is —NR$^{24}$ and the compounds have the general structure (V):

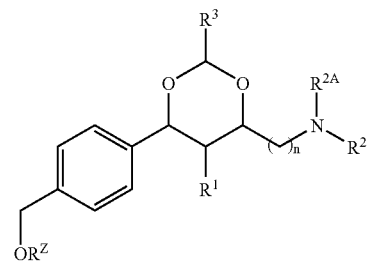

wherein R$^Z$ is as defined generally above and in classes and subclasses herein.

Yet another class of compounds of special interest includes those compounds of formula (III), wherein X is O and the compounds have the general structure (VI):

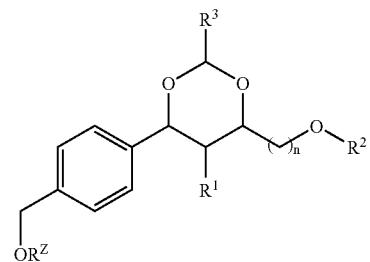

wherein R$^Z$ is as defined generally above and in classes and subclasses herein.

Still another class of compounds of special interest includes those compounds of formula (I), wherein Y is a substituted phenyl moiety, R$^3$ is a phenyl moiety substituted with R$^4$ and the compounds have the general structure (VII):

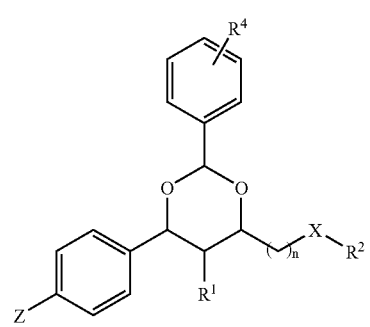

wherein R⁴ is —(CH₂)ᵣN(R⁴ᴬ)₂, —(CH₂)ᵣSR⁴ᴬ, —(CH₂)ᵣOR⁴ᴬ, —(CH₂)ᵣNR⁴ᴬC(=O)R⁴ᴮ, —(CH₂)ᵣC(=O)N(R⁴ᴬ)₂, —S(O)₂R⁴ᴬ, or is an aliphatic, alycyclic, heteroaliphatic, heterocyclic, aryl, heteroaryl, -(aliphatic)aryl, -(aliphatic)heteroaryl, -(heteroaliphatic)aryl, or -(heteroaliphatic)heteroaryl moiety, wherein each occurrence of R⁴ᴮ is independently hydrogen, an aliphatic, alycyclic, heteroaliphatic, heterocyclic, aryl, heteroaryl, -(aliphatic)aryl, -(aliphatic)heteroaryl, -(heteroaliphatic)aryl, or -(heteroaliphatic)heteroaryl moiety; and each occurrence of R⁴ᴬ is independently hydrogen, a protecting group, an aliphatic, alycyclic, heteroaliphatic, heterocyclic, aryl, heteroaryl, -(aliphatic)aryl, -(aliphatic)heteroaryl, -(heteroaliphatic)aryl, or -heteroaliphatic)heteroaryl moiety, or is —C(=O)CH(R⁴ᶜ)NH(SO₂)R⁴ᴰ, —SO₂R⁴ᶜ, —C(=O)R⁴ᶜ, —C(=O)N(R⁴ᶜ)₂, —C(=S)N(R⁴ᶜ)₂, or —C(=O)(CH₂)ₜC(=O)NHR⁴ᶜ, wherein each occurrence of R⁴ᶜ and R⁴ᴰ is independently hydrogen, a protecting group, hydroxyl, protected hydroxyl, or an aliphatic, alycyclic, heteroaliphatic, heterocyclic, aryl, heteroaryl, -(aliphatic)aryl, -(aliphatic)heteroaryl, -(heteroaliphatic)aryl, or -(heteroaliphatic)heteroaryl moiety, wherein r and t are each independently 0–5; and Z is hydrogen, —(CH₂)_qORᶻ, —(CH₂)_qSRᶻ, —(CH₂)_qN(Rᶻ)₂, —C(=O)Rᶻ, —C(=O)N(Rᶻ)₂, or an alkyl, heteroalkyl, aryl, heteroaryl, -(alkyl)aryl, -(alkyl)heteroaryl, -(heteroalkyl)aryl, or -(heteroalkyl)heteroaryl moiety, wherein q is 0–4, and wherein each occurrence of Rᶻ is independently hydrogen, a protecting group, a solid support unit, or an alkyl, cycloalkyl, heteroalkyl, heterocyclic, aryl, heteroaryl, -(alkyl)aryl, -(alkyl)heteroaryl, -(heteroalkyl)aryl, or -heteroalkyl)heteroaryl moiety.

Yet another class of compounds of special interest includes those compounds of formula (VII), wherein Z is —CH₂ORᶻ, and the compounds have the general structure (VIII):

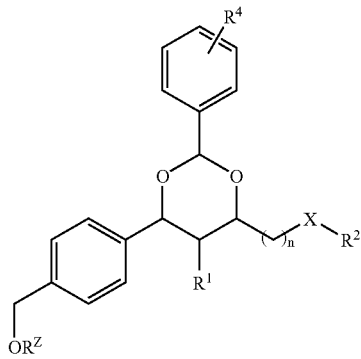

(VIII)

wherein R¹, R², Rᶻ, n and X are as defined generally above or in classes and subclassses herein.

The following compounds are illustrative of certain of the compounds described generally and in classes and subclasses herein:

A number of important subclasses of each of the foregoing classes deserve separate mention; these subclasses include subclasses of each of the foregoing classes in which:

i) compounds of the invention as described above and in classes and subclasses herein wherein R¹ is hydrogen, lower alkyl, or a substituted or unsubstituted phenyl moiety;

ii) compounds of the invention as described above and in classes and subclasses herein wherein R¹ is hydrogen, methyl, or phenyl;

iii) compounds of the invention as described above and in classes and subclasses herein wherein R¹ is hydrogen;

iv) compounds of the invention as described above and in classes and subclasses herein wherein either or both of R², R²ᴬ, or R² and R²ᴬ, taken together with the nitrogen atom to which they are attached, comprise

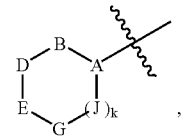

wherein k is an integer from 0–3; A-B, B-D, D-E, E-G, G-J, two or more occurrences of J, and J-A are each connected by a single or double bond; A is CH, C, or N; B is CRᴮ, C(Rᴮ)₂, C(=O), NRᴮ, N, O or S; D is CRᴰ, C(Rᴰ)₂, C(=O), NRᴰ, N, O or S; E is CRᴱ, C(Rᴱ)₂, C(=O), NRᴱ, N, O or S; G is CRᴳ, C(Rᴳ)₂, C(=O), NRᴳ, N, O or S; and each occurrence of J is independently CRᴶ, C(Rᴶ)₂, C(=O), NRᴶ, N, O or S; wherein each occurrence of Rᴮ, Rᴰ, Rᴱ, Rᴳ and Rᴶ is independently hydrogen, halogen, hydroxyl, protected hydroxyl, thiol, protected thiol, amino, protected amino, —COORˣ, —CON(Rʸ)₂, —NRʸCOORˣ, —NRʸCORˣ, or a substituted or unsubstituted, cyclic or acyclic, linear or branched alkyl or heteroalkyl moiety, or a substituted or unsubstituted aryl or heteroaryl moiety, or any two or Rᴮ, Rᴰ, Rᴱ, Rᴳ or Rᴶ taken together comprises a substituted or unsubstituted alicyclic or heterocyclic, moiety or a substituted or unsubstituted aryl or heteroaryl moiety; wherein each occurrence of Rˣ is independently hydrogen, aliphatic, alicyclic, heteroaliphatic, heterocyclic, aryl, heteroaryl, -(alkyl)aryl, -(alkyl)heteroaryl, -(heteroalkyl)aryl, or -(heteroalkyl)heteroaryl; and each occurrence of Rʸ is independently hydrogen, a nitrogen protecting group, acyl, aliphatic, alicyclic, heteroaliphatic, heterocyclic, aryl, heteroaryl, -(alkyl)aryl, -(alkyl)heteroaryl, -(heteroalkyl)aryl, or -(heteroalkyl)heteroaryl;

v) compounds of subset iv) wherein each occurrence of Rᴮ, Rᴰ, Rᴱ, Rᴳ and Rᴶ is independently hydrogen, halogen, hydroxyl, protected hydroxyl, thiol, protected thiol, amino, protected amino, —COOH, —CONH₂, —NHCOOH, —NHCOO(alkyl), —NHCO(alkyl), or a substituted or unsubstituted, cyclic or acyclic, linear or branched alkyl or heteroalkyl moiety, or a substituted or unsubstituted aryl or heteroaryl moiety, or any two or Rᴮ, Rᴰ, Rᴱ, Rᴳ or Rᴶ taken together comprises a substituted or unsubstituted alicyclic or heterocyclic, moiety or a substituted or unsubstituted aryl or heteroaryl moiety;

vi) compounds of the invention as described above and in classes and subclasses herein wherein X is O;

vii) compounds of the invention as described above and in classes and subclasses herein wherein X is S;

viii) compounds of the invention as described above and in classes and subclasses herein wherein X is —N(R²ᴬ)—; wherein R²ᴬ is hydrogen, alkyl, alkenyl, alkynyl, cycloalkyl, heteroalkyl, heterocyclyl, aryl, heteroaryl, -(alkyl)aryl, -(alkyl)heteroaryl, -(heteroalkyl)aryl, -(heteroalkyl)heteroaryl, or either or both of R² and R²ᴬ, or R² and R²ᴬ taken together with the nitrogen atom to which they are attached, forms a substituted or unsubstituted cycloalkyl or heterocyclic moiety, or a substituted or unsubstituted aryl or heteroaryl moiety;

ix) compounds of the invention as described above and in classes and subclasses herein wherein X is —N(R²ᴬ)—; wherein R²ᴬ is hydrogen, lower alkyl, lower cycloalkyl, lower heteroalkyl, heterocyclyl, aryl, or heteroaryl, or either or both of $R^2$ and $R^{2A}$, or $R^2$ and $R^{2A}$ taken together with the nitrogen atom to which they are attached, forms a substituted or unsubstituted cycloalkyl or heterocyclic moiety, or a substituted or unsubstituted aryl or heteroaryl moiety;

x) compounds of the invention as described above and in classes and subclasses herein wherein $R^2$ is one of:

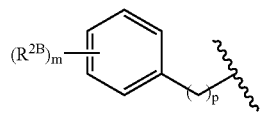
a

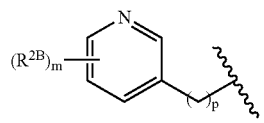
b

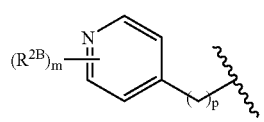
c

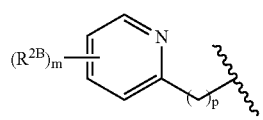
d

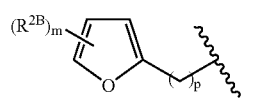
e

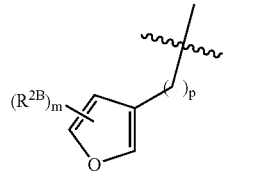
f

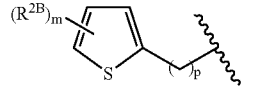
g

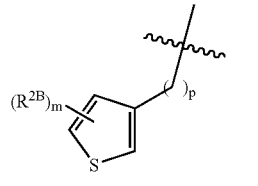
h

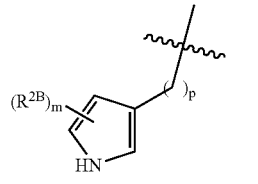
i

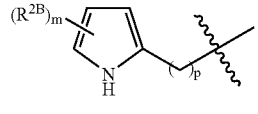
j

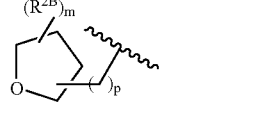
k

-continued

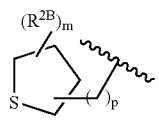
l

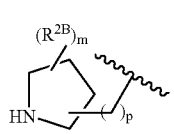
m

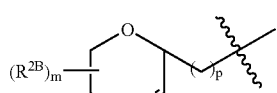
n

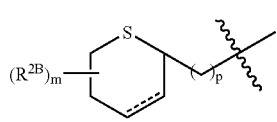
o

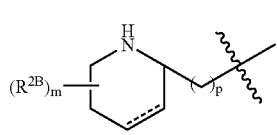
p

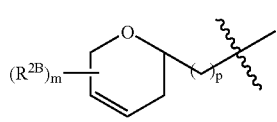
q

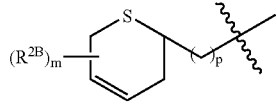
r

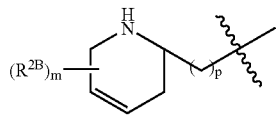
s

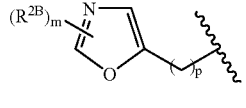
t

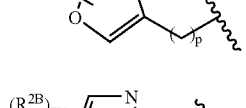
u

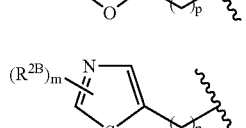
v

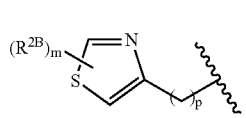
w x

-continued

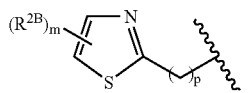
y

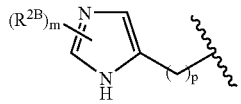
z

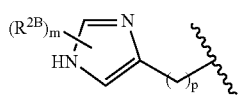
aa

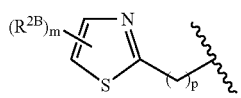
bb

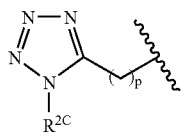
cc

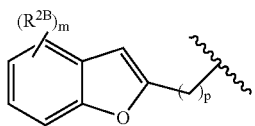
dd

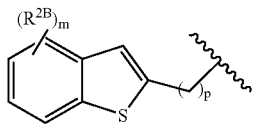
ee

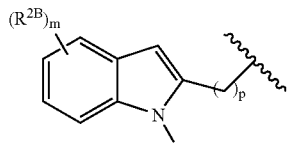
ff

R = H, Alkyl

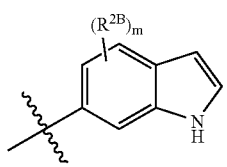
gg

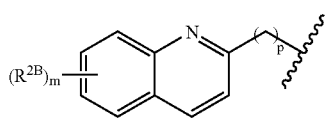
hh

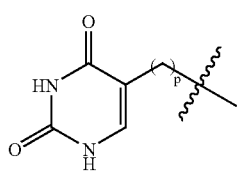
ii

jj n = 0 or 1

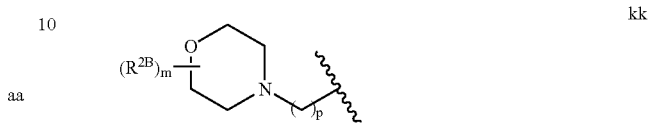
kk

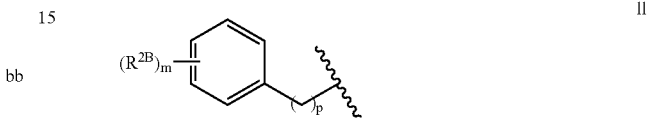
ll

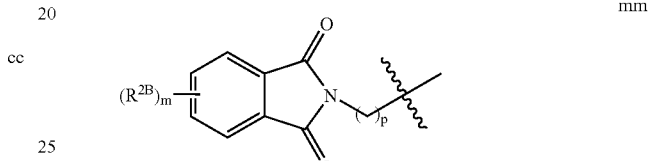
mm

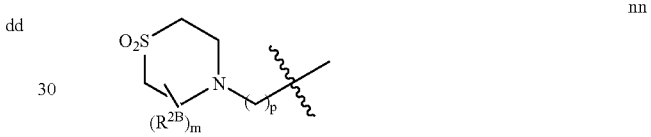
nn

oo wherein m and p are each independently integers from 0 to 3; $q_1$ is an integer from 1 to 6; $R^{2C}$ is hydrogen, lower alkyl or a nitrogen protecting group; and each occurrence of $R^{2B}$ is independently hydrogen, halogen, —CN, or $WR^{W1}$ wherein W is O, S, $NR^{W2}$, —C(=O), —S(=O), —SO$_2$, —C(=O)O—, —OC(=O), —C(=O)$NR^{W2}$, —$NR^{W2}$C(=O); wherein each occurrence of $R^{W1}$ and $R^{W2}$ is independently hydrogen, a protecting group, a prodrug moiety or an alkyl, cycloalkyl, heteroalkyl, heterocyclic, aryl or heteroaryl moiety, or, when W is $NR^{W2}$, $R^{W1}$ and $R^{W2}$, taken together with the nitrogen atom to which they are attached, form a heterocyclic or heteroaryl moiety; or any two adjacent occurrences of $R^{2B}$, taken together with the atoms to which they are attached, form a substituted or unsubstituted, saturated or unsaturated alicyclic or heterocyclic moiety, or a substituted or unsubstituted aryl or heteroaryl moiety;

xi) compounds as described above and in classes and subclasses herein wherein —X—$R^2$ has one of the structures:

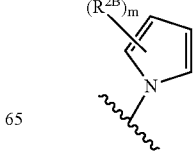
pp

-continued

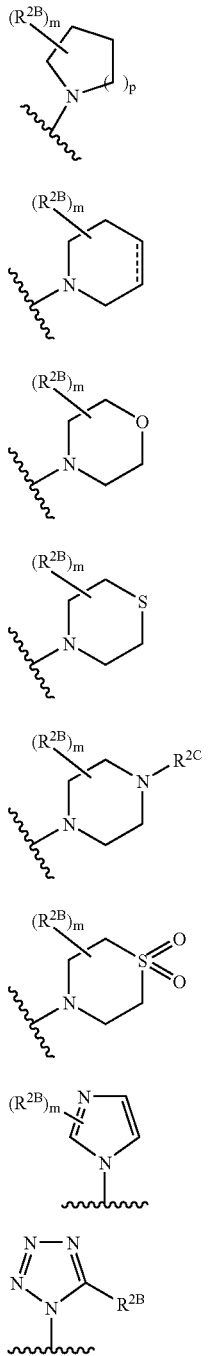

wherein m is an integer from 1 to 4; $R^{2C}$ is hydrogen, lower alkyl or a nitrogen protecting group; and each occurrence of $R^{2B}$ is independently hydrogen, halogen, —CN, or $WR^{W1}$ wherein W is O, S, $NR^{W2}$, —C(=O), —S(=O), —SO$_2$, —C(=O)O—, —OC(=O), —C(=O)NR$^{W2}$, —NR$^{W2}$C(=O); wherein each occurrence of $R^{W1}$ and $R^{W2}$ is independently hydrogen, a protecting group, a prodrug moiety or an alkyl, cycloalkyl, heteroalkyl, heterocyclic, aryl or heteroaryl moiety, or, when W is $NR^{W2}$, $R^{W1}$ and $R^{W2}$, taken together with the nitrogen atom to which they are attached, form a heterocyclic or heteroaryl moiety; or any two adjacent occurrences of $R^{2B}$, taken together with the atoms to which they are attached, form a substituted or unsubstituted, saturated or unsaturated alicyclic or heterocyclic moiety, or a substituted or unsubstituted aryl or heteroaryl moiety;

xii) compounds as described above and in classes and subclasses herein wherein —X—$R^2$ has one of the structures:

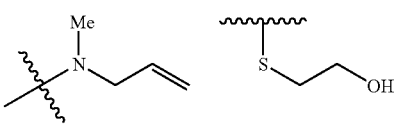

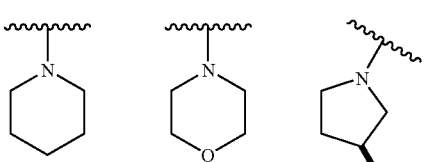

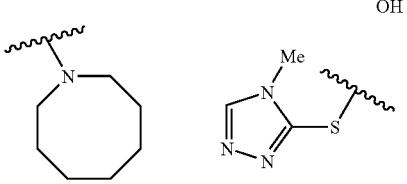

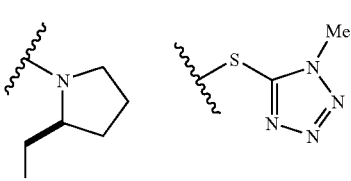

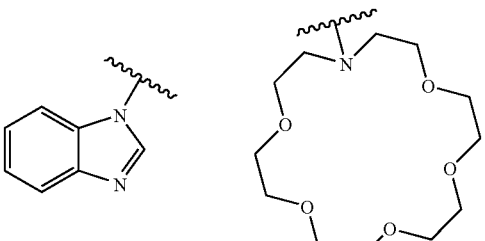

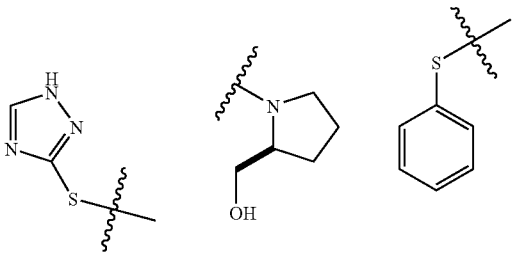

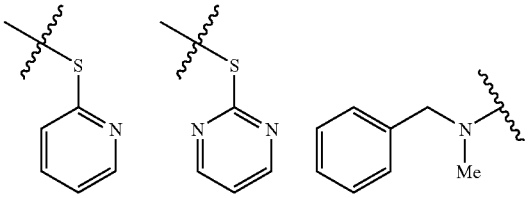

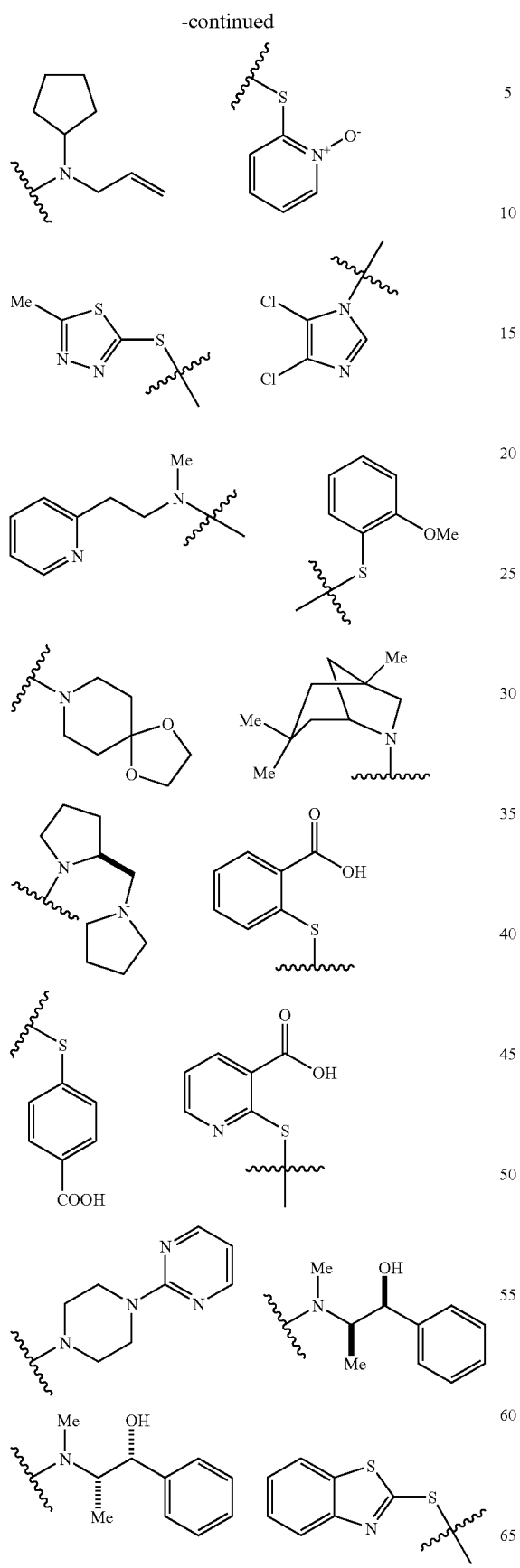

-continued

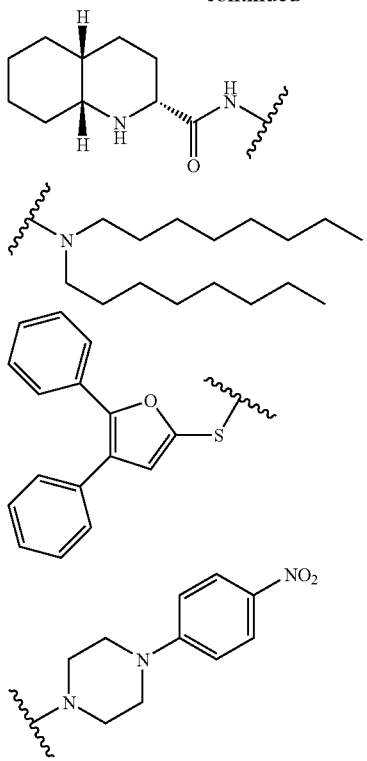

replaced by CO, CO$_2$, COCO, CONR$^{Z1}$, OCONR$^{Z1}$, NR$^{Z1}$NR$^{Z2}$, NR$^{Z1}$NR$^{Z2}$CO, NR$^{Z1}$CO, NR$^{Z1}$CO$_2$, NR$^{Z1}$CONR$^{Z2}$, SO, SO$_2$, NR$^{Z1}$SO$_2$, SO$_2$NR$^{Z1}$, NR$^{Z1}$SO$_2$NR$^{Z2}$, O, S, or NR$^{Z1}$; wherein each occurrence of R$^{Z1}$ and R$^{Z2}$ is independently hydrogen, alkyl, heteroalkyl, aryl, heteroaryl or acyl; and R$^{4A}$ is —C(=O)OR$^{4B}$, —C(=O)NHOR$^{4B}$ or a moiety having the structure:

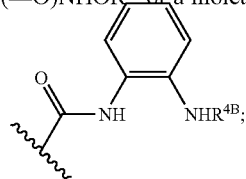

wherein each occurrence of R$^{4B}$ is independently hydrogen, alkyl, heteroalkyl, aryl, heteroaryl or acyl;

xix) compounds of the invention as described above and in classes and subclasses herein wherein R$^3$ is an aryl or heteroaryl moiety substituted with —(CH$_2$)$_r$N(R$^{4C}$)Alk$^1$R$^{4A}$, wherein r is 0 or 1; R$^{4C}$ is hydrogen, a nitrogen protecting group, alkyl, acyl, heteroalkyl, aryl or heteroaryl; R$^{4A}$ comprises a metal chelator; Alk$^1$ is a substituted or unsubstituted C$_{3-7}$alkylene or C$_{3-7}$alkenylene chain wherein up to two non-adjacent methylene units are independently optionally replaced by CO, CO$_2$, COCO, CONR$^{Z1}$, OCONR$^{Z1}$, NR$^{Z1}$NR$^{Z2}$, NR$^{Z1}$NR$^{Z2}$CO, NR$^{Z1}$CO, NR$^{Z1}$CO$_2$, NR$^{Z1}$CONR$^{Z2}$, SO, SO$_2$, NR$^{Z1}$SO$_2$, SO$_2$NR$^{Z1}$, NR$^{Z1}$SO$_2$NR$^{Z2}$, O, S, or NR$^{Z1}$; wherein each occurrence of R$^{Z1}$ and R$^{Z2}$ is independently hydrogen, alkyl, heteroalkyl, aryl, heteroaryl or acyl;

xx) compounds of the invention as described above and in classes and subclasses herein wherein R$^3$ is an aryl or heteroaryl moiety substituted with —(CH$_2$)$_r$N(R$^{4C}$)Alk$^1$R$^{4A}$, wherein r is 0 or 1; R$^{4C}$ is hydrogen, a nitrogen protecting group, alkyl, acyl, heteroalkyl, aryl or heteroaryl; Alk$^1$ is a substituted or unsubstituted C$_{3-7}$alkylene or C$_{3-7}$alkenylene chain wherein up to two non-adjacent methylene units are independently optionally replaced by CO, CO$_2$, COCO, CONR$^{Z1}$, OCONR$^{Z1}$, NR$^{Z1}$NR$^{Z2}$, NR$^{Z1}$NR$^{Z2}$CO, NR$^{Z1}$CO, NR$^{Z1}$CO$_2$, NR$^{Z1}$CONR$^{Z2}$, SO, SO$_2$, NR$^{Z1}$SO$_2$, SO$_2$NR$^{Z1}$, NR$^{Z1}$SO$_2$NR$^{Z2}$, O, S, or NR$^{Z1}$; wherein each occurrence of R$^{Z1}$ and R$^{Z2}$ is independently hydrogen, alkyl, heteroalkyl, aryl, heteroaryl or acyl; and R$^{4A}$ is —C(=O)OR$^{4B}$, —C(=O)NHOR$^{4B}$ or a moiety having the structure:

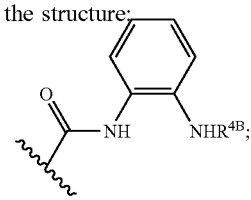

wherein each occurrence of R$^{4B}$ is independently hydrogen, alkyl, heteroalkyl, aryl, heteroaryl or acyl;

xxi) compounds of the invention as described above and in classes and subclasses herein wherein R$^3$ is an aryl or heteroaryl moiety substituted with —(CH$_2$)$_r$N(R$^{4C}$)C(=O)Alk$^2$R$^{4A}$, wherein r is 0 or 1; R$^{4C}$ is hydrogen, a nitrogen protecting group, alkyl, acyl, heteroalkyl, aryl or heteroaryl; R$^{4A}$ comprises a metal chelator; Alk$^2$ is a substituted or unsubstituted C$_{3-6}$alkylene or C$_{3-6}$alkenylene chain wherein up to two non-adjacent methylene units are independently optionally replaced by CO, CO$_2$, COCO, CONR$^{Z1}$, OCONR$^{Z1}$, NR$^{Z1}$NR$^{Z2}$, NR$^{Z1}$NR$^{Z2}$CO, NR$^{Z1}$CO, NR$^{Z1}$CO$_2$, NR$^{Z1}$CONR$^{Z2}$, SO, SO$_2$, NR$^{Z1}$SO$_2$, SO$_2$NR$^{Z1}$, xiii) compounds of the invention as described above and in classes and subclasses herein wherein one or both of R$^2$ and R$^{2A}$ is a substituted or unsubstituted aryl or heteroaryl moiety;

xiv) compounds of the invention as described above and in classes and subclasses herein wherein one or both of R$^2$ and R$^{2A}$ is an aryl or heteroaryl moiety substituted with —COOH, halogen, alkyl, heteroalkyl, aryl, heteroaryl, OH, SH, NO$_2$, NH$_2$, or —NHC(=O)alkyl;

xv) compounds of the invention as described above and in classes and subclasses herein wherein R$^3$ is a substituted aryl or heteroaryl moiety;

xvi) compounds of the invention as described above and in classes and subclasses herein wherein R$^3$ is an aryl or heteroaryl moiety substituted with a moiety having the structure -L-R$^{4A}$ wherein L is a linker and R$^{4A}$ comprises a metal chelator;

xvii) compounds of the invention as described above and in classes and subclasses herein wherein R$^3$ is an aryl or heteroaryl moiety substituted with a moiety having the structure -L-R$^{4A}$ wherein L is a substituted or unsubstituted C$_{4-8}$alkylene or C$_{4-8}$alkenylene chain wherein up to two non-adjacent methylene units are independently optionally replaced by CO, CO$_2$, COCO, CONR$^{Z1}$, OCONR$^{Z1}$, NR$^{Z1}$NR$^{Z2}$, NR$^{Z1}$NR$^{Z2}$CO, NR$^{Z1}$CO, NR$^{Z1}$CO$_2$, NR$^{Z1}$CONR$^{Z2}$, SO, SO$_2$, NR$^{Z1}$SO$_2$, SO$_2$NR$^{Z1}$, NR$^{Z1}$SO$_2$NR$^{Z2}$, O, S, or NR$^{Z1}$; wherein each occurrence of R$^{Z1}$ and R$^{Z2}$ is independently hydrogen, alkyl, heteroalkyl, aryl, heteroaryl or acyl; and R$^{4A}$ comprises a metal chelator;

xviii) compounds of the invention as described above and in classes and subclasses herein wherein R$^3$ is an aryl or heteroaryl moiety substituted with a moiety having the structure -L-R$^{4A}$ wherein L is a substituted or unsubstituted C$_{4-8}$alkylene or C$_{4-8}$alkenylene chain wherein up to two non-adjacent methylene units are independently optionally $NR^{Z1}SO_2NR^{Z2}$, O, S, or $NR^{Z1}$; wherein each occurrence of $R^{Z1}$ and $R^{Z2}$ is independently hydrogen, alkyl, heteroalkyl, aryl, heteroaryl or acyl;

xxii) compounds of the invention as described above and in classes and subclasses herein wherein $R^3$ is an aryl or heteroaryl moiety substituted with $-(CH_2)_rN(R^{4C})C(=O)Alk^2R^{4A}$, wherein r is 0 or 1; $R^{4C}$ is hydrogen, a nitrogen protecting group, alkyl, acyl, heteroalkyl, aryl or heteroaryl; $Alk^2$ is a substituted or unsubstituted $C_{3-6}$alkylene or $C_{3-6}$alkenylene chain wherein up to two non-adjacent methylene units are independently optionally replaced by CO, $CO_2$, COCO, $CONR^{Z1}$, $OCONR^{Z1}$, $NR^{Z1}NR^{Z2}$, $NR^{Z1}NR^{Z2}CO$, $NR^{Z1}CO$, $NR^{Z1}CO_2$, $NR^{Z1}CONR^{Z2}$, SO, $SO_2$, $NR^{Z1}SO_2$, $SO_2NR^{Z1}$, $NR^{Z1}SO_2NR^{Z2}$, O, S, or $NR^{Z1}$; wherein each occurrence of $R^{Z1}$ and $R^{Z2}$ is independently hydrogen, alkyl, heteroalkyl, aryl, heteroaryl or acyl; and $R^{4A}$ is $-C(=O)OR^{4B}$, $-C(=O)NHOR^{4B}$ or a moiety having the structure:

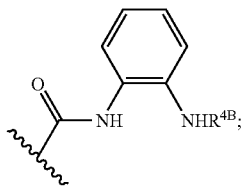

wherein each occurrence of $R^{4B}$ is independently hydrogen, alkyl, heteroalkyl, aryl, heteroaryl or acyl;

xxiii) compounds of the invention as described above and in classes and subclasses herein wherein $R^3$ is an aryl or heteroaryl moiety substituted with $-(CH_2)_rN(R^{4C})C(=O)Alk^2R^{4A}$, wherein r is 0 or 1; $R^{4C}$ is hydrogen, a nitrogen protecting group, alkyl, acyl, heteroalkyl, aryl or heteroaryl; $R^{4A}$ comprises a metal chelator; $Alk^2$ is a substituted or unsubstituted $C_{3-6}$alkylene chain;

xxiv) compounds of the invention as described above and in classes and subclasses herein wherein $R^3$ is an aryl or heteroaryl moiety substituted with $-(CH_2)_rN(R^{4C})C(=O)Alk^2R^{4A}$, wherein r is 0 or 1; $R^{4C}$ is hydrogen, a nitrogen protecting group, alkyl, acyl, heteroalkyl, aryl or heteroaryl; $Alk^2$ is a substituted or unsubstituted $C_{3-6}$alkylene chain; and $R^{4A}$ is $-C(=O)OR^{4B}$, $-C(=O)NHOR^{4B}$ or a moiety having the structure:

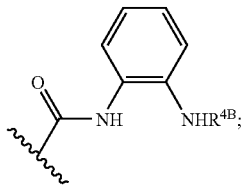

wherein each occurrence of $R^{4B}$ is independently hydrogen, alkyl, heteroalkyl, aryl, heteroaryl or acyl;

xxv) compounds of the invention as described above and in classes and subclasses herein wherein $R^3$ is an aryl or heteroaryl moiety substituted with a moiety having the structure $-L-R^{4A}$ wherein L is $-(CH_2)_rNHC(=O)(CH_2)_t-$, wherein r is 0 or 1; and t is 3, 4 or 5; and $R^{4A}$ comprises a metal chelator;

xxvi) compounds of the invention as described above and in classes and subclasses herein wherein $R^3$ is an aryl or heteroaryl moiety substituted with a moiety having the structure $-L-R^{4A}$ wherein L is $-(CH_2)_rNHC(=O)(CH_2)_t-$, wherein r is 0 or 1; and t is 3, 4 or 5; and $R^{4A}$ is $-C(=O)OR^{4B}$, $-C(=O)NHOR^{4B}$ or a moiety having the structure:

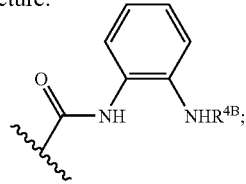

wherein each occurrence of $R^{4B}$ is independently hydrogen, alkyl, heteroalkyl, aryl, heteroaryl or acyl;

xxvii) compounds of the invention as described above and in classes and subclasses herein wherein $R^3$ is one of the following structures:

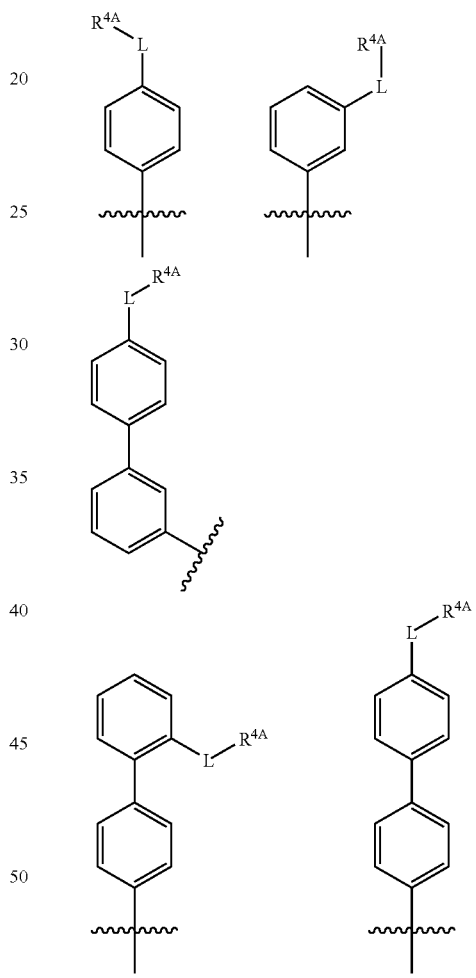

wherein L is a substituted or unsubstituted $C_{4-8}$alkylene or $C_{4-8}$alkenylene chain wherein up to two non-adjacent methylene units are independently optionally replaced by CO, $CO_2$, COCO, $CONR^{Z1}$, $OCONR^{Z1}$, $NR^{Z1}NR^{Z2}$, $NR^{Z1}NR^{Z2}CO$, $NR^{Z1}CO$, $NR^{Z1}CO_2$, $NR^{Z1}CONR^{Z2}$, SO, $SO_2$, $NR^{Z1}SO_2$, $SO_2NR^{Z1}$, $NR^{Z1}SO_2NR^{Z2}$, O, S, or $NR^{Z1}$; wherein each occurrence of $R^{Z1}$ and $R^{Z2}$ is independently hydrogen, alkyl, heteroalkyl, aryl, heteroaryl or acyl; and $R^{4A}$ comprises a metal chelator;

xxviii) compounds of the invention as described above and in classes and subclasses herein wherein $R^3$ is one of the following structures:

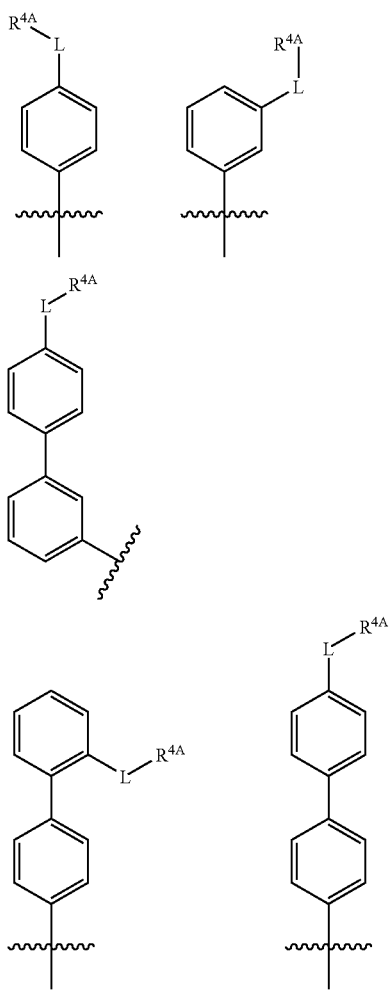

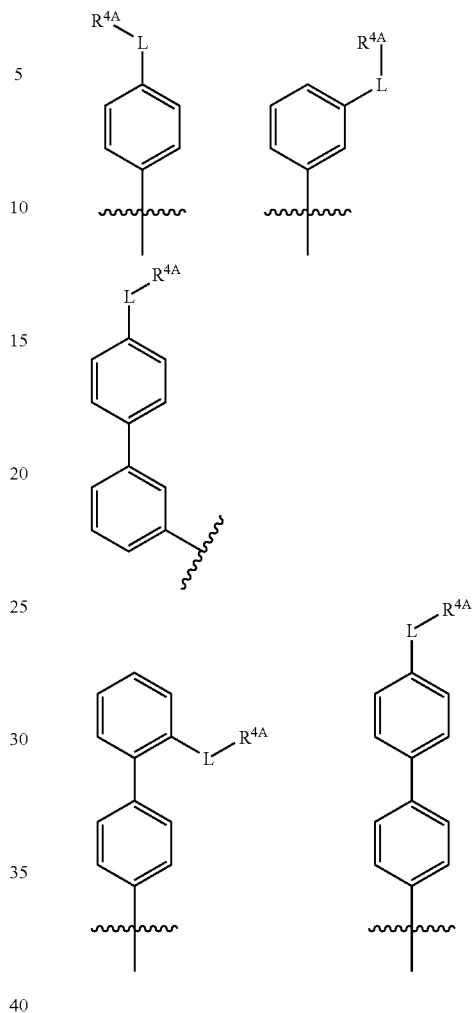

wherein L is a substituted or unsubstituted $C_{4-8}$alkylene or $C_{4-8}$alkenylene chain wherein up to two non-adjacent methylene units are independently optionally replaced by CO, $CO_2$, COCO, $CONR^{Z1}$, $OCONR^{Z1}$, $NR^{Z1}NR^{Z2}$, $NR^{Z1}NR^{Z2}CO$, $NR^{Z1}CO$, $NR^{Z1}CO_2$, $NR^{Z1}CONR^{Z2}$, SO, $SO_2$, $NR^{Z1}SO_2$, $SO_2NR^{Z1}$, $NR^{Z1}SO_2NR^{Z2}$, O, S, or $NR^{Z1}$; wherein each occurrence of $R^{Z1}$ and $R^{Z2}$ is independently hydrogen, alkyl, heteroalkyl, aryl, heteroaryl or acyl; and $R^{4A}$ is —C(O)OR$^{4B}$, —C(=O)NHOR$^{4B}$ or a moiety having the structure:

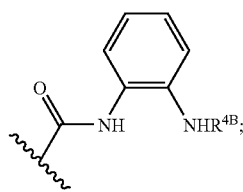

wherein each occurrence of $R^{4B}$ is independently hydrogen, alkyl, heteroalkyl, aryl, heteroaryl or acyl;

xxix) compounds of the invention as described above and in classes and subclasses herein wherein $R^3$ is one of the following structures:

wherein L is —$(CH_2)_rN(R^{4C})Alk^1R^{4A}$, wherein r is 0 or 1; $R^{4C}$ is hydrogen, a nitrogen protecting group, alkyl, acyl, heteroalkyl, aryl or heteroaryl; $Alk^1$ is a substituted or unsubstituted $C_{3-7}$alkylene or $C_{3-7}$alkenylene chain wherein up to two non-adjacent methylene units are independently optionally replaced by CO, $CO_2$, COCO, $CONR^{Z1}$, $OCONR^{Z1}$, $NR^{Z1}NR^{Z2}$, $NR^{Z1}NR^{Z2}CO$, $NR^{Z1}CO$, $NR^{Z1}CO_2$, $NR^{Z1}CONR^{Z2}$, SO, $SO_2$, $NR^{Z1}SO_2$, $SO_2NR^{Z1}$, $NR^{Z1}SO_2NR^{Z2}$, O, S, or $NR^{Z1}$; wherein each occurrence of $R^{Z1}$ and $R^{Z2}$ is independently hydrogen, alkyl, heteroalkyl, aryl, heteroaryl or acyl; and $R^{4A}$ comprises a metal chelator;

xxx) compounds of the invention as described above and in classes and subclasses herein wherein $R^3$ is one of the following structures:

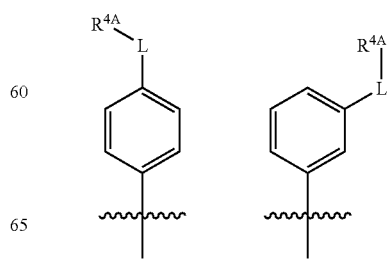

-continued

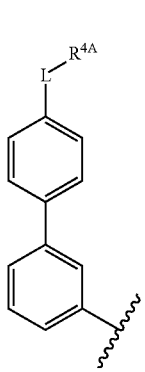

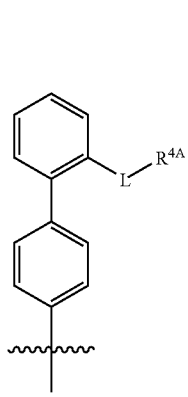
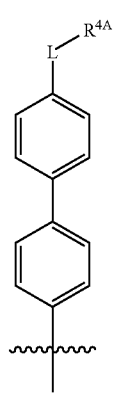

wherein L is —(CH$_2$)$_r$N(R$^{4C}$)Alk$^1$R$^{4A}$, wherein r is 0 or 1; R$^{4C}$ is hydrogen, a nitrogen protecting group, alkyl, acyl, heteroalkyl, aryl or heteroaryl; Alk$^1$ is a substituted or unsubstituted C$_{3-7}$alkylene or C$_{3-7}$alkenylene chain wherein up to two non-adjacent methylene units are independently optionally replaced by CO, CO$_2$, COCO, CONR$^{Z1}$, OCONR$^{Z1}$, NR$^{Z1}$NR$^{Z2}$, NR$^{Z1}$NR$^{Z2}$CO, NR$^{Z1}$CO, NR$^{Z1}$CO$_2$, NR$^{Z1}$CONR$^{Z2}$, SO, SO$_2$, NR$^{Z1}$SO$_2$, SO$_2$NR$^{Z1}$, NR$^{Z1}$SO$_2$NR$^{Z2}$, O, S, or NR$^{Z1}$; wherein each occurrence of R$^{Z1}$ and R$^{Z2}$ is independently hydrogen, alkyl, heteroalkyl, aryl, heteroaryl or acyl; and R$^{4A}$ is —C(=O)OR$^{4B}$, —C(=O)NHOR$^{4B}$ or a moiety having the structure:

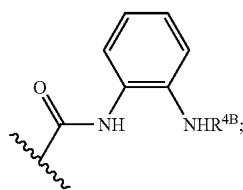

wherein each occurrence of R$^{4B}$ is independently hydrogen, alkyl, heteroalkyl, aryl, heteroaryl or acyl;

xxxi) compounds of the invention as described above and in classes and subclasses herein wherein R$^3$ is one of the following structures:

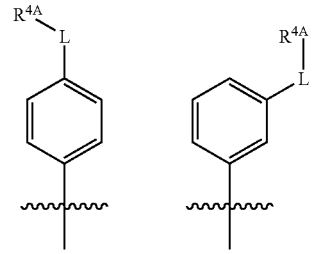

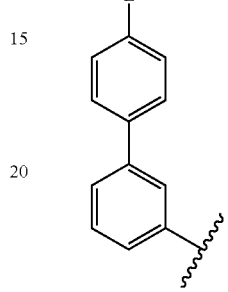

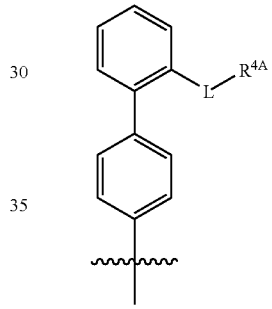

wherein L is —(CH$_2$)$_r$N(R$^{4C}$)C(=O)Alk$^2$R$^{4A}$, wherein r is 0 or 1; R$^{4C}$ is hydrogen, a nitrogen protecting group, alkyl, acyl, heteroalkyl, aryl or heteroaryl; Alk$^2$ is a substituted or unsubstituted C$_{3-6}$alkyldene or C$_{3-6}$alkenylene chain wherein up to two non-adjacent methylene units are independently optionally replaced by CO, CO$_2$, COCO, CONR$^{Z1}$, OCONR$^{Z1}$, NR$^{Z1}$NR$^{Z2}$, NR$^{Z1}$NR$^{Z2}$CO, NR$^{Z1}$CO, NR$^{Z1}$CO$_2$, NR$^{Z1}$CONR$^{Z2}$, SO, SO$_2$, NR$^{Z1}$SO$_2$, SO$_2$NR$^{Z1}$, NR$^{Z1}$SO$_2$NR$^{Z2}$, O, S, or NR$^{Z1}$; wherein each occurrence of R$^{Z1}$ and R$^{Z2}$ is independently hydrogen, alkyl, heteroalkyl, aryl, heteroaryl or acyl; and R$^{4A}$ comprises a metal chelator;

xxxii) compounds of the invention as described above and in classes and subclasses herein wherein R$^3$ is one of the following structures:

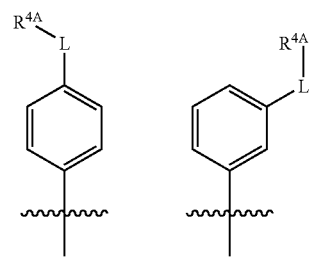

-continued

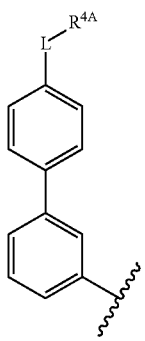

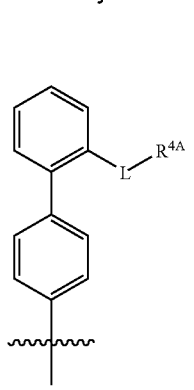 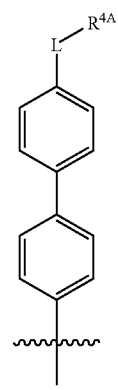

wherein L is —(CH$_2$)$_r$N(R$^{4C}$)C(=O)Alk$^2$R$^{4A}$, wherein r is 0 or 1; R$^{4C}$ is hydrogen, a nitrogen protecting group, alkyl, acyl, heteroalkyl, aryl or heteroaryl; Alk$^2$ is a substituted or unsubstituted C$_{3-6}$alkylene or C$_{3-6}$alkenylene chain wherein up to two non-adjacent methylene units are independently optionally replaced by CO, CO$_2$, COCO, CONR$^{Z1}$, OCONR$^{Z1}$, NR$^{Z1}$NR$^{Z2}$, NR$^{Z1}$NR$^{Z2}$CO, NR$^{Z1}$CO, NR$^{Z1}$CO$_2$, NR$^{Z1}$CONR$^{Z2}$, SO, SO$_2$, NR$^{Z1}$SO$_2$, SO$_2$NR$^{Z1}$, NR$^{Z1}$SO$_2$NR$^{Z2}$, S, or NR$^{Z1}$; wherein each occurrence of R$^{Z1}$ and R$^{Z2}$ is independently hydrogen, alkyl, heteroalkyl, aryl, heteroaryl or acyl; and R$^{4A}$ is —C(=O)OR$^{4B}$, —C(=O)NHOR$^{4B}$ or a moiety having the structure:

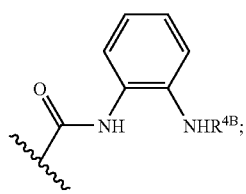

wherein each occurrence of R$^{4B}$ is independently hydrogen, alkyl, heteroalkyl, aryl, heteroaryl or acyl;

xxxiii) compounds of the invention as described above and in classes and subclasses herein wherein R$^3$ is one of the following structures:

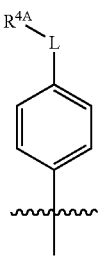 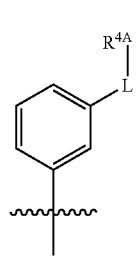

-continued

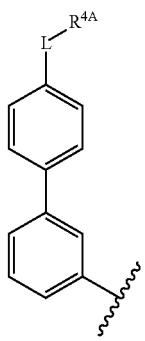

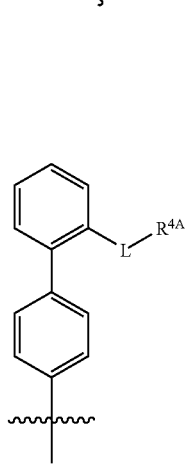 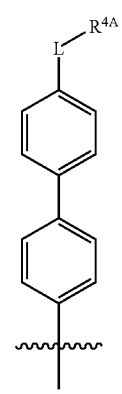

wherein L is —(CH$_2$)$_r$NHC(=O)(CH$_2$)$_t$—, wherein r is 0 or 1; and t is 3, 4 or 5; and R$^{4A}$ comprises a metal chelator;

xxxiv) compounds of the invention as described above and in classes and subclasses herein wherein R$^3$ is one of the following structures:

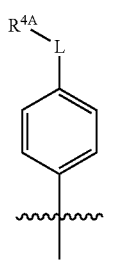 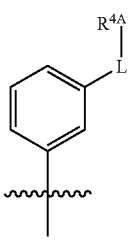

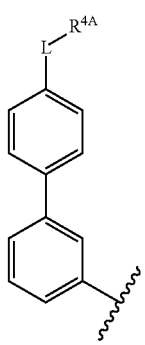

-continued

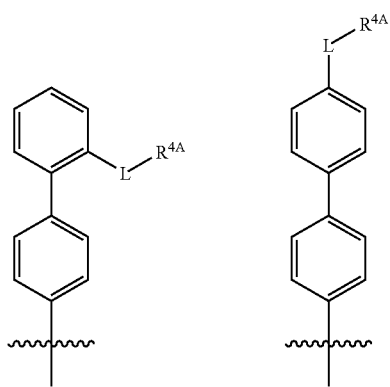

wherein L is —(CH$_2$)$_r$NHC(=O)(CH$_2$)$_t$—, wherein r is 0 or 1; and t is 3, 4 or 5; and R$^{4A}$ is —C(=O)OR$^{4B}$, —C(=O)NHOR$^{4B}$ or a moiety having the structure:

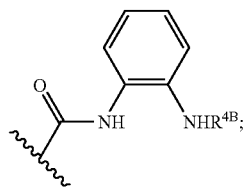

wherein each occurrence of R$^{4B}$ is independently hydrogen, alkyl, heteroalkyl, aryl, heteroaryl or acyl;

xxxv) compounds of the invention as described above and in classes and subclasses herein wherein R$^3$ is one of the following structures:

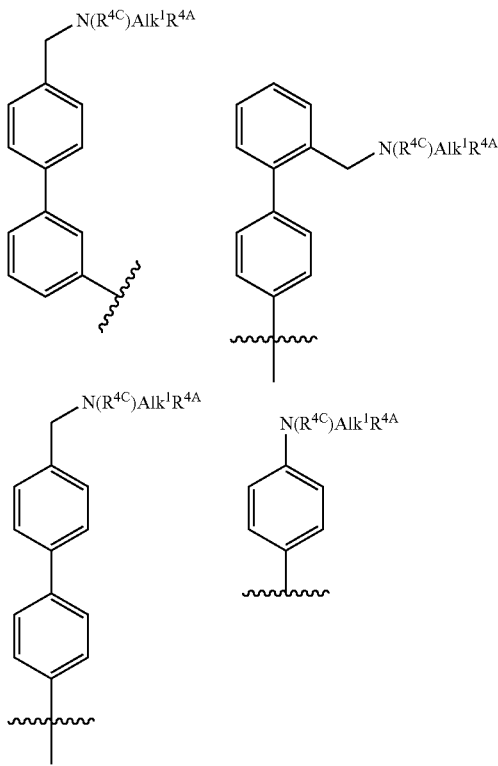

-continued

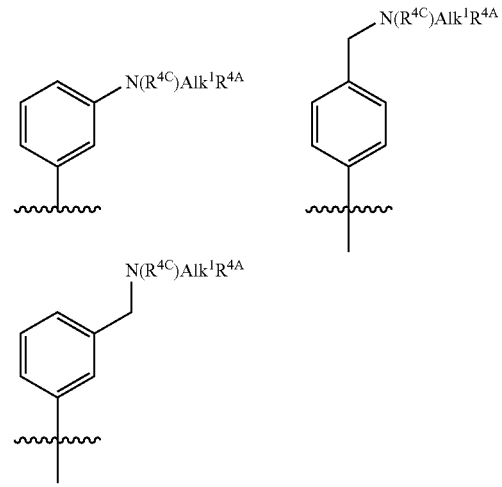

wherein R$^{4C}$ is hydrogen, a nitrogen protecting group, alkyl, acyl, heteroalkyl, aryl or heteroaryl; Alk$^1$ is a substituted or unsubstituted C$_{3-7}$alkylene or C$_{3-7}$alkenylene chain wherein up to two non-adjacent methylene units are independently optionally replaced by CO, CO$_2$, COCO, CONR$^{Z1}$, OCONR$^{Z1}$, NR$^{Z1}$NR$^{Z2}$, NR$^{Z1}$NR$^{Z2}$CO, NR$^{Z1}$CO, NR$^{Z1}$CO$_2$, NR$^{Z1}$CONR$^{Z2}$, SO, SO$_2$, NR$^{Z1}$SO$_2$, SO$_2$NR$^{Z1}$, NR$_{Z1}$SO$_2$NR$^{Z2}$, O, S, or NR$^{Z1}$; wherein each occurrence of R$^{Z1}$ and R$^{Z2}$ is independently hydrogen, alkyl, heteroalkyl, aryl, heteroaryl or acyl; and R$^{4A}$ comprises a metal chelator;

xxxvi) compounds of the invention as described above and in classes and subclasses herein wherein R$^3$ is one of the following structures:

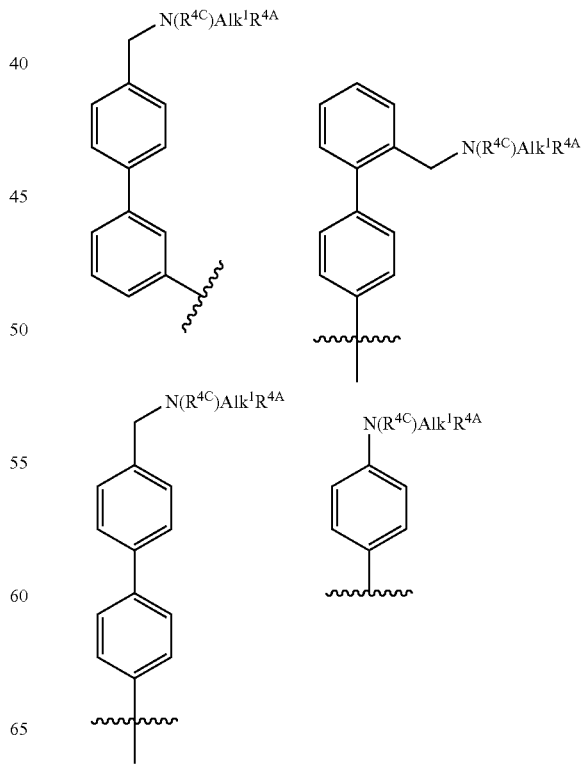

-continued

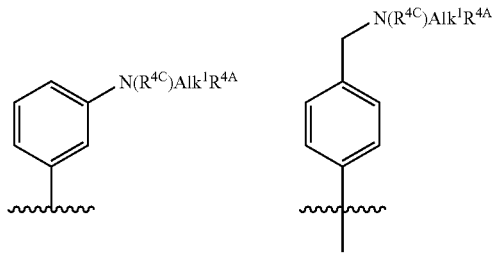

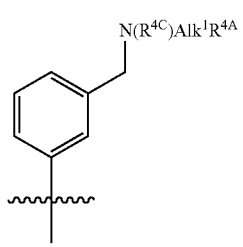

wherein $R^{4C}$ is hydrogen, a nitrogen protecting group, alkyl, acyl, heteroalkyl, aryl or heteroaryl; $Alk^1$ is a substituted or unsubstituted $C_{3-7}$alkylene or $C_{3-7}$alkenylene chain wherein up to two non-adjacent methylene units are independently optionally replaced by CO, $CO_2$, COCO, $CONR^{Z1}$, $OCONR^{Z1}$, $NR^{Z1}NR^{Z2}$, $NR^{Z1}NR^{Z2}CO$, $NR^{Z1}CO$, $NR^{Z1}CO_2$, $NR^{Z1}CONR^{Z2}$, SO, $SO_2$, $NR^{Z1}SO_2$, $SO_2NR^{Z1}$, $NR^{Z1}SO_2NR^{Z2}$, O, S, or $NR^{Z1}$; wherein each occurrence of $R^{Z1}$ and $R^{Z2}$ is independently hydrogen, alkyl, heteroalkyl, aryl, heteroaryl or acyl; and $R^{4A}$ is —C(=O)$OR^{4B}$, —C(=O)$NHOR^{4B}$ or a moiety having the structure:

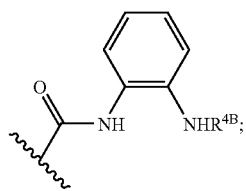

wherein each occurrence of $R^{4B}$ is independently hydrogen, alkyl, heteroalkyl, aryl, heteroaryl or acyl;

xxxvii) compounds of the invention as described above and in classes and subclasses herein wherein $R^3$ is one of the following structures:

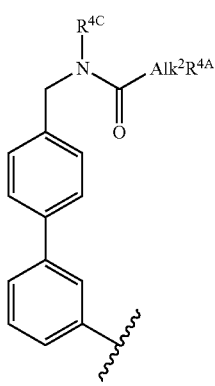

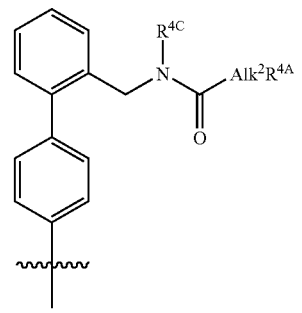

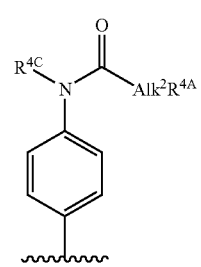
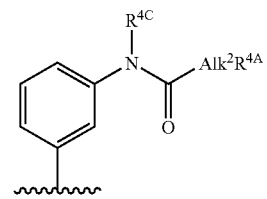

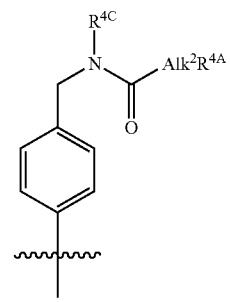
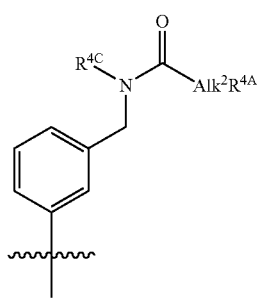

wherein $R^{4C}$ is hydrogen, a nitrogen protecting group, alkyl, acyl, heteroalkyl, aryl or heteroaryl; $Alk^2$ is a substituted or unsubstituted $C_{3-6}$alkylene or $C_{3-6}$alkenylene chain wherein up to two non-adjacent methylene units are independently optionally replaced by CO, $CO_2$, COCO, $CONR^{Z1}$, $OCONR^{Z1}$, $NR^{Z1}NR^{Z2}$, $NR^{Z1}NR^{Z2}CO$, $NR^{Z1}CO$, $NR^{Z1}CO_2$, $NR^{Z1}CONR^{Z2}$, SO, $SO_2$, $NR^{Z1}SO_2$, $SO_2NR^{Z1}$, $NR^{Z1}SO_2NR^{Z2}$, O, S, or $NR^{Z1}$; wherein each occurrence of $R^{Z1}$ and $R^{Z2}$ is independently hydrogen, alkyl, heteroalkyl, aryl, heteroaryl or acyl; and $R^{4A}$ comprises a metal chelator;

xxxviii) compounds of the invention as described above and in classes and subclasses herein wherein $R^3$ is one of the following structures:

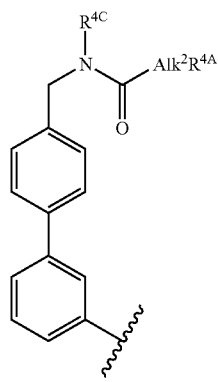

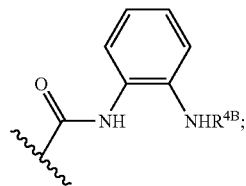

wherein each occurrence of $R^{4B}$ is independently hydrogen, alkyl, heteroalkyl, aryl, heteroaryl or acyl;

xxxix) compounds of the invention as described above and in classes and subclasses herein wherein $R^3$ is one of the following structures:

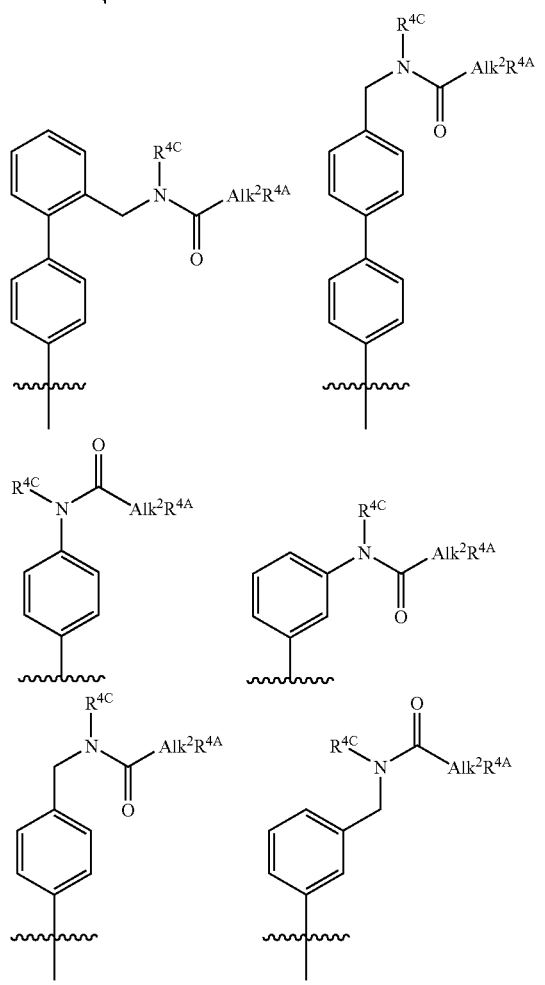

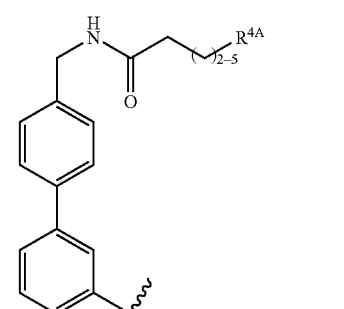

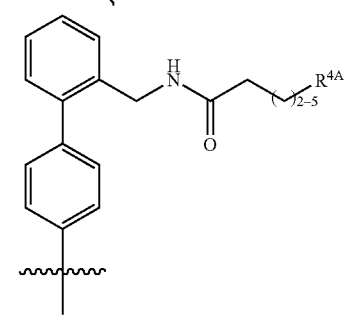

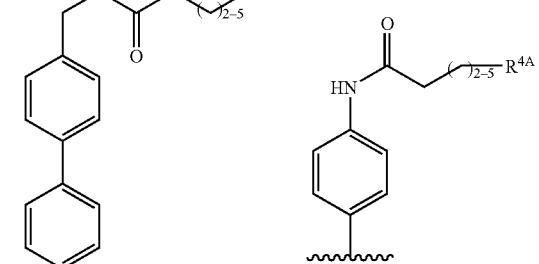

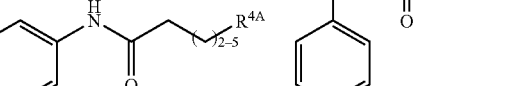

wherein $R^{4C}$ is hydrogen, a nitrogen protecting group, alkyl, acyl, heteroalkyl, aryl or heteroaryl; $Alk^2$ is a substituted or unsubstituted $C_{3-6}$alkylene or $C_{3-6}$alkenylene chain wherein up to two non-adjacent methylene units are independently optionally replaced by CO, $CO_2$, COCO, $CONR^{Z1}$, $OCONR^{Z1}$, $NR^{Z1}NR^{Z2}$, $NR^{Z1}NR^{Z2}CO$, $NR^{Z1}CO$, $NR^{Z1}CO_2$, $NR^{Z1}CONR^{Z2}$, SO, $SO_2$, $NR^{Z1}SO_2$, $SO_2NR^{Z1}$, $NR^{Z1}SO_2NR^{Z2}$, O, S, or $NR^{Z1}$; wherein each occurrence of $R^{Z1}$ and $R^{Z2}$ is independently hydrogen, alkyl, heteroalkyl, aryl, heteroaryl or acyl; and $R^{4A}$ is —C(=O)OR$^{4B}$, —C(=O)NHOR$^{4B}$ or a moiety having the structure:

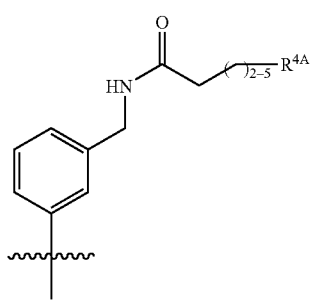

wherein $R^{4A}$ comprises a metal chelator;

xl) compounds of the invention as described above and in classes and subclasses herein wherein $R^3$ is one of the following structures:

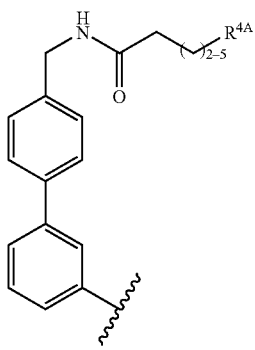

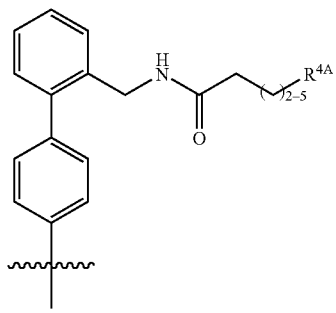

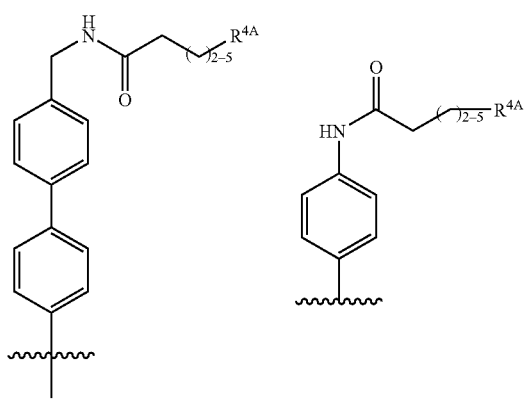

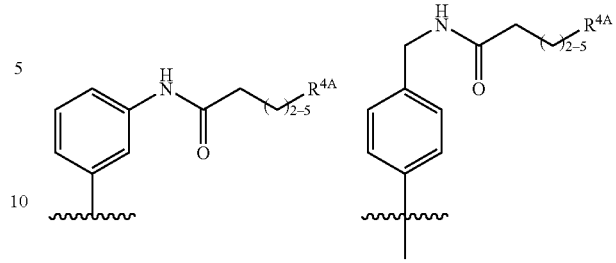

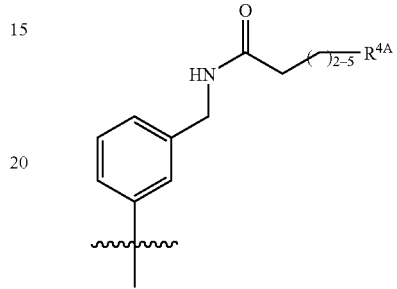

wherein $R^{4A}$ is $-C(=O)OR^{4B}$, $-C(=O)NHOR^{4B}$ or a moiety having the structure:

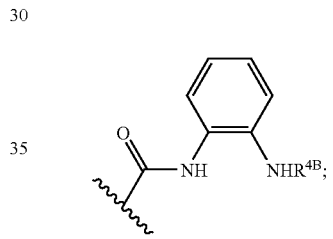

wherein each occurrence of $R^{4B}$ is independently hydrogen, alkyl, heteroalkyl, aryl, heteroaryl or acyl;

xi) compounds of the invention as described above and in classes and subclasses herein wherein $R^{4A}$ is $-C(=O)OH$, $-C(=O)NH_2$ or a moiety having the structure:

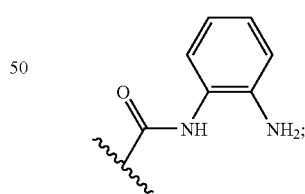

xli) compounds of the invention as described above and in classes and subclasses herein wherein $R^4$ is $-C(=O)(CH_2)_r C(=O)NHR^{4B}$, wherein $R^{4B}$ hydrogen, a protecting group, hydroxyl, protected hydroxyl, or an aliphatic, alycyclic, heteroaliphatic, heterocyclic, aryl, heteroaryl, -(aliphatic)aryl, -(aliphatic)heteroaryl, -(heteroaliphatic)aryl, or -(heteroaliphatic)heteroaryl moiety, wherein r and t are each independently 0–5;

xlii) compounds of the invention as described above and in classes and subclasses herein wherein $R^4$ is $-C(=O)(CH_2)_t C(=O)NHOH$ and t is 3, 4 or 5;

xliii) compounds of the invention as described above and in classes and subclasses herein wherein R⁴ is —C(=O)(CH₂)ₜC(=O)NHOH, t is 3, 4 or 5, and X is S;

xliv) compounds of the invention as described above and in classes and subclasses herein wherein Y is a substituted or unsubstituted aryl or heteroaryl moiety;

xlv) compounds of the invention as described above and in classes and subclasses herein wherein Y is an aryl or heteroayl moiety substituted with —(CH₂)$_q$OR$^Z$, —(CH₂)$_q$SR$^Z$, —(CH₂)$_q$N(R$^Z$)₂, —C(=O)R$^Z$, —C(=O)N(R$^Z$)₂, or an alkyl, heteroalkyl, aryl, heteroaryl, -(alkyl)aryl, -(alkyl)heteroaryl, -(heteroalkyl)aryl, or -(heteroalkyl)heteroaryl moiety, wherein q is 0–4, and wherein each occurrence of R$^Z$ is independently hydrogen, a protecting group, a solid support unit, or an alkyl, heteroalkyl, aryl, heteroaryl, -(alkyl)aryl, -(alkyl)heteroaryl, -(heteroalkyl)aryl, or -(heteroalkyl)heteroaryl moiety;

xlvi) compounds of the invention as described above and in classes and subclasses herein wherein Y is phenyl group substituted with —(CH₂)$_q$OR$^Z$, —(CH₂)$_q$SR$^Z$, —(CH₂)$_q$N(R$^Z$)₂, —C(=O)R$^Z$, —C(=O)N(R$^Z$)₂, or an alkyl, heteroalkyl, aryl, heteroaryl, -(alkyl)aryl, -(alkyl)heteroaryl, -(heteroalkyl)aryl, or -(heteroalkyl)heteroaryl moiety, wherein q is 0–4, and wherein each occurrence of R$^Z$ is independently hydrogen, a protecting group, a solid support unit, or an alkyl, heteroalkyl, aryl, heteroaryl, -(alkyl)aryl, -(alkyl)heteroaryl, -(heteroalkyl)aryl, or -(heteroalkyl)heteroaryl moiety;

xlvii) compounds of the invention as described above and in classes and subclasses herein wherein Y is an aryl or heteroayl moiety substituted with —(CH₂)$_q$OR$^Z$, wherein q is 0–4, and wherein R$^Z$ is independently hydrogen, a protecting group, a solid support unit, or an alkyl, heteroalkyl, aryl, heteroaryl, -(alkyl)aryl, -(alkyl)heteroaryl, -(heteroalkyl)aryl, or -(heteroalkyl)heteroaryl moiety;

xlviii) compounds of the invention as described above and in classes and subclasses herein wherein Y is phenyl group substituted with —(CH₂)$_q$OR$^Z$, wherein q is 0–4, and wherein R$^Z$ is independently hydrogen, a protecting group, a solid support unit, or an alkyl, heteroalkyl, aryl, heteroaryl, -(alkyl)aryl, -(alkyl)heteroaryl, -(heteroalkyl)aryl, or -(heteroalkyl)heteroaryl moiety;

xlix) compounds of the invention as described above and in classes and subclasses herein wherein R$^Z$ is hydrogen or a solid support unit;

xlix) compounds of the invention as described in subsets xlvi and xlviii above wherein the phenyl group is para substituted;

xlx) compounds of the invention as described above and in classes and subclasses herein wherein the core structure has the following stereochemistry:

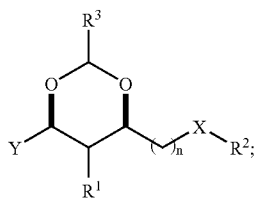

xlxi) compounds of the invention as described above and in classes and subclasses herein wherein the core structure has the following stereochemistry:

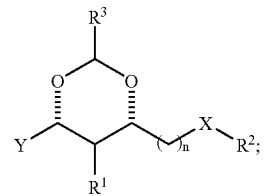

xlxii) compounds of the invention as described above and in classes and subclasses herein wherein the core structure has the following stereochemistry:

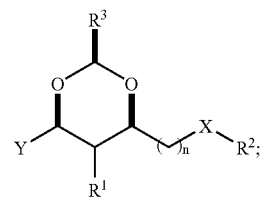

xlxiii) compounds of the invention as described above and in classes and subclasses herein wherein the core structure has the following stereochemistry:

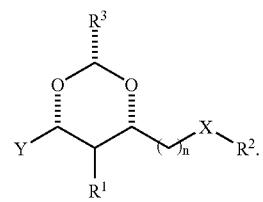

It will be appreciated that for each of the classes and subclasses described above and herein, any one or more occurrences of aliphatic, heteroaliphatic, alkyl, alkenyl, alkynyl, heteroalkyl may independently be substituted or unsubstituted, linear or branched, saturated or unsaturated and any one or more occurrences of aryl, heteroaryl, alicyclic, heteroalicyclic may be substituted or unsubstituted.

The reader will also appreciate that all possible combinations of the variables described in i)-through xlxiii) above (e.g., R¹, R², R³, n, X and Y, among others) are considered part of the invention. Thus, the invention encompasses any and all compounds of formula I generated by taking any possible permutation of variables R¹, R², R³, n, X and Y, and other variables/substituents (e.g., R$^{2A}$, R$^{4A}$, R$^{2B}$, R$^{2C}$, etc.) as further defined for R², R³, and Y, described in i)-through xlxiii) above.

As the reader will appreciate, compounds of particular interest include, among others, those which share the attributes of one or more of the foregoing subclasses. Some of those subclasses are illustrated by the following sorts of compounds:

I) Compounds of the formula (and pharmaceutically acceptable derivatives thereof):

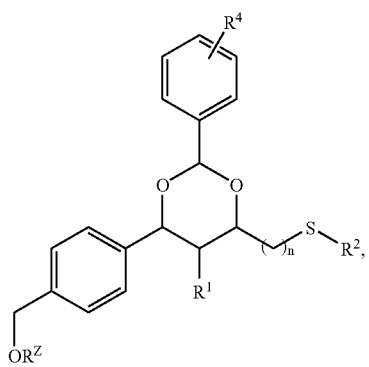

wherein $R^1$, $R^2$, $R^4$, n and $R^Z$ are as described in classes and subclasses herein.

In certain exemplary embodiments, $R^1$ is hydrogen, phenyl or methyl, $R^Z$ is hydrogen or a solid support unit; and $R^2$ is a substituted or unsubstituted alkyl or heteroalkyl moiety, or a substituted or unsubstituted aryl or heteroaryl moiety. In certain embodiments, $R^4$ is —$(CH_2)_rN(R^{4A})_2$, —$(CH_2)_r$SR$^{4A}$, —$(CH_2)_rOR^{4A}$, —$(CH_2)_rNR^{4A}C(=O)R^{4B}$, —$(CH_2)_rC(=O)N(R^{4A})_2$, —$S(O)_2R^{4A}$, or is an aliphatic, alycyclic, heteroaliphatic, heterocyclic, aryl, heteroaryl, -(aliphatic)aryl, -(aliphatic)heteroaryl, -(heteroaliphatic)aryl, or -(heteroaliphatic)heteroaryl moiety, wherein each occurrence of $R^{4B}$ is independently hydrogen, an aliphatic, alycyclic, heteroaliphatic, heterocyclic, aryl, heteroaryl, -(aliphatic)aryl, -(aliphatic)heteroaryl, -(heteroaliphatic)aryl, or -(heteroaliphatic)heteroaryl moiety; and each occurrence of $R^{4A}$ is independently hydrogen, a protecting group, an aliphatic, alycyclic, heteroaliphatic, heterocyclic, aryl, heteroaryl, -(aliphatic)aryl, -(aliphatic)heteroaryl, -(heteroaliphatic)aryl, or -(heteroaliphatic)heteroaryl moiety, or is —$C(=O)$CH$(R^{4C})$NH$(SO_2)R^{4D}$, —$SO_2R^{4C}$, —$C(=O)R^{4C}$, —$C(=O)N(R^{4C})_2$, —$C(=S)N(R^{4C})_2$, or —$C(=O)(CH_2)_tC(=O)NHR^{4C}$, wherein each occurrence of $R^{4C}$ and $R^{4D}$ is independently hydrogen, a protecting group, hydroxyl, protected hydroxyl, or an aliphatic, alycyclic, heteroaliphatic, heterocyclic, aryl, heteroaryl, -(aliphatic)aryl, -(aliphatic)heteroaryl, -(heteroaliphatic)aryl, or -(heteroaliphatic)heteroaryl moiety, wherein r and t are each independently 0–5.

In certain embodiments, when $R^4$ represents a moiety —P-Q, the following groups do not occur simultaneously as defined:

P is selected from the group consisting of substituted or unsubstituted $C_4$–$C_8$ alkylene, $C_4$–$C_8$ alkenylene, $C_4$–$C_8$ alkynylene, and —R-T-U-, wherein R and U are independently absent or represent a $C_2$–$C_7$ alkylene, a $C_2$–$C_7$ alkenylene, or a $C_2$–$C_7$ alkynylene, and T represents O, S or NR$^T$, wherein $R^T$ represents hydrogen, lower alkyl, lower alkenyl, lower alkynyl, aralkyl, aryl or heterocyclyl; and Q is selected from the group consisting of:

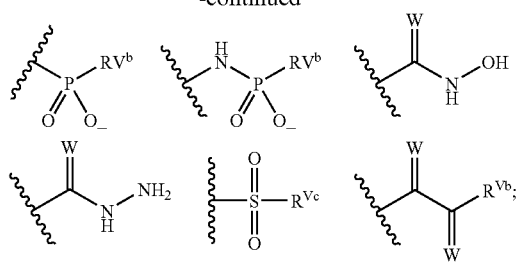

and a boronic acid moiety; wherein W is O or S; V is O, S or —NR$^{Vd}$, wherein $R^{Vd}$ is hydrogen, alkyl, alkoxycarbonyl, aryloxycarbonyl, alkylsulfonyl, arylsulfonyl, or aryl; $R^{Va}$ is hydrogen, alkyl, alkenyl, alkynyl, or aryl; $R^{Vb}$ is hydrogen, alkyl, aryl, alkoxy, aryloxy, amino, hydroxylamino, alkoxylamino or halogen; and $R^{Vc}$ is hydrogen, alkyl, aryl, hydroxyl, alkoxy, aryloxy or amino.

In certain embodiments, when $R^4$ represents a moiety —P-Q, the following groups do not occur simultaneously as defined:

P is selected from the group consisting of

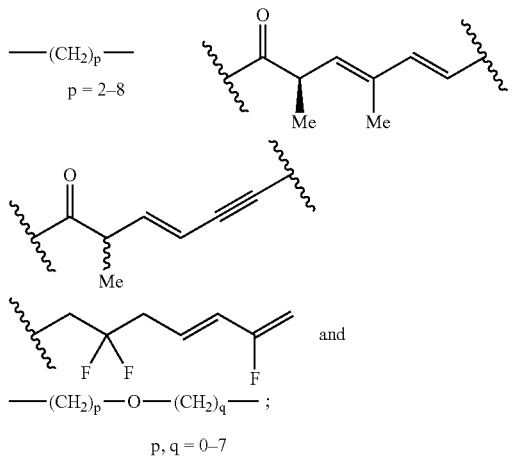

and Q is selected from the group consisting of:

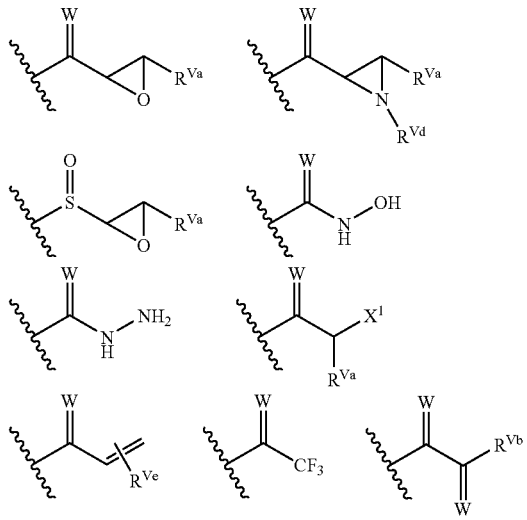

-continued

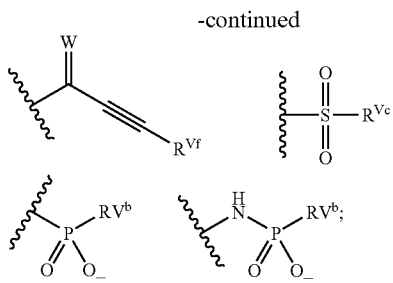

wherein W and $R^{Va\text{-}d}$ are as defined above; $X^1$ is a good leaving group (e.g., diazo, halogen, a sulfate or sulfonate ester such as a tosylate or mesylate); $R^{Ve}$ is hydrogen, alkyl, aryl, alkoxy, aryloxy, halogen; and $R^{Vf}$ is hydrogen, alkyl or halogen.

In certain exemplary embodiments, $R^4$ represents a moiety having the structure -L-$R^4A$ and the compound has the structure:

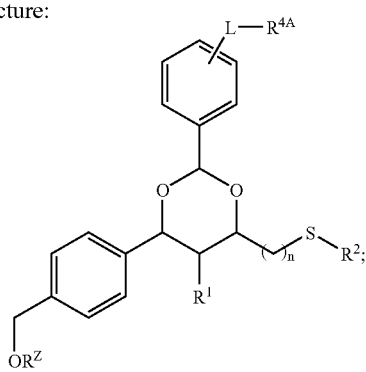

wherein L is a linker and $R^{4A}$ comprises a metal chelator.

In certain embodiments, L is a substituted or unsubstituted $C_{4-8}$alkylene or $C_{4-8}$-alkenylene chain wherein up to two non-adjacent methylene units are independently optionally replaced by CO, $CO_2$, COCO, $CONR^{Z1}$, $OCONR^{Z1}$, $NR^{Z1}NR^{Z2}$, $NR^{Z1}NR^{Z2}CO$, $NR^{Z1}CO$, $NR^{Z1}CO_2$, $NR^{Z1}CONR^{Z2}$, SO, $SO_2$, $NR^{Z1}SO_2$, $SO_2NR^{Z1}$, $NR^{Z1}SO_2NR^{Z2}$, O, S, or $NR^{Z1}$; wherein each occurrence of $R^{Z1}$ and $R^{Z2}$ is independently hydrogen, alkyl, heteroalkyl, aryl, heteroaryl or acyl.

In certain exemplary embodiments, L is —$(CH_2)_r$NHC$(=O)(CH_2)_t$—, wherein r is 0 or 1; and t is 3, 4 or 5.

In certain embodiments, $R^{4A}$ is —C(=O)$OR^{4B}$, —C(=O)NHO$R^{4B}$ or a moiety having the structure:

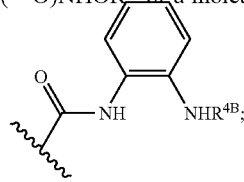

wherein each occurrence of $R^{4B}$ is independently hydrogen, alkyl, heteroalkyl, aryl, heteroaryl or acyl. In certain exemplary embodiments, $R^{4B}$ is hydrogen.

In certain exemplary embodiments, L is —$(CH_2)_r$NHC$(=O)(CH_2)_t$—, wherein r is 0 or 1; t is 3, 4 or 5; and $R^{4A}$ is —C(=O)NHOH.

II) Compounds of the formula (and pharmaceutically acceptable derivatives thereof):

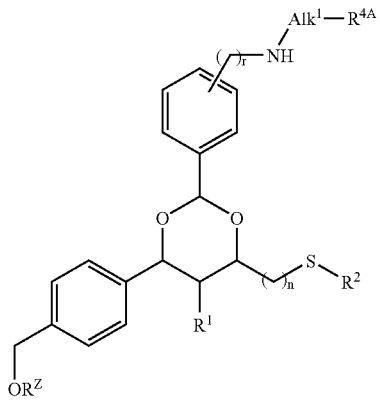

wherein $R^1$, $R^2$, $R^4$, n and $R^Z$ are as described in classes and subclasses herein; r is 0 or 1; $Alk^1$ is a substituted or unsubstituted $C_{4-7}$alkylene or $C_{4-7}$alkenylene chain wherein up to two non-adjacent methylene units are independently optionally replaced by CO, $CO_2$, COCO, $CONR^{Z1}$, $OCONR^{Z1}$, $NR^{Z1}NR^{Z2}$, $NR^{Z1}NR^{Z2}CO$, $NR^{Z1}CO$, $NR^{Z1}CO_2$, $NR^{Z1}CONR^{Z2}$, SO, $SO_2$, $NR^{Z1}SO_2$, $SO_2NR^{Z1}$, $NR^{Z1}SO_2NR^{Z2}$, O, S, or $NR^{Z1}$; wherein each occurrence of $R^{Z1}$ and $R^{Z2}$ is independently hydrogen, alkyl, heteroalkyl, aryl, heteroaryl or acyl; and $R^{4A}$ comprises a metal chelator.

In certain exemplary embodiments, $R^1$ is hydrogen, phenyl or methyl, $R^Z$ is hydrogen or a solid support unit; and $R^2$ is a substituted or unsubstituted alkyl or heteroalkyl moiety, or a substituted or unsubstituted aryl or heteroaryl moiety.

In certain embodiments, $Alk^1$ is a moiety having the structure —C(=O)-$Alk^2$- and the compound has the structure:

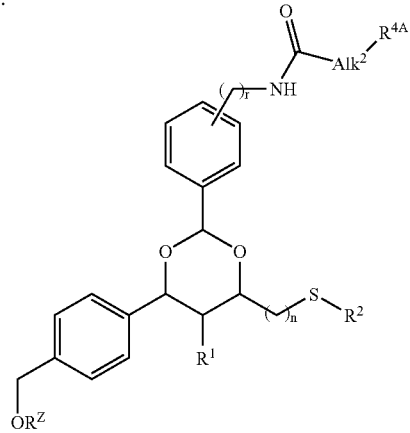

wherein $R^1$, $R^2$, $R^4$, n and $R^Z$ are as described in classes and subclasses herein; r is 0 or 1; $R^{4A}$ comprises a metal chelator and $Alk^2$ is a substituted or unsubstituted $C_{3-6}$alkylene or $C_{3-6}$alkenylene chain wherein up to two non-adjacent methylene units are independently optionally replaced by CO, $CO_2$, COCO, $CONR^{Z1}$, $OCONR^{Z1}$, $NR^{Z1}NR^{Z2}$, $NR^{Z1}NR^{Z2}CO$, $NR^{Z1}CO$, $NR^{Z1}CO_2$, $NR^{Z1}CONR^{Z2}$, SO, $SO_2$, $NR^{Z1}SO_2$, $SO_2NR^{Z1}$, $NR^{Z1}SO_2NR^{Z2}$, O, S, or $NR^{Z1}$; wherein each occurrence of $R^{Z1}$ and $R^{Z2}$ is independently hydrogen, alkyl, heteroalkyl, aryl, heteroaryl or acyl.

In certain exemplary embodiments, $R^1$ is hydrogen, phenyl or methyl; $R^Z$ is hydrogen or a solid support unit; and $R^2$ is a substituted or unsubstituted alkyl or heteroalkyl moiety, or a substituted or unsubstituted aryl or heteroaryl moiety. In certain embodiments, $Alk^2$ is a substituted or unsubstituted $C_{3-6}$alkylene chain.

In certain embodiments, $Alk^2$ is a substituted or unsubstituted $C_{3-6}$alkylene chain; and $R^{4A}$ is as defined immediately above.

III) Compounds of the formula (and pharmaceutically acceptable derivatives thereof):

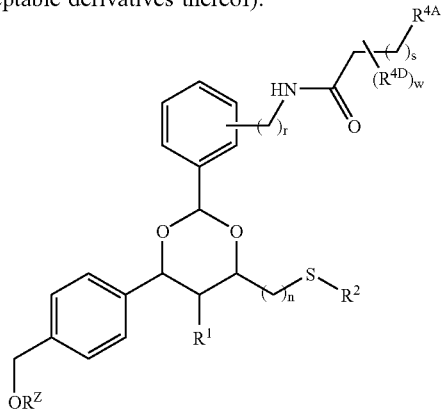

wherein $R^1$, $R^2$, $R^4$, n and $R^Z$ are as described in classes and subclasses herein; r is 0 or 1; s is an integer from 2–5; w is an integer from 0–4; $R^{4A}$ comprises a metal chelator and each occurrence of $R^{4D}$ is independently hydrogen, alkyl, heteroalkyl, cycloalkyl, heterocyclic, alkenyl, alkynyl, aryl, heteroaryl, halogen, CN, $NO_2$, or $WR^{W1}$ wherein W is O, S, $NR^{W2}$, —C(=O), —S(=O), —$SO_2$, —C(=O)O—, —OC(=O), —C(=O)$NR^{W2}$, —$NR^{W2}$C(=O); wherein each occurrence of $R^{W1}$ and $R^{W2}$ is independently hydrogen, a protecting group, a prodrug moiety or an alkyl, cycloalkyl, heteroalkyl, heterocyclic, aryl or heteroaryl moiety, or, when W is $NR^{W2}$ $R^{W1}$ and $R^{W2}$, taken together with the nitrogen atom to which they are attached, form a heterocyclic or heteroaryl moiety; or any two adjacent occurrences of $R^{2B}$, taken together with the atoms to which they are attached, form a substituted or unsubstituted, saturated or unsaturated alicyclic or heterocyclic moiety, or a substituted or unsubstituted aryl or heteroaryl moiety.

In certain exemplary embodiments, $R^1$ is hydrogen, phenyl or methyl; $R^Z$ is hydrogen or a solid support unit; and $R^2$ is a substituted or unsubstituted alkyl or heteroalkyl moiety, or a substituted or unsubstituted aryl or heteroaryl moiety.

In certain embodiments, $R^{4A}$ is —C(=O)$OR^{4B}$, —C(=O)$NHOR^{4B}$ or a moiety having the structure:

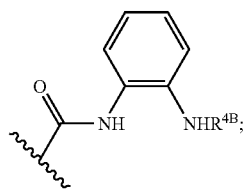

wherein each occurrence of $R^{4B}$ is independently hydrogen, alkyl, heteroalkyl, aryl, heteroaryl or acyl. In certain exemplary embodiments, $R^{4B}$ is hydrogen.

IV) Compounds of the formula (and pharmaceutically acceptable derivatives thereof):

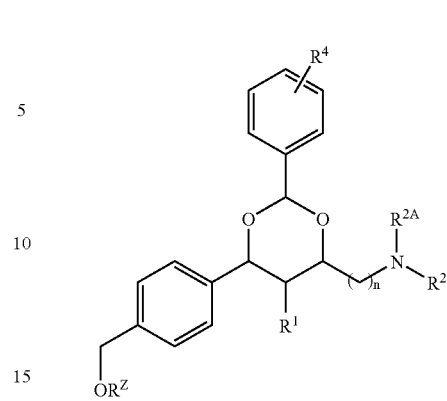

wherein $R^1$, $R^2$, $R^{2A}$, $R^4$, n and $R^Z$ are as described in classes and subclasses herein.

In certain exemplary embodiments, $R^1$ is hydrogen, phenyl or methyl, $R^Z$ is hydrogen or a solid support unit; and either or both of $R^2$ and $R^{2A}$, or $R^2$ and $R^{2A}$ taken together with the nitrogen atom to which they are attached, forms a substituted or unsubstituted cycloalkyl or heterocyclic moiety, or a substituted or unsubstituted aryl or heteroaryl moiety. In certain embodiments, $R^4$ comprises a metal chelator. In certain other embodiments, $R^4$ is —$(CH_2)_rN(R^{4A})_2$, —$(CH_2)_rSR^{4A}$, —$(CH_2)_rOR^{4A}$, —$(CH_2)_rNR^{4A}C(=O)R^{4B}$, $(CH_2)_rC(=O)N(R^{4A})_2$, —$S(O)_2R^{4A}$, or is an aliphatic, alycyclic, heteroaliphatic, heterocyclic, aryl, heteroaryl, -(aliphatic)aryl, -(aliphatic)heteroaryl, -(heteroaliphatic)aryl, or -(heteroaliphatic)heteroaryl moiety, wherein each occurrence of $R^{4B}$ is independently hydrogen, an aliphatic, alycyclic, heteroaliphatic, heterocyclic, aryl, heteroaryl, -(aliphatic)aryl, -(aliphatic)heteroaryl, -(heteroaliphatic)aryl, or -(heteroaliphatic)heteroaryl moiety; and each occurrence of $R^{4A}$ is independently hydrogen, a protecting group, an aliphatic, alycyclic, heteroaliphatic, heterocyclic, aryl, heteroaryl, -(aliphatic)aryl, -(aliphatic)heteroaryl, -(heteroaliphatic)aryl, or -(heteroaliphatic)heteroaryl moiety, or is —C(=O)CH($R^{4C}$)NH($SO_2$)$R^{4D}$, —$SO_2R^{4C}$, —C(=O)$R^{4C}$, —C(=O)N($R^{4C}$)$_2$, —C(=S)N($R^{4C}$)$_2$, or —C(=O)$(CH_2)_tC(=O)NHR^{4C}$, wherein each occurrence of $R^{4C}$ and $R^{4D}$ is independently hydrogen, a protecting group, hydroxyl, protected hydroxyl, or an aliphatic, alycyclic, heteroaliphatic, heterocyclic, aryl, heteroaryl, -(aliphatic)aryl, -(aliphatic)heteroaryl, -(heteroaliphatic)aryl, or -(heteroaliphatic)heteroaryl moiety, wherein r and t are each independently 0–5.

In certain embodiments, when $R^4$ represents a moiety —P-Q, the following groups do not occur simultaneously as defined:

P is selected from the group consisting of substituted or unsubstituted $C_4$–$C_8$ alkylene, $C_4$–$C_8$ alkenylene, $C_4$–$C_8$ alkynylene, and —R-T-U-, wherein R and U are independently absent or represent a $C_2$–$C_7$ alkylene, a $C_2$–$C_7$ alkenylene, or a $C_2$–$C_7$ alkynylene, and T represents O, S or $NR^T$, wherein $R^T$ represents hydrogen, lower alkyl, lower alkenyl, lower alkynyl, aralkyl, aryl or heterocyclyl; and Q is selected from the group consisting of:

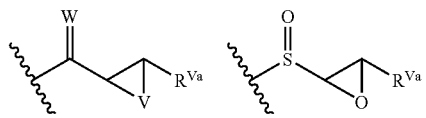

-continued

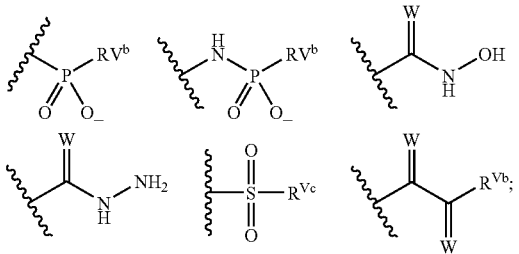

and a boronic acid moiety; wherein W is O or S; V is O, S or —NR$^{Vd}$, wherein R$^{Vd}$ is hydrogen, alkyl, alkoxycarbonyl, aryloxycarbonyl, alkylsulfonyl, arylsulfonyl, or aryl; R$^{Va}$ is hydrogen, alkyl, alkenyl, alkynyl, or aryl; R$^{Vb}$ is hydrogen, alkyl, aryl, alkoxy, aryloxy, amino, hydroxylamino, alkoxylamino or halogen; and R$^{Vc}$ is hydrogen, alkyl, aryl, hydroxyl, alkoxy, aryloxy or amino.

In certain embodiments, when R$^4$ represents a moiety —P-Q, the following groups do not occur simultaneously as defined:

P is selected from the group consisting of

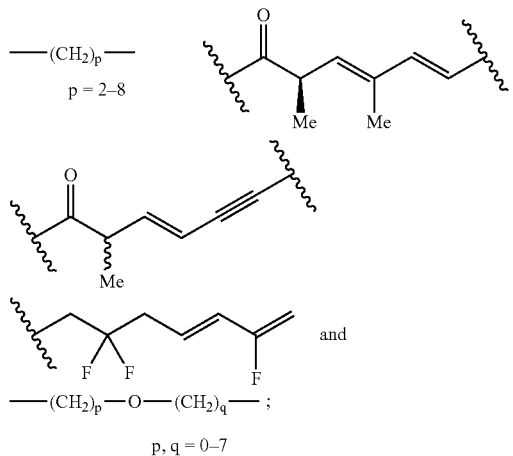

and Q is selected from the group consisting of:

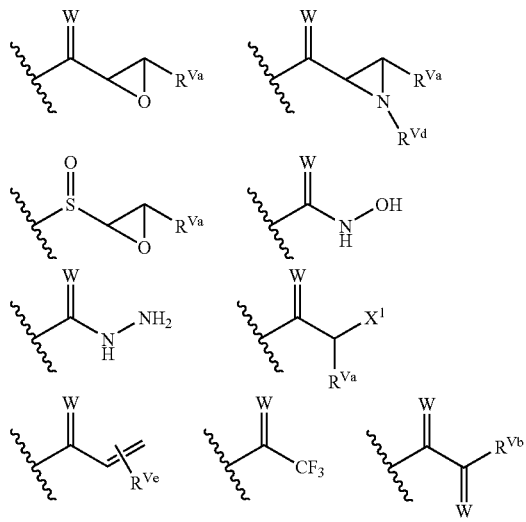

-continued

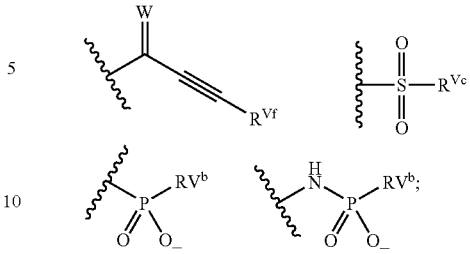

wherein W and R$^{Va-d}$ are as defined above; X$^1$ is a good leaving group (e.g., diazo, halogen, a sulfate or sulfonate ester such as a tosylate or mesylate); R$^{Ve}$ is hydrogen, alkyl, aryl, alkoxy, aryloxy, halogen; and R$^{Vf}$ is hydrogen, alkyl or halogen.

In certain exemplary embodiments, R$^4$ represents a moiety having the structure -L-R$^{4A}$ and the compound has the structure:

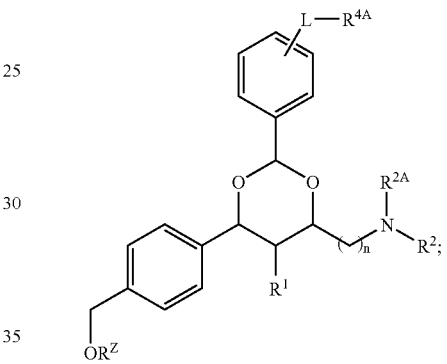

wherein L is a linker and R$^{4A}$ comprises a metal chelator.

In certain embodiments, L is a substituted or unsubstituted C$_{4-8}$alkylene or C$_{4-8}$alkenylene chain wherein up to two non-adjacent methylene units are independently optionally replaced by CO, CO$_2$, COCO, CONR$^{Z1}$, OCONR$^{Z1}$, NR$^{Z1}$NR$^{Z2}$, NR$^{Z1}$NR$^{Z2}$CO, NR$^{Z1}$CO, NR$^{Z1}$CO$_2$, NR$^{Z1}$CONR$^{Z2}$, SO, SO$_2$, NR$^{Z1}$SO$_2$, SO$_2$NR$^{Z1}$, NR$^{Z1}$SO$_2$NR$^{Z2}$, O, S, or NR$^{Z1}$; wherein each occurrence of R$^{Z1}$ and R$^{Z2}$ is independently hydrogen, alkyl, heteroalkyl, aryl, heteroaryl or acyl.

In certain exemplary embodiments, L is —(CH$_2$)$_r$NHC(=O)(CH$_2$)$_t$—, wherein r is 0 or 1; and t is 3, 4 or 5.

In certain embodiments, R$^{4A}$ is —C(=O)OR$^{4B}$, —C(=O)NHOR$^{4B}$ or a moiety having the structure:

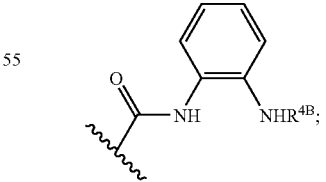

wherein each occurrence of R$^{4B}$ is independently hydrogen, alkyl, heteroalkyl, aryl, heteroaryl or acyl. In certain exemplary embodiments, R$^{4B}$ is hydrogen.

In certain exemplary embodiments, L is —(CH$_2$)$_r$NHC(=O)(CH$_2$)$_t$—, wherein r is 0 or 1; t is 3, 4 or 5; and R$^{4A}$ is —C(=O)NHOH.

In certain embodiments, either or both of $R^2$ and $R^{2A}$, or $R^2$ and $R^{2A}$ taken together with the nitrogen atom to which they are attached, forms a substituted or unsubstituted cycloalkyl or heterocyclic moiety, or a substituted or unsubstituted aryl or heteroaryl moiety.

V) Compounds of the formula (and pharmaceutically acceptable derivatives thereof):

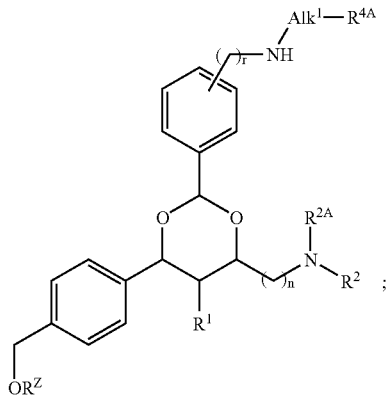

wherein $R^1$, $R^2$, $R^{2A}$, $R^4$, n and $R^Z$ are as described in classes and subclasses herein; r is 0 or 1; $Alk^1$ is a substituted or unsubstituted $C_{4-7}$alkylene or $C_{4-7}$alkenylene chain wherein up to two non-adjacent methylene units are independently optionally replaced by CO, $CO_2$, COCO, $CONR^{Z1}$, $OCONR^{Z1}$, $NR^{Z1}NR_{Z2}$, $NR^{Z1}NR^{Z2}CO$, $NR^{Z1}CO$, $NR^{Z1}CO_2$, $NR^{Z1}CONR^{Z2}$, SO, $SO_2$, $NR^{Z1}SO_2$, $SO_2NR^{Z1}$, $NR^{Z1}SO_2NR^{Z2}$, O, S, or $NR^{Z1}$; wherein each occurrence of $R^{Z1}$ and $R^{Z2}$ is independently hydrogen, alkyl, heteroalkyl, aryl, heteroaryl or acyl; and $R^{4A}$ comprises a metal chelator.

In certain exemplary embodiments, $R^1$ is hydrogen, phenyl or methyl, $R^Z$ is hydrogen or a solid support unit; and $R^2$ is a substituted or unsubstituted alkyl or heteroalkyl moiety, or a substituted or unsubstituted aryl or heteroaryl moiety.

In certain embodiments, $Alk^1$ is a moiety having the structure —C(=O)-$Alk^2$- and the compound has the structure:

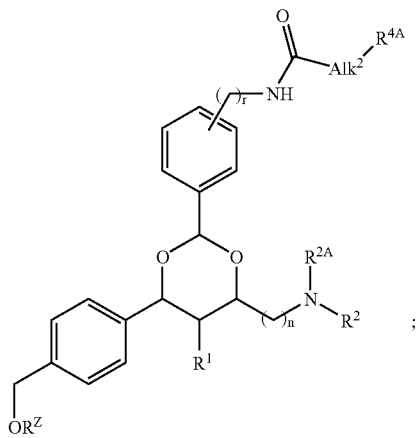

wherein $R^1$, $R^2$, $R^4$, n and $R^Z$ are as described in classes and subclasses herein; r is 0 or 1; $R^{4A}$ comprises a metal chelator and $Alk^2$ is a substituted or unsubstituted $C_{3-6}$alkylene or $C_{3-6}$alkenylene chain wherein up to two non-adjacent methylene units are independently optionally replaced by CO, $CO_2$, COCO, $CONR^{Z1}$, $OCONR^{Z1}$, $NR^{Z1}NR^{Z2}$, $NR^{Z1}NR^{Z2}CO$, $NR^{Z1}CO$, $NR^{Z1}CO_2$, $NR^{Z1}CONR^{Z2}$, SO, $SO_2$, $NR^{Z1}SO_2$, $SO_2NR^{Z1}$, $NR^{Z1}SO_2NR^{Z2}$, O, S, or $NR^{Z1}$; wherein each occurrence of $R^{Z1}$ and $R^{Z2}$ is independently hydrogen, alkyl, heteroalkyl, aryl, heteroaryl or acyl.

In certain exemplary embodiments, $R^1$ is hydrogen, phenyl or methyl; $R^Z$ is hydrogen or a solid support unit; and $R^2$ is a substituted or unsubstituted alkyl or heteroalkyl moiety, or a substituted or unsubstituted aryl or heteroaryl moiety. In certain embodiments, $Alk^2$ is a substituted or unsubstituted $C_{3-6}$alkylene chain.

In certain embodiments, $R^{4A}$ is —C(=O)$OR^{4B}$, —C(=O)$NHOR^{4B}$ or a moiety having the structure:

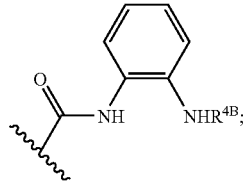

wherein each occurrence of $R^{4B}$ is independently hydrogen, alkyl, heteroalkyl, aryl, heteroaryl or acyl. In certain exemplary embodiments, $R^{4B}$ is hydrogen.

In certain embodiments, $Alk^2$ is a substituted or unsubstituted $C_{3-6}$alkylene chain; and $R^{4A}$ is as defined immediately above.

In certain embodiments, either or both of $R^2$ and $R^{2A}$, or $R^2$ and $R^{2A}$ taken together with the nitrogen atom to which they are attached, forms a substituted or unsubstituted cycloalkyl or heterocyclic moiety, or a substituted or unsubstituted aryl or heteroaryl moiety.

VI) Compounds of the formula (and pharmaceutically acceptable derivatives thereof):

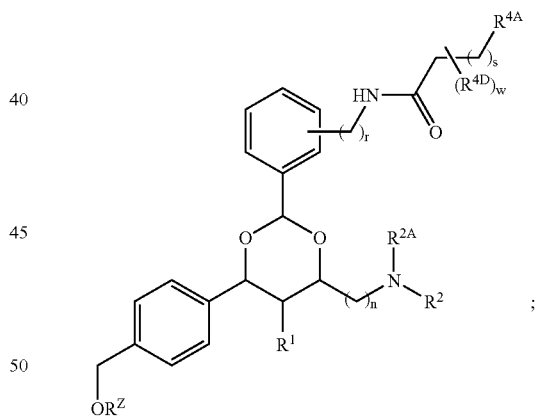

wherein $R^1$, $R^2$, $R^{2A}$, $R^4$, n and $R^Z$ are as described in classes and subclasses herein; r is 0 or 1; s is an integer from 2–5; w is an integer from 0–4; $R^{4A}$ comprises a metal chelator and each occurrence of $R^{4D}$ is independently hydrogen, alkyl, heteroalkyl, cycloalkyl, heterocyclic, alkenyl, alkynyl, aryl, heteroaryl, halogen, CN, $NO_2$, or $WR^{W1}$ wherein W is O, S, $NR^{W2}$, —C(=O), —S(=O), —$SO_2$, —C(=O)O—, —OC(=O)—, —C(=O)NR$^{W2}$, —$NR^{W2}$C(=O); wherein each occurrence of $R^{W1}$ and $R^{W2}$ is independently hydrogen, a protecting group, a prodrug moiety or an alkyl, cycloalkyl, heteroalkyl, heterocyclic, aryl or heteroaryl moiety, or, when W is $NR^{W2}$ $R^{W1}$ and $R^{W2}$, taken together with the nitrogen atom to which they are attached, form a heterocyclic or heteroaryl moiety; or any two adjacent occurrences of $R^{2B}$, taken together with the atoms to which they are attached, form a substituted or unsubstituted, saturated or unsaturated alicyclic or heterocyclic moiety, or a substituted or unsubstituted aryl or heteroaryl moiety.

In certain exemplary embodiments, $R^1$ is hydrogen, phenyl or methyl; $R^Z$ is hydrogen or a solid support unit; and $R^2$ is a substituted or unsubstituted alkyl or heteroalkyl moiety, or a substituted or unsubstituted aryl or heteroaryl moiety.

In certain embodiments, $R^{4A}$ is $-C(=O)OR^{4B}$, $-C(=O)NHOR^{4B}$ or a moiety having the structure:

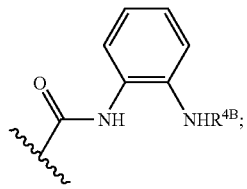

wherein each occurrence of $R^{4B}$ is independently hydrogen, alkyl, heteroalkyl, aryl, heteroaryl or acyl. In certain exemplary embodiments, $R^{4B}$ is hydrogen.

In certain embodiments, either or both of $R^2$ and $R^{2A}$, or $R^2$ and $R^{2A}$ taken together with the nitrogen atom to which they are attached, forms a substituted or unsubstituted cycloalkyl or heterocyclic moiety, or a substituted or unsubstituted aryl or heteroaryl moiety.

In certain exemplary embodiments, for compounds of classes I–VI above, $R^2$ is one of:

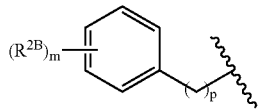 a

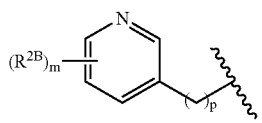 b

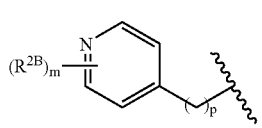 c

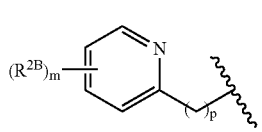 d

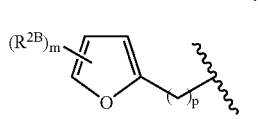 e

 f

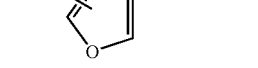

-continued

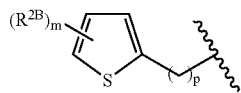 g

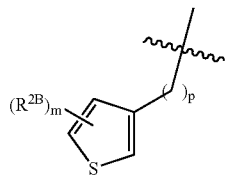 h

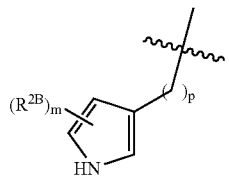 i

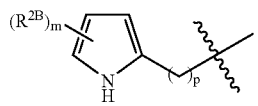 j

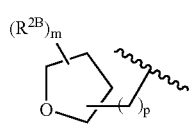 k

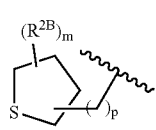 l

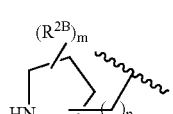 m

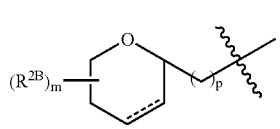 n

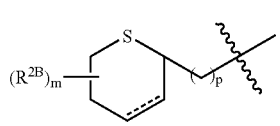 o

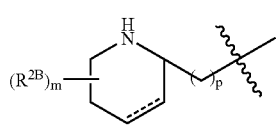 p

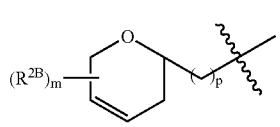 q

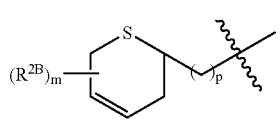 r

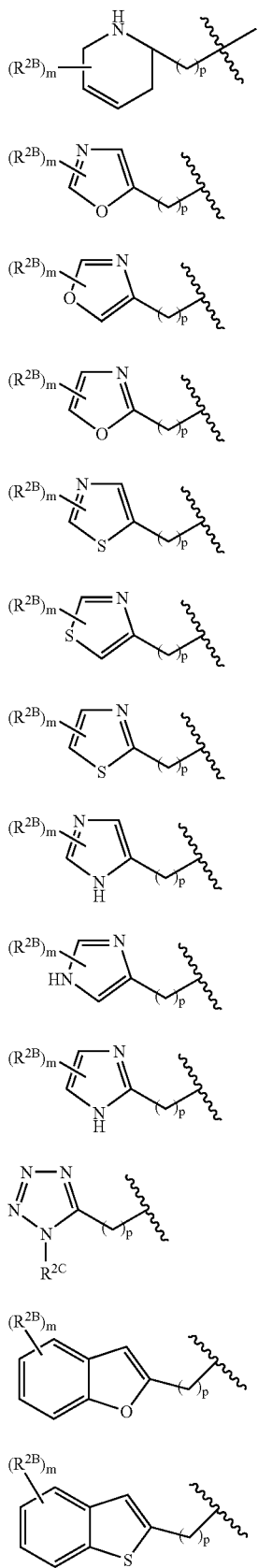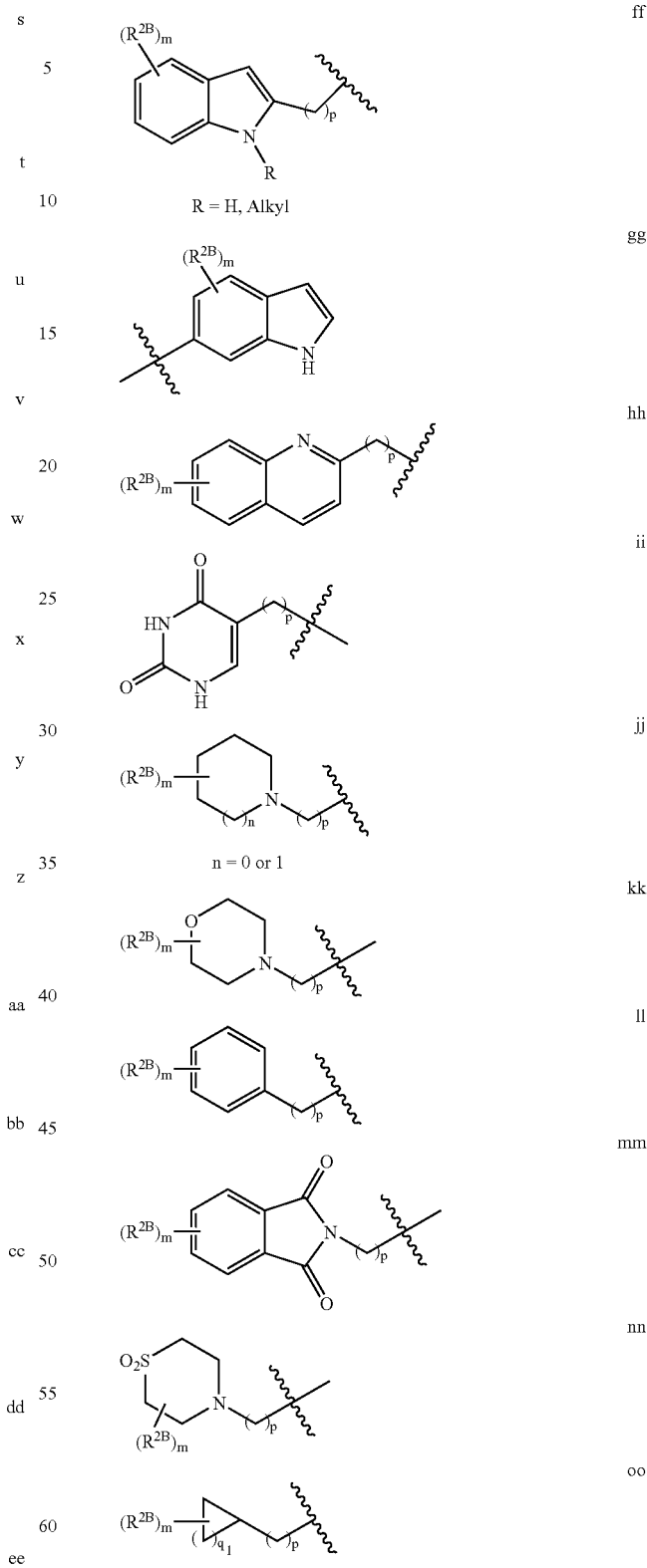
wherein m and p are each independently integers from 0 to 3; $q_1$ is an integer from 1 to 6; $R^{2C}$ is hydrogen, lower alkyl or a nitrogen protecting group; and each occurrence of $R^{2B}$ is independently hydrogen, halogen, —CN, or WR$^{W1}$ wherein W is O, S, NR$^{W2}$, —C(=O), —S(=O), —SO$_2$, —C(=O)O—, —OC(=O), —C(=O)NR$^{W2}$, —NR$^{W2}$C(=O); wherein each occurrence of R$^{W1}$ and R$^{W2}$ is independently hydrogen, a protecting group, a prodrug moiety or an alkyl, cycloalkyl, heteroalkyl, heterocyclic, aryl or heteroaryl moiety, or, when W is NR$^{W2}$, R$^{W1}$ and R$^{W2}$, taken together with the nitrogen atom to which they are attached, form a heterocyclic or heteroaryl moiety; or any two adjacent occurrences of R$^{2B}$, taken together with the atoms to which they are attached, form a substituted or unsubstituted, saturated or unsaturated alicyclic or heterocyclic moiety, or a substituted or unsubstituted aryl or heteroaryl moiety.

In certain exemplary embodiments, for compounds of classes IV–VI above, either or both of R$^2$, R$^{2A}$, or R$^2$ and R$^{2A}$, taken together with the nitrogen atom to which they are attached, comprise

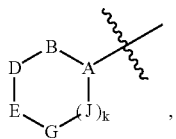

wherein k is an integer from 0–3; A-B, B-D, D-E, E-G, G-J, two or more occurrences of J, and J-A are each connected by a single or double bond; A is CH, C, or N; B is CR$^B$, C(R$^B$)$_2$, C(=O), NR$^B$, N, O or S; D is CR$^D$, C(R$^D$)$_2$, C(=O), NR$^D$, N, O or S; E is CR$^E$, C(R$^E$)$_2$, C(=O), NR$^E$, N, O or S; G is CR$^G$, C(R$^G$)$_2$, C(=O), NR$^G$, N, O or S; and each occurrence of J is independently CR$^J$, C(R$^J$)$_2$, C(=O), NR$^J$, N, O or S; wherein each occurrence of R$^B$, R$^D$, R$^E$, R$^G$ and R$^J$ is independently hydrogen, halogen, hydroxyl, protected hydroxyl, thiol, protected thiol, amino, protected amino, —COOR$^x$, —CON(R$^y$)$_2$, —NR$^y$COOR$^x$, —NR$^y$COR$^x$, or a substituted or unsubstituted, cyclic or acyclic, linear or branched alkyl or heteroalkyl moiety, or a substituted or unsubstituted aryl or heteroaryl moiety, or any two or R$^B$, R$^D$, R$^E$, R$^G$ or R$^J$ taken together comprises a substituted or unsubstituted alicyclic or heterocyclic, moiety or a substituted or unsubstituted aryl or heteroaryl moiety; wherein each occurrence of R$^x$ is independently hydrogen, aliphatic, alicyclic, heteroaliphatic, heterocyclic, aryl, heteroaryl, -(alkyl)aryl, -(alkyl)heteroaryl, -(heteroalkyl)aryl, or (heteroalkyl)heteroaryl; and each occurrence of R$^y$ is independently hydrogen, a nitrogen protecting group, acyl, aliphatic, alicyclic, heteroaliphatic, heterocyclic, aryl, heteroaryl, -(alkyl)aryl, -(alkyl)heteroaryl, -(heteroalkyl)aryl, or (heteroalkyl)heteroaryl.

In certain exemplary embodiments, for compounds of classes IV—VI above, either or both of R$^2$, R$^{2A}$, or R$^2$ and R$^{2A}$, taken together with the nitrogen atom to which they are attached, comprise

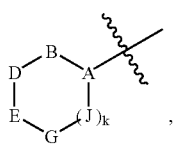

wherein k is an integer from 0–3; A-B, B-D, D-E, E-G, G-J, two or more occurrences of J, and J-A are each connected by a single or double bond; A is CH, C, or N; B is CR$^B$, C(R$^B$)$_2$, C(=O), NR$^B$, N, O or S; D is CR$^D$, C(R$^D$)$_2$, C(=O), NR$^D$, N, O or S; E is CR$^E$, C(R$^E$)$_2$, C(=O), NR$^E$, N, O or S; G is CR$^G$, C(R$^G$)$_2$, C(=O), NR$^G$, N, O or S; and each occurrence of J is independently CR$^J$, C(R$^J$)$_2$, C(=O), NR$^J$, N, O or S; wherein each occurrence of R$^B$, R$^D$, R$^E$, R$^G$ and R$^J$ is independently hydrogen, halogen, hydroxyl, protected hydroxyl, thiol, protected thiol, amino, protected amino, —COOH, —CONH$_2$, —NHCOOH, —NHCOO(alkyl), —NHCO(alkyl), or a substituted or unsubstituted, cyclic or acyclic, linear or branched alkyl or heteroalkyl moiety, or a substituted or unsubstituted aryl or heteroaryl moiety, or any two or R$^B$, R$^D$, R$^E$, R$^G$ or R$^J$ taken together comprises a substituted or unsubstituted alicyclic or heterocyclic, moiety or a substituted or unsubstituted aryl or heteroaryl moiety.

In certain exemplary embodiments, for compounds of classes IV–VI above, one or both of R$^2$ and R$^{2A}$ is a substituted or unsubstituted aryl or heteroaryl moiety.

In certain exemplary embodiments, for compounds of classes IV–VI above, one or both of R$^2$ and R$^{2A}$ is an aryl or heteroaryl moiety substituted with —COOH, halogen, alkyl, heteroalkyl, aryl, heteroaryl, OH, SH, NO$_2$, NH$_2$, or —NHC(=O)alkyl.

In certain exemplary embodiments, for compounds of classes I–VI above, R$^{4A}$ is —C(=O)OH, —C(=O)NHOH or a moiety having the structure:

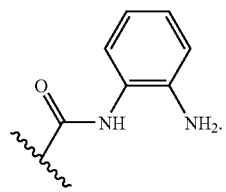

In certain exemplary embodiments, for compounds of classes I–VI above, R$^{4A}$ is —C(=O)NHOH.

In certain exemplary embodiments, for compounds of classes I–VI above, the compound core structure has the following stereochemistry:

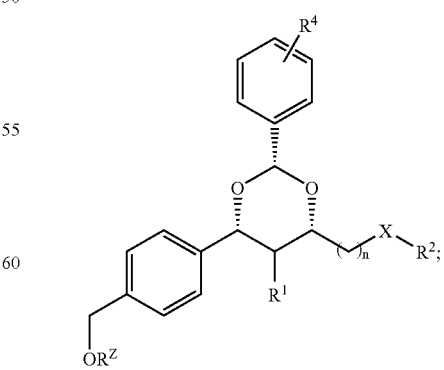

wherein X is S or NR$^{2A}$ and R$^4$ is as further defined in I–VI above.

In certain exemplary embodiments, for compounds of classes I–VI above, the compound core structure has the following stereochemistry:

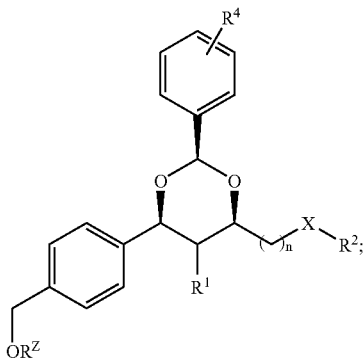

wherein X is S or NR$^{2A}$ and R$^4$ is as further defined in I–VI above.

It will also be appreciated that for each of the subgroups I–VI described above, a variety of other subclasses are of special interest, including, but not limited to those classes described above i)–xlxiii) and classes, subclasses and species of compounds described above and in the examples herein.

Some of the foregoing compounds can comprise one or more asymmetric centers, and thus can exist in various isomeric forms, e.g., stereoisomers and/or diastereomers. Thus, inventive compounds and pharmaceutical compositions thereof may be in the form of an individual enantiomer, diastereomer or geometric isomer, or may be in the form of a mixture of stereoisomers. In certain embodiments, the compounds of the invention are enantiopure compounds. In certain other embodiments, mixtures of stereoisomers or diastereomers are provided.

Furthermore, certain compounds, as described herein may have one or more double bonds that can exist as either the Z or E isomer, unless otherwise indicated. The invention additionally encompasses the compounds as individual isomers substantially free of other isomers and alternatively, as mixtures of various isomers, e.g., racemic mixtures of stereoisomers. In addition to the above-mentioned compounds per se, this invention also encompasses pharmaceutically acceptable derivatives of these compounds and compositions comprising one or more compounds of the invention and one or more pharmaceutically acceptable excipients or additives.

Compounds of the invention may be prepared by crystallization of compound of formula (I) under different conditions and may exist as one or a combination of polymorphs of compound of general formula (I) forming part of this invention. For example, different polymorphs may be identified and/or prepared using different solvents, or different mixtures of solvents for recrystallization; by performing crystallizations at different temperatures; or by using various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffractogram and/or other techniques. Thus, the present invention encompasses inventive compounds, their derivatives, their tautomeric forms, their stereoisomers, their polymorphs, their pharmaceutically acceptable salts their pharmaceutically acceptable solvates and pharmaceutically acceptable compositions containing them.

2) Synthetic Overview:

As described above, the present invention provides novel compounds, specifically compounds having the following general structure:

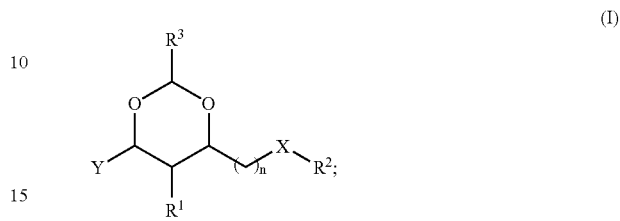

(I)

wherein R$^1$–R$^3$, n, X and Y are as defined generally above and in classes and subclasses herein.

It will be appreciated that for compounds as generally described above, certain classes of compounds are of special interest. For example, one class of compounds of special interest includes those compounds wherein the compound has the stereochemistry as shown in Formula (III$^A$):

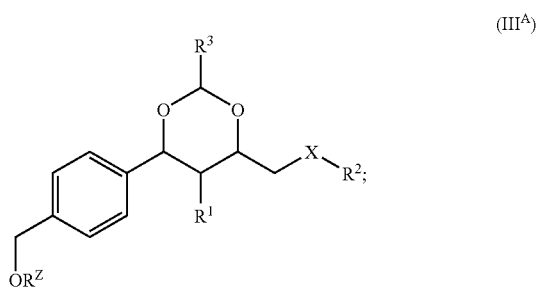

(III$^A$)

wherein R$^Z$ is as defined generally above and in classes and subclasses herein.

Another class of compounds of special interest includes those compounds wherein R$^3$ is a substituted phenyl group and the compound has the structure as shown in Formula (VIII$^A$):

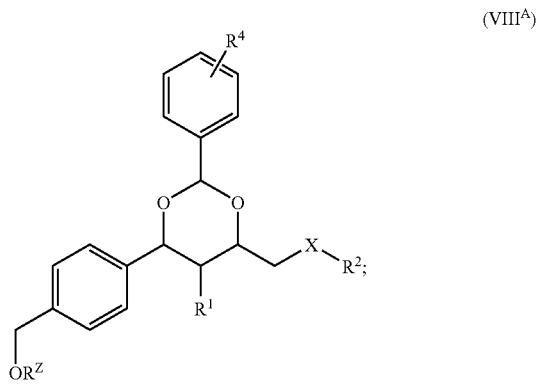

(VIII$^A$)

wherein R$^1$, R$^2$, R$^Z$, n and X are as defined generally above or in classes and subclassses herein.

Another class of compounds of special interest includes those compounds wherein R', R$^0$ and R$^{3'}$ are each hydrogen and the compound has the structure as shown in Formula (IX):

(IX)

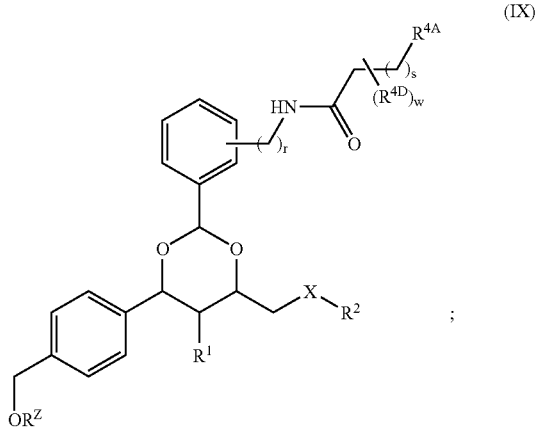

wherein R¹, R², R⁴, n and $R^Z$ are as described in classes and subclasses herein; r is 0 or 1; s is an integer from 2–5; w is an integer from 0–4; $R^{4A}$ comprises a metal chelator and each occurrence of $R^{4D}$ is independently hydrogen, alkyl, heteroalkyl, cycloalkyl, heterocyclic, alkenyl, alkynyl, aryl, heteroaryl, halogen, CN, NO₂, or $WR^{W1}$ wherein W is O, S, $NR^{W2}$, C(=O), —S(=O), —SO₂, —C(=O)O—, —OC(=O), —C(=O)$NR^{W2}$, —$NR^{W2}$C(=O); wherein each occurrence of $R^{W1}$ and $R^{W2}$ is independently hydrogen, a protecting group, a prodrug moiety or an alkyl, cycloalkyl, heteroalkyl, heterocyclic, aryl or heteroaryl moiety, or, when W is $NR^{W2}$, $R^{W1}$ and $R^{W2}$, taken together with the nitrogen atom to which they are attached, form a heterocyclic or heteroaryl moiety; or any two adjacent occurrences of $R^{2B}$, taken together with the atoms to which they are attached, form a substituted or unsubstituted, saturated or unsaturated alicyclic or heterocyclic moiety, or a substituted or unsubstituted aryl or heteroaryl moiety.

In yet another aspect of the invention, methods for producing intermediates useful for the preparation of compounds of formulae (III^A), (VIII^A) and (IX) are provided.

In another aspect of the invention, a method for the synthesis of the core structure (III^A) is provided, one method comprising steps of:

providing an epoxy alcohol having the structure:

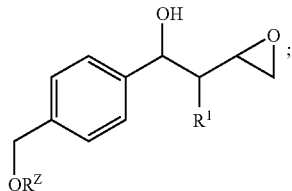

reacting the epoxy alcohol with a reagent having the structure R²XH under suitable conditions to generate a diol having the core structure:

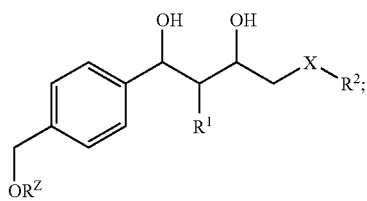

reacting the diol with a reagent having the structure R₃CH(OMe)₂ under suitable conditions to generate a scaffold having the core structure:

(III^A)

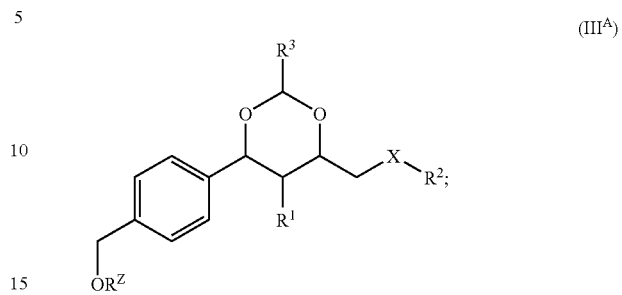

wherein R¹ is hydrogen, or an aliphatic, alicyclic, heteroaliphatic, heterocyclic, aromatic or heteroaromatic moiety;

R² is hydrogen, a protecting group, or an aliphatic, alicyclic, heteroaliphatic, heterocyclic, aromatic or heteroaromatic moiety;

X is —O—, —C($R^{2A}$)₂—, —S—, or —$NR^{2A}$—, wherein $R^{2A}$ is hydrogen, a protecting group, or an aliphatic, alicyclic, heteroaliphatic, heterocyclic, aromatic or heteroaromatic moiety;

or wherein two or more occurrences of R² and $R^{2A}$, taken together, form an alicyclic or heterocyclic moiety, or an aryl or heteroaryl moiety;

R³ is an aliphatic, alicyclic, heteroaliphatic, heterocyclic, aromatic or heteroaromatic moiety; and $R^Z$ is an aliphatic, alicyclic, heteroaliphatic, heterocyclic, aromatic or heteroaromatic moiety and is attached to a solid support.

In certain embodiments, the method further comprises cleaving the core structure (III) from the solid support to which it is attached.

In certain exemplary embodiments, the epoxy alcohol has the structure:

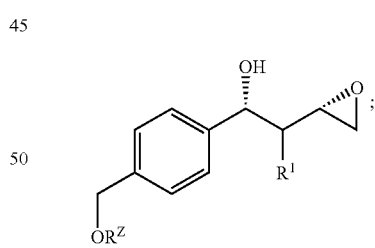

the diol has the structure:

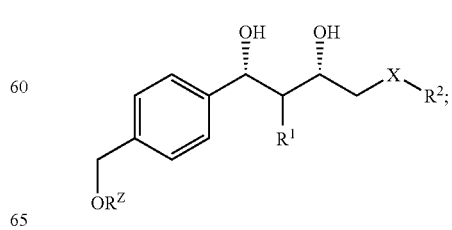

and the core scaffold has the structure:

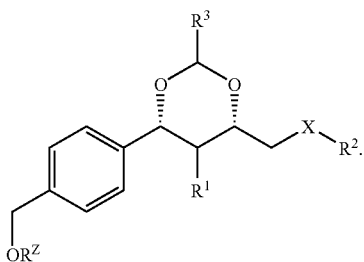

In certain other exemplary embodiments, the epoxy alcohol has the structure:

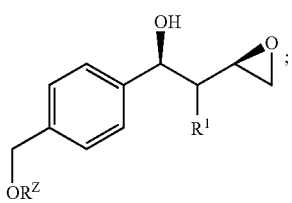

the diol has the structure:

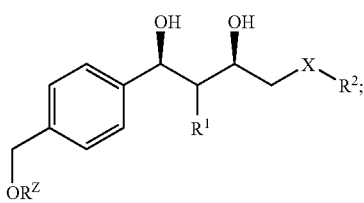

and the the core scaffold has the structure:

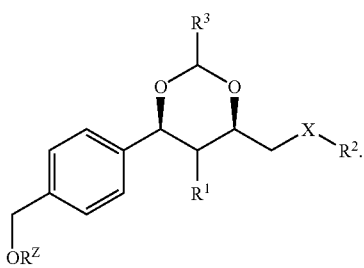

In certain embodiments, $R^3$ has the following structure:

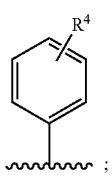

and the method described above generates the structure:

(VIII$^A$)

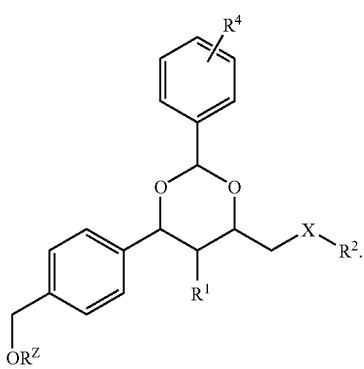

In another aspect of the invention, a method for the synthesis of the core structure (IX) is provided, one method comprising steps of:

providing an epoxy alcohol having the structure:

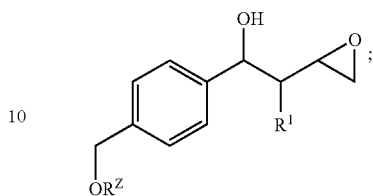

reacting the epoxy alcohol with a reagent having the structure $R^2XH$ under suitable conditions to generate a diol having the core structure:

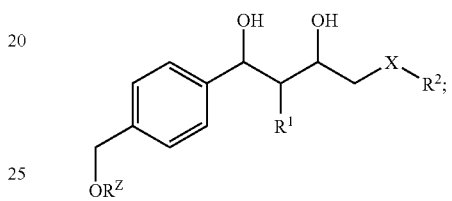

subjecting the diol with a reagent having the structure:

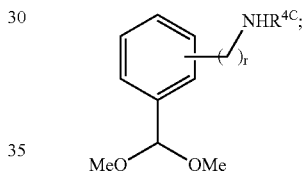

wherein $R^{4C}$ is a nitrogen protecting group;
to suitable conditions to generate an amine having the structure:

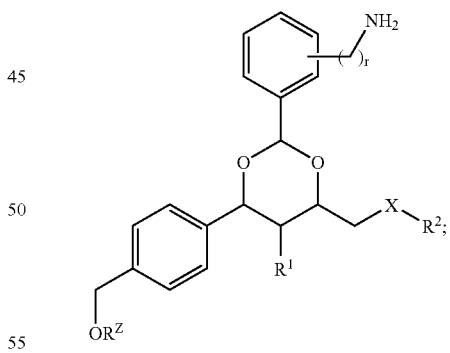

reacting the amine with a reagent having the structure:

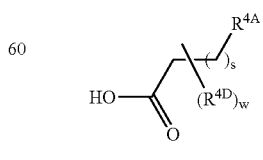

under suitable conditions to generate a scaffold having the core structure:

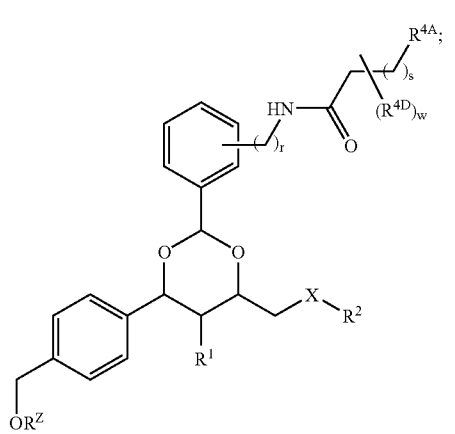

(IX)

wherein R¹ is hydrogen, or an aliphatic, alicyclic, heteroaliphatic, heterocyclic, aromatic or heteroaromatic moiety;

R² is hydrogen, a protecting group, or an aliphatic, alicyclic, heteroaliphatic, heterocyclic, aromatic or heteroaromatic moiety;

X is —O—, —C(R$^{2A}$)$_2$—, —S—, or —NR$^{2A}$—, wherein R$^{2A}$ is hydrogen, a protecting group, or an aliphatic, alicyclic, heteroaliphatic, heterocyclic, aromatic or heteroaromatic moiety;

or wherein two or more occurrences of R² and R$^{2A}$, taken together, form an alicyclic or heterocyclic moiety, or an aryl or heteroaryl moiety;

r is 0 or 1;

s is an integer from 2–5;

w is an integer from 0–4;

R$^{4A}$ comprises a metal chelator;

each occurrence of R$^{4D}$ is independently hydrogen, alkyl, heteroalkyl, cycloalkyl, heterocyclic, alkenyl, alkynyl, aryl, heteroaryl, halogen, CN, NO$_2$, or WR$^{W1}$ wherein W is O, S, NR$^{W2}$, —C(=O), —S(=O), —SO$_2$, —C(=O)O—, —OC(=O), —C(=O)NR$^{W2}$, —NR$^{W2}$C(=O); wherein each occurrence of R$^{W1}$ and R$^{W2}$ is independently hydrogen, a protecting group, a prodrug moiety or an alkyl, cycloalkyl, heteroalkyl, heterocyclic, aryl or heteroaryl moiety, or, when W is NR$^{W2}$, R$^{W1}$ and R$^{W2}$, taken together with the nitrogen atom to which they are attached, form a heterocyclic or heteroaryl moiety; or any two adjacent occurrences of R$^{2B}$, taken together with the atoms to which they are attached, form a substituted or unsubstituted, saturated or unsaturated alicyclic or heterocyclic moiety, or a substituted or unsubstituted aryl or heteroaryl moiety; and R$^Z$ is an aliphatic, alicyclic, heteroaliphatic, heterocyclic, aromatic or heteroaromatic moiety and is attached to a solid support.

In certain embodiments, the method further comprises cleaving the core structure (IX) from the solid support to which it is attached.

In certain exemplary embodiments, the epoxy alcohol has the structure:

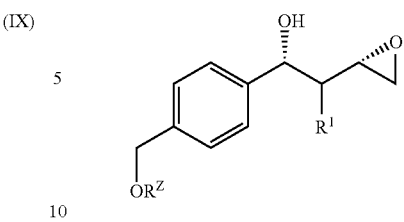

the diol has the structure:

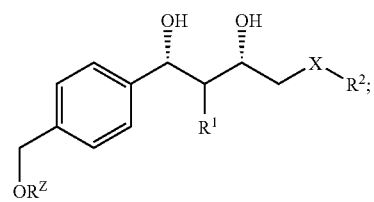

the amine has the structure:

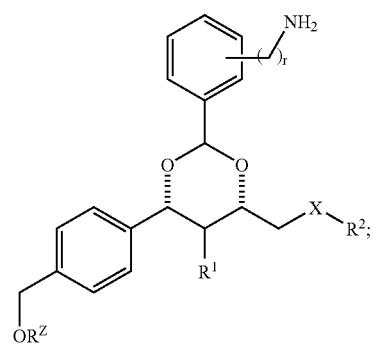

and the core scaffold (IX) has the structure:

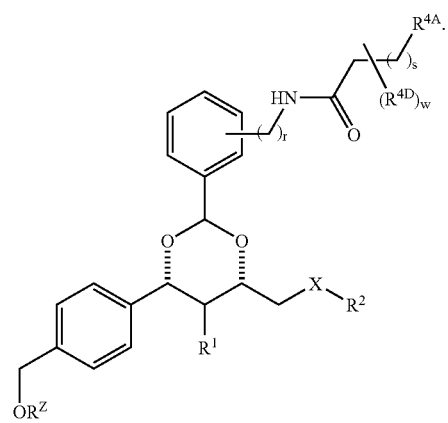

In certain exemplary embodiments, the epoxy alcohol has the structure:

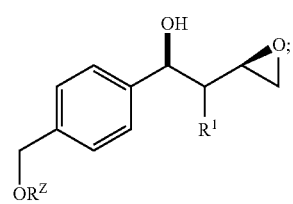

the diol has the structure:

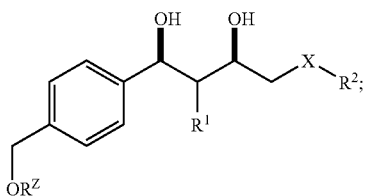

the amine has the structure:

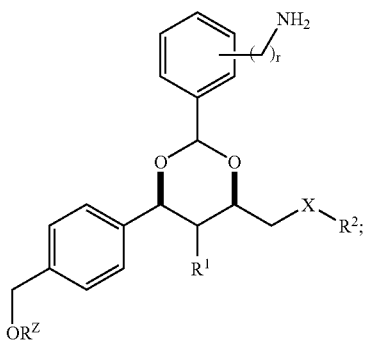

and the core scaffold has the structure (IX):

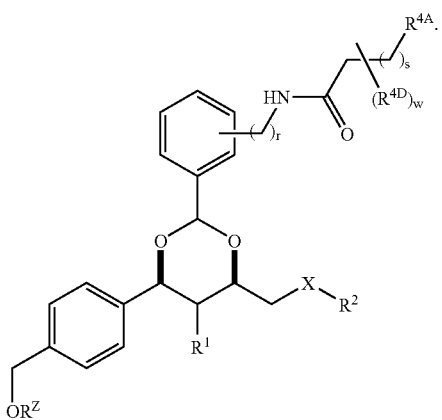

In certain embodiments, the methods described above are carried out in solution phase, and $R^Z$ is not attached to a solid support.

Diversification:

It will also be appreciated that each of the components used in the synthesis of inventive compounds can be diversified either before synthesis or alternatively after the construction of the core structure of formula (I). As used herein, the term "diversifying" or "diversify" means reacting an inventive compound (I) or any of the precursor fragments (or any classes or subclasses thereof) at one or more reactive sites to modify a functional moiety or to add a functional moiety (e.g., nucleophilic addition of a substrate). Described generally herein are a variety of schemes to assist the reader in the synthesis of a variety of compounds, either by diversification of the intermediate components or by diversification of the core structures as described herein, and classes and subclasses thereof. It will be appreciated that a variety of diversification reactions can be employed to generate compounds other than those described in the Exemplification herein. As but a few examples, where a double bond is present in the compound structure, epoxidation and aziridation can be conducted to generate epoxide and aziridine derivatives of compounds described herein. For additional guidance available in the art, the practitioner is directed to "Advanced Organic Chemistry", March, J. John Wiley & Sons, 2001, 5$^{th}$ ed., the entire contents of which are hereby incorporated by reference.

3) Pharmaceutical Compositions

As discussed above, the present invention provides novel compounds having antitumor and antiproliferative activity, and thus the inventive compounds are useful for the treatment of cancer.

Accordingly, in another aspect of the present invention, pharmaceutical compositions are provided, which comprise any one of the compounds described herein (or a prodrug, pharmaceutically acceptable salt or other pharmaceutically acceptable derivative thereof), and optionally comprise a pharmaceutically acceptable carrier. In certain embodiments, these compositions optionally further comprise one or more additional therapeutic agents. Alternatively, a compound of this invention may be administered to a patient in need thereof in combination with the administration of one or more other therapeutic agents. For example, additional therapeutic agents for conjoint administration or inclusion in a pharmaceutical composition with a compound of this invention may be an approved chemotherapeutic agent, or it may be any one of a number of agents undergoing approval in the Food and Drug Administration that ultimately obtain approval for the treatment of protozoal infections and/or any disorder associated with cellular hyperproliferation. In certain other embodiments, the additional therapeutic agent is an anticancer agent, as discussed in more detail herein. In certain other embodiments, the compositions of the invention are useful for the treatment of protozoal infections.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or a pro-drug or other adduct or derivative of a compound of this invention which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in *J. Pharmaceutical Sciences*, 66: 1–19 (1977), incorporated herein by reference. The salts can be prepared in situ during the final isolation and purification of the compounds of the invention, or separately by reacting a free base or free acid function with a suitable reagent, as described generally below. For example, a free base function can be reacted with a suitable acid. Furthermore, where the compounds of the invention carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, non-toxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hernisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Additionally, as used herein, the term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moeity advantageously has not more than 6 carbon atoms. Examples of particular esters include formates, acetates, propionates, butyrates, acrylates and ethylsuccinates.

Furthermore, the term "pharmaceutically acceptable prodrugs" as used herein refers to those prodrugs of the compounds of the present invention which are, within the scope of sound medical judgment, suitable for use in contact with the issues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

As described above, the pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include (poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose and starch. Such dosage forms may also comprise, as in normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The present invention encompasses pharmaceutically acceptable topical formulations of inventive compounds. The term "pharmaceutically acceptable topical formulation", as used herein, means any formulation which is pharmaceutically acceptable for intradermal administration of a compound of the invention by application of the formulation to the epidermis. In certain embodiments of the invention, the topical formulation comprises a carrier system. Pharmaceutically effective carriers include, but are not limited to, solvents (e.g., alcohols, poly alcohols, water), creams, lotions, ointments, oils, plasters, liposomes, powders, emulsions, microemulsions, and buffered solutions (e.g., hypotonic or buffered saline) or any other carrier known in the art for topically administering pharmaceuticals. A more complete listing of art-known carriers is provided by reference texts that are standard in the art, for example, Remington's Pharmaceutical Sciences, 16th Edition, 1980 and 17th Edition, 1985, both published by Mack Publishing Company, Easton, Pa., the disclosures of which are incorporated herein by reference in their entireties. In certain other embodiments, the topical formulations of the invention may comprise excipients. Any pharmaceutically acceptable excipient known in the art may be used to prepare the inventive pharmaceutically acceptable topical formulations. Examples of excipients that can be included in the topical formulations of the invention include, but are not limited to, preservatives, antioxidants, moisturizers, emollients, buffering agents, solubilizing agents, other penetration agents, skin protectants, surfactants, and propellants, and/or additional therapeutic agents used in combination to the inventive compound. Suitable preservatives include, but are not limited to, alcohols, quaternary amines, organic acids, parabens, and phenols. Suitable antioxidants include, but are not limited to, ascorbic acid and its esters, sodium bisulfite, butylated hydroxytoluene, butylated hydroxyanisole, tocopherols, and chelating agents like EDTA and citric acid. Suitable moisturizers include, but are not limited to, glycerine, sorbitol, polyethylene glycols, urea, and propylene glycol. Suitable buffering agents for use with the invention include, but are not limited to, citric, hydrochloric, and lactic acid buffers. Suitable solubilizing agents include, but are not limited to, quaternary ammonium chlorides, cyclodextrins, benzyl benzoate, lecithin, and polysorbates. Suitable skin protectants that can be used in the topical formulations of the invention include, but are not limited to, vitamin E oil, allatoin, dimethicone, glycerin, petrolatum, and zinc oxide.

In certain embodiments, the pharmaceutically acceptable topical formulations of the invention comprise at least a compound of the invention and a penetration enhancing agent. The choice of topical formulation will depend or several factors, including the condition to be treated, the physicochemical characteristics of the inventive compound and other excipients present, their stability in the formulation, available manufacturing equipment, and costs constraints. As used herein the term "penetration enhancing agent" means an agent capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, Percutaneous Penetration Enhancers, Maibach H. I. and Smith H. E. (eds.), CRC Press, Inc., Boca Raton, Fla. (1995), which surveys the use and testing of various skin penetration enhancers, and Buyuktimkin et al., Chemical Means of Transdermal Drug Permeation Enhancement in Transdermal and Topical Drug Delivery Systems, Gosh T. K., Pfister W. R., Yum S. I. (Eds.), Interpharm Press Inc., Buffalo Grove, Ill. (1997). In certain exemplary embodiments, penetration agents for use with the invention include, but are not limited to, triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate) and N-methyl pyrrolidone.

In certain embodiments, the compositions may be in the form of ointments, pastes, creams, lotions, gels, powders, solutions, sprays, inhalants or patches. In certain exemplary embodiments, formulations of the compositions according to the invention are creams, which may further contain saturated or unsaturated fatty acids such as stearic acid, palmitic acid, oleic acid, palmito-oleic acid, cetyl or oleyl alcohols, stearic acid being particularly preferred. Creams of the invention may also contain a non-ionic surfactant, for example, polyoxy-40-stearate. In certain embodiments, the active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are made by dissolving or dispensing the compound in the proper medium. As discussed above, penetration enhancing agents can also be used to increase the flux of the compound across the skin. The rate can be controlled by either providing a rate controlling membrane or by dispersing the compound in a polymer matrix or gel.

It will also be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another immunomodulatory agent, anticancer agent or agent useful for the treatment of psoriasis), or they may achieve different effects (e.g., control of any adverse effects).

For example, other therapies or anticancer agents that may be used in combination with the inventive compounds of the present invention include surgery, radiotherapy (in but a few examples, γ-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), to name a few. For a more comprehensive discussion of updated cancer therapies see, The Merck Manual, Seventeenth Ed. 1999, the entire contents of which are hereby incorporated by reference. See also the National Cancer Institute (CNI) website (www.nci.nih.gov) and the Food and Drug Administration (FDA) website for a list of the FDA approved oncology drugs (www.fda.gov/cder/cancer/druglistframe).

In certain embodiments, the pharmaceutical compositions of the present invention further comprise one or more additional therapeutically active ingredients (e.g., chemotherapeutic and/or palliative). For purposes of the invention, the term "Palliative" refers to treatment that is focused on the relief of symptoms of a disease and/or side effects of a therapeutic regimen, but is not curative. For example, palliative treatment encompasses painkillers, antinausea medications and anti-sickness drugs. In addition, chemotherapy, radiotherapy and surgery can all be used palliatively (that is, to reduce symptoms without going for cure; e.g., for shrinking tumors and reducing pressure, bleeding, pain and other symptoms of cancer).

Additionally, the present invention provides pharmaceutically acceptable derivatives of the inventive compounds, and methods of treating a subject using these compounds, pharmaceutical compositions thereof, or either of these in combination with one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or a prodrug or other adduct or derivative of a compound of this invention which upon administration to a patient in need is capable of providing, directly or indirectly, a compound as otherwise described herein, or a metabolite or residue thereof.

4) Research Uses, Pharmaceutical Uses and Methods of Treatment

Research Uses

According to the present invention, the inventive compounds may be assayed in any of the available assays known in the art for identifying compounds having antiprotozoal, HDAC inhibitory and/or antiproliferative activity. For example, the assay may be cellular or non-cellular, in vivo or in vitro, high- or low-throughput format, etc.

Thus, in one aspect, compounds of this invention which are of particular interest include those which:
exhibit HDAC-inhibitory activity;
exhibit the ability to inhibit HDAC1;
exhibit the ability to inhibit HDAC6;

exhibit the ability to modulate the glucose-sensitive subset of genes downstream of Ure2p;

exhibit cytotoxic or growth inhibitory effect on cancer cell lines maintained in vitro or in animal studies using a scientifically acceptable cancer cell xenograft model; and/or exhibit a therapeutic profile (e.g., optimum safety and curative effect) that is superior to existing chemotherapeutic agents.

As detailed in the exemplification herein, in assays to determine the ability of compounds to inhibit cancer cell growth certain inventive compounds may exhibit $IC_{50}$ values $\leq 100$ µM. In certain other embodiments, inventive compounds exhibit $IC_{50}$ values $\leq 50$ µM. In certain other embodiments, inventive compounds exhibit $IC_{50}$ values $\leq 40$ µM. In certain other embodiments, inventive compounds exhibit $IC_{50}$ values $\leq 30$ µM. In certain other embodiments, inventive compounds exhibit $IC_{50}$ values $\leq 20$ µM. In certain other embodiments, inventive compounds exhibit $IC_{50}$ values $\leq 10$ µM. In certain other embodiments, inventive compounds exhibit $IC_{50}$ values $\leq 7.5$ µM. In certain embodiments, inventive compounds exhibit $IC_{50}$ values $\leq 5$ µM. In certain other embodiments, inventive compounds exhibit $IC_{50}$ values $\leq 2.5$ µM. In certain embodiments, inventive compounds exhibit $IC_{50}$ values $\leq 1$ µM. In certain embodiments, inventive compounds exhibit $IC_{50}$ values $\leq 0.75$ µM. In certain embodiments, inventive compounds exhibit $IC_{50}$ values $\leq 0.5$ µM. In certain embodiments, inventive compounds exhibit $IC_{50}$ values $\leq 0.25$ µM. In certain embodiments, inventive compounds exhibit $IC_{50}$ values $\leq 0.1$ µM. In certain other embodiments, inventive compounds exhibit $IC_{50}$ values $\leq 75$ nM. In certain other embodiments, inventive compounds exhibit $IC_{50}$ values $\leq 50$ nM. In certain other embodiments, inventive compounds exhibit $IC_{50}$ values $\leq 25$ nM. In certain other embodiments, inventive compounds exhibit $IC_{50}$ values $\leq 10$ nM. In other embodiments, exemplary compounds exhibited $IC_{50}$ values $\leq 7.5$ nM. In other embodiments, exemplary compounds exhibited $IC_{50}$ values $\leq 5$ nM.

Pharmaceutical Uses and Methods of Treatment

In general, methods of using the compounds of the present invention comprise administering to a subject in need thereof a therapeutically effective amount of a compound of the present invention. As discussed above, the compounds of the invention are selective inhibitors of histone deacetylases and, as such, are useful in the treatment of disorders modulated by histone deacetylases. For example, compounds of the invention may be useful in the treatment of cancer. Accordingly, in yet another aspect, according to the methods of treatment of the present invention, tumor cells are killed, or their growth is inhibited by contacting said tumor cells with an inventive compound or composition, as described herein.

Thus, in another aspect of the invention, methods for the treatment of cancer are provided comprising administering a therapeutically effective amount of a compound of formula (I), as described herein, to a subject in need thereof. In certain embodiments, a method for the treatment of cancer is provided comprising administering a therapeutically effective amount of an inventive compound, or a pharmaceutical composition comprising an inventive compound to a subject in need thereof, in such amounts and for such time as is necessary to achieve the desired result. In certain embodiments of the present invention a "therapeutically effective amount" of the inventive compound or pharmaceutical composition is that amount effective for killing or inhibiting the growth of tumor cells. The compounds and compositions, according to the method of the present invention, may be administered using any amount and any route of administration effective for killing or inhibiting the growth of tumor cells. Thus, the expression "amount effective to kill or inhibit the growth of tumor cells", as used herein, refers to a sufficient amount of agent to kill or inhibit the growth of tumor cells. The exact amount required will vary from subject to subject, depending on the species, age, and general condition of the subject, the severity of the infection, the particular anticancer agent, its mode of administration, and the like.

In certain embodiments, the method involves the administration of a therapeutically effective amount of the compound or a pharmaceutically acceptable derivative thereof to a subject (including, but not limited to a human or animal) in need of it. In certain embodiments, the inventive compounds as useful for the treatment of cancer (including, but not limited to, glioblastoma, retinoblastoma, breast cancer, cervical cancer, colon and rectal cancer, leukemia, lymphoma, lung cancer (including, but not limited to small cell lung cancer), melanoma and/or skin cancer, multiple myeloma, non-Hodgkin's lymphoma, ovarian cancer, pancreatic cancer, prostate cancer and gastric cancer, bladder cancer, uterine cancer, kidney cancer, testicular cancer, stomach cancer, brain cancer, liver cancer, or esophageal cancer).

In certain embodiments, the inventive anticancer agents are useful in the treatment of cancers and other proliferative disorders, including, but not limited to breast cancer, cervical cancer, colon and rectal cancer, leukemia, lung cancer, melanoma, multiple myeloma, non-Hodgkin's lymphoma, ovarian cancer, pancreatic cancer, prostate cancer, and gastric cancer, to name a few. In certain embodiments, the inventive anticancer agents are active against leukemia cells and melanoma cells, and thus are useful for the treatment of leukemias (e.g., myeloid, lymphocytic, myelocytic and lymphoblastic leukemias) and malignant melanomas. In still other embodiments, the inventive anticancer agents are active against solid tumors.

In certain embodiments, the inventive compounds also find use in the prevention of restenosis of blood vessels subject to traumas such as angioplasty and stenting. For example, it is contemplated that the compounds of the invention will be useful as a coating for implanted medical devices, such as tubings, shunts, catheters, artificial implants, pins, electrical implants such as pacemakers, and especially for arterial or venous stents, including balloon-expandable stents. In certain embodiments inventive compounds may be bound to an implantable medical device, or alternatively, may be passively adsorbed to the surface of the implantable device. In certain other embodiments, the inventive compounds may be formulated to be contained within, or, adapted to release by a surgical or medical device or implant, such as, for example, stents, sutures, indwelling catheters, prosthesis, and the like. For example, drugs having antiproliferative and anti-inflammatory activities have been evaluated as stent coatings, and have shown promise in preventing retenosis (See, for example, Presbitero P. et al., "Drug eluting stents do they make the difference?", *Minerva Cardioangiol,* 2002, 50(5):431–442; Ruygrok P. N. et al., "Rapamycin in cardiovascular medicine", *Intern. Med. J.,* 2003, 33(3):103–109; and Marx S. O. et al., "Bench to bedside: the development of rapamycin and its application to stent restenosis", *Circulation,* 2001, 104(8):852–855, each of these references is incorporated herein by reference in its entirety). Accordingly, without wishing to be bound to any particular theory, Applicant proposes that inventive compounds having antiproliferative effects can be used as stent coatings and/or in stent drug delivery devices, inter alia for the prevention of restenosis or reduction of restenosis rate. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. A variety of compositions and methods related to stent coating and/or local stent drug delivery for preventing restenosis are known in the art (see, for example, U.S. Pat. Nos. 6,517,889; 6,273,913; 6,258,121; 6,251,136; 6,248,127; 6,231,600; 6,203,551; 6,153,252; 6,071,305; 5,891,507; 5,837,313 and published U.S. patent application No.: US2001/0027340, each of which is incorporated herein by reference in its entirety). For example, stents may be coated with polymer-drug conjugates by dipping the stent in polymer-drug solution or spraying the stent with such a solution. In certain embodiment, suitable materials for the implantable device include biocompatible and nontoxic materials, and may be chosen from the metals such as nickel-titanium alloys, steel, or biocompatible polymers, hydrogels, polyurethanes, polyethylenes, ethylenevinyl acetate copolymers, etc. In certain embodiments, the inventive compound is coated onto a stent for insertion into an artery or vein following balloon angioplasty.

The compounds of this invention or pharmaceutically acceptable compositions thereof may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device.

Within other aspects of the present invention, methods are provided for expanding the lumen of a body passageway, comprising inserting a stent into the passageway, the stent having a generally tubular structure, the surface of the structure being coated with (or otherwise adapted to release) an inventive compound or composition, such that the passageway is expanded. In certain embodiments, the lumen of a body passageway is expanded in order to eliminate a biliary, gastrointestinal, esophageal, tracheal/bronchial, urethral and/or vascular obstruction.

Methods for eliminating biliary, gastrointestinal, esophageal, tracheal/bronchial, urethral and/or vascular obstructions using stents are known in the art. The skilled practitioner will know how to adapt these methods in practicing the present invention. For example, guidance can be found in U.S. Patent Publication No.: 2003/0004209 in paragraphs [0146]–[0155], which paragraphs are hereby incorporated herein by reference.

Another aspect of the invention relates to a method for inhibiting the growth of multidrug resistant cells in a biological sample or a patient, which method comprises administering to the patient, or contacting said biological sample with a compound of formula I or a composition comprising said compound.

Additionally, the present invention provides pharmaceutically acceptable derivatives of the inventive compounds, and methods of treating a subject using these compounds, pharmaceutical compositions thereof, or either of these in combination with one or more additional therapeutic agents.

Another aspect of the invention relates to a method of treating or lessening the severity of a disease or condition associated with a proliferation disorder in a patient, said method comprising a step of administering to said patient, a compound of formula I or a composition comprising said compound.

It will be appreciated that the compounds and compositions, according to the method of the present invention, may be administered using any amount and any route of administration effective for the treatment of cancer and/or disorders associated with cell hyperproliferation. For example, when using the inventive compounds for the treatment of cancer, the expression "effective amount" as used herein, refers to a sufficient amount of agent to inhibit cell proliferation, or refers to a sufficient amount to reduce the effects of cancer. The exact amount required will vary from subject to subject, depending on the species, age, and general condition of the subject, the severity of the diseases, the particular anticancer agent, its mode of administration, and the like.

The compounds of the invention are preferably formulated in dosage unit form for ease of administration and uniformity of dosage. The expression "dosage unit form" as used herein refers to a physically discrete unit of therapeutic agent appropriate for the patient to be treated. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts (see, for example, Goodman and Gilman's , "The Pharmacological Basis of Therapeutics", Tenth Edition, A. Gilman, J. Hardman and L. Limbird, eds., McGraw-Hill Press, 155–173, 2001, which is incorporated herein by reference in its entirety).

Another aspect of the invention relates to a method for inhibiting histone deacetylase activity in a biological sample or a patient, which method comprises administering to the patient, or contacting said biological sample with a compound of formula I or a composition comprising said compound.

Furthermore, after formulation with an appropriate pharmaceutically acceptable carrier in a desired dosage, the pharmaceutical compositions of this invention can be administered to humans and other animals orally, rectally, parenterally, intracisternally, intravaginally, intraperitoneally, topically (as by powders, ointments, creams or drops), bucally, as an oral or nasal spray, or the like, depending on the severity of the infection being treated. In certain embodiments, the compounds of the invention may be administered at dosage levels of about 0.001 mg/kg to about 50 mg/kg, from about 0.01 mg/kg to about 25 mg/kg, or from about 0.1 mg/kg to about 10 mg/kg of subject body weight per day, one or more times a day, to obtain the desired therapeutic effect. It will also be appreciated that dosages smaller than 0.001 mg/kg or greater than 50 mg/kg (for example 50–100 mg/kg) can be administered to a subject. In certain embodiments, compounds are administered orally or parenterally.

Treatment Kit

In other embodiments, the present invention relates to a kit for conveniently and effectively carrying out the methods in accordance with the present invention. In general, the pharmaceutical pack or kit comprises one or more containers filled with one or more of the ingredients of the pharmaceutical compositions of the invention. Such kits are especially suited for the delivery of solid oral forms such as tablets or capsules. Such a kit preferably includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Alternatively, placebo dosages, or calcium dietary supplements, either in a form similar to or distinct from the dosages of the pharmaceutical compositions, can be included to provide a kit in which a dosage is taken every day. Optionally associated with such container(s) can be a notice in the form prescribed by a governmental agency regulating the manufacture, use or sale of pharmaceutical products, which notice reflects approval by the agency of manufacture, use or sale for human administration.

Equivalents

The representative examples which follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that, unless otherwise indicated, the entire contents of each of the references cited herein are incorporated herein by reference to help illustrate the state of the art. The following examples contain important additional information, exemplification and guidance which can be adapted to the practice of this invention in its various embodiments and the equivalents thereof These and other aspects of the present invention will be further appreciated upon consideration of the following Examples, which are intended to illustrate certain particular embodiments of the invention but are not intended to limit its scope, as defined by the claims.

Exemplification

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

1) General Description of Synthetic Methods:

The practitioner has a well-established literature of heterocycle (e.g., 1,3-dioxane) chemistry to draw upon, in combination with the information contained herein, for guidance on synthetic strategies, protecting groups, and other materials and methods useful for the synthesis of the compounds of this invention.

The various references cited herein provide helpful background information on preparing compounds similar to the inventive compounds described herein or relevant intermediates, as well as information on formulation, uses, and administration of such compounds which may be of interest.

Moreover, the practitioner is directed to the specific guidance and examples provided in this document relating to various exemplary compounds and intermediates thereof.

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

According to the present invention, any available techniques can be used to make or prepare the inventive compounds or compositions including them. For example, a variety of a variety combinatorial techniques, parallel synthesis and/or solid phase synthetic methods such as those discussed in detail below may be used. Alternatively or additionally, the inventive compounds may be prepared using any of a variety of solution phase synthetic methods known in the art.

It will be appreciated as described below, that a variety of inventive compounds can be synthesized according to the methods described herein. The starting materials and reagents used in preparing these compounds are either available from commercial suppliers such as Aldrich Chemical Company (Milwaukee, Wis.), Bachem (Torrance, Calif.), Sigma (St. Louis, Mo.), or are prepared by methods well known to a person of ordinary skill in the art following procedures described in such references as Fieser and Fieser 1991, "Reagents for Organic Synthesis", vols 1–17, John Wiley and Sons, New York, N.Y., 1991; Rodd 1989 "Chemistry of Carbon Compounds", vols. 1–5 and supps, Elsevier Science Publishers, 1989; "Organic Reactions", vols 1–40, John Wiley and Sons, New York, N.Y., 1991; March 2001, "Advanced Organic Chemistry", 5th ed. John Wiley and Sons, New York, N.Y.; and Larock 1990, "Comprehensive Organic Transformations: A Guide to Functional Group Preparations", $2^{nd}$ ed. VCH Publishers. These schemes are merely illustrative of some methods by which the compounds of this invention can be synthesized, and various modifications to these schemes can be made and will be suggested to a person of ordinary skill in the art having regard to this disclosure.

The starting materials, intermediates, and compounds of this invention may be isolated and purified using conventional techniques, including filtration, distillation, crystallization, chromatography, and the like. They may be characterized using conventional methods, including physical constants and spectral data.

1) Synthesis of Exemplary Compounds:

Unless otherwise indicated, starting materials are either commercially available or readily accessibly through laboratory synthesis by anyone reasonably familiar with the art.

Described generally below, are procedures and general guidance for the synthesis of compounds as described generally and in subclasses and species herein.

I. EXAMPLE 1

Synthesis of 1,3-dioxanes for Use as HDAC Inhibitors

Post-translational modification of proteins through acetylation and deacetylation of lysine residues has a critical role in regulating their cellular functions (Kouzarides, T. *EMBO J* 2000, 19, 1176). While small molecule probes for specific protein kinases and phosphatases exist, probes of histone acetyl transferases and deacetylases are limited due to their lack of selectivity. Described below is the synthesis of a library of 1,3-dioxanes and the discovery of certain selective small molecule inhibitors of histone deacetylases (HDACs). Thousands of such compounds using the one bead-one stock solution format ((a) Stemson et al. *J. Am. Chem. Soc.* 2001, 123, 1740–1747; (b) Blackwell et al. *Chem. Biol.* 2001, 8, 1167–1182 (c) Clemons et al. *Chem. Biol.* 2001, 8, 1183–1195) for synthesis have been described below.

HDACs are zinc hydrolases that modulate gene expression through deacetylation of the N-acetyl-lysine residues of histone proteins and other transcriptional regulators (Hassig et al. *Curr. Opin. Chem. Biol.* 1997, 1, 300–308). HDACs participate in cellular pathways that control cell shape and differentiation, and an HDAC inhibitor has been shown effective in treating an otherwise recalcitrant cancer (Warrell et al. *J. Natl. Cancer Inst.* 1998, 90, 1621–1625). Nine human HDACs have been characterized ((a) Taunton et al. *Science* 1996, 272, 408–411; (b) Yang et al. *J. Biol. Chem.* 1997, 272, 28001–28007. (c) Grozinger et al. *Proc. Natl. Acad. Sci. U.S.A.* 1999, 96, 4868–4873. (d) Kao et al. *Genes Dev.* 2000, 14, 55–66. (e) Hu et al. *J. Biol. Chem.* 2000, 275, 15254–15264. (f) Zhou et al. *Proc. Natl. Acad. Sci. U.S.A.* 2001, 98, 10572–10577) and two inferred (Venter et al. *Science* 2001, 291, 1304–1351); these members fall into two related classes (class I and II). No small molecules are known that selectively target either the two classes or individual members of this family (for example ortholog-selective HDAC inhibitors have been reported: (a) Meinke et al. *J. Med. Chem.* 2000, 14, 4919–4922; (b) Meinke, et al. *Curr. Med. Chem.* 2001, 8, 211–235).

The natural products trapoxin (Kijima et al. *J. Biol. Chem.* 1993, 268, 22429–22435) (TPX) and trichostatin A (Tsuji et al. *J. Antibiot.* 1976, 29, 1–6) (TSA) are potent inhibitors and useful probes of HDACs, but their lack of selectivity among family members limits their ability to dissect the functions of individual members. The absence of atomic resolution structures of human HDACs complicates a structure-based solution to this problem; therefore, we have undertaken a screening-based approach. Based on sequence alignments of HDACs and structural analyses of natural HDAC inhibitors (FIG. 1), including TPX and TSA, a synthetic pathway was conceived leading to 7200 1,3-dioxanes, all biased towards HDAC inhibition. Representative compounds that resulted from this pathway were shown to inhibit two different human HDACs; the varied structures of the dioxanes and their tendency to inhibit HDACs suggest that suitable screening methods may identify the sought after, specific inhibitors.

While not wishing to be bound by any particular theory, structural rationale for HDAC inhibition is suggested from the X-ray crystal structure of TSA-bound HDAC-like protein (HDLP), an HDAC ortholog from the thermophilic bacterium *Aquifex aeolicus* (Finnin et al. *Nature* 1999, 401, 188–193). In this structure, the hydroxamic acid of TSA penetrates a narrow, hydrophobic channel and chelates a buried zinc ion. The substructural organization of most HDAC inhibitors can be rationalized in light of the HDLP structure. Inhibitors typically possess metal-binding functionality, and a cap substructure that interacts with amino acids at the entrance of the N-acetyl lysine-binding channel. The cap and the metal-binding functionality are connected by a linker, often a 5–6 atom hydrocarbon chain (Jung et al. *J. Med. Chem.* 1999, 42, 4669–4679). Synthetic molecules incorporating these substructural elements are likely to inhibit HDAC enzymes.

Comparison of amino acid sequences around the active site was used to infer structural differences between individual HDAC family members that could be exploited in the design of selective inhibitors. Most of the amino acids that contact TSA in the HDLP structure are conserved across all HDACs. However, this conservation diverges for amino acids at the solvent-exposed rim of the channel, indicating that this is a selectivity-deternining region (FIG. 1). The most significant sequence differences are observed between class I and class II HDACs. The sequence diversity in the rim of the N-acetyl lysine-binding channel suggests that selective inhibitors may be identified from collections of compounds having varied cap groups, since these groups would be expected to interact with the rim residues. It is also of note that an Arg265Pro single nucleotide polymorphism has been recently identified in the rim region of HDAC3, (Wolfsberg et al. *Nature* 2001, 409, 824–826) providing the structural rationale for polymorph-specific design of HDAC inhibitors. By synthesizing molecules that possess diversity elements targeted towards regions predicted to be structurally divergent, discovery of selective inhibitors may be possible.

The synthetic plan (FIG. 2) generates diversity in the cap region of the small molecules by using the split-pool synthesis technique. The chain length for the hydrocarbon linker ranges from 3–6 methylene groups so that the orientation of the cap relative to the enzyme channel is varied. The 1,3-dioxane is a rigid core that can be synthesized stereoselectively and with enormous structural diversity (Sternson et al. *J. Am. Chem. Soc.* 2001, 123, 1740–1747).

To simplify structure determination of synthetic products, an adaptation of the encoding strategy reported by Still and co-workers (Ohlmeyer et al. *Proc. Natl. Acad. Sci. U.S.A.* 1993, 90, 10922–10926) was used entailing covalent [Rh (OCOCPh$_3$)$_2$]$_2$-mediated attachment of electrophoric diazoketone tags to individual, high capacity polystyrene synthesis beads. These tags can be removed oxidatively after the synthesis and analyzed by GC.

Two portions of a silane-derivatized polystyrene resin were tagged with two diazoketones, and, then, enantiomeric γδ-epoxy alcohols attached to afford modified polystyrene support (1). The resin was pooled, split, encoded for the subsequent reactions with 50 combinations of six diazoketones, and reacted with 50 nucleophile building blocks to generate 100 1,3-diols (2) in high purity. The solid-supported 1,3-diols were pooled and split into six portions that were reacted with Fmoc-amino dimethylacetal building blocks under HCl catalysis to form 600 Fmoc-amino-1,3-dioxanes (3). The resin was tagged with six combinations of three diazoketones to encode the ketalization reactions. To encode the subsequent reactions, the resin was pooled and split into four portions and reacted with four combinations of three diazoketones. After Fmoc removal, these pools were reacted with TESC1 to protect free hydroxyls incorporated from the nucleophile building blocks. The amino-1,3-dioxane resin was reacted with four diacid building blocks: pyridine-activated glutaric anhydride or PyBOP-activated monophthalimidomethylester diacids (Nefkens et al. *Recueil* 1963, 82, 941–953). Treatment with hydrazine generated 2400 carboxyamides (4). One third of these carboxyamide beads was set aside for screening experiments. The high purity of these reaction products indicates that the phthalimidomethylester is well-suited for carboxylic acid protection in solid phase organic synthesis where ester hydrolysis can be difficult due to the poor aqueous swelling properties of polystyrene resins. The remaining carboxyamides were split into two portions. One portion was reacted with diisopropylcarbodiimide (DIC) and phenylenediamine to generate 2400 o-aminoanilides (6). Reaction of the remaining portion of resin 4 with O-2-methoxypropanehydroxylamine in the presence of PyBOP generated 2400 protected hydroxamic acids (5). The 2-methoxypropane protecting group worked better for this reaction as O-TBDMS protection gave impure reaction products and O-allyl and O-THP protecting groups were not sufficiently labile to be removed under conditions compatible with every synthesized compound. Treatment of resin 5 with PPTS generated 2400 hydroxamic acids (7). The purity of the reaction products at each synthetic step was determined by LC-MS analysis of the crude material cleaved from single beads. For every reaction product analyzed (50 out of 50), GC analysis of the electrophoric tags allowed their structures to be inferred. In each instance, the mass of the structure inferred was consistent with the LC-MS data.

The 7200 polystyrene beads were arrayed and cleaved in the one bead-one stock solution format to generate 7200 stock solutions. To demonstrate the ability of the synthesized compounds to inhibit HDAC, we synthesized two compounds (8 and 9) representative of the molecules in the library, and measured IC50s against HDAC1 and HDAC6. Calculated IC50s of ~1 μM were similar to the IC50s of the substructure 10, indicating that the 1,3-dioxane portion of the molecules is not detrimental to HDAC inhibition. In contrast, a compound with a shorter hydrocarbon linker (11) than those used in the library synthesis weakly inhibited HDAC1 and HDAC6 (IC50s>50 μM).

II. Experimentals for Example I

Figure 4:
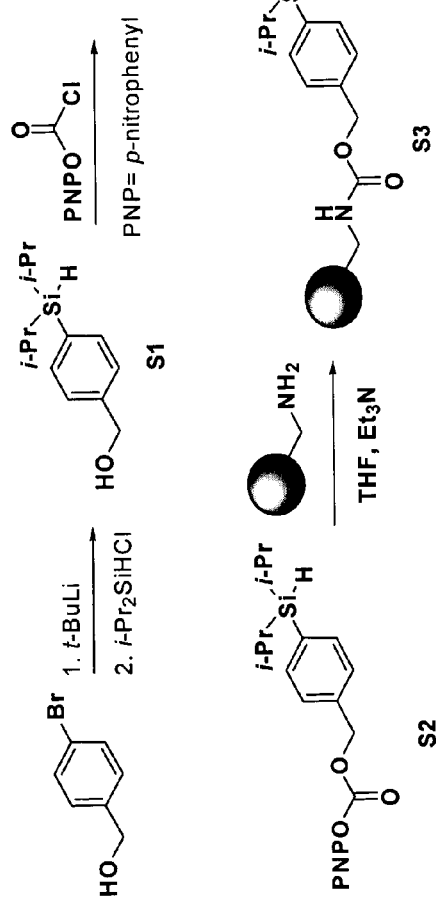
FIG. 4 depicts the synthesis of linker S3.

A) Silyl Linker Synthesis (FIG. 4)

4-(Diisopropylsilanyl)-phenyl methanol (S1). To a stirred suspension of sodium hydride (2.60 g, 108 mmol) in THF (430 mL) was added a THF (50 mL) solution of 4-bromobenzyl alcohol (18.2 g, 97.3 mmol). The mixture was heated to 45° C. for 3 h and, then, cooled to −65° C. A 1.80 M solution of tert-butyllithium (114 mL) was added to the reaction. After 30 minutes, chlorodiisopropylsilane (17.6 mL, 102 mmol) was added, and the reaction was warmed to room temperature, stirred overnight, and quenched with saturated $(NH_4)_2SO_4$ (15 mL). The resulting mixture was filtered through celite and $Na_2SO_4$, concentrated in vacuo, and then dissolved in hexanes (400 mL). This solution was washed with water (400 mL), brine (250 mL), then dried over $Na_2SO_4$, filtered, and concentrated in vacuo to obtain a yellow oil (23 g). Flash column chromatography (silica gel, 20% ethyl acetate/hexanes) provided S1 (17.5 g, 81%) as a colorless oil. $^1H$ NMR (400 MHz, $CDCl_3$): δ 7.52 (d, 2H, J=1.8 Hz), 7.51 (d, 2H, J=1.8 Hz), 4.70 (d, 2H, J=6.1 Hz), 3.94 (t, 1H, J=3.1 Hz), 1.64 (t, 1H, J=6.1 Hz), 1.23 (m, 2H), 1.06 (d, 6H, J=7.3 Hz), 0.98 (d, 6H, J=7.3 Hz). CI/MS ($NH_3$): 240 ($M+NH_4^+$).

Carbonic acid 4-(diisopropyl-silanyl)-benzyl ester 4-nitrophenyl ester (S2). To a solution of silane S2 (0.60 g, 2.7 mmol) in $CH_2Cl_2$ (10 mL) was added 2,6-lutidine (0.040 mL, 3.5 mmol) followed by 4-nitrophenyl chloroformate (0.60 g, 3 mmol). After 45 minutes, the reaction was concentrated in vacuo. Flash column chromatography (silica gel, 20% ether/hexanes) furnished carbonate (S2) (1.05 g, 100%) as a pale yellow oil that solidified on standing. $^1H$ NMR (400 MHz, $CDCl_3$): δ 8.28 (d, 2H, J=9.5 Hz), 7.56 (d, 2H, J=8.1 Hz), 7.42 (d, 2H, J=8.1 Hz), 7.40 (d, 2H, J=9.5 Hz), 5.30 (s, 1H), 3.96 (t, 1H, J=3.1 Hz), 1.23 (m, 2H), 1.07 (d, 6H, J=7.3 Hz), 0.99 (d, 6H, J=7.3 Hz). FAB/MS: 410 ($M+Na^+$).

Diisopropylphenylsilane resin (S3). PS AM $NH_2$ resin (1.5 g, 1.41 mmol, 1.0 equiv.) was placed in a 20 mL fritted polypropylene tube. A solution of carbonate, S2, (1.7 g, 4.4 mmol, 3.1 equiv.) in THF (12 mL) with $Et_3N$ (0.558 mL, 4.0 mmol, 4.0 equiv.) was added. The reaction was allowed to proceed for 48 h with rotary mixing. The yellow resin was filtered and washed extensively with $H_2O$ and THF until the resin was white to yield diisopropylphenylsilane resin (S3).

Figure 6:
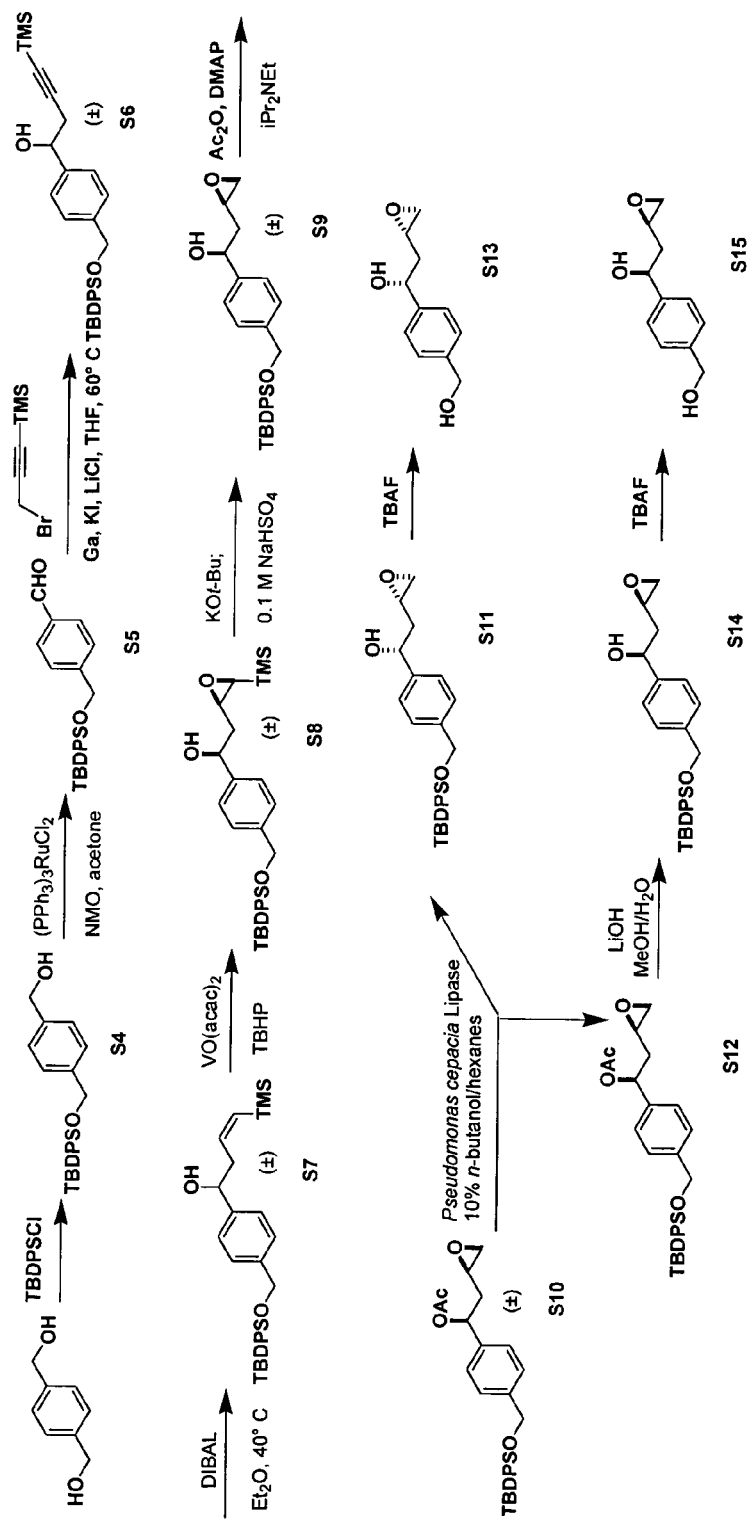
FIG. 6 depicts the synthesis of epoxyol S15.

B) γ,δ-Epoxy Alcohol Synthesis (FIG. 6)

4-(tert-Butyldiphenylsilanoxymethyl)phenyl methanol (S4). To 1,4-benzenedimethanol (25 g, 180 mmol) in DMF (450 mL) with imidazole (9.2 g, 140 mmol) was added tert-butyldiphenylsilyl chloride (12 mL, 45 mmol). After 24 h the solvent was removed in vacuo and the residue was diluted with water (300 mL). The mixture was extracted with $CH_2Cl_2$ (2×150 mL), and the organic layers were dried over $Na_2SO_4$. Flash column chromatography (silica gel, 30% ethyl acetate/hexanes) provided alcohol S4 (14.8 g, 87%) as a colorless oil. $^1H$ NMR (400 MHz, $CDCl_3$): δ (dd, 4H, J=8.0 Hz, 1.5 Hz), 7.35 (m, 10H), 4.77 (s, 2H), 4.70 (s, 2H), 1.10 (s, 9H).

4-(tert-Butyldiphenylsilanoxymethyl)benzaldehyde (S5). To a solution of alcohol S4 (14.5 g, 39.4 mmol) in acetone (200 mL) with N-methylmorpholine oxide (6.9 g, 59 mmol) was added, portionwise, $RuCl_2(PPh_3)_3$ (0.76 g, 0.79 mmol). After 25 min, the solvent was removed in vacuo. Flash column chromatography (silica gel, 30% ether/hexanes) furnished a white, waxy solid (10.9 g, 74%). $^1H$ NMR (400 MHz, $CDCl_3$): δ 10.01 (s, 1H), 7.85 (d, 2H, J=8.3 Hz), 7.68 (d, 4H, J=6.3 Hz), 7.51 (d, 2H, J=8.3 Hz), 7.38 (m, 6H), 4.84 (s, 2H), 1.11 (s, 9H).

(±)-1-[4-(tert-Butyldiphenylsilanoxymethyl)phenyl]-4-(trimethylsilanyl)-but3-yn-1-ol (S6). A flame dried, three-necked flask was charged with aldehyde S5 (9.0 g, 24 mmol) in THF (150 mL), LiCl (1.2 g, 29 mmol), KI (8.0 g, 48 mmol), gallium pellets (2.5 g, 36 mmol), and 3-(trimethylsilyl)propargyl bromide (6.8 mL, 48 mmol). After refluxing for 14 h, the reaction was diluted with ether (300 mL). The resulting mixture was extracted with water (2×100 mL), and the aqueous extracts were back extracted with ether (4×50 mL). The organic extracts were dried over $MgSO_4$ and purified by flash column chromatography (silica gel, 20% ether/hexanes) to generate alkyne S6 as a yellow oil (7.9 g, 68%; 86% based on recovered starting material). $^1H$ NMR (500 MHz, $CDCl_3$): δ 7.69 (d, 4H, J=7.8 Hz), 7.40 (m, 10H), 4.86 (m, 1H), 4.76 (s, 2H), 2.66 (d, 1H, J=7.1 Hz), 2.41 (d, 1H, J=3.3 Hz), 1.09 (s, 9H), 0.16 (s, 9H).

(±)-1-[4-(tert-Butyldiphenylsilanoxymethyl)phenyl)]-4-(trimethylsilanyl)-but3-en-1-ol (S7). A flame dried, three-necked flask charged with alkyne S6 (16.8 g, 34.5 mmol) in ether (20 mL) was cooled to 0° C. DIBAL (12.5 mL, 70 mmol) was added dropwise over 30 minutes with the reaction temperature kept below 20° C. The solution was heated to 38° C. After 3 h, the reaction was cooled to 0° C.

and MeOH (1 mL) was added dropwise followed by Na$_2$SO$_4$.10H$_2$O (50 g, CAUTION-EXOTHERM) and celite (20 g). The reaction was filtered, and the solvent was removed in vacuo. Flash column chromatography (silica gel, 20% ether/hexanes) provided olefin S7 (10.9 g, 65%) as a colorless oil. $^1$H NMR (400 MHz, CDCl$_3$): δ 7.70 (dd, 4H, J=8.1 Hz, 1.5 Hz), 7.40 (m, 10H), 4.86 (m, 1H), 4.76 (s, 2H), 2.66 (d, 1H, J=7.1 Hz), 2.41 (d, 1H, J=3.3 Hz), 1.09 (s, 9H), 0.16 (s, 9H). FAB/MS: 511 (M+Na$^+$).

(±)-1-[4-(tert-Butyldiphenylsilanoxymethyl)phenyl]-2-[3-(trimethylsilanyl)oxiranyl]-ethanol (S8). To a solution of azeotropically dried (2×20 mL toluene) alcohol S7 (15.5 g, 31.7 mmol) in CH$_2$Cl$_2$ (250 mL) at 0° C. was added vanadyl acetylacetonate (0.27 g, 1.0 mmol) and tert-butyl hydroperoxide (9.3 mL of a 5.4 M solution in dichloroethane, 50 mmol). After 24 h, Me$_2$S (5 mL) was added to quench the reaction. The mixture was concentrated and immediately purified by flash column chromatography (silica gel, 25% to 50% ether/hexanes gradient). Epoxide S8 was obtained as a colorless oil (8.0 g, 50%). $^1$H NMR (500 MHz, CDCl$_3$): δ 7.69 (m, 2H), 7.44–7.33 (m, 12H), 4.98 (ddd, 1H, J=8.9 Hz, 4.9 Hz, 2.5 Hz), 4.77 (s, 2H), 3.26 (ddd, 1H, J=8.9 Hz, 5.2 Hz, 3.5 Hz), 2.60 (d, 1H, J=2.5 Hz), 2.24 (d, 1H, J=5.2 Hz), 2.11 (ddd, 1H, J=14.4 Hz, 4.5 Hz, 3.5 Hz), 1.78 (ddd, 1H, J=14.4 Hz, 8.9 Hz, 8.9 Hz), 1.09 (s, 9H), 0.15 (s, 9H). CI/MS (NH$_3$): 522 (M+NH$_4^+$).

(±)-1-[4-(tert-Butyldiphenysilanoxymethyl)phenyl]-2-oxiranyl-ethanol (S9). To a solution of epoxide S8 (0.53 g, 1.1 mmol) in THF (10.5 mL) at 0° C. was added potassium tert-butoxide (1.3 mL of a 1.0 M solution in THF, 1.3 mmol). After 18 minutes, 0.1 M NaHSO$_4$ (27 mL) was added, and the reaction was warmed to room temperature. After 4 h, the reaction was quenched with NaHCO$_3$ (0.6 g), concentrated in vacuo, and then extracted with ether (4×40 mL). The combined organic layers were dried over Na$_2$SO$_4$, filtered, and concentrated in vacuo to obtain an orange oil (0.42 g). This was purified by flash column chromatography (silica gel, 35% ethyl acetate/hexanes) to obtain epoxide S9 as a pale yellow oil (0.30 g, 67%). $^1$H NMR (500 MHz, CDCl$_3$): δ 7.69 (d, 2H, J=6.8 Hz), 7.44–7.33 (m, 12H), 4.85 (t, 1H, J=6.1 Hz), 4.77 (s, 2H), 3.03 (m, 1H), 2.77 (dd, 1H, J=4.9 Hz, 4.9 Hz), 2.52 (dd, 1H, J=4.9 Hz, 3.0 Hz), 2.33 (s, 1H), 2.07 (ddd, 1H, J=14.5 Hz, 5.0 Hz, 5.0 Hz), 1.90 (ddd, 1H, J=14.5 Hz, 7.5 Hz, 7.5 Hz), 1.09 (s, 9H). CI/MS (NH$_3$): 450 (M+NH$_4^+$).

(±)-Acetic acid 1-[4-(tert-butyldiphenylsilanoxymethyl)phenyl]-2-oxiranyl-ethyl ester (S10). To a solution of alcohol S9 (779 mg, 1.80 mmol) in CH$_2$Cl$_2$ (18 mL) at 0° C. was added acetic anhydride (0.28 mL, 3.0 mmol) and N,N-diisopropylethylamine (0.52 mL, 3.0 mmol) in CH$_2$Cl$_2$ (4.4 mL), followed by 4-(dimethylamino)pyridine (0.044 g, 0.36 mmol). After 15 minutes, the solution was warmed to room temperature. The reaction was diluted with CH$_2$Cl$_2$ (25 mL) and washed with water (25 mL), 1 N citric acid (25 mL), and brine (25 mL). The combined aqueous layers were extracted with CH$_2$Cl$_2$ (3×25 mL) and then the combined organic layers were washed with brine (20 mL), dried over Na$_2$SO$_4$, filtered, and concentrated in vacuo. The crude oil was purified by flash column chromatography (silica gel, 20% ethyl acetate/hexanes) to obtain ester S10 as a colorless oil (774 mg, 1.63 mmol, 91%). $^1$H NMR (400 MHz, CDCl$_3$): δ 7.69 (m, 2H), 7.44–7.34 (m, 12H), 5.96 (t, 1H, J=7.0 Hz), 4.76 (s, 2H), 2.88 (m, 1H), 2.70 (dd, 1H, J=4.8 Hz, 4.8 Hz), 2.41 (dd, 1H, J=4.8 Hz, 2.2 Hz), 2.14 (ddd, 1H, J=14.0 Hz, 7.0 Hz, 7.0 Hz), 2.10 (s, 3H), 2.01 (ddd, 1H, J=14.0 Hz, 7.0 Hz, 5.0 Hz), 1.09 (s, 9H). FAB/MS: 497 (M+Na$^+$).

Enzymatic kinetic resolution of S10. To a stirred solution of *Pseudomonas cepacia* Lipase (0.88 g, Altus Biologics Catalyst #20 ChiroCLEC™-PC) in 10% n-butanol/hexanes (88 mL) was added a solution of ester S10 (0.76 g, 1.60 mmol) in acetone (4.5 mL). The kinetic resolution was followed by chiral HPLC (10% ethanol/hexanes, 1 mL/min. R,R-whelk-01 column). After 25 h, additional catalyst was added (0.13 g). After 35 h, the reaction was filtered through a silica gel plug (200 g) with 65% ether/hexanes. The filtrate was concentrated in vacuo and purified by flash column chromatography (65% ether/hexanes) to afford (1S)-acetic acid 1-[4-(tert-butyldiphenylsilanyloxymethyl)phenyl]-2-oxiranyl-ethyl ester (S12) (0.39 g, 102% yield, 94% ee) and (1R)-1-[4-(tert-butyldiphenylsilanyloxymethyl)phenyl]2-oxiranyl-ethanol (0.31 g, 90% yield, 100% ee) (S11). Mosher ester analysis for the determination of absolute configuration is presented below. Enantiomeric excess was determined by chiral HPLC (Table S1).

TABLE S1

Distribution over time of enantiomeric starting materials ((S)-ROAc) and (R)-ROAc) and single product ((S)-ROH) reported as percent total integrated peak area.

| Time | (S)-ROAc (R$_t$ = 7.72 min.) | (S)-ROH (R$_t$ = 8.29 min.) | (R)-ROAc (R$_t$ = 12.10 min.) |
| --- | --- | --- | --- |
| 20 h | 50% | 45% | 5% |
| 26 h | 50% | 47% | 3% |
| 35 h | 50% | 49% | 1% |

(1S)-1-[4-(tert-Butyldiphenylsilanyloxymethyl)phenyl]-2-oxiranyl-ethanol (S14). To a vigorously stirred methanol (21 mL) solution of ester (S12) (0.36 g, 0.76 mmol) was added LiOH.H$_2$O (0.072 g, 1.70 mmol) in water (7 mL). After 1 h, the reaction was diluted with ether (50 mL) and washed with brine (50 mL). The aqueous layer was extracted with ether (3×50 mL) and the combined organics were washed with brine (50 mL), dried over sodium sulfate, filtered, and concentrated in vacuo. The residue was purified by flash column chromatography (silica gel, 65% ether/hexanes) to obtain alcohol S14 as a colorless oil (0.31 g, 93%). $^1$H NMR (500 MHz, CDCl$_3$): δ 7.69 (d, 2H, J=6.8 Hz), 7.44–7.33 (m, 12H), 4.85 (t, 1H, J=6.1 Hz), 4.77 (s, 2H), 3.03 (m, 1H), 2.77 (dd, 1H, J=4.9 Hz, 4.9 Hz), 2.52 (dd, 1H, J=4.9 Hz, 3.0 Hz), 2.33 (s, 1H), 2.07 (ddd, 1H, J=14.5 Hz, 5.0 Hz, 5.0 Hz), 1.90 (ddd, 1H, J=14.5 Hz, 7.5 Hz, 7.5 Hz), 1.09 (s, 9H). CI/MS (NH$_3$): 450 (M+NH$_4^+$).

(1S)-1-(4-Hydroxymethylphenyl)-2-oxiranyl-ethanol (S15). To a solution of silyl alcohol (S14) (0.32 g, 0.74 mmol) in THF (1.14 mL) was added tetrabutylammonium fluoride hydrate (0.29 g, 1.10 mmol). After 2 h, another portion of tetrabutylammonium fluoride hydrate (0.048 mg, 0.18 mmol) was added. After 3 h, the reaction was concentrated with an N$_2$ stream and purified by flash column chromatography (silica gel, 3% isopropyl alcohol/ethyl acetate) to obtain alcohol S15 as a colorless oil (0.11 g, 77%). $^1$H NMR (400 MHz, CDCl$_3$): δ 7.40–7.35 (m, 4H), 4.98 (t, 1H, J=Hz), 4.69 (d, 2H, J=3.7 Hz), 3.02 (m, 1H), 2.76 (dd, 1H, J=4.8 Hz, 4.0 Hz), 2.51 (dd, 1H, J=4.8 Hz, 2.6 Hz), 2.44 (d, 1H, J=2.2 Hz, OH), 2.06 (ddd, 1H, J=14.0 Hz, 4.8 Hz, 4.0 Hz), 1.86 (ddd, 1H, J=14.0 Hz, 8.0 Hz, 8.0 Hz), 1.70 (broad s, 1H). CI-HRMS (NH$_3$) m/z calcd for C$_{11}$H$_{18}$NO$_3$ 212.1287, found 212.1285.

(1R)-1-(4-Hydroxymethylphenyl)-2-oxiranyl-ethanol (S13). $^1$H NMR (400 MHz, CDCl$_3$): δ 7.40–7.35 (m, 4H), 4.98 (t, 1H, J=Hz), 4.69 (d, 2H, J=3.7 Hz), 3.02 (m, 1H), 2.76 (dd, 1H, J=4.8 Hz, 4.0 Hz), 2.51 (dd, 1H, J=4.8 Hz, 2.6 Hz), 2.44 (d, 1H, J=2.2 Hz, OH), 2.06 (ddd, 1H, J=14.0 Hz, 4.8 Hz, 4.0 Hz), 1.86 (ddd, 1H, J=14.0 Hz, 8.0 Hz, 8.0 Hz), 1.70 (broad s, 1H). CI-HRMS (NH$_3$) m/z calcd for C$_{11}$H$_{18}$NO$_3$ 212.1287, found 212.1285.

Figure 5:
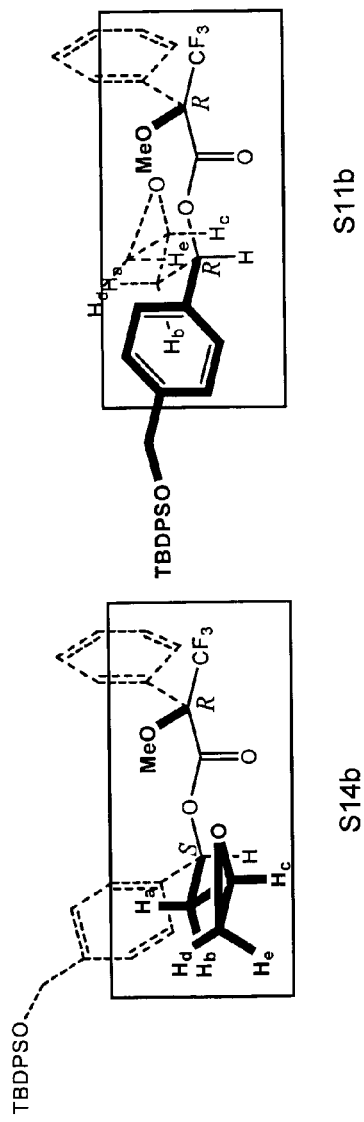
FIG. 5 depicts Mosher ester derivitization.

Mosher Ester Derivatization for Determination of Absolute Configuration (FIG. 5)

(R)-(+)-MTPA Ester of (1R)-1-[4-(tert-Butyl-diphenyl-silanyloxymethyl)phenyl]-2-oxiranyl-ethanol (S11b). To a stirred CH$_2$Cl$_2$ (0.1 mL) solution of (R)-(+)-α-methoxy-α-(trifluoromethyl)phenylacetic acid (3.3 mg, 0.014 mmol), 1-{3-(dimethylamino)propyl]-3-ethylcarbodiimide hydrochloride (2.6 mg, 0.014 mmol), and (dimethylamino)pyridine (0.5 mg, 0.004 mmol), was added a CH$_2$Cl$_2$ (0.15 mL) solution of alcohol (S11) (5.0 mg, 0.012 mmol). After 6 h, the reaction was concentrated under an N$_2$ stream and immediately purified by flash column chromatography (silica gel, 20% ethyl acetate/hexanes) to obtain Mosher ester S11b as a colorless oil (2.8 mg, 0.0043 mmol, 31%). $^1$H NMR (400 MHz, CDCl$_3$): δ 7.68 (m, 2H), 7.44–7.31 (m, 19H), 6.13 (dd, 1H, J=6.8 Hz, 6.8 Hz), 4.77 (s, 2H), 3.46 (s, 3H), 2.74 (m, 1H, H$_c$), 2.65 (dd, 1H, J=4.4 Hz, 4.4 Hz, H$_d$), 2.38 (dd, 1H, J=4.4 Hz, 2.4 Hz, H$_e$), 2.26 (ddd, 1H, J=13.6 Hz, 6.8 Hz, 6.8 Hz, H$_a$), 1.98 (ddd, 1H, J=13.6 Hz, 6.8 Hz, 5.4 Hz, H$_b$), 1.10 (s, 9H). FAB/MS: 671 (M+Na$^+$).

(R)-(+)-MTPA Ester of (1S)-1-[4-(tert-Butyl-diphenyl-silanyloxymethyl)-phenyl]-2-oxiranyl-ethanol (S14b). $^1$H NMR (400 MHz, CDCl$_3$): δ 7.69 (m, 2H), 7.45–7.20 (m, 19H), 6.08 (dd, 1H, J=6.8 Hz, 6.8 Hz), 4.76 (s, 2H), 3.56 (s, 3H), 2.84 (m, 1H, H$_c$), 2.71 (dd, 1H, J=4.4 Hz, 4.4 Hz, H$_d$), 2.44 (dd, 1H, J=4.4 Hz, 2.4 Hz, H$_e$), 2.22 (ddd, 1H, J=13.6 Hz, 6.8 Hz, 6.8 Hz, H$_a$), 2.09 (ddd, 1H, J=13.6 Hz, 6.8 Hz, 4.4 Hz, H$_b$), 1.10 (s, 9H). FAB/MS: 671 (M+Na$^+$).

TABLE S2

Chemical Shift Differences Between Diastereomers S11b and S14b.

| Proton | H$_a$ | H$_b$ | H$_c$ | H$_d$ | H$_e$ |
|---|---|---|---|---|---|
| δS-δR (ppm) | +0.11 | −0.04 | +0.10 | +0.19 | +0.06 |

Table S2 summarizes the observed differences in proton chemical shifts (Δδ) between the (R)-(+)-MPTA esters of the two enantiomers, S14 and S11. H$_a$–H$_e$ in S11b are predicted to be upfield of H$_a$–H$_e$ in S14b due to the diamagnetic current of the MPTA phenyl ring. The observed Δδ values agree with the predicted Δδ values except in the case of H$_b$. Although it is difficult to predict the exact orientation of H$_b$ relative to the shielding cones of the other phenyl rings in S11b and S14b, the discrepancy between the observed and predicted Δδ's for H$_b$ is most likely due to the secondary effect of these rings.

Figure 7:
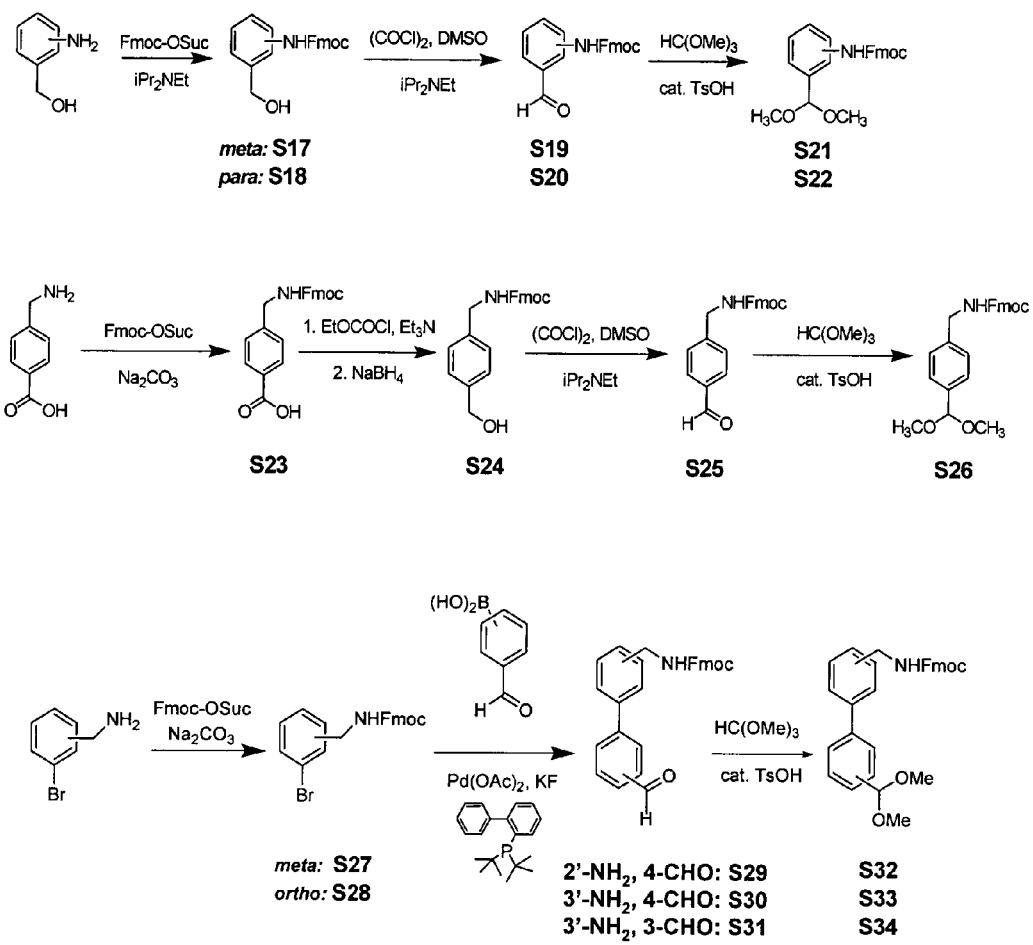
FIG. 7 depicts the synthesis of exemplary reagents S32, S33 and S34.

Fmoc-amino Dimethyl Acetal Synthesis (FIG. 7)

(3-Hydroxymethylphenyl)carbamic acid 9H-fluoren-9-ylmethyl ester (S17). To a solution of 3-aminobenzyl alcohol (10 g, 81 mmol) in CH$_2$Cl$_2$ (800 mL) and pyridine (8 mL, 100 mmol) was added 9-fluorenylmethyloxycarbonyl-N-hydroxysuccinimide (30 g, 90 mmol) and this heated to 30° C. After 24 h, precipitate had formed. The reaction was filtered and the precipitate was washed with cold CH$_2$Cl$_2$ to give alcohol S17 (21.4 g, 76%) as a beige solid. $^1$H NMR (500 MHz, CDCl$_3$): δ 7.78 (d, 2H, J=7.8 Hz), 7.61 (d, 2H, J=7.3 Hz), 7.42 (t, 2H, J=7.3 Hz), 7.38 (s, 1H), 7.33 (t, 2H, J=7.3 Hz), 7.31 (m, 2H), 7.05 (m, 1H), 6.75 (br s, 1H), 4.64 (s, 2H), 4.54 (d, 2H, J=6.4 Hz), 4.27 (t, 1H, J=6.4 Hz). ESI-HRMS m/z calcd for C$_{22}$H$_{20}$NO$_3$ 346.1443, found 346.1427.

(4-Hydroxymethyl-phenyl)-carbamic acid 9H-fluoren-9-ylmethyl ester (S18). To a solution of 4-aminobenzyl alcohol (12.3 g, 100 mmol) in THF (195 mL) and N,N-diisopropylethylamine (17.5 mL, 100 mmol) was added 9-fluorenylmethyloxycarbonyl-N-hydroxysuccinimide (33.8 g, 100 mmol). After 16 h, the reaction was diluted with CH$_2$Cl$_2$ and poured into 1 N hydrogen chloride. The aqueous layer was extracted with CH$_2$Cl$_2$. The combined organics were dried over magnesium sulfate, filtered, and concentrated to give a yellow solid. This solid was washed with CH$_2$Cl$_2$ to give alcohol S18 as a pale yellow solid (23 g, 66%). $^1$H NMR (400 MHz, d$_6$-DMSO): δ 9.66 (broad s, 1H), 7.90 (d, 2H, J=7.6 Hz), 7.74 (d, 2H, J=7.3 Hz), 7.42 (dd, 2H, J=7.6 Hz, 7.6 Hz), 7.35 (d, 2H, J=7.7 Hz), 7.34 (dd, 2H, J=7.3 Hz, 7.3 Hz), 7.19 (d, 2H, J=7.7 Hz), 5.07 (t, 1H, J=4.4 Hz), 4.46 (d, 2H, J=6.4 Hz), 4.40 (d, 2H, J=4.4 Hz), 4.29 (t, 1H, J=6.4 Hz). ESI/MS: 368 (M+Na$^+$).

(3-Formylphenyl)carbamic acid 9H-fluoren-9-ylmethyl ester (S19). To a stirred, −78° C. CH$_2$Cl$_2$ (200 mL) solution of oxalyl chloride (7.8 mL, 89 mmol) was added DMSO (12.7 mL, 178 mmol) in CH$_2$Cl$_2$ (40 mL). After 10 minutes, alcohol S17 (23.7 g, 68.7 mmol) in CH$_2$Cl$_2$ (65 mL) and DMSO (20 mL) was added over 15 minutes. After 20 minutes, N,N-diisopropylethylamine (60.0 mL, 344 mL) in CH$_2$Cl$_2$ (20 mL) was added over 10 minutes and stirred an additional 5 min. The solution was warmed to 0° C. and quenched with water (150 mL). The layers were separated and the aqueous layer was extracted with CH$_2$Cl$_2$ (200 mL). The combined organics were washed with brine (150 mL), dried over MgSO$_4$, filtered, and concentrated in vacuo to obtain a yellow solid. The crude solid was recrystallized (ethyl acetate and hexanes) to obtain a pale yellow solid (11.93 g). The mother liquor was concentrated in vacuo and then purified by flash column chromatography (silica gel, 30% ethyl acetate/hexanes) to obtain a pale yellow solid (6.21 g). Total yield: 18.1 g (77%). $^1$H NMR (500 MHz, d$_6$-DMSO): δ 10.1 (broad s, 1H), 9.94 (s, 1H), 8.06 (m, 1H), 7.89 (d, 2H, J=7.3 Hz), 7.75 (d, 2H, J=7.3 Hz), 7.74 (m, 1H), 7.52 (m, 2H), 7.41 (dd, 2H, J=7.3 Hz, 7.3 Hz), 7.34 (dd, 2H, J=7.3 Hz), 4.52 (d, 2H, J=6.4 Hz), 4.32 (t, 1H, J=6.4 Hz). APCI/MS: 344 (M+H$^+$)

(4-Formyl-phenyl)-carbamic acid 9H-fluoren-9-ylmethyl ester (S20). $^1$H NMR (500 MHz, d$_6$-DMSO): δ 10.20 (broad s, 1H), 9.84 (s, 1H), 7.91 (d, 2H, J=7.8 Hz), 7.81 (d, 2H, J=7.6 Hz), 7.75 (d, 2H, J=7.3 Hz), 7.64 (d, 2H, J=7.6 Hz), 7.42 (dd, 2H, J=7.3 Hz), 7.35 (dd, 2H, J=7.3 Hz), 4.55 (d, 2H, J=6.4 Hz), 4.32 (t, 1H, J=6.4 Hz). APCI/MS: 344 (M+H$^+$).

(3-Dimethoxymethylphenyl)carbamic acid 9H-fluoren-9-ylmethyl ester (S21). To a vigorously stirred mixture of methanol (250 mL) containing aldehyde S19 (18 g, 53 mmol) and p-toluenesulfonic acid monohydrate (2.5 g, 13 mmol) was added trimethyl orthoformate (39 mL, 360 mmol). After 1.5 h of moderate heating (flask equipped with short path to drive reaction forward), the reaction was quenched with a 1:1 mixture of saturated sodium bicarbonate and water (150 mL) and diluted with CH$_2$Cl$_2$ (200 mL). The aqueous layer was extracted with CH$_2$Cl$_2$ and the combined organic layers were washed with brine, dried over Na$_2$SO$_4$, and concentrated in vacuo to give dimethyl acetal S21 (20 g, 100%) as a pale yellow solid which was used without further purification. $^1$H NMR (500 MHz, d$_6$-DMSO): δ 9.77 (s, 1H), 7.90 (d, 2H, J=7.3 Hz), 7.74 (d, 2H, J=7.3 Hz), 7.55 (br s, 1H), 7.42 (dd, 2H, J=7.3 Hz, 7.3

Hz), 7.41 (m, 1H) 7.34 (dd, 2H, J=7.3 Hz, 7.3 Hz), 7.26 (dd, 1H, J=7.8 Hz, 7.8 Hz), 6.99 (d, 1H, J=7.3), 5.32 (s, 1H), 4.44 (d, 2H, J=6.8 Hz), 4.30 (t, 1H, J=6.8 Hz), 3.21 (s, 6H). APCI/MS: 412 (M+Na+).

(4-Dimethoxymethyl-phenyl)-carbamic acid 9H-fluoren-9-ylmethyl ester (S22). $^1$H NMR (400 MHz, d$_6$-DMSO): δ 9.75 (broad s, 1H), 7.90 (d, 2H, J=7.3 Hz), 7.74 (d, 2H, J=7.3 Hz), 7.42 (m, 4H), 7.34 (dd, 2H, J=7.3 Hz, 7.3 Hz), 7.25 (d, 2H, J=8.4 Hz), 5.30 (s, 1H), 4.47 (d, 2H, J=6.6 Hz), 4.30 (t, 1H, J=6.6 Hz), 3.20 (s, 6H). ESI/MS: 412 (M+Na+).

4-[(9H-Fluoren-9-ylmethoxycarbonylamino)-methyl]-benzoic acid (S23). To 4-aminomethyl-benzoic acid (10.6 g, 70.1 mmol) in dioxane (130 mL) was added 9% aqueous Na$_2$CO$_3$ (150 mL) followed by 9-fluorenylmethyloxycarbonyl-N-hydroxysuccinimide (26 g, 77 mmol). The solution was heated to 40° C. for 12 h and then cooled to room temperature. The reaction was acidified with 1 M HCl (500 mL), and extracted with ether (300 mL) to obtain acid S23 as a fluffy white solid (25.9 g, 69.4 mmol, 99%). $^1$H NMR (500 MHz, d$_6$-DMSO): δ 12.85 (broad s, 1H), 7.90 (m, 4H), 7.70 (m, 2H), 7.39 (m, 2H), 7.31 (m, 4H), 4.37 (d, 2H, J=6.8 Hz), 4.24 (d, 2H, J=5.8 Hz), 4.23 (t, 1H, J=6.8 Hz). APCI/MS: 372 (M+H+).

(4-Hydroxymethylbenzyl)-carbamic acid 9H-fluoren-9-ylmethyl ester (S24). To a solution of acid (S27) (23.3 g, 62.4 mmol) and triethylamine (8.7 mL, 62 mmol) in THF (150 mL) at −7° C. was added ethyl chloroformate (6.0 mL, 62 mmol) over 30 minutes. After an additional 30 minutes, the mixture was filtered through celite and the filter pad was rinsed with THF. NaBH$_4$ (9.0 g, 240 mmol) was added to the filtrate, followed by dropwise addition of methanol (38 mL) over 1 h at 10° C. After 1.5 h, the reaction was quenched with 3 M HCl and diluted with water and CH$_2$Cl$_2$. After 1 h of vigorous stirring, the layers were separated and the aqueous layer extracted with CH$_2$Cl$_2$ (2×150 mL). The combined organic layers were washed with brine, dried over MgSO$_4$, filtered, and concentrated in vacuo to give alcohol (S24) (15.7 g, 70%) which was used without further purification. $^1$H NMR (500 MHz, d$_6$-DMSO): δ 7.88 (d, 2H, J=7.3 Hz), 7.82 (t, 1H, J=6.3 Hz, NH), 7.69 (d, 2H, J=7.3 Hz), 7.41 (dd, 2H, J=7.3 Hz, 7.3 Hz), 7.31 (dd, 2H, J=7.3 Hz), 7.23 (d, 2H, J=8.1 Hz), 7.15 (d, 2H, J=8.1 Hz), 5.13 (broad s, 1H), 4.45 (s, 2H), 4.33 (d, 2H, J=6.5 Hz), 4.22 (t, J=6.5 Hz), 4.15 (d, 2H, J=6.3 Hz). APCI/MS: 360 (M+H+).

(4-Formylbenzyl)-carbamic acid 9H-fluoren-9-ylmethyl ester (S25). $^1$H NMR (500 MHz, d$_6$-DMSO): δ 10.02 (s, 1H), 7.88 (d, 2H, J=7.6 Hz), 7.87 (d, 2H, J=7.6 Hz), 7.70 (d, 2H, J=7.8), 7.51 (d, 2H, J=7.8), 7.42 (dd, 2H, J=7.6 Hz, 7.6 Hz), 7.33 (dd, 2H, J=7.6 Hz, 7.6 Hz), 7.13 (m, 1H, NH), 4.45 (d, 2H, J=6.4 Hz), 4.42 (d, 2H, J=6.8 Hz), 4.25 (t, 1H, J=6.8 Hz). ESI/MS: 380 (M+Na+).

(4-Dimethoxymethylbenzyl)-carbamic acid 9H-fluoren-9-ylmethyl ester (S26). $^1$H NMR (500 MHz, d$_6$-DMSO): δ 7.88 (d, 2H, J=7.3 Hz), 7.85 (t, 1H, J=5.9 Hz), 7.68 (d, 2H, J=7.3 Hz), 7.41 (dd, 2H, J=7.3 Hz, 7.3 Hz), 7.31 (m, 4H), 7.20 (d, 2H, J=7.8 Hz), 4.33 (d, 2H, J=6.8 Hz), 4.20 (t, 1H, J=6.8 Hz), 4.17 (d, 2H, J=5.9 Hz), 3.21 (s, 6H). APCI/MS: 426 (M+Na+).

(3-Bromobenzyl)-carbamic acid 9H-fluoren-9-ylmethyl ester (S27). To 3-bromobenzylamine hydrochloride (16.0 g, 71.9 mmol) was added aqueous 9% Na$_2$CO$_3$ (211 mL) followed by 9-fluorenylmethyloxycarbonyl-N-hydroxysuccinimide (25.5 g, 75.5 mmol) in dioxane (211 mL). This was stirred 30 minutes, then diluted with CH$_2$Cl$_2$ (200 mL). The layers were separated and the aqueous layer was extracted with CH$_2$Cl$_2$. The combined organic layers were washed with 1 M HCl, brine, dried over magnesium sulfate, filtered, and concentrated in vacuo. The resulting solid was purified by recrystallization (ethyl acetate/hexanes) to obtain a fluffy, white solid (24 g, 59 mmol, 82%). $^1$H NMR (400 MHz, d$_6$-DMSO): δ 7.90 (t, 1H, J=6.2 Hz), 7.88 (d, 2H, J=7.5 Hz), 7.68 (d, 2H, J=7.5 Hz), 7.43 (m, 4H), 7.32 (dd, 2H, J=7.5 Hz, 7.5 Hz), 7.26 (d, 1H, J=7.7 Hz), 7.20 (d, 1H, J=7.3 Hz), 4.35 (d, 2H, J=6.6 Hz), 4.22 (t, 1H, J=6.6 Hz), 4.17 (d, 2H, J=6.2 Hz). ESI/MS: 408 (M+H+).

(2-Bromobenzyl)-carbamic acid 9H-fluoren-9-ylmethyl ester (S28). 1H NMR (400 MHz, d$_6$-DMSO): δ 7.89 (d, 2H, J=7.5 Hz), 7.88 (t, 1H, J=6.2 Hz, NH), 7.71 (d, 2H, J=7.5 Hz), 7.58 (d, 1H, J=7.5 Hz), 7.42 (dd, 2H, J=7.5 Hz, 7.5 Hz), 7.35 (dd, 1H, J=7.5 Hz, 7.5 Hz), 7.32 (dd, 2H, J=7.5 Hz, 7.5 Hz), 7.20 (dd, 1H, J=7.5 Hz, 7.5 Hz), 7.19 (d, 1H, J=7.5 Hz), 4.38 (d, 2H, J=6.6 Hz), 4.24 (t, 1H, J=6.6 Hz), 4.19 (d, 2H, J=6.2 Hz). APCI/MS: 408 (M+H+).

(4'-Formylbiphenyl-2-ylmethyl)-carbamic acid 9H-fluoren-9-ylmethyl ester (S29). 4-Formylphenylboronic acid (4.97 g, 33.2 mmol), aryl bromide S28 (9.0 g, 22 mmol), KF (3.8 g, 66 mmol), biphenyl-2-yl-di-tert-butyl-phosphane (0.26 g, 0.884 mmol), and palladium(II) acetate (0.099 g, 0.44 mmol) were charged into an oven-dried flask. After one evacuation/backfill cycle with Ar, the solids were dissolved in THF (45 mL) and heated moderately (30° C.) with stirring. After 24 h, the reaction was diluted with CH$_2$Cl$_2$ and was washed with 1 M NaOH. The aqueous layer was extracted with CH$_2$Cl$_2$ and the combined organics were then washed with brine, dried over Na$_2$SO$_4$, filtered, and concentrated in vacuo. The crude solid was purified by flash column chromatography (silica gel, 30% ethyl acetate/hexanes) to obtain a white solid (6.0 g, 63%). $^1$H NMR (400 MHz, d$_6$-DMSO): δ 10.04 (s, 1H), 7.95 (d, 2H, J=8.2 Hz), 7.88 (d, 2H, J=7.5 Hz), 7.82 (t, 1H, J=5.9 Hz, NH), 7.67 (d, 2H, J=7.5 Hz), 7.59 (d, 2H, J=8.2 Hz), 7.43–7.30 (m, 7H), 7.24 (d, 1H, J=7.7 Hz), 4.29 (d, 2H, J=7.0 Hz), 4.19 (t, 1H, J=7.0 Hz), 4.12 (d, 2H, J=5.9 Hz). APCI/MS: 434 (M+H+).

(4'-Formylbiphenyl-3-ylmethyl)-carbamic acid 9H-fluoren-9-ylmethyl ester (S30). 4-Formylphenylboronic acid (5.0 g, 33 mmol), aryl bromide S27 (9.0 g, 22 mmol), KF (3.8 g, 66 mmol), biphenyl-2-yl-di-tert-butyl-phosphane (0.26 g, 0.88 mmol), and palladium(II) acetate (0.099 g, 0.44 mmol) were charged into an oven-dried flask. After one evacuation/backfill cycle with Ar, the solids were dissolved in THF (45 mL) and heated to reflux with stirring. After 5 h, the reaction was diluted with ethyl acetate, filtered through a celite pad and washed with 1 M NaOH. The aqueous layer was extracted with ethyl acetate and the combined organics were then washed with brine, dried over MgSO$_4$, filtered, and concentrated in vacuo to afford an orange oil (13 g). The crude oil was purified by flash column chromatography (silica gel, 30% ethyl acetate/hexanes) to obtain aldehyde S29 as a yellow oil (5.7 g, 60%). $^1$H NMR (400 MHz, CDCl$_3$): δ 10.06 (s, 1H), 7.95 (d, 2H, J=8.2 Hz), 7.76 (d, 2H, J=7.5 Hz), 7.74 (d, 2H, J=8.2 Hz), 7.59 (d, 2H, J=7.5 Hz), 7.56 (m, 1H), 7.55 (s, 1H), 7.46 (dd, 1H, J=7.9 Hz, 7.9 Hz), 7.39 (dd, 2H, J=7.5 Hz, 7.5 Hz), 7.33 (m, 1H), 7.29 (dd, 2H, J=7.5 Hz, 7.5 Hz), 5.16 (broad s, 1H), 4.48 (d, 2H, J=7.0 Hz), 4.47 (s, 2H), 4.24 (t, 1H, J=7.0 Hz). ESI/MS: 456 (M+Na+).

(3'-Formylbiphenyl-3-ylmethyl)-carbamic acid 9H-fluoren-9-ylmethyl ester (S31). $^1$H NMR (400 MHz, CDCl$_3$): δ 10.08 (s, 1H), 8.08 (s, 1H), 7.87 (d, 1H, J=7.7 Hz), 7.84 (d, 1H, J=8.1 Hz), 7.76 (d, 2H, J=7.3 Hz), 7.61 (dd, 1H, J=7.7 Hz, 7.7 Hz), 7.60 (d, 2H, J=7.3 Hz), 7.55 (m, 1H), 7.54 (s, 1H), 7.46 (dd, 1H, J=8.1 Hz, 8.1 Hz), 7.39 (dd, 2H, J=7.3 Hz, 7.3 Hz), 7.32 (m, 1H), 7.39 (dd, 2H, J=7.3 Hz, 7.3 Hz), 5.19 (broad s, 1H) 4.47 (d, 2H, J=7.0 Hz) 4.46 (s, 2H), 4.12 (t, 1H, J=7.0 Hz). APCI/MS: 456 (M+Na$^+$).

(4'-Dimethoxymethylbiphenyl-2-ylmethyl)-carbamic acid 9H-fluoren-9ylmethyl ester (S32). To a vigorously stirred mixture of methanol (250 mL) containing aldehyde (S29) (17.0 g, 39.3 mmol) and p-toluenesulfonic acid monohydrate (0.75 g, 3.9 mmol) was added trimethyl orthoformate (17 mL, 160 mmol). After 1.5 h of moderate heating (flask equipped with short path to drive reaction forward), the reaction was quenched with a 1:1 mixture of saturated sodium bicarbonate and water (150 mL) and diluted with CH$_2$Cl$_2$ (200 mL). The aqueous layer was extracted with CH$_2$Cl$_2$ and the combined organic layers were washed with brine, dried over Na$_2$SO$_4$, and concentrated in vacuo to give a pale yellow solid (17.5 g, 36.6 mmol, 93%) which was used without further purification. $^1$H NMR (400 MHz, d$_6$-DMSO): δ 7.88 (d, 2H, J=7.7 Hz), 7.79 (t, 1H, J=5.9 Hz), 7.68 (d, 2H, J=7.3 Hz), 7.43–7.30 (m, 11H), 7.19 (d, 1H, J=7.0 Hz), 5.40 (s, 1H), 4.29 (d, 2H, J=7.0 Hz), 4.20 (t, 1H, J=7.0 Hz), 4.11 (d, 2H, J=5.9 Hz), 3.25 (s, 6H). FAB/MS: 502 (M+Na$^+$).

(4'-Dimethoxymethylbiphenyl-3-ylmethyl)-carbamic acid 9H-fluoren-9-ylmethyl ester (S33). $^1$H NMR (400 MHz, d$_6$-DMSO): δ 7.91 (t, 1H, J=6.1 Hz), 7.87 (d, 2H, J=7.5 Hz), 7.68 (d, 2H, J=7.5 Hz), 7.63 (d, 2H, J=8.4 Hz), 7.55 (s, 1H), 7.53 (m, 1H), 7.45 (d, 1H, J=8.4 Hz), 7.38 (m, 4H), 7.27 (dd, 2H, J=7.5 Hz, 7.5 Hz), 7.21 (d, 1H, J=7.3 Hz), 5.43 (s, 1H), 4.33 (d, 2H, J=7.0 Hz), 4.24 (d, 2H, J=6.1 Hz), 4.23 (t, 1H, J=7.0 Hz), 3.26 (s, 6H). ESI/MS: 502 (M+Na$^+$).

(3'-Dimethoxymethyl-biphenyl-3-ylmethyl)-carbamic acid 9H-fluoren-9ylmethyl ester (S34). $^1$H NMR (400 MHz, d$_6$-DMSO): δ 7.94 (t, 1H, J=5.9 Hz), 7.87 (d, 2H, J=7.5 Hz), 7.68 (d, 2H, J=7.5 Hz), 7.60 (m, 1H), 7.59 (s, 1H), 7.52 (m, 2H), 7.47 (dd, 1H, J=7.3 Hz), 7.43–7.37 (m, 4H), 7.27 (dd, 2H, J=7.5 Hz, 7.5 Hz), 7.22 (d, 1H, J=7.3 Hz), 5.42 (s, 1H), 4.33 (d, 2H, J=7.0 Hz), 4.26 (d, 2H, J=5.9 Hz), 4.22 (t, 1H, J=7.0 Hz), 3.25 (s, 6H). ESI/MS: 502 (M+Na$^+$).

Methylphthalimidomonoester Synthesis

Suberic acid methylphthalimidomonoester (S35). To a mixture of suberic acid (5.0 g, 29 mmol) in DMF (40 mL) with dicyclohexylamine (8.0 mL, 40 mmol) was added chloromethylphthalimide (6.1 g, 31 mmol) and the reaction was heated to 60° C. for 5 h. The reaction was diluted with CH$_2$Cl$_2$ (500 mL) and washed with 0.1 M NaHSO$_4$ (3×200 mL). The aqueous layers were back extracted with CH$_2$Cl$_2$ (5×100 mL) and the organic layers were combined and dried over MgSO$_4$, filtered, and concentrated in vacuo. The crude residue was purified by flash column chromatography (silica gel, 7% MeOH/CH$_2$Cl$_2$) to yield suberic acid methylphthalimidomonoester as a white solid (3.41 g, 35%). $^1$H NMR (500 MHz, CD$_3$OD): δ 7.94 (dd, 2H, J=5.6 Hz, 2.9 Hz), 7.86 (dd, 2H, J=5.6 Hz, 2.9 Hz), 5.68 (s, 2H), 2.32 (t, 2H, J=7.3 Hz), 2.24 (t, 2H, J=7.3 Hz), 1.68 (m, 4H), 1.32 (m, 4H).

Adipic acid methylphthalimidomonoester (S36). $^1$H NMR (500 MHz, CDCl$_3$): δ 7.93 (dd, 2H, J=5.4 Hz, 2.9 Hz), 7.79 (dd, 2H, J=5.4 Hz, 2.9 Hz), 5.72 (s, 2H), 2.35 (td, 4H, J=6.8 Hz, 2.0 Hz), 1.67 (m, 4H). ESI-HRMS m/z calcd for C$_{15}$H$_{15}$NO$_6$Na 328.0797; found 328.0801.

Pimelic acid methylphthalimidomonoester (S37). $^1$H NMR (500 MHz, CDCl$_3$): δ 7.93 (dd, 2H, J=5.4 Hz, 2.9 Hz), 7.79 (dd, 2H, J=5.4 Hz, 2.9 Hz), 5.72 (s, 2H), 2.33 (m, 4H), 1.64 (m, 4H), 1.36 (m, 2H). ESI-HRMS m/z calcd for C$_{16}$H$_{17}$NO$_6$Na 342.0954; found 342.0967.

Building Block Selection and Demonstration Compound Synthesis

Figures 8A, 8B:
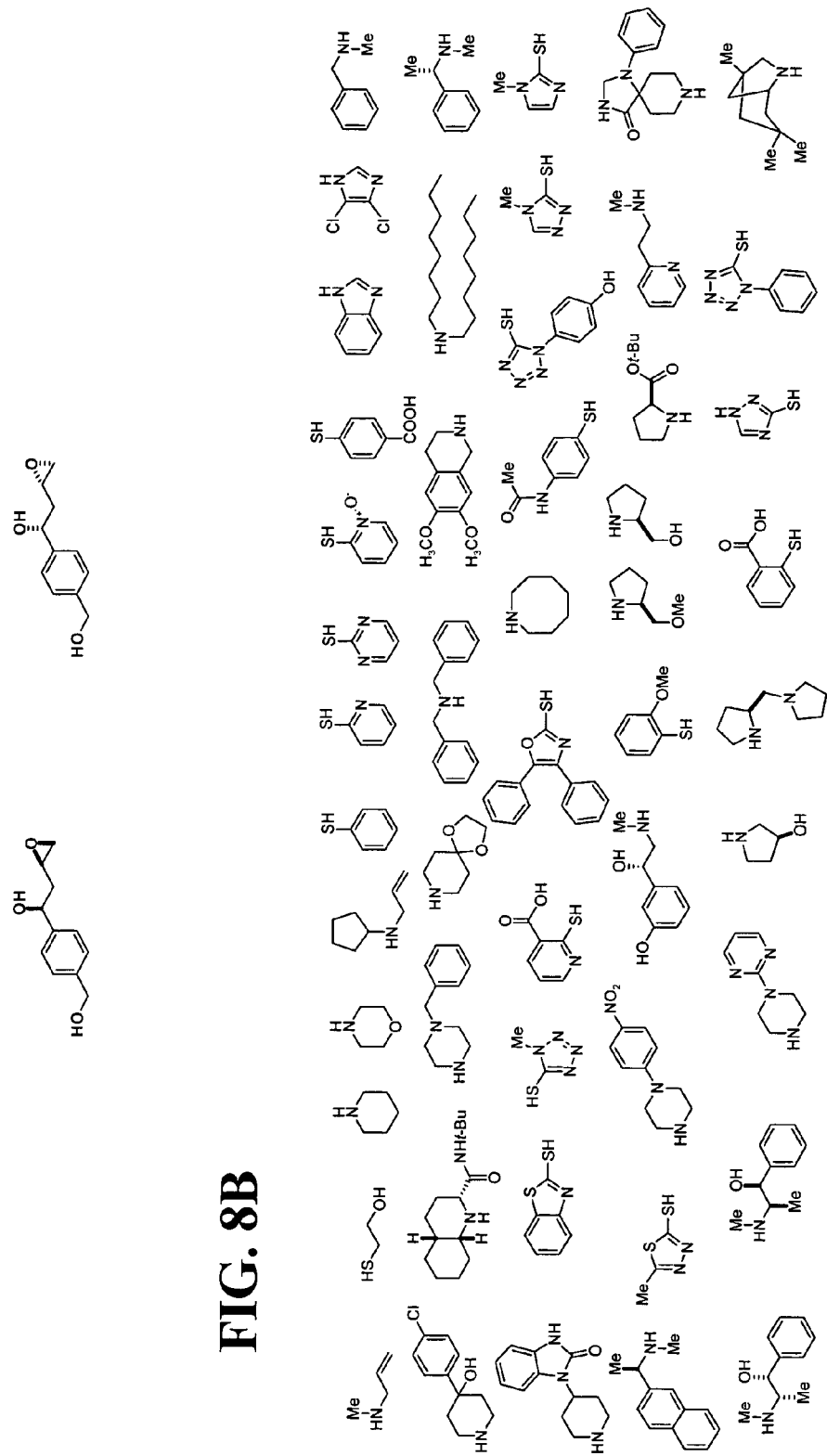
FIG. 8 depicts exemplary building blocks used for a 7200 member 1,3-dioxane library. (A) γ,δ-epoxy alcohol building blocks, (B) amine and thiol building blocks, (C) Fmoc-amino dimethyl acetal building blocks, and (D) diacid building blocks.
Figure 8C:
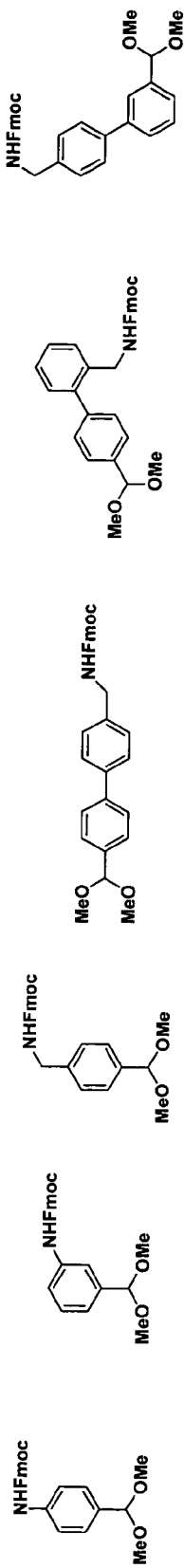
Figure 8D:
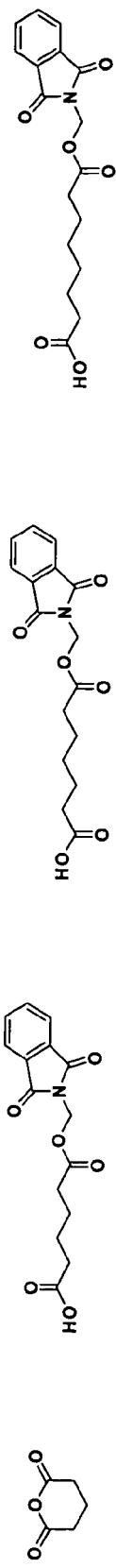

Nucleophile, acetal, and diacid building blocks were selected after analysis of their reactions with model substrates. LC-MS analysis of crude reaction products after HF.pyr cleavage permitted selection of building blocks that underwent reaction with >90% purity (FIG. 8).

Figure 9A:
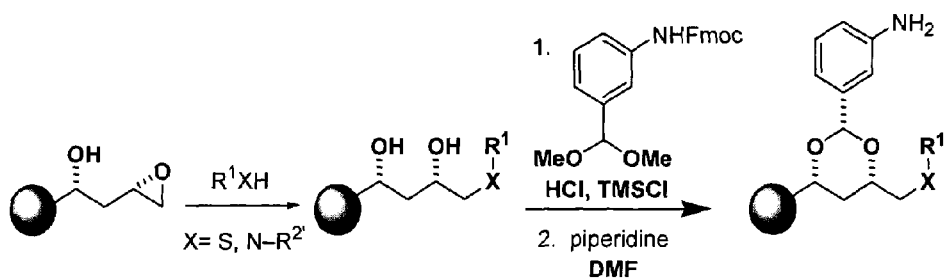
FIG. 9 depicts (a) selection of nucleophilic building blocks; (b) selection of Fmoc-amino dimethyl acetal building blocks; and (c) selection of diacid building blocks.

Procedure for selection of nucleophile building blocks. Nucleophilic building blocks were selected after a two step reaction sequence in order to assess the compatibility of different nucleophiles with both the epoxide opening conditions and the acidic ketalization conditions (FIG. 9A).

Figure 9B:
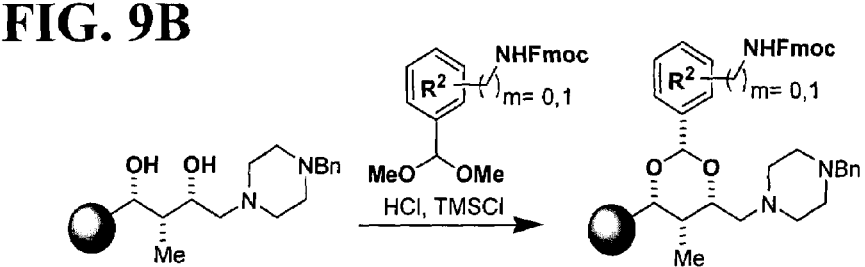

Procedure for selection of Fmoc-amino dimethylacetal building blocks. Fmoc-amino dimethylacetal building blocks were selected by acetal formation with a 1,3-diol known to be one of the most challenging substrates in the library for this reaction (FIG. 9B).

Figure 9C:
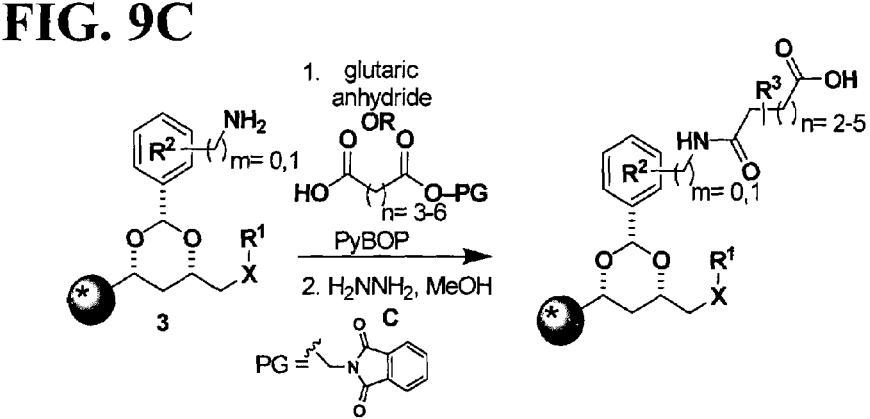

Procedure for selection of diacid building blocks. Diacid building blocks were selected by reaction with a variety of amino-1,3-dioxanes to ensure appropriate reactivity and purity (FIG. 9C). Several sample hydroxamic acid compounds were also made to demonstrate the purity of the crude reaction products.

(±)-Pentanedioic acid 4-[4-(benzothiazol-2-ylsulfanylmethyl)-6-(4-hydroxymethyl-phenyl)-[1,3]dioxan-2-yl]-benzylamide hydroxyamide (8). $^1$H NMR (500 MHz, CD$_3$OD): δ 7.82 (d, 2H, J=8.1 Hz), 7.46–7.31 (m, 9H), 7.19 (d, 2H, J=7.8 Hz), 5.75 (s, 1H), 4.95 (dd, 1H, J=11.0, 1.8 Hz), 4.58 (s, 2H), 4.41 (m, 1H), 4.33 (s, 2H), 3.69 (dd, 1H, J=13.7 Hz, 4.4 Hz), 3.60 (dd, 1H, J=13.7 Hz, 7.3 Hz), 2.26 (t, 2H, J=7.3 Hz), 2.11 (t, 2H, J=7.3 Hz), 2.07 (m, 1H), 1.92 (quint, 2H, J=7.3 Hz), 1.79 (m, 1H). APCI/MS: 630 (M+Na$^+$).

(±)-Octanedioic acid {3-[4-(benzothiazol-2-ylsulfanylmethyl)-6-(4-hydroxymethyl-phenyl)-[1,3]dioxan-2-yl]-phenyl}-amide hydroxyamide (9). $^1$H NMR (500 MHz, CD$_3$OD): δ 7.83 (t, 2H, J=9.3 Hz), 7.72 (s, 1H), 7.57 (dt, 1H, J=7.8 Hz, 1.5 Hz), 7.46–7.40 (m, 3H), 7.36–7.32 (m, 3H), 7.22 (t, 1H, J=7.8 Hz), 7.18 (d, 1H, J=7.8 Hz), 5.76 (s, 1H), 4.95 (dd, 1H, J=11.0, 2.2 Hz), 4.59 (s, 2H), 4.43 (m, 1H), 3.71 (dd, 1H, J=13.7 Hz, 4.4 Hz), 3.59 (dd, 1H, J=13.7 Hz, 7.3 Hz), 2.35 (t, 2H, J=7.3 Hz), 2.15–2.05 (m, 3H), 1.79 (m, 1H), 1.69 (t, 2H, J=6.8 Hz), 1.62 (t, 2H, J=7.3 Hz), 1.38 (m, 4H). APCI/MS: 636 (M+H$^+$).

Library Synthesis and Post-synthetic Characterization

General procedure for molecular encoding of reactions. To each batch of resin was added a solution in CH$_2$Cl$_2$ (3.18 mL) that was 8.4 mM in each tag assigned to that reaction. After 45 min of agitation, a solution of [Rh(OCOCPh$_3$)$_2$]$_2$ in CH$_2$Cl$_2$ (3.18 mL of a 4.4 mg/mL solution) was added and the reactions were agitated for 16 h. Reactions were filtered and washed THF (2×15 min) and CH$_2$Cl$_2$ (3×1 h). Resin was dried under vacuum.

General procedure for molecular decoding of reactions. To a single bead in a glass HPLC vial insert was added a 0.24 M solution of CAN in 5:1 THF/H$_2$O (5 μL) followed by decane (8 μL). The inserts were placed in an HPLC vial, capped, and heated at 37° C. for 21 h. The insert was then removed from the vial, sonicated for 1 min and centrifuged briefly. The top decane layer was carefully removed and transferred to a clean glass HPLC insert. A 1:1 solution of N,O-bistrimethylsilylacetamide in decane (1 μL) was added to the decane solution and quickly centrifuged for 30 s. The insert was placed in a GC autosampler vial for EC-GC analysis. EC-GC data was obtained on a Hewlett Packard 6890 gas chromatograph fitted with a 7683 series injector and autosampler, split-splitless inlet, μ-ECD detector, and a J&W DB1 15 m×0.25 mm×0.25 μm column. (Gradient start temperature: 110° C.; hold 1 min, ramp 45° C./min to 250° C., hold 2 min, ramp 15° C./min to 325° C., hold 2 min. Flow rate: constant flow, 1 mL/min. Inlet was purged at 1 min with flow rate 60 mL/min, reduced to 20 mL/min at 2 min).

Solid Phase Synthesis Procedures

Representative procedure for γ,δ-epoxy alcohol resins (1). Diisopropylphenylsilane resin, S3, (0.76 g, 0.59 mmol, 1.0 equiv.) was split into two portions and encoded for the subsequent γ,δ-epoxy alcohol building blocks. The resin was placed in an oven-dried 25 mL round bottom flask under Ar. To remove atmospheric water from the resin, it was washed with anhydrous THF (3×10 mL over 30 min) followed by anhydrous $CH_2Cl_2$ (2×10 mL over 20 min). A small-bore cannula was used to remove the solvents. The resin was suspended in $CH_2Cl_2$ (5 mL) and trichloroisocyanuric acid (0.081 g, 0.35 mmol, 1.2 equiv.) was added. After 1 h, a white precipitate had developed and the resin was filtered via cannula and washed with THF (2×10 mL) followed by $CH_2Cl_2$ (2×10 mL). γ,δ-Epoxy alcohol (0.10 g, 0.53 mmol, 1.8 equiv.) was azeotropically dried (3×10 mL toluene) and dissolved in $CH_2Cl_2$ (1 mL) with i-$Pr_2$NEt (0.092 μL, 0.53 mmol, 1.8 equiv.) and DMAP (0.013 g, 0.11 mmol, 0.4 equiv.). The solution was added to the activated resin and allowed to stand for 4 h. The resin was washed 3×DMF and 5×THF to give γ,δ-epoxy alcohol resin (1).

1,3-diol resin (2). γ,δ-Epoxy alcohol resin, 1, were pooled, suspended in DMF (15 mL), and mixed on a rotary shaker for 1.5 h followed by mixing in THF (15 mL) for 2 h. The resin was filtered and dried under vacuum. The dried resin (19 mg, 0.6 mequiv./g avg, 0.011 mmol, 1.0 equiv.) was split into fifty portions and encoded for the subsequent reaction. To each of the fifty resin portions was added the appropriate nucleophile (0.3 mmol, 27 equiv.) followed by i-PrOH (0.3 mL). In the case of thiol building blocks or amine hydrochloride salts, one equivalent of i-$Pr_2$NEt (0.051 mL, 0.30 mmol, 27 equiv.) was added and the vials were flushed with Ar, capped, and allowed to stand in an oven at 50° C. 24 h. The reactions were filtered and washed with DMF (10×5 min) and THF (10×5 min) to give 1,3-diol resin (2). Twelve beads were individually cleaved with 19:1 THF/HF.pyr. The tagged beads were decoded, and the crude reaction mixtures were analyzed by LC (See FIG. S7 in Sternson et al. "Synthesis of 7200 Small Molecules Based on a Substructural Analysis of the Histone Deacetylase Inhibitors Trichostatin and Trapoxin", Org. Lett., 2001, 3(26):4239–4242, Supporting Information).

1,3-Dioxane resin (3). After pooling, 1,3-diol resin, 2, was split into six equal portions (0.19 g, 0.55 mequiv./g avg, 0.10 mmol, 1.0 equiv.) and treated with Fmoc-amino dimethylacetal building blocks (1.1 mmol., 11 equiv.) in a solution of 0.05 M HCl in anhydrous 1,4-dioxane (3.5 mL) and TMSCI (0.35 mL, 2.8 mmol, 28 equiv.). After 4 h, the reaction was quenched with anhydrous pyridine (2 mL), filtered, and washed with DMF (4×10 min) and THF (4×10 min). The resin was treated with 0.2 M pyridinium para-toluenesulfonate in 10% MeOH-THF (2×5 mL) for 2 h. The resin was filtered and washed with DMF (4×10 min), THF (2×10 min), and $CH_2Cl_2$ (2×10 min). The pools were then encoded for the previous reaction. The resin was pooled, split into four portions, and encoded for the following reaction. Ten beads were individually cleaved with 19:1 THF/HF.pyr. The tagged beads were decoded, and the crude reaction mixtures were analyzed by LC-MS (See FIG. 58 in Sternson et al. "Synthesis of 7200 Small Molecules Based on a Substructural Analysis of the Histone Deacetylase Inhibitors Trichostatin and Trapoxin", Org. Lett., 2001, 3(26):4239–4242, Supporting Information). The encoded resin was treated with 20% piperidine-DMF (3×10 mL) for 30 min and then washed with $CH_2Cl_2$ (4×10 min) and dried under vacuum. The resin was suspended in $CH_2Cl_2$ (3 mL) with i-$Pr_2$NEt (0.26 mL, 1.5 mmol) and DMAP (0.012 g, 0.1 mmol) and TESCI (0.15 mL, 0.9 mmol) was added. After 2 h, the resin was washed with $CH_2Cl_2$ (4×10 min) to give 1,3-dioxane resin (3).

Carboxylic Acid-1,3-dioxane Resin (4).

(i) 1,3-Dioxane resin (3, 0.30 g) was suspended in DMF (2 mL) with pyridine (0.18 mL, 2 mmol) and glutaric anhydride was added (0.11 g, 1 mmol). After 10 h, the reaction was filtered and washed with DMF (4×10 min), THF (2×10 min), and $CH_2Cl_2$ (2×10 min).

(ii) 1,3-Dioxane resin (3, 0.30 g) was added to 2:1 DMF/$CH_2Cl_2$ (2 mL) with acid (2 mmol), PyBOP (0.99 g, 1.9 mmol), and i-$Pr_2$NEt (0.44 mL, 2.5 mmol). After 12 h, the reactions were filtered and washed with DMF (4×10 min), THF (2×10 min), and $CH_2Cl_2$ (2×10 min). The resin was suspended in 1 M hydrazine in MeOH (1.5 mL, 1.5 mmol) and the mixture was heated to 55° C. After 12 h, the reactions were filtered and washed with DMF (4×10 min), THF (2×10 min), and $CH_2Cl_2$ (2×10 min). The resin was pooled and split into three equal portions. One third of the resin was set aside for biological testing. Nine beads were individually cleaved with 19:1 THF/HF.pyr. The tagged beads were decoded, and the crude reaction mixtures were analyzed by LC-MS.

o-Aminoanilide 1,3-dioxane resin (6). One third of the carboxylic acid 1,3-dioxane resin (5, 0.43 g) was combined with 1-hydroxybenzotriazole (0.076 g, 0.56 mmol) and 1,2-phenylenediamine (0.080 g, 0.74 mmol). A solution of i-$Pr_2$NEt (0.21 mL, 1.2 mmol) in $CH_2Cl_2$ (2 mL) was added followed by diisopropylcarbodiimide (0.095 mL, 0.60 mmol). After 4 h, the reaction was filtered and washed with DMF (4×10 min), THF (2×10 min), and $CH_2Cl_2$ (2×10 min). Ten beads were individually cleaved with 18:1:1 THF/HF.pyr/pyr. The tagged beads were decoded, and the crude reaction mixtures were analyzed by LC-MS.

Hydroxamic acid 1,3-dioxane resin (7). One third of the carboxylic acid 1,3-dioxane resin (5, 0.43 g) was suspended in DMF (2 mL) with PyBOP (0.3 g, 0.58 mmol), i-$Pr_2$NEt (0.21 mL, 1.2 mmol), and O-(2-methoxypropane)-hydroxylamine (0.08 g, 0.76 mmol). After 5 h, the reaction was filtered and washed with DMF (4×10 min). The resin was then treated with 0.2 M pyridinium para-toluenesulfonate in 10% MeOH-THF (2×5 mL) for 2 h. The resin was filtered and washed with DMF (4×10 min), THF (2×10 min), $CH_2Cl_2$ (2×10 min). Ten beads were individually cleaved with 19:1 THF/HF.pyr. The tagged beads were decoded, and the crude reaction mixtures were analyzed by LC-MS.

Post-synthetic Characterization

After key steps in the library synthesis single beads were cleaved and analyzed for the purity of the attached compounds and to confirm proper encoding of the bead. The HPLC UV traces of these single bead cleavages are shown. In all cases, the molecular ion in the MS trace of the major peak corresponded to the mass predicted by the encoding reactions. The lower purity for the library synthesis versus the model reactions demonstrates the potential for discrepancy in results between model reactions and products from a library synthesis that occurs at the final steps.

LC-MS analysis was performed on a Micromass Platform LCZ-MS coupled to a Waters 2690 HPLC. Analyses were run using either an APCI or an ES interface with positive-negative ionization mode switching. Chromatography was over a 3.5 μm Waters Symmetry C18 column (50 mm×2.1 mm i.d.) eluting at 0.4 mL/min with a gradient of 15–100% B over 10 min (A=water+0.1% formic acid; B=acetonitrile+ 0.1% formic acid). A 5 μL sample of the solution was injected.

Library Cleavage Elution Studies

To ensure that our high-throughput process for library cleavage would yield stock solution concentrations sufficient for multiple phenotypic and protein-binding assays, a model study was performed.

Compound S35 was synthesized on 20 milligrams (182 beads) of γ,δ-epoxyol functionalized resin (1). Nineteen beads were set aside for single bead cleavage and elution experiments. The remaining beads were treated with 18:1:1 THF/Hf.pyr/pyr for two hours. The cleavage reaction was quenched with TMSOMe and the resultant solution separated from the beads. The beads were then washed with THF for one day to ensure maximum extraction of S35 from the polymer matrix. Purification of the combined extracts by silica gel chromatography resulted in recovery of 56 nmol/ bead.

S35

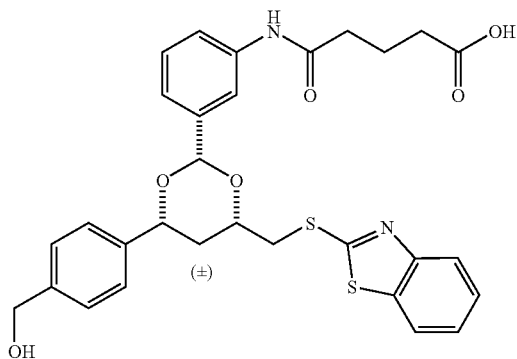

Nineteen uncleaved beads were arrayed into a 384-well plate (one bead/well). Ten beads were treated with 18:1:1 THF/HF.pyr/pyr (20 μL/well) for two hours. The remaining nine beads were treated with this cleavage solution for five hours. The reactions were quenched with TMSOMe (20 μL/well) and the solution in each well evaporated over fifteen minutes. Compound S35 was then eluted from each bead with 20 minute washes using 20 μL DMF. A two-wash protocol was determined to be optimal (single bead yield did not increase with additional washes). Eluent was then removed using a centrifugal vacuum evaporator (GeneVac) and the dried material in each well dissolved in 5 μL of DMF. The amount of compound in each well was determined spectrophotometrically by comparison to a standard curve generated from purified S35.

Two hour cleavage was sufficient to obtain single bead yields which were comparable, on average, to the bulk cleavage yield. However, five hour cleavage minimized bead-to-bead deviations, presumably because the longer reaction time enables full reagent penetration into the polymer support.

Compound Cleavage and Formation of Arrayed Stock Solutions.

Resin was distributed into twenty-one 384-well polypropylene plates (Genetix, 50 μL well volume) using a bead arraying tool to give a single bead per well. Each well was treated with a solution of 18:1:1 THF/HF.pyr/pyr (20 μL). After 2 h, TMSOMe (20 μL) was added to quench the HF. The solvent was allowed to evaporate and the beads were washed with DMF (3×15 μL×40 min) and distributed into daughter plates. DMF was removed with a centrifugal vacuum evaporator (GeneVac). Compounds will be dissolved in a polar solvent prior to biological assay.

The 2 h cleavage protocol was selected, despite more consistent stock solution concentrations using a 5 h protocol, because exposing model compounds to 18:1:1 THF/HF.pyr/ pyr for longer than 2 h decreased their purity.

Biological Assay Procedures

Cell culture and Transfections. TAg-Jurkat cells were transfected by electroporation with 5 μg of FLAG-epitope-tagged pBJ5 constructs (as described in ref. 5c) for expression of recombinant proteins. Cells were harvested 48 h posttransfection.

HDAC assays. [$^3$H]Acetate-incorporated histones were isolated from butyrate-treated HeLa cells by hydroxyapatite chromatography (as described in Tong, et al. *Nature* 1997, 395, 917–921. ) Immunoprecipitates were incubated with 1.4 μg (10,000 dpm) histones for 3 h at 37° C. HDAC activity was determined by scintillation counting of the ethyl acetate-soluble [$^3$H]acetic acid (as described in Taunton, et al., *Science* 1996, 272, 408–411). Compounds were added in DMSO such that final assay concentrations were 1% DMSO. IC50s were calculated using Prism 3.0 software. Curve fitting was done without constraints using the program's Sigmoidal-Dose Response parameters. All data points were acquired in duplicate and IC50s are calculated from the composite results of at least two separate experiments.

Identification and Characterization of a Selective Tubulin Deacetylase Inhibitor In a pilot experiment, 352 hydroxamic acids from our HDAC-biased 1,3-dioxane library were screened in a pair of assays designed to identify molecules that selectively inhibit either histone deacetylation or tubulin deacetylation. One compound, JCWII114 (shown below), potently and selectively inhibited tubulin deacetylation but had no visible effect on histone deacetylation.

Structure of JCWII114, a selective tubulin deacetylase inhibitor:

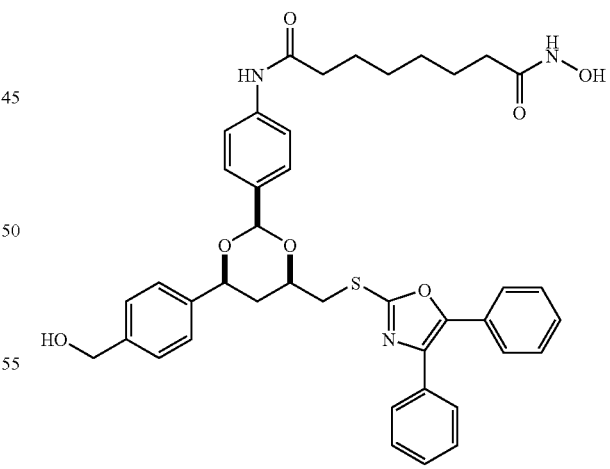

Figure 10:
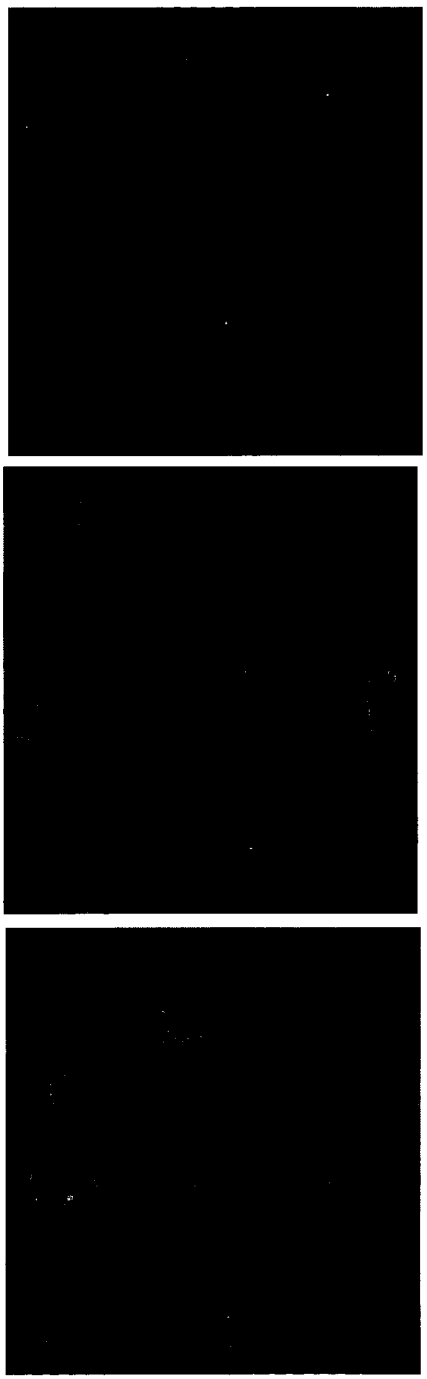
FIG. 10 depicts anti-acetyl-lysine 40 tubulin (red) and anti-acetyl-histone (green) immunofluorescence BS-C-1 cells (14 h treatment).
Figure 10:
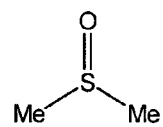
Figure 10:
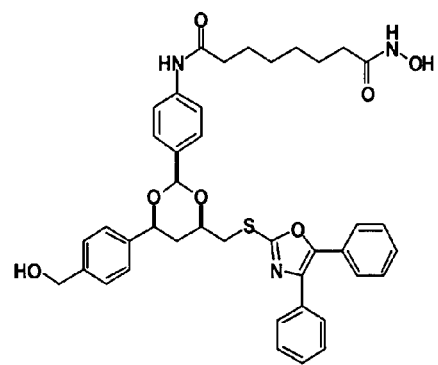
Figure 10:
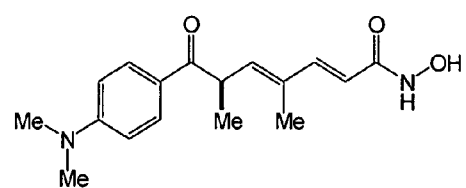
Figure 11:
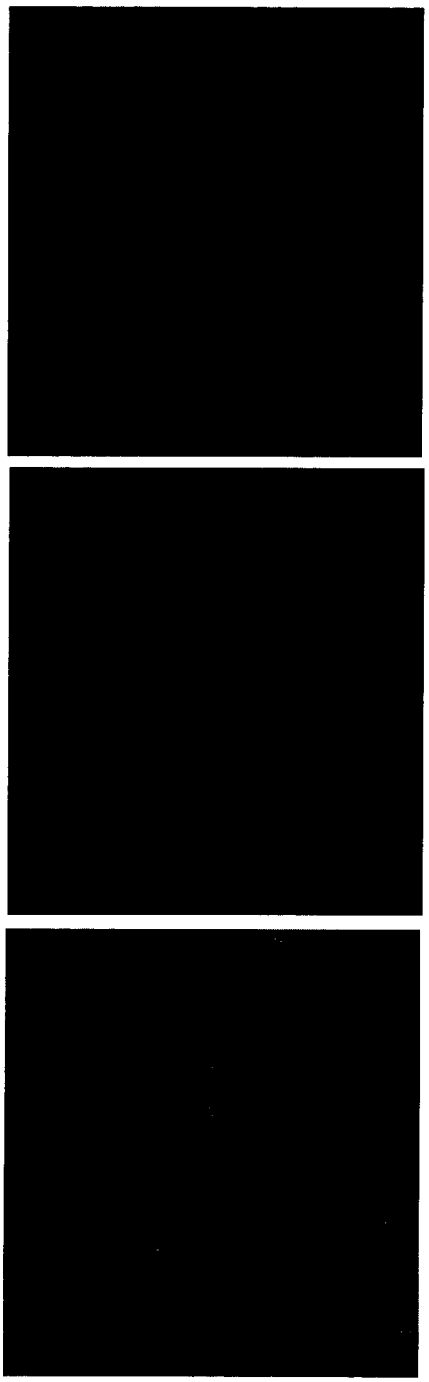
FIG. 11 depicts anti-acetyl-lysine 40 tubulin (red) and anti-acetyl-histone (green) immunofluorescence BS-C-1 cells (14 h treatment).
Figure 11:
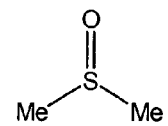
Figure 11:
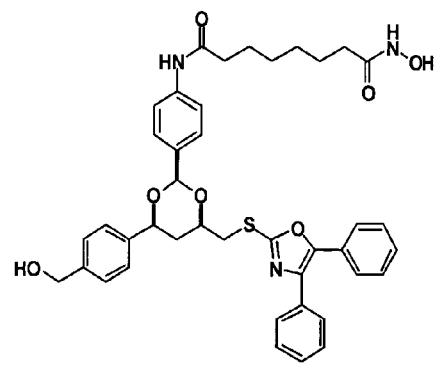
Figure 11:
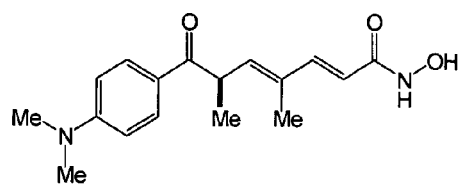
Figure 12:
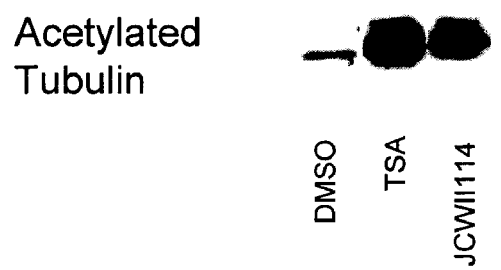
FIG. 12 depicts the effect of inventive compound JCWII114 on acetylated tubulin and acetylated histone H3 in A549 cells (5 h treatment).
Figure 12:
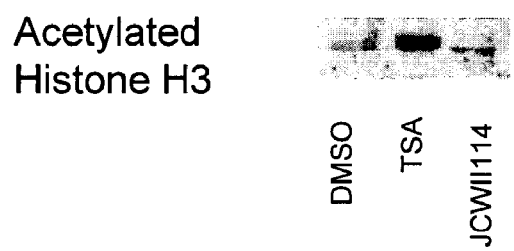
Figure 13A:
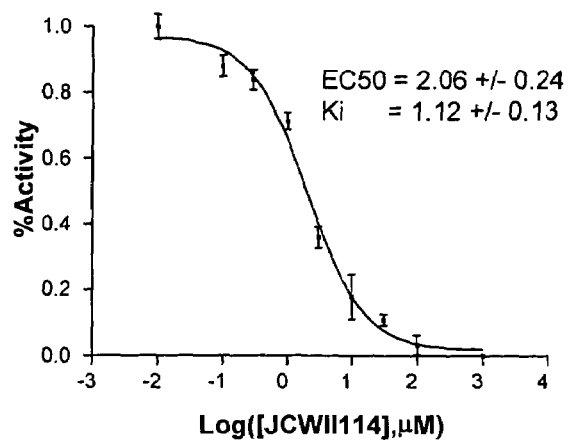
FIG. 13 depicts exemplary concentration response curves for inhibition of HDAC1, 4 and 6. (A) Concentration response curve for inhibition of HDAC1 Fluor de Lys Deacetylation by inventive compound JCWII114; (B) Concentration response curve for inhibition of HDAC4 Fluor de Lys Deacetylation by inventive compound JCWII114; and (C) Concentration response curve for inhibition of HDAC6 Fluor de Lys Deacetylation by inventive compound JCWII114.
Figure 13B:
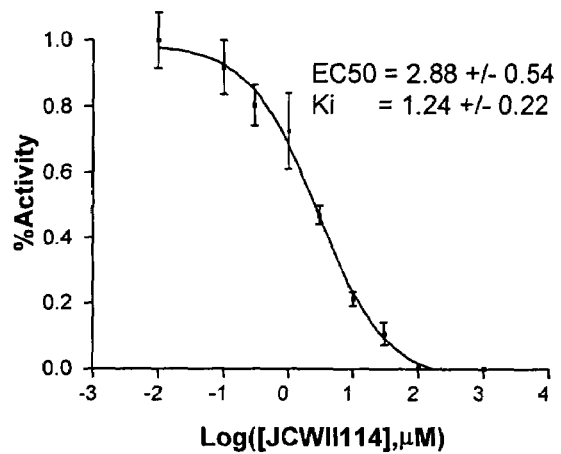
Figure 13C:
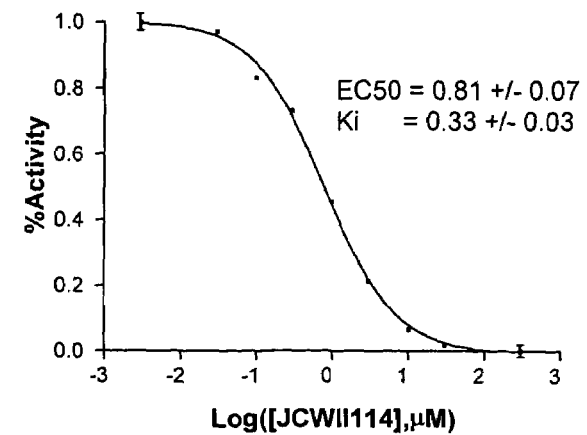

This result was confirmed by immunofluorescence microscopy (FIG. 10) and Western blot analysis (FIG. 12). Furthermore, in an in vitro enzyme inhibition assay, JCWII114 exhibited 3-fold selectivity for HDAC6 over HDAC1 and HDAC4 (FIG. 13). This, along with other data that implicate HDAC6 as the tubulin deacetylase, suggests that HDAC6 is the target of JCWII114. Studies to confirm that HDAC6 is a tubulin deacetylase and that it is the relevant target of JCWII114 are described in more detail in Example 7 below. JCWII114 is also designated "tubacin" (See Example 7 below).

Figure 14:
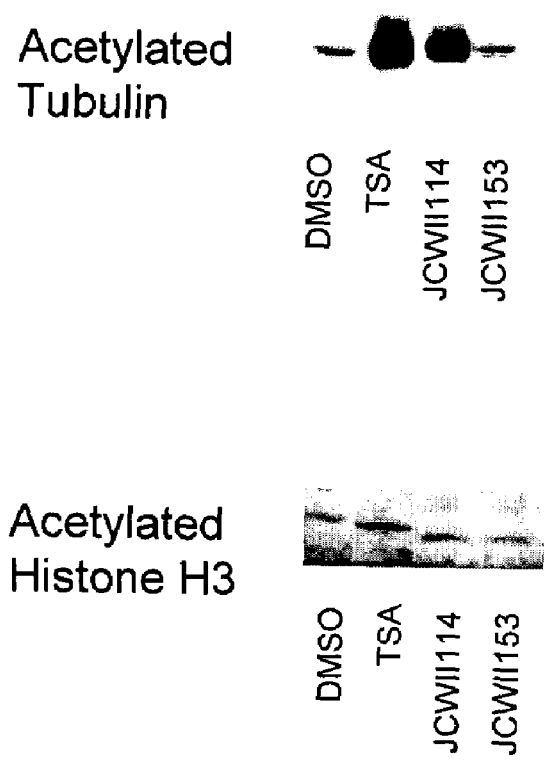
FIG. 14 depicts the effect of inventive compound JCWII153 (the carboxylic acid analog of JCWII114) on acetylated tubulin and acetylated histone H3 in A549 cells (5 h treatment). TSA treatment was carried out at 300 nM; JCWII114 was carried out at 2 µM; JCWII153 treatment was carried out at 2 µM.

The carboxylic acid analogue of JCWII114 did not affect histone or tubulin deacetylation according to Western blot analysis (FIG. 14). This result both validates our use of the hydroxamic acid functionality to generate an HDAC-biased library, as well as suggests that JCWII114 is, in fact, inhibiting a deacetylase rather than affecting some other pathway that regulates acetylation of tubulin.

Structure of JCWII153, the carboxylic acid analogue of JCWII114.

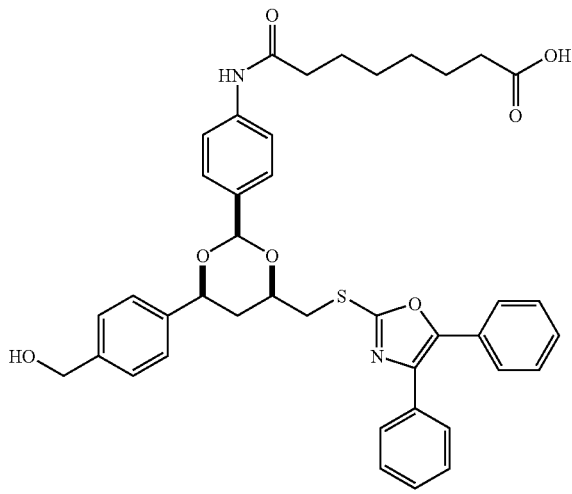

Figure 16:
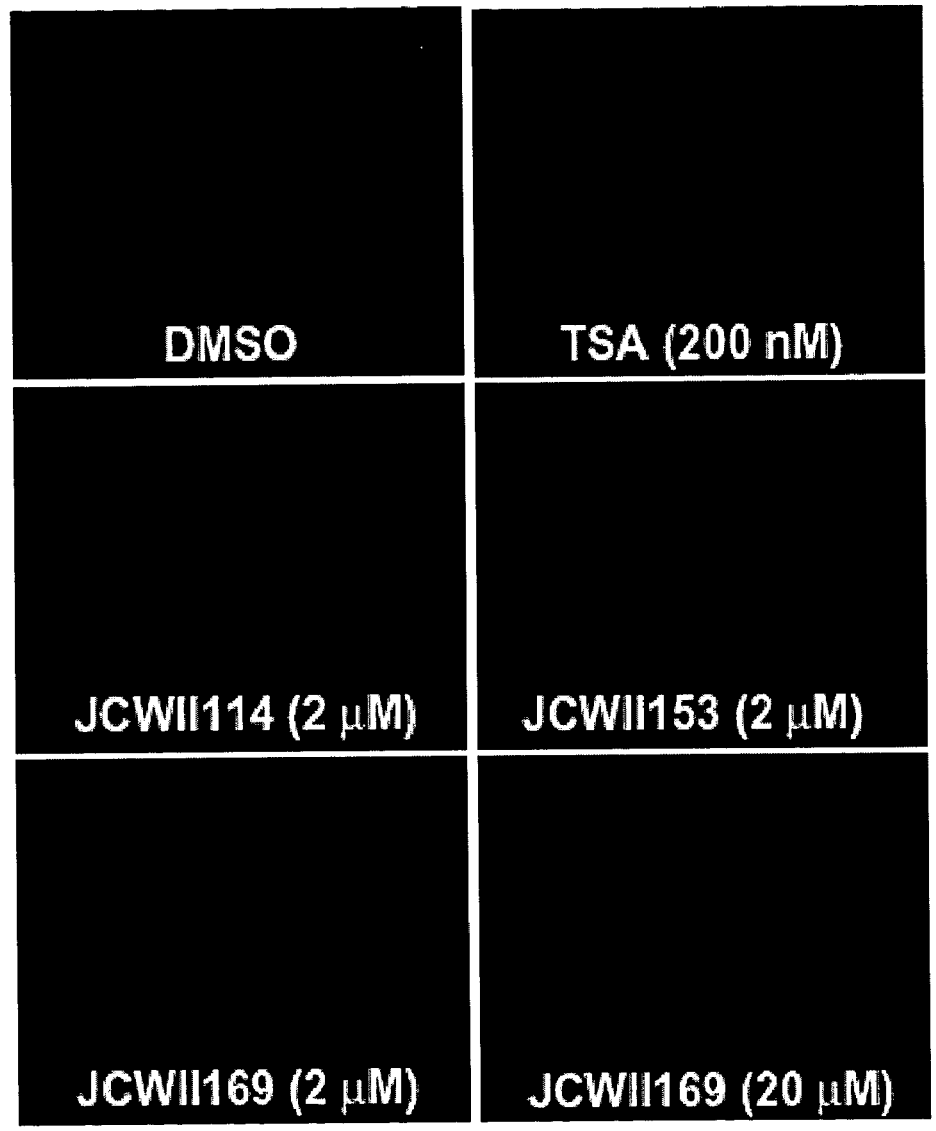
FIG. 16 depicts the effect of inventive compound JCWII114 analogs on total acetylated lysine levels in A549 cells (18 h treatment).
Figure 17A:
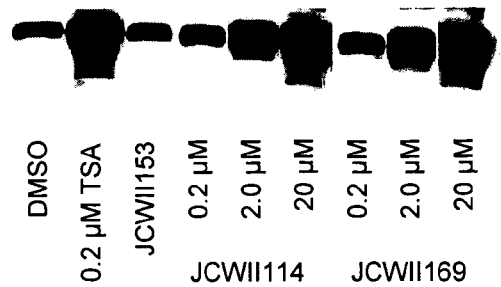
FIG. 17 depicts exemplary enantiomers and their potency and selectivity. (A) Acetylated Tubulin; (B) Acetylated Histone H3; and (C) Structures of inventive compounds tested. Enantiomers JCWII114 and JCWII169 have similar potency and selectivity in A549 cells (5 h treatment).
Figure 17B:
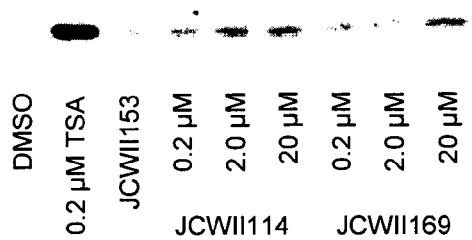
Figure 17C:
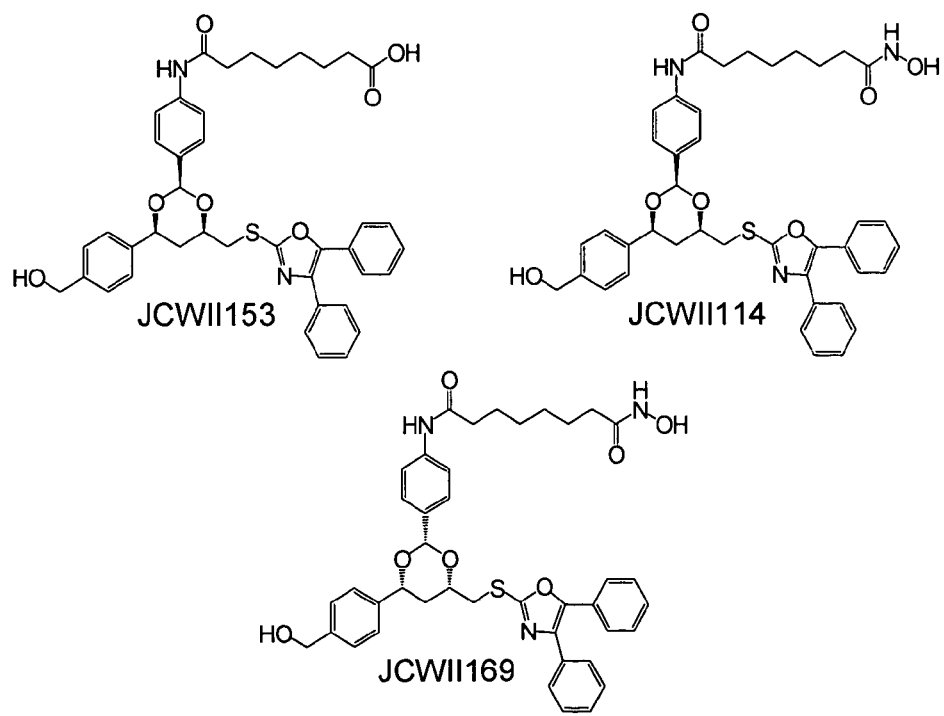

JCWII169, the enantiomer of JCWII114 was analyzed by immunofluorescence microscopy (FIGS. 15 and 16) and Western blot (FIG. 17). No significant difference in selectivity or potency was observed between JCWII169 and JCWII114.

JCWII114 appears to be a truly selective tubulin deacetylase inhibitor. Unlike trichostatin, trapoxin, and other indiscriminate HDAC inhibitors, JCWII114 has no apparent affect on the cell cycle or on cell morphology. Whereas with previous HDAC inhibitors the effects of histone and tubulin deacetylation were intertwined, JCWII114 will allow us to unravel cellular processes directly affected by the acetylation state of tubulin from those affected by the acetylation state of histones.

Screening the Entire HDAC-biased Library for Selective Tubulin and Histone Deacetylase Inhibitors Based on the success of our pilot screen, we proceeded to assay the full library (2400 hydroxamic acids, 2400 carboxylic acids, and 2400 ortho-aminoanilides) both find additional potent and selective deacetylase inhibitors, and learn what structural elements, if any, are responsible for potency and selectivity. Our data demonstrate unequivocally the importance of the hydroxamic acid functionality in conferring potency. A more detailed study is described in Example 6 below.

III. EXAMPLE 2

Synthesis of 1,3-dioxanes and use in Multiple Phenotypic and Protein-binding Assays As described above, the compounds of the invention are useful as inhibitors of HDAC. In addition, small molecules, such as the compounds of the invention, provide a means to modulate rapidly and therefore dissect the circuitry of biological networks (Mitchison et al. *Chem. Biol.* 1994, 1, 3–6; Schreiber et al. *Bioorg. Med. Chem.* 1998, 6, 1127–1152). Such compounds can be discovered using phenotypic (Mayer et al. *Science* 1999, 286, 971–974) or protein-binding assays (MacBeath et al. *J. Am. Chem. Soc.* 1999, 121, 7967–7968). Phenotypic assays can be used to identify small molecules that modulate a specific cellular or organismic pathway without prior knowledge of the protein components of the pathway. Protein-binding assays, often used in drug discovery efforts, can also be used to identify reagents for exploring protein function in subsequent biological assays. By determining the pathways and processes altered by the small molecule, the functions of its target can be elucidated. Both strategies are capable of providing insight into complex processes.

The use of small molecules to dissect biological function is being accelerated by high throughput screening of large collections of small molecules (Mayer et al. *Science* 1999, 286, 971–974). Advances in the use of robotics and the miniaturization of phenotypic and protein binding assays have facilitated rapid screening of large compound collections. However, the production of small molecule libraries has not matched the advances in screening technology. The development of solid phase organic synthesis has increased productivity in organic synthesis through simplification of purification protocols, permitting reactions to be automated and run in parallel (Bunin et al. *J. Am. Chem. Soc.* 1992, 114, 10997–10998; DeWitt et al. *Proc. Natl. Acad. Sci. U.S.A.* 1993, 90, 6909–6913). This approach has gained widespread acceptance because milligram quantities of each small molecule can be generated for screening in multiple biological assays; however, issues of cost and labor typically limit library sizes to hundreds of compounds. Millions of distinct compounds can be synthesized through a variation of solid phase synthesis that treats each solid phase particle (commonly, derivatized polystyrene beads) as a separate reaction vessel. By splitting and pooling (Furka et al *Int. J. Pept. Protein Res.* 1991, 37, 487–493; Lam et al. *Nature* 1991, 354, 82–84; Houghten et al. *Nature* 1991, 354, 84–86) the collection of synthesis beads over a reaction sequence, all possible combinations of a large matrix of building blocks can be accessed, generating an enormous amplification in the number of different compounds produced for a small number of reactions (Tan et al. *J. Am. Chem. Soc.* 1999, 121, 9073–9087). Despite the introduction of the split-pool synthetic method over a decade ago, it has not gained widespread use due to challenges in compound identification, minute quantities of released compounds, and the resulting tendency to screen molecules as mixtures. By addressing these issues, we have developed a split-pool synthetic approach to generate arrayed stock solutions of single 1,3-dioxane compounds sufficient for multiple phenotypic and protein-binding assays. Synthesis of a small demonstration library of 1890 molecules (a precursor step to a larger 50,000 compound library), structure determination of active compounds, and biological activities in multiple assays are discussed.

A high capacity solid support and a silicon linker enable the synthesis of small molecules in quantities sufficient for multiple phenotypic and protein-binding assays. A fundamental challenge to the production of stock solutions from a split-pool library suitable for multiple biological assays is the release of sufficient compound from the synthesis resin. To generate the concentrations of small molecule necessary for phenotypic assays in cell culture and in multicellular organisms, 5–10 mM stock solutions in 5–10 µL of DMSO or DMF are desirable. When using miniaturized assays (assay volumes 2–40 µL), this permits hundreds of assays to be performed at screening concentrations of up to 100 µM after dilution into an assay plate. To obtain sufficient quantities of arrayed small molecule stock solutions for multiple assays, 500 µm aminomethyl polystyrene beads (Rapp Polymere- Tubingen, Germany) with a loading capacity of 85 nmol/bead were used. These beads have ~5-fold larger diameter than the commonly used synthesis resin, with ~100-fold greater quantity of attached small molecule. Synthesis resin with a capacity of 50–100 nmol/bead is sufficient to generate 10 mM stock solutions in 5 µL of DMSO.

Figure 18:
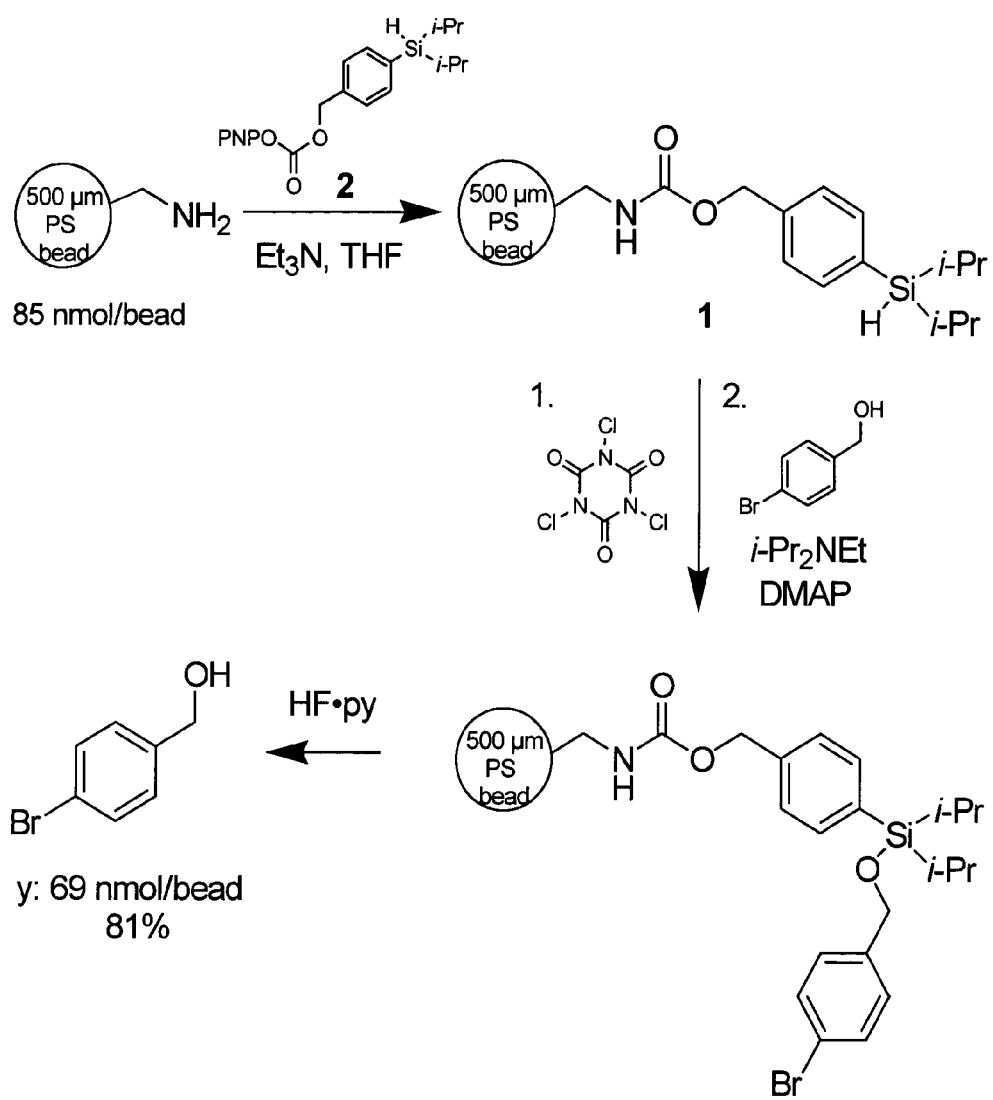
FIG. 18 depicts synthesis of an exemplary solid support unit (solid support and linker).
Figure 19:
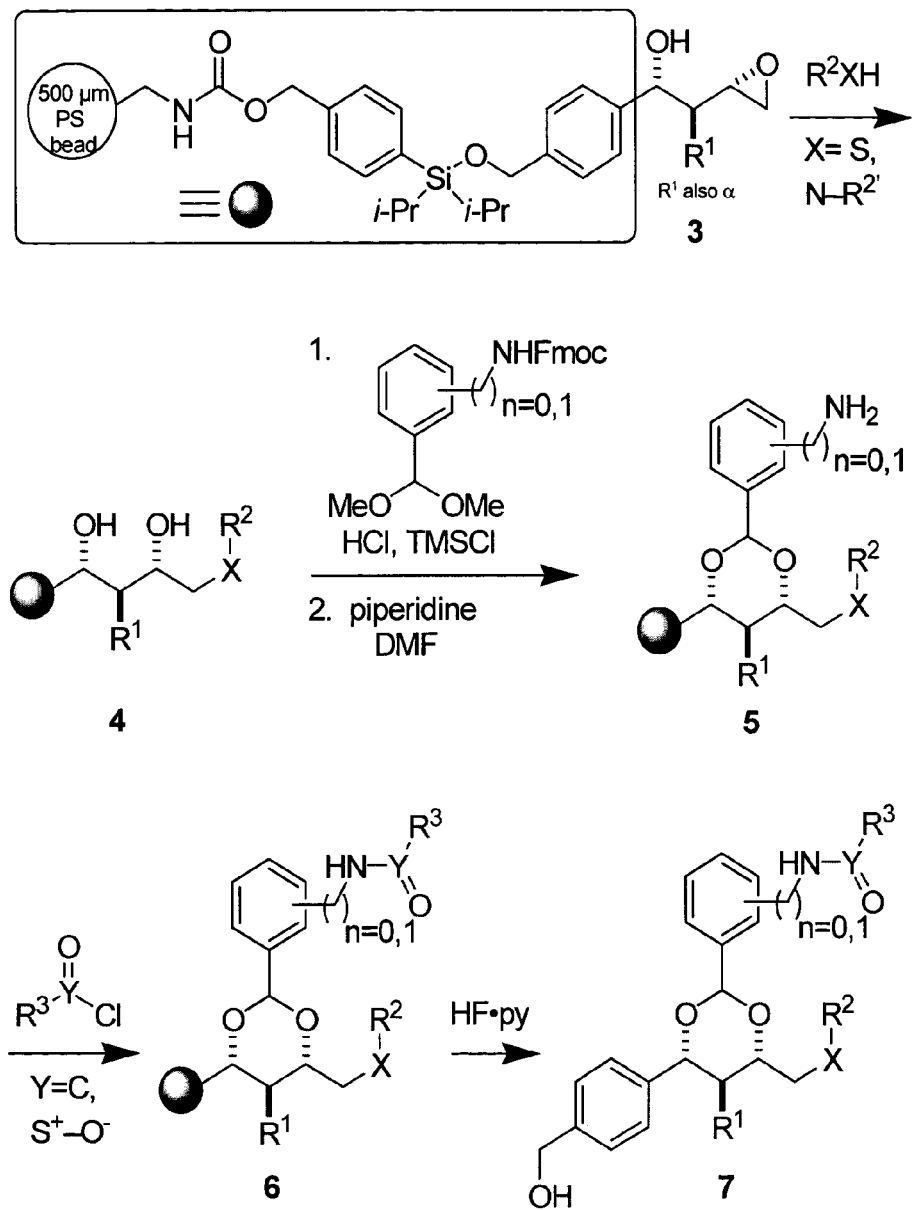
FIG. 19 depicts an exemplary synethetic scheme.

An acid and base-stable diisopropylphenylsilyl ether linker (1) was developed for the 1,3-dioxane synthesis to permit mild fluoride mediated cleavage of the small molecules (FIG. 18). Despite the availability of many acid and base stable linkers (Hu et al. *Tetrahedron Lett.* 1998, 39, 2711–2714) few of these exhibit stability to both of these sets of reaction conditions as required by our 1,3-dioxane library synthesis (FIG. 19). Additionally, chemically robust linkers typically require harsh cleavage conditions that are not compatible with a wide variety of chemical functionality present in the 1,3-dioxane library. To avoid post-synthetic purification strategies, the reagent used for cleavage of the small molecule at the end of the synthesis should be removed easily, preferably by evaporation, further limiting the possible linker chemistries to be employed. Alkylsilyl ether chemistry was focused on which is widely used in organic synthesis because silyl ethers are often stable to both acid and base, but they are cleaved under mild conditions with fluoride. A common source of fluoride, HF.pyridine (HF.py), can be quenched with TMSOMe yielding volatile byproducts thereby obviating the need for purification after compound cleavage. The diisopropylphenylsilyl linker 1 was developed with these considerations in mind.

The diisopropylphenylsilane linker, activated as a paranitrophenyl carbonate (2), was attached to aminomethyl polystyrene synthesis resin through a carbamate linkage. Oxidation of silane 1 with trichloroisocyanuric acid generated a silyl chloride that was reacted with alcohol building blocks. To illustrate the intrinsic yield of attachment and release for silyl linker 1, 4-bromobenzyl alcohol was attached and then cleaved with HF.py in 81% yield, releasing 69 nmol/bead on average. This amount is sufficient to prepare ~10 mM stock solutions by addition of 5–10 µL of DMSO. Due to the development of miniaturized phenotypic and protein binding assays utilizing robotic liquid transfer of 4–40 nL droplets on the tips of specially machined pins (Lipinski et al. *Adv. Drug Delivery Rev.* 1997, 23, 3–25) these stock solutions can be assayed hundreds of times at 50–100 µM assay concentrations.

Split-pool library synthesis. The discovery of small molecule partners for uncharacterized proteins can provide powerful tools to explore biology. While many guidelines exist for the molecular structure of drugs (Lindsley et al. *J. Am. Chem. Soc.* 2000, 122, 422–423) the only generally accepted criterion for structures of protein-binding small molecules is that they should contain elements to restrict their degrees of conformational freedom. Bias towards "pharmacophore" or natural product structures can provide inspiration for a synthesis (Schreiber et al. *Science* 2000, 287, 1964–1969; Bunin et al. *J. Am. Chem. Soc.* 1992, 114, 10997–10998) but there is no inherent requirement to adhere to these structural motifs for the synthesis of small molecule partners to uncharacterized proteins. Some considerations for such diversity-oriented organic syntheses have been provided.

The 1,3-dioxane structure (FIG. 19) was selected for split-pool synthesis because it is a rigid core that can be synthesized stereoselectively with high purity in the presence of diverse ancillary functional groups. Building blocks for the library were selected through a series of quality control experiments involving liquid chromatography-mass spectrometry (LC-MS) analysis of the building blocks in model reactions on 500 µm polystyrene beads. The building blocks that underwent test reactions with >90% purity were selected for the synthesis. Although our intention is to synthesize a library of 50,000 1,3-dioxane molecules, we first demonstrated our strategy for producing split-pool libraries as arrayed stock solutions by synthesizing a 1890 (theoretical) member library synthesized from a subset of the tested building blocks.

Figures 20A, 20B:
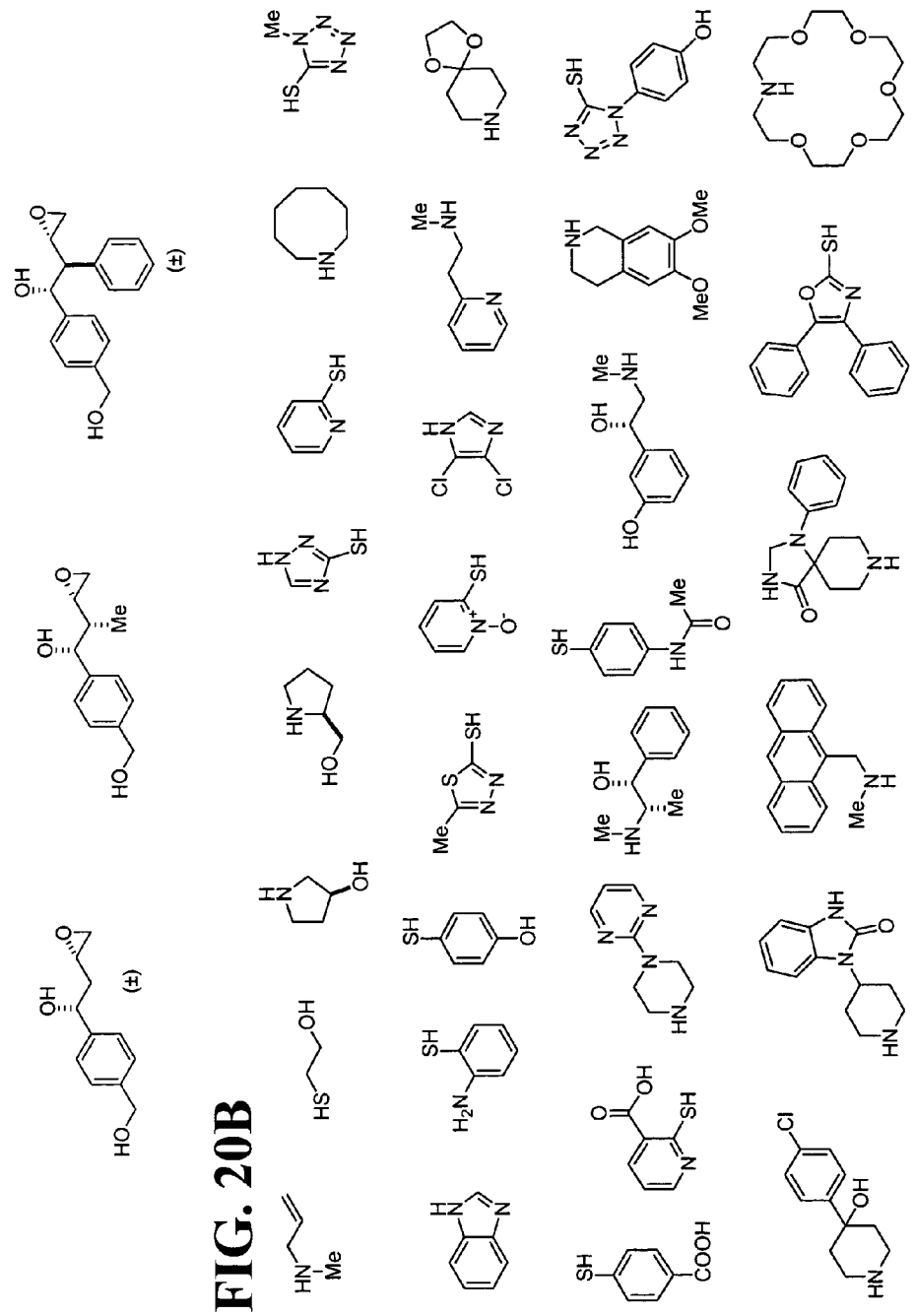
FIG. 20 depicts exemplary (A) epoxy alcohol building blocks, (B) amine and thiol building blocks, (C) Fmoc-amino dimethylacetal building blocks and (D) electrophile building blocks.
Figure 20C:
Figure 20D:
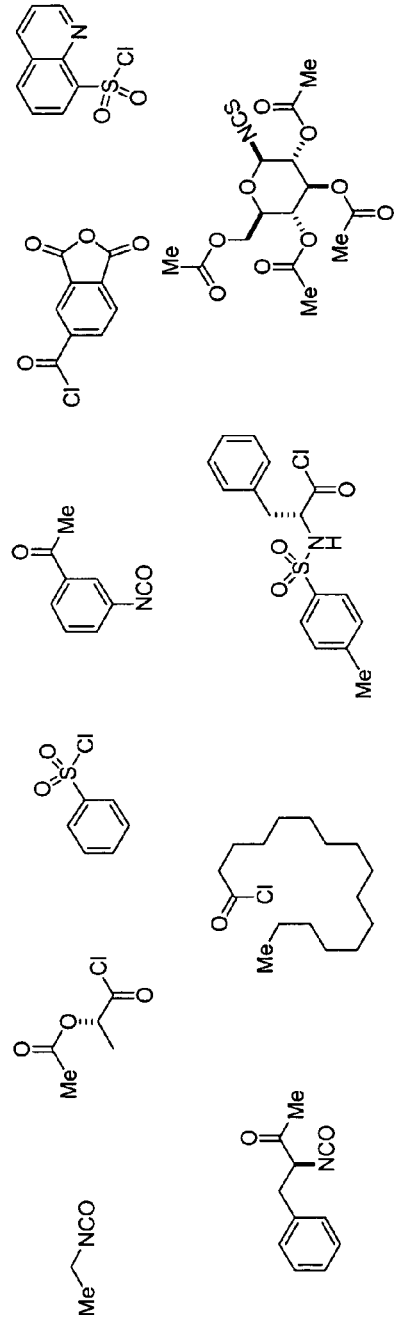

Three γ,δ-epoxy alcohols (FIG. 20) were attached to the polystyrene solid support through the diisopropylphenylsilyl ether linkage in 90% of the theoretical yield (theoretical yield based on loading/cleavage sequence of 4-bromobenzyl alcohol). The epoxy alcohol derivatized resin (3) was pooled and then split into 30 vessels with a diverse set of secondary amine and thiol building blocks (FIG. 20B) to generate 90 different 1,3-diols (4) in quantitative yield, a portion of which were set aside for screening in biological assays. The solid supported 1,3-diols were pooled and split into two portions that were reacted with Fmoc-aminodimethyl acetal building blocks (FIG. 20C) in 0.05 M HCl in dioxane and TMSCl to furnish 180 Fmoc-amino-1,3-dioxanes in 85–95% yield. The use of TMSCl as a dehydrating agent was important for consistently driving the reaction to completion. The diisopropylphenylsilyl ether linkage was stable to 0.05 M HCl in anhydrous dioxane for 4 h; however, yield and purity were substantially reduced with higher HCl concentrations or with longer reaction time. Dimethylacetal building blocks were used for 1,3-dioxane formation because the corresponding aldehydes reacted slowly when forming the cis,cis-5-methyl-1,3-dioxanes. This is presumably due to the development of four gauche interactions with the axial C5 methyl group as no difficulties were observed in forming the trans,trans-5-phenyl-1,3-dioxanes which have only two gauche interactions with the C5 phenyl group. Dimethylacetal building blocks led to the unwanted formation of mixed acetals with hydroxyl functionality present in the nucleophile building blocks. Because it was considered desirable to maintain free hydroxyl functionality due to considerations of molecular diversity, these acyclic acetals were removed by treatment of the resin with 0.2 M pyridinium para-toluenesulfonate in 9:1 THF-MeOH. The resin was then pooled and treated with piperidine to effect Fmoc removal, washed with TMSCl to protect any free hydroxyls, and the solid supported amines (5) were split and reacted with 10 electrophiles (FIG. 20D) to generate 1800 amides, ureas, thioureas, and sulfonamides (6). Two equivalents of aminomethyl polystyrene were used for the synthesis, thus 3780 compounds (3600 1,3-dioxanes and 180 1,3-diols) were synthesized in two days with only 48 reactions.

Concentrations of arrayed stock solutions. Traditionally, split-pool libraries are screened as mixtures, requiring deconvolution strategies to identify the active compounds (Erb et al. *Proc. Natl. Acad Sci. U.S.A.* 1994, 91, 11422–11426; Freier et al. *J Med. Chem.* 1995, 38, 344–352). Mixtures are prone to high false positive and false negative frequency, and they demand considerable labor when identifying the active components from multiple assays. In order to segregate each synthetic compound for the preparation of arrayed stock solutions, the collection of beads with attached 1,3-dioxanes was distributed into eleven 384 well polypropylene plates using a bead arraying tool. The 1,3-dioxanes (7) were released from the beads by treatment with HF.py for 1.5 h followed by TMSOMe to quench the excess HF as volatile byproducts. Solvent evaporation and addition of 5 μL DMSO generated stock solutions of individual compounds. The concentration of a representative stock solution from the library was spectrophotometrically determined to be 6.7 mM by comparison to a standard curve calculated from a purified bulk sample of the relevant compound (8 in FIG. 21).

To study bead-to-bead variability of the amount of released compound, eleven synthesis beads with attached 1,3-dioxane 8 were synthesized, arrayed, cleaved under the above conditions, and analyzed using spectrophotometry. After soaking the beads in 5 μL of DMSO for 14 days, the stock solution concentrations were between 1.9 mM and 10.1 mM (median concentration: 6.2 mM, mean concentration: 5.4 mM). This variance in the concentration is likely the result of small variations in bead diameter which, due to the cubic relationship of diameter to volume, leads to a spread in the amount of compound attached within the bead and, thus, in the concentration of the stock solutions.

Bulk cleavage of the beads used above liberated 59 nmol/bead of compound 8 which was determined by dividing the amount of isolated compound after cleavage, bead washing, and chromatography by the number of beads cleaved. Using this value, the theoretical mean stock solution concentration in 5 μL of DMSO is 11.9 mM. The discrepancy between the theoretical mean concentration of 11.9 mM and the observed mean concentration of 5.4 mM can be attributed to several factors. The lower than expected concentration is due, in part, to the absorption of atmospheric water by the DMSO stock solutions over time leading to an increase in solution volume with a corresponding decrease in concentration. Over 14 days, the stock solutions were observed to undergo a volume increase of ~40%. In the future, wet DMSO or solvents that absorb less water will be tested. Correction for the volume increase would give a mean concentration of 7.6 mM, still less than the theoretical mean concentration. The remaining difference in observed versus theoretical concentration is likely due to inefficient extraction of the cleaved compound out of the bead. We have observed that DMSO does not swell polystyrene beads, and extraction of compound remaining in the bead after cleavage may be slow, especially for large diameter beads. The development of miniaturized, highly parallel bead washing procedures or the use of solvents with better swelling properties may diminish this concentration discrepancy.

Despite concentrations below the theoretical value, the dilution of these stock solutions into cell based assays permit, on average, 50 μM screening concentrations at 1% final DMSO concentration. We have found that this is sufficient to discover biologically active molecules in a wide variety of protein-binding and phenotypic assays using the one compound-one bead approach.

Post-synthetic purity analysis of the arrayed stock solutions. The post-synthetic purity of the library was analyzed by liquid chromatography on ten randomly selected stock solutions from each of the ten final acylation reactions (100 beads). Of the selected stock solutions, 47% were >90% pure after 4 synthetic steps and 76% were >70% pure. Incomplete acylation, over-acylation and oxidation were responsible for 23% of the solutions being <90% pure. These inefficiencies with the final acylation step have been addressed by slight alterations in the synthetic method. Specifically, the acylation reaction times have been extended to ensure the completion of this reaction in all cases, and the triethylsilyl protecting group is used instead of trimethylsilyl protection to prevent acylation of ancillary hydroxyl groups in the final step of the synthesis.

It appears that, excluding the final acylation reaction, the molecules were synthesized reliably with high purity (most undesired products could be attributed to the acylation step). Although all of the building blocks used for the acylation reactions were shown to give the desired product with >90% purity in test systems, it is not surprising that reaction performance for the full range of building block combinations yields some compounds with lower than expected purity. This difficulty in predicting reaction success is magnified in a split-pool synthesis during the final diversity steps. Because it is untenable to perform reaction optimization on every reaction in a library synthesis, this post-synthesis quality control analysis will be important to producing the larger 50,000 compound library with the highest possible purity. These considerations lead us to predict that future libraries based on slight optimizations of this chemistry will show >90% purity for ~70% of the compounds.

Use of mass spectrometry for molecular structure determination. The structures of compounds in the stock solutions were determined using LC-MS (Brummel et al. *Science* 1994, 264, 399–402) with atmospheric pressure chemical ionization (APCI) or electrospray ionization (ESI). Direct infusion APCI and ESI-MS analysis was not successful due to competing signals from byproducts derived from extensive manipulations of organic solvents in plastic vessels that are required by the use of HF.py. Liquid chromatography was used to separate the small molecule of interest from these largely polymeric impurities. One difficulty in using mass as a unique identifier for compounds in split-pool libraries is the limited number of integer masses in the range relevant to small molecules (250–1000 amu). Our strategy to decrease the mass redundancy was to segregate the beads from the final 10 synthetic reactions into separate stock plates, thereby reducing the problem of distinguishing between 1800 possible masses to distinguishing between 180 masses.

Figure 21A:
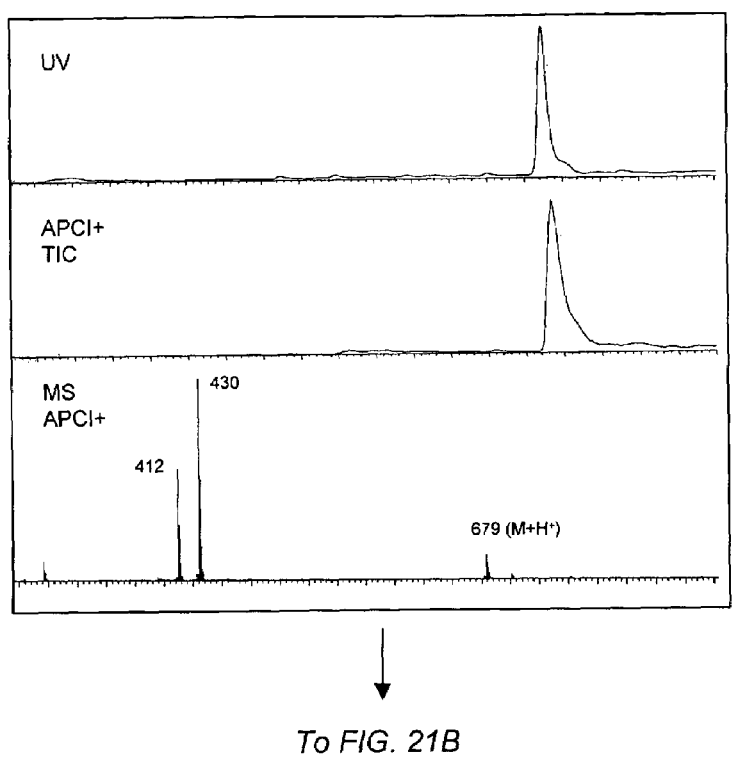
FIG. 21 depicts structure determination procedure for the 1,3-dioxane library. (A) from LC-MS: UV absorbance trace, total ion count (TIC) trace (APCI+) and mass spectrum under the major peak. The molecular ion (M+1) is 679 amu. (B) Determination of precursor amine mass. (C) All possible combinations of epoxyalcohol, nucleophile, and acetal building block masses. The mass being referenced, 564 amu results from two possible combinations of building blocks represented in the two possible structures. (D) Fragments with masses of 429 and 411 amu are consistent only with structure 8. (E) Sample from the synthesis of the proposed structure 8 (trace A) shows the same retention time as a mixture of the synthesized compound and a sample from the original stock solution (trace B).
Figure 21B:
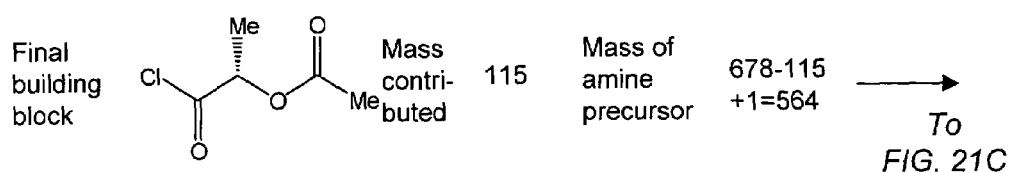
Figure 22A:
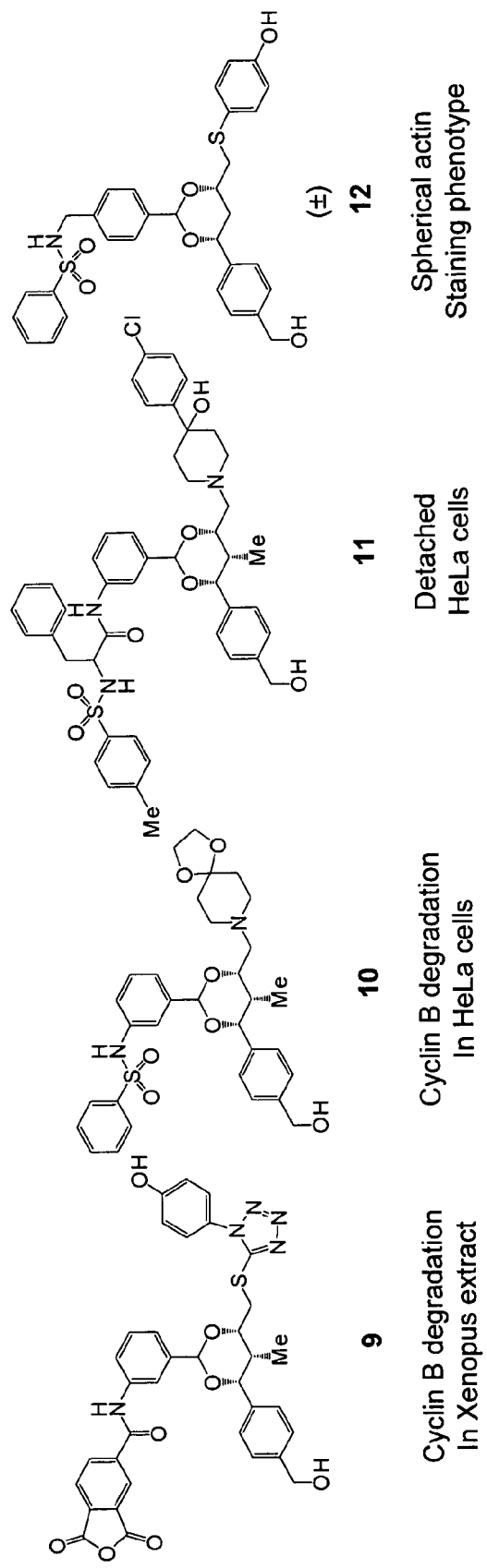
FIG. 22 depicts molecules identified to show activity in phenotypic and protein-binding assays: (A) molecules showing activity in a variety of phenotypic assays in *Xenopuslaevis* extract and in HeLa cells; (B) 1,3-diol 13 causes a wavy notochord phenotype (arrow) in Zebrafish embryos 24 h post fertilization; and (C) FKBP12 ligand identified using a small molecule microarray (a magnified portion of the array is shown).
Figure 22B:
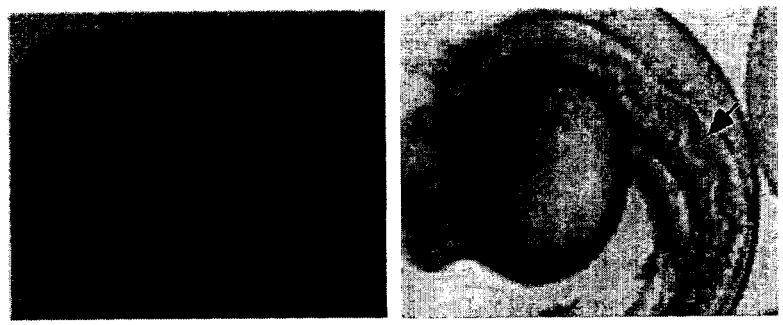
Figure 22B:
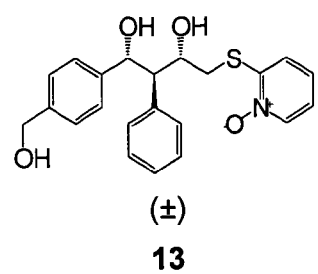
Figure 22C:
Figure 22C:
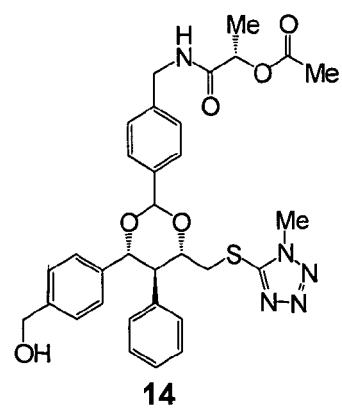

A representative example of the structure determination procedure is illustrated in FIG. 4. After LC-MS analysis of a portion (5%) of the stock solution, the molecular ion was identified (FIG. 21A). Because the beads were not pooled after the last synthetic step, the mass of the final building block was known. Subtraction of this mass from the molecular ion gave the mass of the 1,3-dioxane intermediate, 5 (FIG. 21B). Comparison to a table of the 180 possible 1,3-dioxane masses (FIG. 21C) generated from all combinations of the epoxy alcohol, nucleophile and acetal fragments allowed, in this case, two possible molecular structures with the same mass to be assigned (FIG. 21D). In most cases, the structures of molecules with redundant integer masses were distinguished by a reliable fragmentation of the 1,3-dioxane ring involving elimination of the aldehyde fragment. The appearance of peaks at 429 amu and 411 amu correspond, respectively, to the products from fragmentation of the 1,3-dioxane ring and from subsequent elimination of water. These fragments can be used to unambiguously distinguish between the two 1,3-dioxane constitutional isomers. The proposed 1,3-dioxane, 8, was synthesized and liquid chromatography showed that a mixture of the synthesized compound and the compound from the stock solution gave only one peak that had an identical retention time with the synthesized compound 8 (FIG. 21E).

Features such as isotope patterns and LC retention times were also used in some cases to resolve redundancies. Mass considerations did not influence the choice of desired building blocks, and some mass redundancies existed even after fragment analysis. In these cases two or more molecules would be synthesized and tested separately. The reliability of this structure determination approach was assessed by identification of a molecule from each of the final ten acylation reactions and resynthesis of the proposed structure. Comparison of the retention times by LC-MS showed that this procedure predicted the correct structure ten out of ten times.

Identification of biologically active 1,3-dioxane molecules and related structures. Arrayed stock solutions of single compounds from a split-pool library permit compounds to be tested individually in multiple assays. Using less than 10% by volume of the 1,3-dioxane stock solutions, we have performed five phenotypic assays and over fifty protein-binding experiments in duplicate. Results of these screens are reported here, but, in most cases, the targets have not yet been pursued. However, these experiments confirm that molecules from the library are entering cells and interacting directly with protein targets, validating our approach to screen from split-pool libraries in multiple assays.

Biologically active 1,3-dioxanes have been identified in phenotypic assays in cell culture, zebrafish, and *Xenopus laevis* oocyte extract (FIG. 22). Three structurally related phthallic anhydride derivatives (one example, compound 9, is shown) showed inhibitory activity in a miniaturized (4 μL assay volume) *Xenopus laevis* oocyte extract assay that indicates modulation of the cyclin B degradation pathway (Hughes et al. *J. Med. Chem.* 1998, 41, 3804–3811). A similar cyclin B degradation assay in HeLa cells (30 μL assay volume) revealed sulfonamide 10 to have inhibitory activity (Note: the use of LC-MS for structure determination is most amenable to moderately sized split-pool libraries (100–5000 compounds). For larger libraries the combined use of LC-MS structure determination and molecular encoding has been utilized). Neither set of compounds was active in both assay systems.

High throughput microscopy of HeLa cells in approximately 2500 single-compound assays using compounds from the 1,3-dioxane library showed cell detachment (induced by 11) and an altered actin staining phenotype (induced by 12). The cellular basis of these phenotypes has not been investigated. No phenotypes consistent with mitotic arrest were observed.

A cytoblot assay in HeLa cells based on the accumulation of phosphorylated nucleolin protein has proven useful for identification of compounds that disrupt mitotic cell cycle progression, including ones that act by novel mechanisms (Mayer et al. *Science* 1999, 286, 971–974). No molecules in the 1,3-dioxane library led to the accumulation of phosphorylated nucleolin protein. Consistent with observations in the cell staining assays (see above), this indicates that the compounds in the library do not target the mitotic machinery.

To determine the effect of these compounds on whole organism development, a phenotypic assay was performed using 16-cell zebrafish (*Danio rerio*) embryos (Stockwell et al. *Chem. Biol.* 1999, 6, 71–83) with 1300 compounds from the 1,3-dioxane library. Embryos treated with a 1,3-diol precursor (13) to the dioxanes at 60 μM developed folds in the anterior trunk region of the notochord at 18 h post-fertilization (FIG. 22B; embryo shown at 24 h post-fertilization for clarity). The folded notochord phenotype has also been observed through genetic mutant screens[32] for the $gul^{m208}$ and $lev^{m531}$ mutations. The 1,3-diol (13) may target these gene products or other proteins involved in the same biological pathway. Dissection of the pathways involved in notochord development may be complemented by small molecule ligands for proteins in those pathways.

In addition to phenotypic assays, over fifty protein-binding assays have been performed with the 1,3-dioxane library using small molecule microarrays (MacBeath et al. *J. Am. Chem. Soc.* 1999, 121, 7967–7968; Peterson et al. *Proc. Natl. Acad. Sci. U.S.A.* 2000, 97, 12965–12969). The microarrays were constructed by covalent attachment of 1 nL of each stock solution to a glass slide using a contact printing robot. Labeled proteins were used to probe the microarray for small molecule partners. Small molecules that bind to human FKBP12 (14), histone deacetylase-1, calmodulin, and a variety of fusion proteins derived from the yeast proteome and glutathione-S-transferase have been identified (Stemple et al. *Development* 1996, 123, 117–128).

IV. Experimentals for Example 2

Diisopropylphenylsilane resin (1). PS AM NH$_2$ resin (1.5 g, 1.41 mmol, 1.0 equiv.) was placed in a 20 mL fritted polypropylene tube. A solution of carbonate, 2, (1.7 g, 4.4 mmol, 3.1 equiv.) in THF (12 mL) with Et$_3$N (0.558 mL, 4.0 mmol, 4.0 equiv.) was added. The reaction was allowed to proceed for 48 h with rotary mixing. The yellow resin was filtered and washed extensively with H$_2$O and THF until the resin was white to yield diisopropylphenylsilane resin (1).

Representative procedure for γ,δ-epoxy alcohol resins (3). Diisopropylphenylsilane resin, 1, (0.48 g, 0.37 mmol, 1.0 equiv.) was placed in an oven-dried 25 mL round bottom flask under Ar. To remove atmospheric water from the resin, it was washed with anhydrous THF (3×10 mL over 30 min) followed by anhydrous CH$_2$Cl$_2$ (2×10 mL over 20 min). A small bore cannula was used to remove the solvents. The resin was suspended in CH$_2$Cl$_2$ (3.0 mL) and trichloroisocyanuric acid (0.115 g, 0.5 mmol, 1.4 equiv.) was added. After 1 h a white precipitate had developed and the resin was filtered via cannula and washed with THF (2×10 mL) followed by CH$_2$Cl$_2$ (2×10 mL). γ,δ-Epoxy alcohol (0.82 mmol, 2.2 equiv.) was azeotropically dried (4×toluene) and dissolved in CH$_2$Cl$_2$ (2.5 mL) with i-Pr$_2$NEt (0.14 mL, 0.82 mmol, 2.2 equiv.) and DMAP (0.019 g, 0.15 mmol, 0.4 equiv.). The solution was added to the activated resin and allowed to stand for 4 h. The resin was washed 3×DMF and 5×THF to give γ,δ-epoxy alcohol resin (3).

1,3-diol resin (4). γ,δ-Epoxy alcohol resin, 3, were pooled, suspended in DMF (15 mL), and mixed on a rotary shaker for 1.5 h followed by mixing in THF (15 mL) for 2 h. The resin was filtered and dried under vacuum. The dried resin (17 mg, 0.63 mequiv./g avg, 0.011 mmol, 1.0 equiv.) was split into thirty 0.5 dram glass Wheaton vials. To each of the thirty resin portions was added the appropriate nucleophile (0.2 mmol, 18 equiv.) followed by i-PrOH (0.2 mL). In the case of thiols or amine hydrochloride salts, one equivalent of i-Pr$_2$NEt (35 μL, 0.2 mmol, 18 equiv.) was added and the vials were flushed with Ar, capped, and allowed to stand in a 50° C. oven for 24 h. The reactions were filtered and washed 15×DMF 15×THF to give 1,3-diol resin (4). Approximately six beads from each reaction were set aside for biological assays.

1,3-Dioxane resin (5). After pooling, 1,3-diol resin, 4, was split into two equal portions (0.28 g, 0.58 mequiv./g avg, 0.162 mmol, 1.0 equiv.) and treated with Fmoc-amino dimethyl acetal building blocks (3.2 mmol., 20 equiv.) in a solution of 0.05 M HCl in anhydrous 1,4-dioxane (4.65 mL) and TMSCI (0.24 mL, 1.9 mmol, 12 equiv.). After 4 h, the reaction was quenched with anhydrous 2,6-lutidine (2 mL), filtered, and washed 4×DMF and 4×THF. The resin was treated with 0.2 M pyridinium para-toluenesulfonate in 10% MeOH-THF (2×10 mL) for 2 h. The resin was pooled and treated with 20% piperidine-DMF (3×15 mL) for 15 min and then washed 5×THF and dried under vacuum. To the resin in $CH_2Cl_2$ (10 mL), a solution of TMSC1 (0.22 mL, 1.7 mmol, 10 equiv.) and i-$Pr_2$NEt (0.44 mL, 2.5 mmol, 15 equiv.) in $CH_2Cl_2$ (5 mL) was added and mixed on a rotary shaker for 1 h. The resin was washed with 10% MeOH-THF for 1 h followed by 5×THF to give 1,3-dioxane resin (5).

Acyl-1,3-dioxane resin (6). 1,3-Dioxane resin, 5, was split in ten equal portions (0.06 g, 0.54 mequiv./g avg, 0.032 mmol, 1 equiv.) into 1 dram Wheaton vials and suspended in $CH_2Cl_2$ (acid and sulfonyl chlorides: 2 mL; isocyanates and isothiocyanate: 1 mL) with 2,6-lutidine (acid and sulfonyl chlorides: 0.07 mL, 0.6 mmol, 19 equiv.; isocyanates and isothiocyanate: none added). The electrophile was added (acid and sulfonyl chlorides: 0.4 mmol, 12 equiv.; isocyanates and isothiocyanate: 1 mmol, 31 equiv.) and the reactions were mixed on a rotary shaker (acid and sulfonyl chlorides: 6 h; isocyanates and isothiocyanate: 12 h). The reactions were washed 5×DMF and 5×THF and dried under vacuum to give acyl-1,3-dioxane resin (6).

Resynthesis of 1,3-dioxanes was Performed by Adaptation of the Above Procedure (αS)2-acetoxy)-N-[[4-[(4S,6R)-4-[[(4,5-diphenyl-2-oxazolyl)thio]methyl]-6[4(hydroxymethyl)phenyl]-1,3-dioxan2-yl]phenyl]methyl-propionamide (8)

$^1$H NMR (500 MHz, $CD_3COCD_3$): δ 7.76 (s, 1H), 7.64 (dd, 2H, J=8.3, 1.5), 7.56 (dd, 2H, J=8.3, 2.0), 7.48 (d, 2H, J=8.3), 7.46–7.34 (m, 8H), 7.25 (d, 2H, J=8.3), 5.85 (s, 1H), 5.11 (q, 1H, J=6.8), 5.08 (dd, 1H, J=11.2, 2.4), 4.62 (d, 2H, J=6.1), 4.51 (m, 1H), 4.39 (m, 2H), 4.17 (t, 1H, J=6.1),3.67 (dd, 1H, J=13.7, 4.4),3.56 (dd, 1H, J=13.7, 7.3), 2.17 (dt, 1H, J=13.2, 2.4), 1.84 (dd, 1H, J=13.2, 11.2), 1.41 (d, 2H, J=6.8). ESI-HRMS m/z calcd for $C_{31}H_{31}NO_6S_2Na$, found.

(±)-N-[3-[(4S,5R,6R)-4-(1,4-dioxa-8-azaspiro [4.5]dec-8-ylmethyl)6-[4(hydroxymethyl)phenyl]-5-methyl-1,3-dioxan-2-yl]phenyl-benzenesulfonamide (10):

$^1$H NMR (500 MHz, $CDCl_3$): δ 7.78 (d, 2H, J=8.3), 7.55 (t, 1H, J=7.8), 7.45 (t, 2H, J=7.8), 7.4–7.2 (m, 7H), 7.04 (d, 1H, J=7.3), 6.81 (s, 1H), 5.71 (s, 1H), 5.08 (s, 1H), 4.77 (d, 1H, J=8.3), 4.70 (s, 2H), 4.00 (d, 2H, J=5.4), 3.98 (obs, 1H), 3.97 (d, 2H, J=5.4), 3.65 (d, 1H, J=12.2), 3.32 (d, 1H, J=13.2), 3.2–3.0 (m, 3H), 2.25 (td, 2H, J=13.2, 3.4), 1.96 (q, 1H, J=6.4), 1.87 (m, 2H), 0.68 (d, 3H, J=6.4). ESI-HRMS m/z calcd for $C_{32}H_{39}N_2O_7S$ 595.2478, found 595.2501.

(αS)-N-[3-[(4S,5R,6R)-4-[[4-(4-chlorophenyl)-4-hydroxy-1-piperidinyl]methyl]-6-[4-(hydroxymethyl)phenyl] 5-methyl-1,3-dioxan-2-yl]phenyl-α-[[(4-methylphenyl)sulfonyl]amino]-benzenepropanamide (11)

$^1$H NMR (500 MHz, $CD_3COCD_3$): δ 9.45 (br s, 1H), 7.76 (br s, 1H), 7.61 (d, 2H, J=8.3), 7.60 (obs, 1H), 7.55 (m, 1H), 7.33 (m, 9H), 7.17 (m, 7H), 7.14 (br s, 1H), 5.82 (s, 1H), 5.22 (s, 1H), 4.75 (m, 1H), 4.64 (s, 2H), 4.22 (m, 1H), 3.2–2.8 (m, 8H), 3.11 (dd, 1H, J=13.7, 6.3), 3.09 (dd, 1H, J=13.7, 8.3), 2.21 (s, 3H), 2.13 (br q, 1H, J=6.8), 1.81 (m, 2H), 0.74 (d, 3H, J=6.8). ESI-HRMS m/z calcd for $C_{46}H_{51}ClN_3O_7S$ 824.3136, found 824.3142.

(±)-N-[[4-(4R,6S)-4-[4-(hydroxymethyl)phenyl]-6-[[4-hydroxyphenyl)thio]methyl]-1,3-dioxan-2-yl]phenyl]methyl-benzenesulfonamide (12)

$^1$H NMR (500 MHz, $CD_3COCD_3$): δ 8.51 (s, 1H), 7.89 (d, 2H, J=7.3), 7.64 (t, 1H, J=4.9), 7.59 (d, 2H, J=7.3), 7.43 (d, 2H, J=8.1), 7.35 (m, 6H), 7.27 (d, 2H, J=8.1), 6.94 (t, 1H, J=6.3), 6.82 (d, 2H, J=8.3), 5.74 (s, 1H), 4.97 (dd, 1H, J=11.2, 2.4), 4.62 (d, 2H, J=6.3), 4.16 (obs t, 1H, J=6.3), 4.15 (obs, 1H), 4.14 (d, 2H, J=6.3), 3.12 (dd, 1H, J=13.7, 6.8), 2.99 (dd, 1H, J=13.7, 5.9), 2.13 (dt, 1H, J=13.2, 2.4), 1.65 (app q, 1H, J=13.2). ESI-HRMS m/z calcd for $C_{31}H_{31}NO_6S_2Na$ 600.1491, found 600.1515.

(±)-(1R,2S,3S)-1-[4-(hydroxymethyl)phenyl]-4-[(1-oxido-2-pyridinyl)thio]-2-phenyl-1,3-butanediol (13)

$^1$H NMR (500 MHz, $CD_3OD$): δ 8.27 (d, 1H, J=8.2), 7.39 (td, 1H, J=10.1, 1.8), 7.19 (m, 2H), 7.12 (m, 6H), 7.03 (dd, 2H, J=10.1, 1.8), 5.24 (d, 1H, J=11.4), 4.53 (td, 1H, J=9.6, 3.4), 4.47 (s, 2H), 3.28 (t, 1H, J=11.4), 3.07 (dd, 1H, J=16.7, 3.4), 2.82 (dd, 1H, J=16.7, 9.6). ESI-HRMS m/z calcd for $C_{32}H_{36}N_5O_6S$, found.

(αS)-2-acetyloxy)-N-[[4-[(4R,5S,6S)-4-[4-(hydroxymethyl)phenyl]-6-[[4,5-diphenyl-2-oxazolyl)thio]methyl]61, 3-dioxan-2-yl]phenyl]methyl-propionamide (14)

$^1$H NMR (500 MHz, $CD_3COCD_3$): δ 7.81 (br s, 1H), 7.45 (d, 2H, J=7.8), 7.31 (d, 2H, J=8.3), 7.24 (m, 9H), 6.10 (s, 1H), 5.23 (d, 1H, J=10.3), 5.12 (q, 1H, J=6.8), 4.74 (qd, 1H, J=8.2, 2.9), 4.52 (d, 2H, J=6.8), 4.43 (m, 2H), 4.10 (t, 1H, J=5.9), 3.92 (s, 3H), 3.45 (dd, 1H, J=13.6, 2.9), 3.38 (dd, 1H, J=13.6, 8.2), 3.19 (t, 1H, J=10.3), 2.09 (s, 3H), 1.42 (d, 3H, J=6.8). ESI-HRMS m/z calcd for $C_{32}H_{36}N_5O_6S$ 618.2386, found 618.2410.

Bead cleavage and formation of arrayed stock solutions. Acyl-1,3-dioxane resin (6) was distributed into ten 384 well polypropylene plates (Corning Costar, 40 μL well volume) using a bead arraying tool to give a single bead per well. A solution of 5% HF.py in THF (15 μL) was added to each well and sealed with foil for 1.5 h. Methoxytrimethylsilane (5 μL) was added using the Hydra 384 liquid transfer instrument (Robbins Scientific) equipped with Teflon coated needles. The solvent was evaporated and the Hydra 384 was used to add DMSO (5 μL) to the wells.

Use of mass spectrometry for molecular structure determination. LC-MS analysis was performed on a Micromass Platform LCZ-MS coupled to a Waters 2690 HPLC. Analyses were run using either an APCI or an ES interface with positive-negative ionization mode switching. Chromatography was over a 3.5 μm Waters Symmetry C18 column (50 mm×2.1 mm i.d.) eluting at 0.4 mL/min with a gradient of 15–100% B over 10 min (A=water+0.1% formic acid; B=acetonitrile+0.1% formic acid). An aliquot (0.25 μL) of the DMSO stock solution was removed and added to $CH_3CN$ (15 μL) in a glass autosampler vial insert. A 5 μL sample of the solution was injected.

V. EXAMPLE 3

Use of 1,3-dioxanes as Modulators of a Glucose-sensitive Subset of Genes Downstream of Ure2p The progress in identifying and expressing all human proteins (Wiemann et al. *Genome Res.* 2001, 11, 422–435) presents an opportunity to develop a small-molecule modulator for every protein function. Small molecule approaches to study protein function have illuminated diverse fields of biology. Examples include tetrodotoxin, which enabled the dissection of the action potential (Narahashi et al. *J. Gen. Physiol.* 1964, 47, 965–974), and agonists of peroxisome-proliferator-activated receptor γ such as rosiglitazone, which illuminated the regulation of adipogenesis (Lehmann et al. *J. Biol. Chem.* 1995, 12953–12956). However, in most cases no small molecule that can modulate the function of a protein of interest is known, and there is currently no efficient method of identifying these biological probes. Using the example of the yeast protein Ure2p, general two-step method has been demonstrated that does not require a high-resolution structure or a previously characterized small molecule known to bind the protein. First, diversity oriented synthesis is used to produce structurally complex and diverse small molecules efficiently. Second, the resulting compounds are screened for their ability to bind a protein of interest by using small-molecule microarrays, a technique for extremely high-throughput parallel-binding assays. Cell-based studies can subsequently determine which functions of the protein are modulated by each small molecule.

Figure 23A:
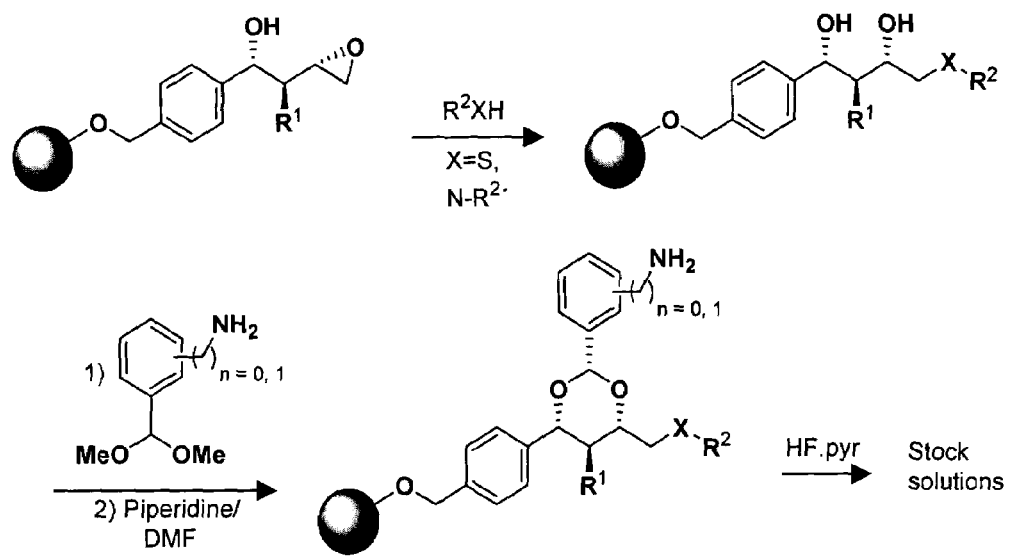
FIG. 23 depicts depicts the library synthesis and identification of uretupamine. (A) Outline of the diversity-oriented synthesis leading to uretupamine and other library members. (B) An expanded view of 64 compound spots on the 3,780-member small molecule microarray (~800 spots cm$^{-2}$). Cy5 labelled Ure2p was passed over a microarray of the 1,3-dioxane small molecule library, and the resulting slide was washed three times and scanned for fluorescence. The spot corresponding to uretupamine A is shown.
Figure 23B:
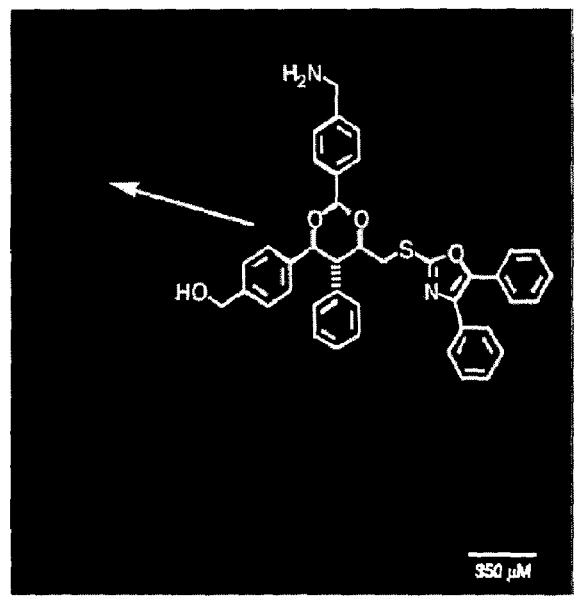

The yeast protein Ure2p has been widely studied in several different contexts. Ure2p is the central repressor of genes involved in nitrogen metabolism (Coschigano et al. *Mol. Cell Biol.* 1991, 11, 822–832), is capable of switching to a prion form (Wickner et al. *Science* 1994, 264, 566–569), and is part of a signalling cascade downstream of the Tor proteins (Hardwick et al. *Proc. Natl. Acad. Sci. U.S.A.* 1999, 96, 14866–14870; Cardenas et al. *Genes Dev.* 1999, 13, 3271–3279). Because there is no known small molecule that binds to Ure2p, a collection of 3,780 structurally complex 1,3-dioxane small molecules was screened resulting from a diversity-oriented synthesis (See, FIG. 23A). The molecules are structurally unbiased towards any particular protein target and can be used to identify specific probes for many different proteins. This collection of molecules had been prepared with a 'one bead-one stock' solution technology platform with the use of macrobeads (FIG. 23A) followed by automated compound cleavage and the generation of 5-mM stock solutions in 5 µl of N,N-dimethylformamide (Sternson et al. *J. Am. Chem. Soc.* 2001, 123, 1740–1747; Blackwell et al. *Chem. Biol.* 2001, 8, 1167–1182; Clemons et al. *Chem. Biol.* 2001, 8, 1183–1195). The small molecules were arrayed in high-density on glass slides (~800 spots/cm$^2$, 1 nl of each compound per slide) with a quill-pin contact-printing robot. These microarrays were probed with fluorescently labeled Ure2p, enabling the protein-binding properties of each molecule to be tested in parallel with minimal protein consumption (protein solution: 20 mg/ml, 0.2 ml). This method has been used to detect known interactions such as that between FKPB12 and a synthetic pipecolyl a-ketoamide and is applied here to the identification of novel small molecule-protein interactions with compounds. Eight compound spots on the microarrays showed reproducible binding to labelled Ure2p (see FIG. 23B for one such spot in an 8×8 spot array where each spot is derived from a single-compound stock solution derived from the diversity oriented synthesis).

Figure 24A:
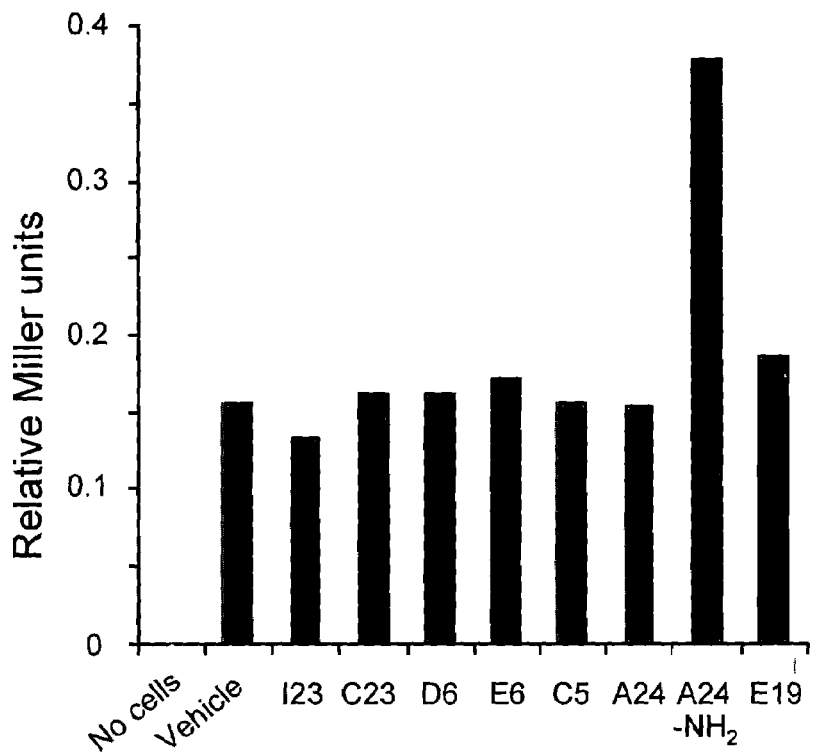
FIG. 24 depicts studies in vivo, dose response and structure-activity relationships of uretupamine. (A) A yeast strain (DB26-3A) growing in YPD medium expressing a PUT1-lacZ reporter was treated with 50 nM rapamycin or with a compound that had been detected to bind to labelled Ure2p on a small-molecule microarray. After 90 min of treatment at 30° C., a standard liquid b-galactosidase assay was performed. Data are expressed in fold Miller units compared with treatment with 50 nM rapamycin for 90 minutes. DB26-3A (MAT-a ura3-52 ade2 PUT1-lacZ) was a gift from M. Brandriss. Vehicle: samples treated with N,N-dimethylformamide (DMF), the vehicle into which library compounds were dissolved (B): Uretupamine A was resynthesized and tested in the b-galactosidase assay by using the PUT1-lacZ reporter at the concentrations indicated for 60 min at 30 C in YPD medium. (C) Compounds derived from the uretupamine A structure were synthesized to explore structure-activity relationships. Listed are b-galactosidase assay results of treatment with each compound at 100 μM (asterisk designates 50 μM) for 60 min at 30 C in YPD medium. Data are in percentage Miller units compared with treating with 50 nM rapamycin for 60 min. Ac, acetate; MDPO, 2-mercapto-4,5-diphenyloxazole; MBO, 2-mercaptobenzoxazole; Ph, phenyl. (D) Binding of uretupamine B to Ure2p was determined by using surface plasmon resonance (BIAcore 3000) to have a dissociation constant of 7.5 μM. Data points were acquired in triplicate. Ure2p was immobilized to CM5 sensor chips by injection of 100 μg/ml Ure2p in 10 mM sodium acetate pH 4.5 in accordance with the manufacturer's procedures. The reference cell was derivatized with antibodies against glutathione S-transferase (GST) followed by GST capture. Small-molecule binding measurements and dissociation were in PBS/Tween-20 containing 10% DMF flow rate 5 μl/min).
Figure 24B:
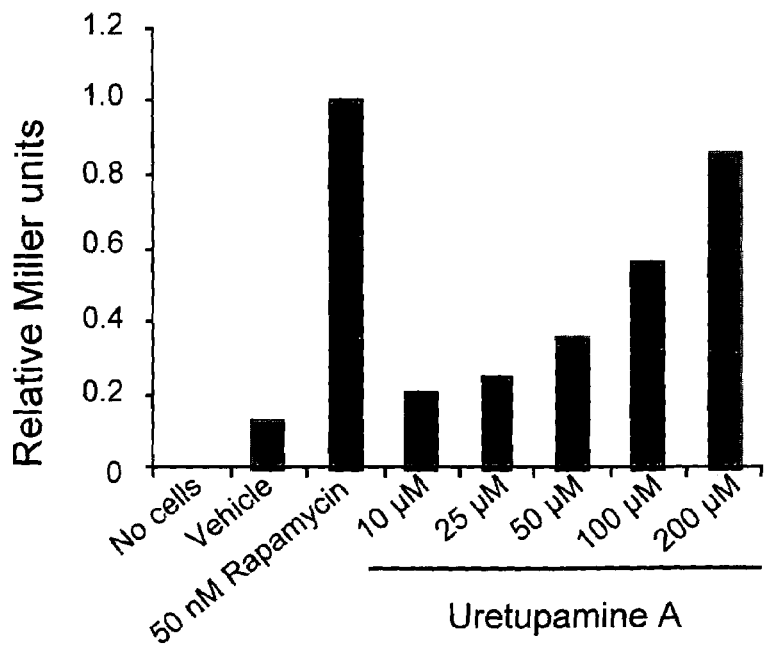

To determine cellular activity, the molecules comprising these spots were resynthesized and tested for the modulation of endogenous Ure2p function with a PUT1-lacZ reporter system because PUT1 expression is known to be repressed by URE2. In addition to the positive control of rapamycin, one of the eight compounds activated this reporter (FIG. 24A). The compound, which was named uretupamine A, gave a concentration dependent dose response that at higher concentrations approached the levels of reporter gene activation induced by rapamycin (FIG. 24B).

Figure 24C:
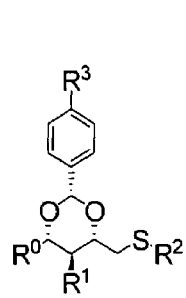
Figure 24D:
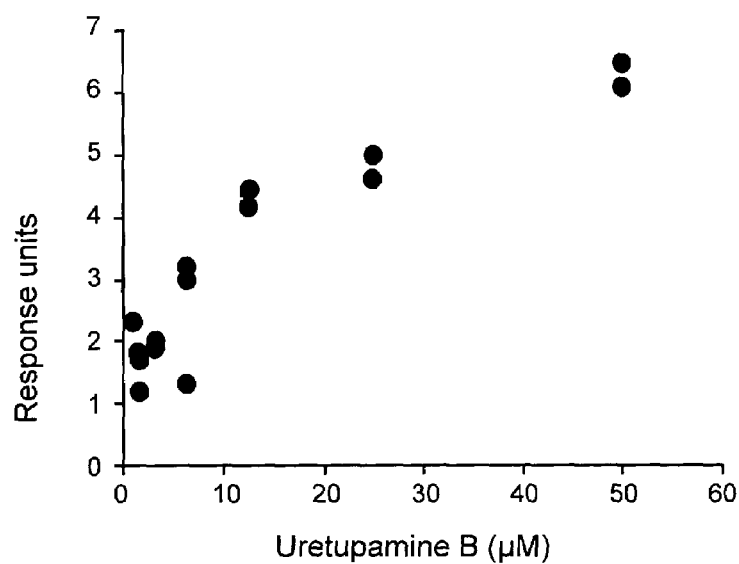

To explore structure-activity relationships, a series of compounds were synthesized with systematic variations in the structure of uretupamine A (FIG. 24C). Specific atomic interactions are believed to be responsible for uretupamine binding because most modifications of its structure resulted in a complete loss of activity (FIG. 24C). Uretupamine A was rendered functionally inactive by acylation of the primary amine, replacement of the diphenyloxazole moiety with a phenyl group or a benzoxazole group or modification of the benzyl alcohol moiety (FIG. 24C). However, the C-5 position of the dioxane ring was tolerant to the modification. Because the potency of uretupamine A was attenuated by poor solubility at higher concentrations in yeast medium, a more soluble derivative was synthesized, uretupamine B, which lacked the C-5 phenyl group on the dioxane ring (FIG. 24C). As expected uretupamine B was more potent than uretupamine A (FIG. 24C). Surface plasmon resonance was used to obtain a binding constant for uretupamine A and B binding to purified Ure2p. This demonstrated that uretupamine A and B bound to Ure2p with equilibrium dissociation constants of 18.1 and 7.5 µM, respectively (FIG. 24D), which is consistent with their potencies in cells.

Figures 25A, 25B, 25C:
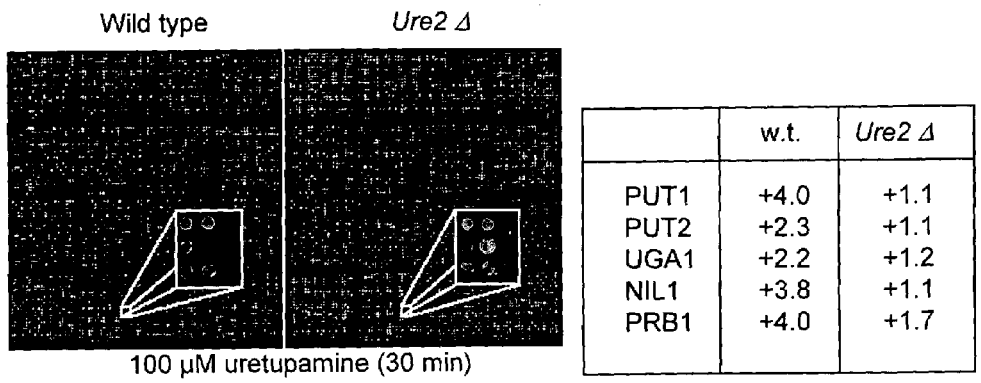
FIG. 25 depicts transcription profiling of treatment with uretupamine. (A) The left microarray corresponds to wildtyupe cells (PM38) treated with vehicle (DMF) versus wild type (w.t.) cells treated for 30 min with uretupamine A at 100 μM. The right microarray corresponds to ure2Δ cells (PH2) treated with vehicle versus ure2Δ cells treated for 30 min with uretupamine A at 100 μM. Profiles were obtained as described (Hardwick et al. *Proc. Natl. Acad. Sci. USA* 1999, 96, 14866–14870). At the right are shown specific gene inductions of some URE2-dependent genes from the microarrays. PM38 (MATaleu2-3, 112 ura3-52), PM71 (MATaleu2-3, 112 ura3-52 gln3Δ5::LEU2), MS221 (MATaura3-52 nil1::hisG), PH2 (MATaleu2-3, 112 ura3-52 ure2Δ12::URA3) were gifts from B. Magasanik and M. Brandriss. (B) The transcription profiles of wild-type cells (PM38), ure2Δ cells (PH2), gln3Δ cells (PM71) and nil1Δ cells (MS221) grown in YPD medium treated for 30 min with 100 μM uretupamine B were obtained. The geometric means of gene inductions of the sets listed are shown. (C) An analysis was performed based on treating individual profiles as high-dimensional vectors and then examining the ratios of their magnitudes as a measure of relative activity (Shamji et al. *Curr. Biol.* 2000, 10, 1574–1581; Kuruvilla et al. *Genome Biol.* 2002, 3(3), 0011.1–0011.11).

To determine the precise effects and specificity of uretupamine, whole-genome transcription profiling was used in wild-type cells as well as an otherwise isogenic ure2D strain-a 'targetless' strain (Marton et al. *Nature Med.* 1998, 4, 1293–1301). (Complete transcription profiling data are publicly available at http://www.schreiber.chem.harvard.edu) Both uretupamine A and B upregulated only a subset of genes (including PUT1, PUT2, PRB1, NIL1 and UGA11) known to be under the control of Ure2p (FIGS. 25A,B). The expression of other genes (including GAP1, MEP2, A AGP1, BAT2 and DAL5) controlled by Ure2p was essentially unchanged (FIGS. 25A,B). The compounds had little or no effect on either set of genes in a targetless ure2Δ strain, an otherwise identical strain lacking only the gene encoding the putative protein to which uretupamines A and B bind (FIGS. 25A,B). This result suggests that a small molecule readily obtained from diversity-oriented synthesis and screening with the use of smallmolecule microarrays has nearly complete cellular specificity for its screening partner, at least as judged by its global effects on the mRNA levels of treated cells.

Although Ure2p-controlled genes are normally thought of as responsive to nitrogen quality, the subset of genes induced by uretupamine (PUT1, PUT2, PRB1, NIL1, and UGA1) has been shown to be upregulated when glucose is removed from the media. The mechanism for this differential regulation of Ure2p-controlled genes in response to different nutrient signals is not understood. Ure2p represses transcription factors Gln3p and Nil1p, which might be differentially regulated to achieve this effect. To test this hypothesis, uretupamine B was profiled in gln3Δ and nil1Δ strains. Remarkably, it was found that deleting GLN3 had little effect on the actions of uretupamine, whereas deleting NIL1 abrogated its actions (FIG. 25B). Further confirmation for this selectivity comes from whole-genome vector-based comparisons of four profiles; these comparisons show that URE2 and NIL1, but not GLN3, are critical for uretupamine action (FIG. 25C). Northern blot analysis confirmed the effect of uretupamine B on PUT1 expression (normalized to ACT1 expression) in wild-type, gln3Δ and nil1Δ strains.

The fact that the binding of uretupamine to Ure2p induces the expression of glucose-sensitive genes in a NIL-1 dependent manner suggests that Ure2p might itself be the target of a glucose-sensitive pathway. This is in contrast to a glucose-sensitive pathway impinging on Nil1p, bypassing Ure2p.

Because Ure2p is a phosphoprotein, the phosphorylation state of Ure2p was examined after different types of nutrient shift. Wild-type cells were shifted from the high-quality nitrogen source, ammonium sulphate, to the low quality nitrogen source proline. Cells were also shifted from the high-quality (fermentable) energy source glucose to the low-quality (non-fermentable) energy sources acetate or glycerol. Surprisingly, Ure2p was not dephosphorylated when ammonium sulphate was removed but was dephosphorylated when glucose was removed (FIG. 26A). These data indicate that signals not previously thought to regulate Ure2p after its phosphorylation state, whereas signals previously thought to regulate Ure2p do not alter its phosphorylation state. Identical results were obtained for cells transferred from a glucose-containing medium and for cells of a different background (W303). Other stresses (such as 1M NaCl, 1 M sorbitol, pH 9.5 or heat shock) known to upregulate Ure2p-dependent genes did not cause Ure2p dephosphorylation (FIG. 26B). These data suggest that Ure2p is part of a signalling pathway that specifically responds to glucose.

Figures 26D, 26E:
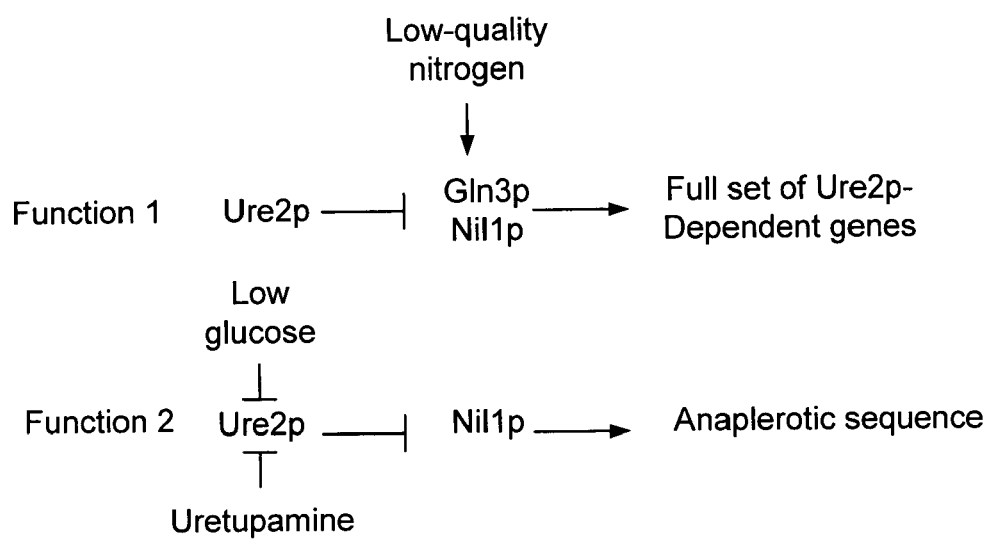
FIG. 26 depicts glucose-sensitive signalling and a model of Ure2p function. (A): A wild type strain (PM38) was grown to mid-exponential phase in synthetic glucose (dextrose) (SD)-ammonium sulphate (AS) medium, washed with PBS and split into either SD-AS medium, SD-AS medium containing 50 nM rapamycin, SD-proline medium, synthetic acetate-AS medium or synthetic glycerol-AS medium, then incubated with shaking for 1 h at 30° C. Control: the sample split into SD-AS medium. Synthetic medium consisted of 1.7 g of YNB medium, without amino acids and without AS, 2% carbon sourced, 0.1% nitrogen source and auxotrophic supplements when needed (leucine 120 mg I$^{-1}$, uracil 20 mg I$^{-1}$). Whole cell lysates were blotted with anti-Ure2p antibodies kindly provided by R. Wickner as described previously. A previous report claimed that Ure2p dephosphorylation does occur upon nitrogen limitation but those authors examined cells shifted from a rich medium to a synthetic-nitrogen-limited medium, thus changing many variables of the medium simultaneously. In experiments conducted herein, cells were shifted from a synthetic medium containing 0.1% ammonium sulphate as a high quality nitrogen source to an otherwise identical medium containing 0.1% proline as a low-quality nitrogen source. Inspection of published Ure2p immunoblots under similar conditions also supports the lack of a mobility shift (see, Edskes et al. *Genetics* 1999, 153, 585–594; Edskes et al. *Proc. Natl. Acad. Sci. U.S.A.* 2000, 97, 6625–6629). (B): A wild-type strain (PM38) was treated for 1 h with no drug, 50 nM rapamycin, salt stress (1M NaCl), high osmolarity (1M sorbitol) or high pH (pH 9.5). (C) A wild-type strain (PM38) was shifted from an SD-AS medium to a synthetic acetate—AS medium and incubated with shaking for 30 min at 30° C. This transcription profile was compared to the profile of the same strain shifted from SD-AS to synthetic ethanol-AS medium. The expression of various subsets of genes was compared between profiles by using vector algebra and the results are presented in a colorimetric comparison array. (D) Inspection of Ure2p-dependent genes reveals that uretupamine-sensitive genes behave similarly when cells are shifted to ethanol or acetate, whereas uretupamine-insensitive genes behave differently. (E) Nitrogen quality regulates the Ure2p-Gln3p/Nil1p complex by signalling to Gln3p/Nil1p, whereas low glucose concentration regulates the complex by signalling to Ure2p. Low glucose concentration leads to dephosphorylation of Ure2p to induce a specific set of genes involved in an anaplerotic sequence, a state mimicked by uretupamine.

Kornberg and Krebs first proposed that on energy sources such as acetate, metabolic sequences called anaplerotic are activated to replenish tricarboxylic-acid-cycle intermediates (Kornberg et al. Nature 1957, 179, 988–991). Yease cells growning in acetate-containing media have been shown to accumulate ammonia (Bogonez et al. Biochim. Biophys. Acta, 1983, 733, 234–241), which leads to the following paradox. Ammonia would repress the expression of Ure2p-dependent genes, including those thought to promote survival on acetate as part of an anaplerotic sequence (PUT1, PUT2 and UGA1). It is possible that acetate-induced Ure2p-dephosphorylation protects the anaplerotic sequence from this repression by ammonia. The transcription profile was performed of yeast shifted from glucose to acetate and compared it with that of cells shifted from glucose to ethanol. Genome-wide analysis showed that Ure2p dependent genes were differentially affected by the two transitions (FIG. 26C). Unlike ethanol, acetate caused the downregulation of some Ure2p-dependent genes, but, like ethanol, acetate induced those genes activated by uretupamine (FIG. 26D). Taken together, these data suggest that Ure2p-dephosphorylation stabilizes the induction of genes for an anaplerotic sequence when other cellular forces might repress the expression of these same genes (FIG. 26E).

The approach described herein to uncovering the role of Ure2p in glucose signalling is rooted in the principles of reverse genetics. A method of modulating Ure2p function selectively was desired to examine the resulting phenotype. Because uretupamine modulates only a subset of Ure2p function, its effects are more specific than those resulting from deletion of the URE2 gene. This property of uretupamine highlights the multifunctionality of individual proteins and addresses the challenge in proteomics to identify and control all possible inputs and outputs of each protein. With uretupamine, a functional connection has been demonstrated between Ure2p, Nil1p and glucose levels. A means to control this system more selectively than any physiological stimulus or genetic deletion has been demonstrated. Diversity-oriented synthesis and small-molecule microarrays provide a potentially systematic method for acquiring powerful probes, where different small molecules can modulate different aspects of a protein's function, preceding the discovery of a genetic allele of a similar phenotype.

VI. EXAMPLE 4

In Vivo Activity

Although a variety of methods can be utilized, one exemplary method by which the in vivo activity of the inventive compounds is determined is by subcutaneously transplanting a desired tumor mass in mice. Drug treatment is then initiated when tumor mass reaches approximately 100 mm$^3$ after transplantation of the tumor mass. A suitable composition, as described in more detail above, is then administered to the mice, preferably in saline and also preferably administered once a day at doses of 5, 10 and 25 mg/kg, although it will be appreciated that other doses can also be administered. Body weight and tumor size are then measured daily and changes in percent ratio to initial values are plotted. In cases where the transplanted tumor ulcerates, the weight loss exceeds 25–30% of control weight loss, the tumor weight reaches 10% of the body weight of the cancer-bearing mouse, or the cancer-bearing mouse is dying, the animal is sacrificed in accordance with guidelines for animal welfare.

VII. EXAMPLE 5

Assays to Identify Potential Antiprotozoal Compounds by Inhibition of Histone Deacetylase.

As detailed in U.S. Pat. No. 6,068,987, inhibitors of histone deacetylases may also be useful as antiprotozoal agents. Described therein are assays for histone deacetylase activity and inhibition and describe a variety of known protozoal diseases. The entire contents of U.S. Pat. No. 6,068,987 are hereby incorporated by reference.

VIII. EXAMPLE 6

Multi-dimensional Chemical Genetic Analysis of a Combinatorial Library of Deacetylase Inhibitors Using Cell-Based Assays Systematic chemical genetics aims to explore the space representing interactions between small molecules and biological systems. Beyond measuring binding interactions and enzyme inhibition, measuring changes in the activity of proteins in intact signaling networks is necessary. Toward this end, chemical space was partitioned into regions with different biological activities using a panel of cell-based assays and small molecule, "chemical genetic modifiers." In certain embodiments, this methodology was used for the discovery of 617 small molecule inhibitors of histone deacetylases from a multidimensional screen of the 1,3-dioxane library of the invention (See examples 1 and 2). Following decoding of chemical tags and re-synthesis, the selectivity of one inhibitory molecule (tubacin) toward α-tubulin deacetylation, and another (histacin) toward histone deacetylation was demonstrated. These small molecules will facilitate dissecting the role of acetylation in a variety of cell biological processes.

Models of complex biological systems highlight the interdependent and robust nature of biochemical networks [See for example, 1. Jeong, H., Tombor, B., Albert, R., Oltvai, Z. N., Barabasi, A. L. (2000). The large scale organization of metabolic networks. Nature 407, 651–654; 2. Albert, R., Jeong, H., Barabasi, A. L. (2000). Error and attack tolerance of complex networks. Nature 406, 378–382; 3. Maslov, S. and Sneppen, K. (2002). Specificity and stability in topology of protein networks. Science 296, 910–913; and 4. Mitchison, T. J. (1994). Towards a pharmacological genetics. Chem. Biol. 1, 3–6]. The development of experimental methods to modulate selectively the functions of individual nodes (representing proteins) in these networks is one aim of chemical genetics. Although chemical genetics is modeled after classical genetics, especially with respect to the logic of phenotype-based screening, it differs from classical genetics in the use of small molecules, rather than mutations, to perturb the function(s) of gene products [See for example, 1. Schreiber, S. L. and Bernstein, B. E. (2002). Signaling network model of chromatin. Cell, 111, 771–8; 2. Stockwell, B. R. (2000). Chemical genetics: ligand-based discovery of gene function. Nat. Rev. Genet. 1, 116–125; 3. Specht, K. M. and Shokat, K. M. (2002). The emerging power of chemical genetics. Curr. Opin. Cell Biol. 14, 155–159; 4. Schreiber, S. L. (2000). Target-oriented and diversity-oriented organic synthesis in drug discovery. Science. 287, 1964–1969; 5. Haggarty, S. J, Mayer, T. U., Miyamoto, D. T., Fathi, R., King, R. W., Mitchison, T. J., and Schreiber, S. L. (2000). Dissecting cellular processes using small molecules: identification of colchicine-like, taxol-like and other small molecules that perturb mitosis. Chem. Biol. 7, 275–286; and 6. Schreiber, S. L. (2003). Chemical Genetics. C&E News, 81, 51–61]. Given the temporal control offered by small molecules, and the ability to use combinations of small molecule modulators, chemical genetics promises to complement the use of pure genetic analysis to study a wide range of biological systems. Although the use of ribonucleic acid interference (RNAi) and related phenomena now provides a powerful reverse genetic approach for functional genomics, the inability to selectively target individual functions of proteins, to directly disrupt protein-protein interactions, and the extended temporal scale required for RNAi, limits the general application of this approach.

Diversity-oriented organic synthesis is increasingly providing complex and effective small molecule modulators of biological processes [See for example, 1. Schreiber, S. L. (2000). Target-oriented and diversity-oriented organic synthesis in drug discovery. Science. 287, 1964–1969; 2. Schreiber, S. L. (2003). Chemical Genetics. C&E News, 81, 51–61]. Challenges for chemical genetics include: 1) determining which of these molecules have specific effects upon biological systems (at various levels of resolution from proteins to whole organisms) and, 2) determining the structural and physiochemical properties of molecules that specify associated biological activities. These efforts will benefit from the systematic "mapping" of small molecules to positions in a multidimensional chemical space derived from molecular and/or biological descriptors. Toward this end, a multidimensional chemical genetic (MDCG) approach has been developed, using high-throughput phenotypic assays to partition chemical space into regions of different biological activities, as well as to partition biological space into regions with differential chemical activity (See, Haggarty et al., "Multidimensional Chemical Genetic Analysis of Diversity-Oriented Synthesis-Derived Deacetylate Inhibitors Using Cell-Based Assays", Chem. Biol., 10, 383–396 (2003)).

Figure 27A:
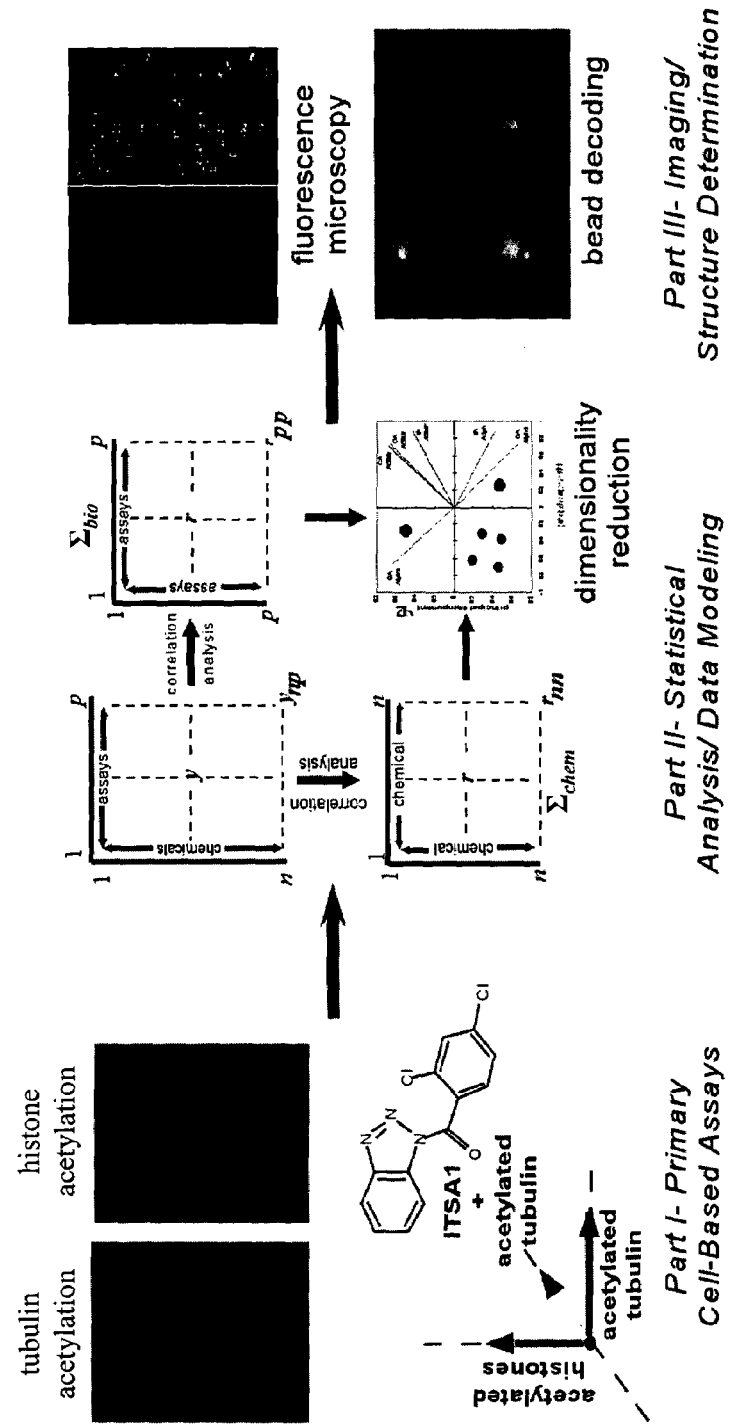
FIG. 27 depicts an overview of multidimensional chemical genetic analysis. (A) The three part protocol involved in screening of 7,392 diversity-oriented synthesis-derived deacetylase inhibitors. Chemical genetic information is obtained as 'object-observations' and arranged in a matrix, denoted by S. Each column ($y_j$) in S is a descriptor which corresponds to a phenotype from a cell-based or biochemical assay. Each row ($x_i$) in S is an object which corresponds to a chemical. An element (m, n) of S, encodes information about chemical m for descriptor n. [ITSA1 is a chemical genetic modifier that suppresses TSA-induced histone and α-tubulin acetylation; See, for example, Koeller, K. M., Haggarty, S. J., Perkins, B. D., Leykin, I., Wong, J. C., Kao, M. C., and Schreiber. S. L. (2003). Chemical Genetic Modifier Screens: small molecule trichostatin suppressors as probes of intracellular histone and tubulin acetylation. *Chem. Biol.* 10(5):397–4101]. (B) Summary of small molecules based upon a 1,3-dioxane structure and combinatorics of the full library. (C) Summary of screens performed and abbreviations used for the assays.

Similar to other research endeavors requiring multidimensional analysis, chemical genetic information can be arranged in a matrix, denoted S, consisting of an ordered array of columns and rows (FIG. 27A). Each column ($y_j$) in S, is a descriptor corresponding to a cell-based or biochemical assay, and is denoted by a bold-face, lower case letter subscripted j (where j=1 to n). Similarly, each row ($x_i$) in S corresponds to a chemical, and is denoted by a bold-face, lower case letter subscripted i (where i=1 to m). Accordingly, an element (m, n) of S encodes information about chemical m for descriptor n.

Geometrically, considering the elements of S as coordinates, chemicals (or assays) can be modeled as vectors, $x_i=[e_1, e_2, \ldots, e_n]$, in an n- (or m-) dimensional vector space. By defining the Euclidean distance D between two vectors (e.g., $x_1$ and $x_2$) in this vector space to be: $D_{12}^2=\Sigma[(x_1-x_2)^2]$, the space of chemical genetic observation can be considered as a metric space. That means that the relative distance D between chemicals $x_i$ (or assays $y_j$), in other words their proximity, becomes informative with respect to similarity between the particular descriptors considered. Accordingly, in analyzing chemical genetic data obtained from screening small molecule libraries, small molecules $x_i$ (or assays $y_j$) can be considered to be functionally similar if they are closely positioned (i.e., within a specified radius) in the underlying descriptor space. Since similarity between small molecules is determined by the pattern of interaction with biological systems, the corresponding distance metric D complements the definition of similarity obtained from calculated molecular descriptors based on chemical structure. Furthermore, since similarity in cell-based assays results from patterns of small molecules interacting with expressed gene products, the corresponding distance metric D complements the definition of similarity obtained from DNA sequence or gene expression analysis.

As part of this on-going effort, MDCG analysis has been applied to identify selective inhibitors of the family of zinc-dependent deacetylase enzymes typified by the histone deacetylases (HDACs) [See for example, 1. Boffa, L. C., Vidali, G., Mann, R. S., and Allfrey, V. G. (1978). Suppression of histone deacetylation in vivo and in vitro by sodium butyrate. J. Biol. Chem. 253, 3364–3366; 2. Yoshida, M., Kikima, M., Akita, M. and Beppu, T. (1990). Potent and specific inhibition of mammalian histone deacetylasse both in vivo and in vitro by trichostatin A. J. Biol. Chem. 265, 17174–17179; 3. Kijima, M., Yoshida, M., Sugita, K., Horinouchi, S., and Beppu, T. (1993). Trapoxin, an antitumor cyclic tetrapeptide is an irreversible inhibitor of mammalian histone deacetylases. J. Biol. Chem. 268, 22429–22435; 4. Taunton, J., Hassig, C. A., and Schreiber, S. L. (1996). A mammalian histone deacetylase related to the yeast transcriptional regulator rpd3p. Science 272, 408–411; 5. Grozinger, C. M., and Schreiber, S. L. (2002). Deacetylase enzymes: biological functions and the use of small molecule inhibitors. Chem. Biol. 9, 3–16; 6. Polevoda, B., and Sherman, F. (2002). The diversity of acetylated proteins. GenomeBiol. 3, reviews0006; 7. Khochbin, S., Verdel, A., Lemercier, C., and Seigneurin-Berny, D. (2001) Functional significance of histone deacetylase diversity. Curr. Opin. Genet. Dev. 11, 162–166; 8. Remiszewski, S. W. (2002). Recent advances in the discovery of small molecule histone deacetylase, inhibitors. Curr. Opin. Drug Discov. Devel. 5, 487–499; and 9. Johnstone, R. W. (2002). Histone-deacetylase inhibitors: novel drugs for the treatment of cancer. Nat. Rev. Drug Discov. 1, 287–299). Motivations behind the use of chemical genetic modifiers (e.g., ITSA1, "inhibitor of trichostatin A-1") in dissecting the role of HDACs in regulating cell cycle progression are described elsewhere [See, Koeller, K. M., Haggarty, S. J., Perkins, B. D., Leykin, I., Wong, J. C., Kao, M. C., and Schreiber. S. L. (2003). Chemical Genetic Modifier Screens: small molecule trichostatin suppressors as probes of intracellular histone and tubulin acetylation. Chem. Biol. 10(5):397–410]. The use of one selective inhibitor of α-tubulin deacetylation (tubacin) discovered in this analysis to dissect the function of HDAC6 as an α-tubulin deacetylase [Hubbert, C., Guardiola, A., Shao, R., Kawaguchi, Y., Ito, A., Nixon, A., Yoshida, M., Wang, X. F., and Yao, T. P. (2002). HDAC6 is a microtubule-associated deacetylase. Nature 417, 455–458] in mediating cell cycle progression, microtubule stability, and cell motility is described in Example 7. See, also, Haggarty, S. J., Koeller, K. M., Wong, J. C., Grozinger, C. M., and Schreiber. S. L. (2003). Domain-selective small molecule inhibitor of HDAC6-mediated tubulin deacetylation. Proc.

*Natl. Acad. Sci. USA.* 100, 4389–4394. Finally, a study toward the structural and physiochemical basis for the in vivo selectivity of HDAC inhibitors discovered in this analysis has been reported in Wong, J. C., Hong, R., and Schreiber, S. L. (2003). Structural biasing elements for in-cell histone deacetylase paralog selectivity. *J. Am. Chem. Soc.* 125(19):5586–7.

Results

Library Design and Outline of Multidimensional Chemical Genetic Analysis

The stereoselective synthesis of a small molecule library based on a 1,3-dioxane diversity element is described herein; See, in particular, Examples 1 and 2 above [See also, FIG. 27B; and Sternson, S. M., Wong, J. C., Grozinger, C. M., and Schreiber, S. L. (2001). Synthesis of 7200 small molecules based on a substructural analysis of the histone deacetylase inhibitors trichostatin and trapoxin. Org. Lett. 3, 4239–4242]. Each small molecule contains a metal-chelating functional group (e.g., o-aminoanilide, carboxylic acid, or hydroxamic acid) at position R' (See, FIG. 27B). Without wishing to be bound to any particular theory, it is thought that, since HDACs are zinc-dependent hydrolases [See for example, Finnin, M. S., Donigian, J. R., Cohen, A., Richon, V. M., Rifkind, R. A., Marks, P. A., Breslow, R., and Pavletich, N. P. (1999). Structures of a histone deacetylase homologue bound to the TSA and SAHA inhibitors. *Nature* 401, 188–193], metal chelators "bias" the inventive library toward deacetylase inhibition. Prior to screening the full 7,392-member library, a pilot screen of five representative small molecules indicated that these compounds inhibited HDACs 1, 4 and 6 in vitro, and four of five also induced α-tubulin acetylation (low µM range; data not shown) [See for example, Pipemo, G., and Fuller, M. T. (1985). Monoclonal antibodies specific for an acetylated form of alpha-tubulin recognize the antigen in cilia and flagella from a variety of organisms. *J. Cell Biol.* 101, 2085–2094]. Consequently, since determining the relative activity and selectivity of these small molecules was one objective, a line of study became identifying compounds that caused a differential increase in α-tubulin acetylation and histone acetylation as indicators of cytoplasmic and nuclear deacetylase inhibition, respectively.

Based on our previous success using miniaturized cytoblot cell-based assays [See for example, 1. Haggarty, S. J, Mayer, T. U., Miyamoto, D. T., Fathi, R., King, R. W., Mitchison, T. J., and Schreiber, S. L. (2000). Dissecting cellular processes using small molecules: identification of colchicine-like, taxol-like and other small molecules that perturb mitosis. *Chem. Biol.* 7, 275–286; and 2. Stockwell, B. R., Haggarty, S. J., and Schreiber, S. L. (1999). High-throughput screening of small molecules in miniaturized mammalian cell-based assays involving post-translational modifications. *Chem. Biol.* 6, 71–83], a three-part screen compatible with the amount of compound available from a "one bead-one stock solution" approach to chemical genetics was developed [See for example, 1. Walling, L. A., Peters, N. R., Horn, E. J., and King, R. W. (2001). New technologies for chemical genetics. *J. Cell Biochem. Suppl.* 37, 7–12; 2. Blackwell, H. E., Perez, L., Stavenger, R. A., Tallarico, J. A., Cope Eatough, E., Foley, M. A., and Schreiber, S. L. (2001). A one-bead, one-stock solution approach to chemical genetics: part 1. *Chem. Biol.* 8, 1167–1182; 3. Clemons, P. A., Koehler, A. N., Wagner, B. K., Sprigings, T. G., Spring, D. R., King, R. W., Schreiber, S. L., and Foley, M. A. (2001). A one-bead, one-stock solution approach to chemical genetics: part 2. *Chem. Biol.* 8, 1183–1195]. Using antibodies specific to the acetylated state of α-tubulin and acetylated histones (FIG. 27A Part I) [See for example, Piperno, G., and Fuller, M. T. (1985). Monoclonal antibodies specific for an acetylated form of alpha-tubulin recognize the antigen in cilia and flagella from a variety of organisms. *J. Cell Biol.* 101, 2085–2094], assay conditions were optimized separately using HDAC inhibitor trichostatin A (TSA) as a positive control for inhibition of both histone and α-tubulin deacetylation [See for example, 1. Yoshida, M., Kikima, M., Akita, M. and Beppu, T. (1990). Potent and specific inhibition of mammalian histone deacetylasse both in vivo and in vitro by trichostatin A. *J. Biol. Chem.* 265, 17174–17179; and 2. Koeller, K. M., Haggarty, S. J., Perkins, B. D., Leykin, I., Wong, J. C., Kao, M. C., and Schreiber. S. L. (2003). Chemical Genetic Modifier Screens: small molecule trichostatin suppressors as probes of intracellular histone and tubulin acetylation. *Chem. Biol.* 10(5):397–410]. The antibody utilized to evaluate the level of histone acetylation (anti-acetylated lysine antibody) reacts with a variety of proteins by western blotting. However, under cytoblot conditions, this antibody recognized predominantly nuclear proteins, as judged by fluorescence microscopy. Thus, without wishing to be bound to any particular theory, we propose that the acetylated lysine cytoblot is effectively a measure of histone acetylation, as histones are the predominant nuclear acetylated proteins. The chemical genetic modifier ITSA1 (FIG. 27C), which suppresses (reduces) the ability of TSA to increase acetylation levels of both α-tubulin and histones [Koeller, K. M., Haggarty, S. J., Perkins, B. D., Leykin, I., Wong, J. C., Kao, M. C., and Schreiber. S. L. (2003). Chemical Genetic Modifier Screens: small molecule trichostatin suppressors as probes of intracellular histone and tubulin acetylation. *Chem. Biol.* 10(5):397–410], was introduced as another variable in the screening strategy. ITSA1 suppresses hydroxamic acid-based (such as TSA), but not epoxy ketone-based (such as trapoxin) deacetylase inhibitors. Thus, using ITSA1 in our screen allowed identification of both "TSA-like" and "trapoxin-like" small molecule deacetylase inhibitors, based on the ability to be suppressed by ITSA1.

Following cytoblot analysis, statistical properties were calculated for each of the screening datasets (FIG. 27A Part II). Using an empirically determined threshold for bioactivity, a discrete model of these data was constructed in the form of a chemical genetic network and topological properties of the resulting graph calculated. To determine global relationships between assay variables and regions of different bioactivity, both clustering and principal component analysis were used. Subsequently, small molecules of interest were retested from the sample stock solution by fluorescence microscopy (FIG. 27A Part III). This secondary assay allowed assessment of selectivity in an independent manner, and to determine whether small molecule "hits" had other effects on cellular morphology, viability, and chromatin conformation.

Screening Results

Figure 28A:
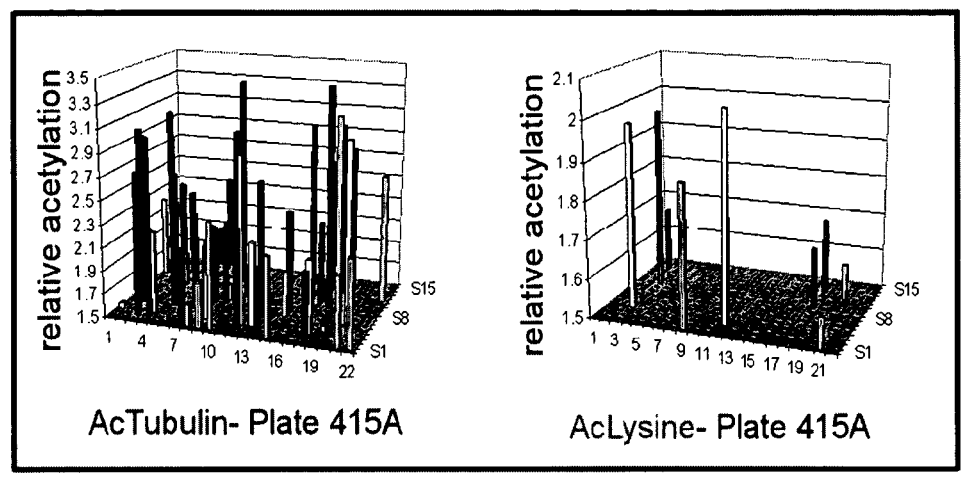
FIG. 28 depicts a statistical analysis of the biological activity of the 1,3-dioxane library. (A) Example of raw screening data of one 384-well plate from the AcTubulin and AcLysine assays with the relative acetylation level corresponding to the fold-change in signal compared to background. (B) Average (n=7 plates) correlation of duplicate plates within the set of hydroxamic acids. (C) Box-plot showing summary of statistical properties of the screening data from the three structural classes of deacetylase inhibitors after averaging duplicate data and $Log_2$-transformation. Top and bottom numbers (black) are the highest and lowest extremes, respectively. Blue numbers are the median values and red numbers the mean value for each distribution. The inner box represents the upper and lower bound of the third and first quartile, respectively, which contains 50% of the distribution. The upper and lower bars represent 1.5-times the spread of the third to first quartile with black/white dots representing small molecules outside this range. (D) Number of bioactive small molecules and distribution amongst the three structural classes using a normalized acetylation value of 1.5 as the criterion.
Figure 28B:
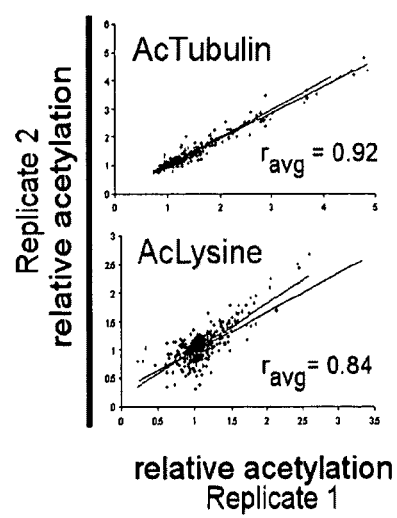
Figure 28C:
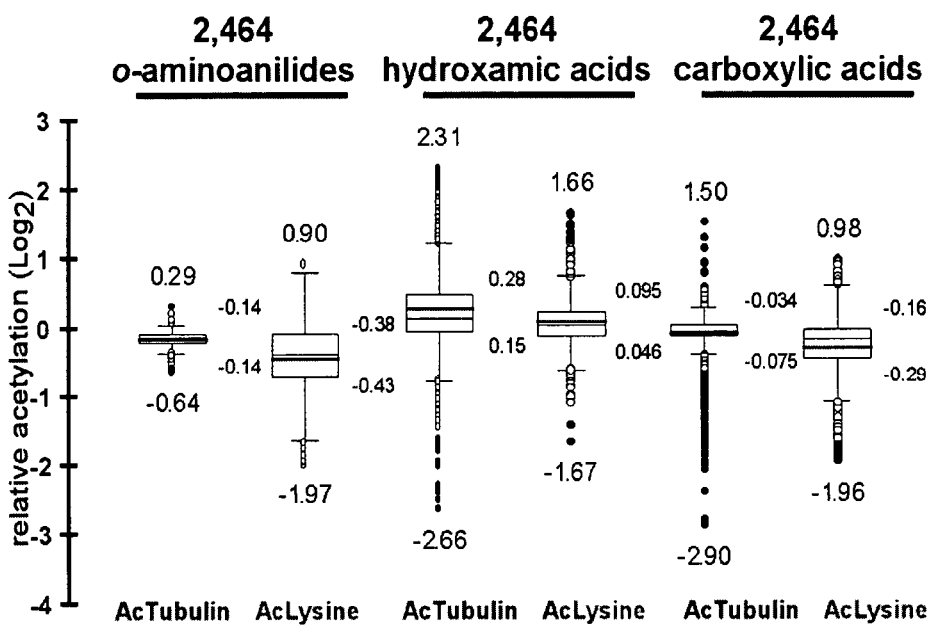
Figure 28D:
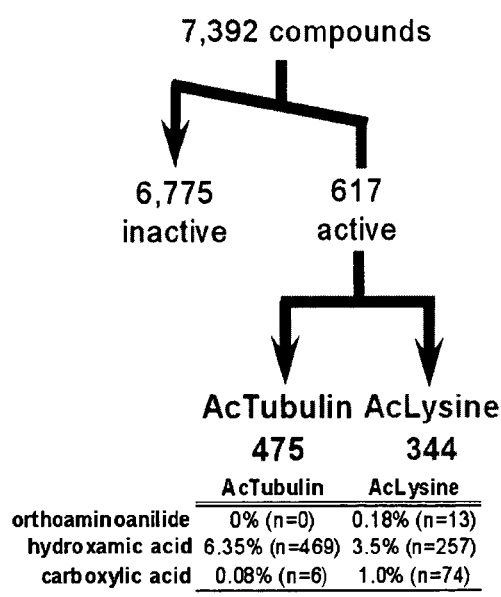

A summary of the cell-based assays performed is shown in FIG. 27C. Following robotic pin-transfer [Walling, L. A., Peters, N. R., Horn, E. J., and King, R. W. (2001). New technologies for chemical genetics. J. Cell Biochem. Suppl. 37, 7–12], the 1,3-dioxane-based small molecules (~2–5 µM depending upon efficiency of synthesis and amount of compound pin-transferred) were incubated with cells for a total of 18 hours. The entire collection of 7,392 molecules was screened (in duplicate) in the AcTubulin and AcLysine cytoblot assays (e.g., (FIG. 28A). A subset of the library was then further evaluated in three other acetylation-based assays, including one involving the suppressor ITSA1. Correlation between replicates was strong, with r=0.84 (p-value<0.05) representing the minimum correlation between duplicate plates containing hydroxamic acids (FIG. 28B). Values from replicates were standardized to a control from each plate, averaged, and $Log_2$-transformed to reduce the skewness and kurtosis prior to fitting to a normal distribution. Statistical properties pertaining to each R' biasing element (i.e., metal chelator) in the library are shown in the box-plots in FIG. 28C. Since diversity position R' was encoded spatially, as well as by tagging, we were able to determine the relative distribution of bioactive small molecules amongst the three biasing elements. Under the assumption of equal synthetic efficiency and purity, the hydroxamic acids were assessed to be most active and the o-aminoanilides least active in both the AcTubulin and AcLysine assays (FIG. 28D).

Figure 29A:
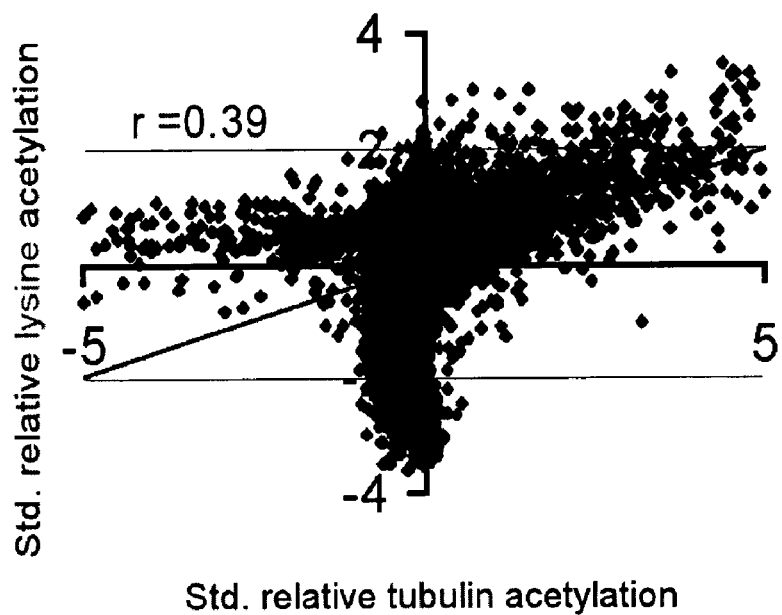
FIG. 29 depicts a correlation between AcTubulin and AcLysine assays and suppression of α-tubulin acetylation by ITSA1. (A) Linear correlation of the normalized acetylation values of the 7,392 members of the 1,3-dioxanes in the AcLysine and AcTubulin assays. (B) 617 of the total library members with bioactivity using a 1.5-fold increase in the normalized acetylation value as the criterion (blue, active in both the AcTubulin and AcLysine assays; green, active in only the AcLysine assay; red, active only the AcTubulin assay). (C) Venn diagram of the 617 bioactive small molecules deconvoluted into selective and overlapping sets. (D) ITSA1 (50 μM) suppressed the increased α-tubulin acetylation (yellow line) induced by most, but not all, of the top 100 ranked positives in the AcTubulin assay (red line.
Figure 29B:
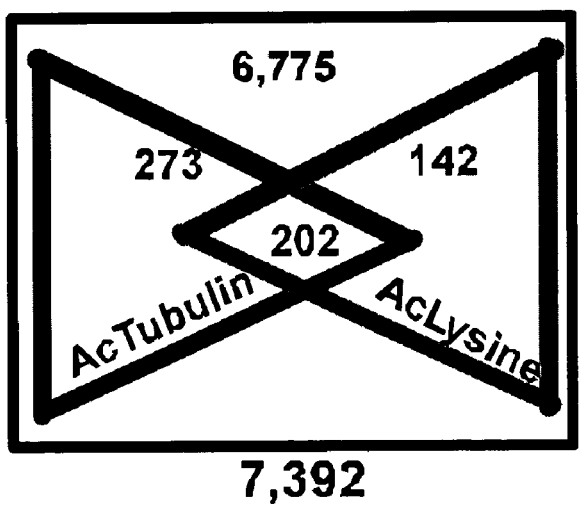
Figure 29C:
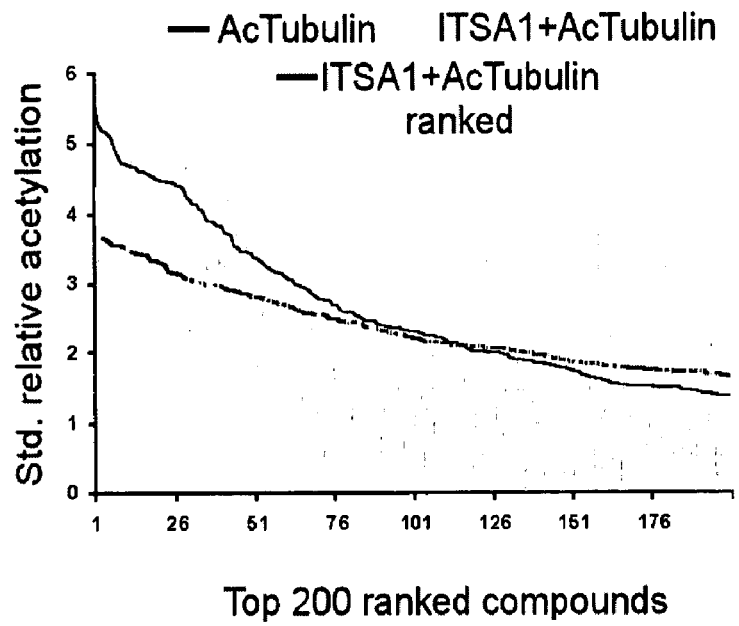

After separately fitting relative acetylation data from the AcTubulin and AcLysine assays to a normal distribution, a value corresponding to a 1.5-fold or greater increase was chosen as the criterion for bioactivity. Accordingly, 617 small molecules were active in at least one assay, with 475 small molecules active in the AcTubulin assay, and 344 small molecules active in the AcLysine assay (FIG. 28D). Overall, a significant correlation (r=0.39, p-value <0.05) exists between the normalized acetylation level in the AcTubulin versus the AcLysine assays (FIG. 29A). Indeed, deconvolution of the 617 hit compounds into those specific for the AcTubulin (273) or the AcLysine (142) assay, revealed that 202 (33%) molecules scored in both assays (FIGS. 29B, C).

Because there was an unequal distribution of positives toward those small molecules containing hydroxamic acids at diversity position R' in both the AcTubulin and AcLysine cytoblots, we focused subsequent screening efforts on the 2,464-member hydroxamic acid subset of the 1,3-dioxane library. These compounds were screened in the AcTubulin assay in the presence of chemical genetic modifier ITSA1, which suppresses trichostatin-induced histone and α-tubulin acetylation [Koeller, K. M., Haggarty, S. J., Perkins, B. D., Leykin, I., Wong, J. C., Kao, M. C., and Schreiber. S. L. (2003). Chemical Genetic Modifier Screens: small molecule trichostatin suppressors as probes of intracellular histone and tubulin acetylation. *Chem. Biol.* 10(5):397–410]. Two additional assays were employed to measure acetylation of histone H3 (AcHisH3), and histone H4 (AcHisH4). Using the same statistical analyses and threshold used for the AcTubulin and AcLysine assays, 137 small molecules caused increased α-tubulin acetylation in the presence of ITSA1, 229 caused an increase in AcHisH3, and 231 caused an increase in AcHisH4.

Suppression of α-tubulin Acetylation by the Chemical Genetic Modifier ITSA1

Figure 29D:
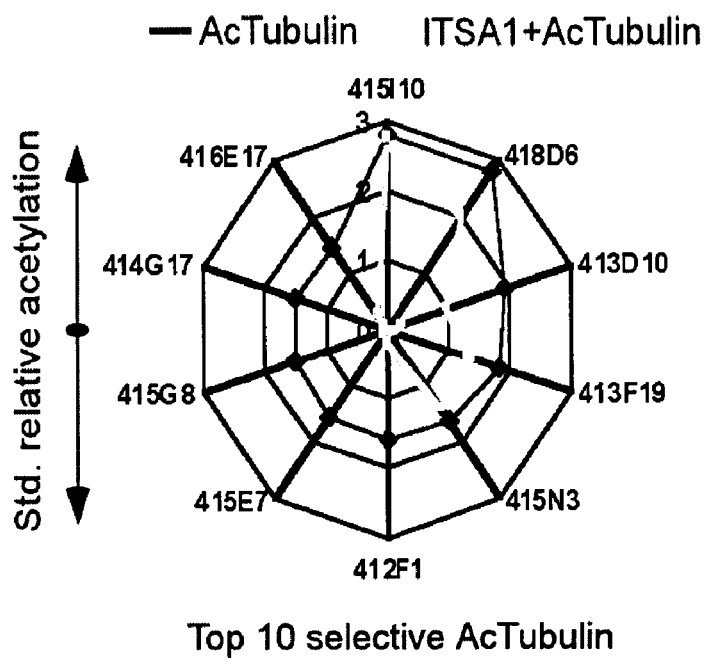

Over the hydroxamic acid subset, the correlation between the AcTubulin and AcTubulin+ITSA1 assays remained significant (r=0.65, p-value <0.05). However, in the AcTubulin+ITSA1 cytoblot, reduction in the number of positives (137 versus 475) indicates that ITSA1 effectively suppressed many of the inducers of α-tubulin acetylation. ITSA1-resistant small molecules are, in general, among the most potent inducers of α-tubulin acetylation (FIG. 29D). Interestingly, not all of the hydroxamic acids that induced α-tubulin acetylation were suppressed by ITSA1, making it unlikely that ITSA1 reacts directly with this functional group.

Representation of Screening Results as a Chemical Genetic Network

Figure 30A:
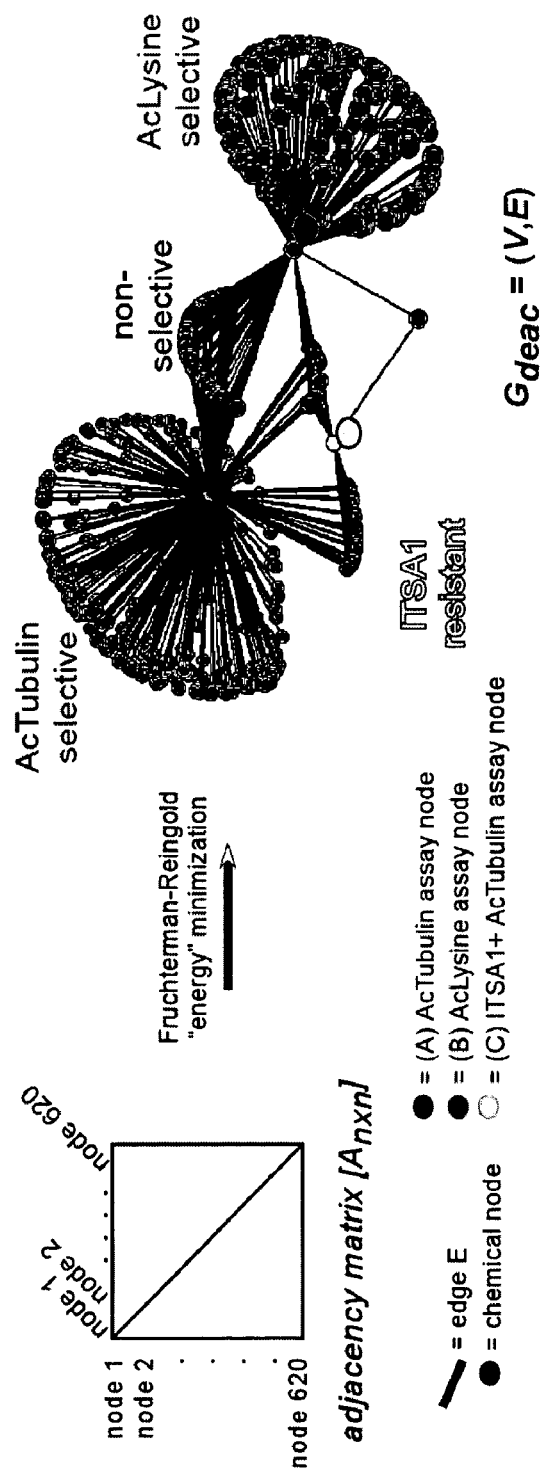
FIG. 30 depicts a chemical genetic network from screening data. (A) Adjacency matrix and resulting graph ($G_{deac}$) after applying the Fruchterman-Reingold "energy" minimization algorithm. Nodes represent either assays or small molecules according to the indicated colors. Edges (black lines) connect bioactive small molecules to the corresponding assay. (B) 'Retrosynthetic analysis' of $G_{deac}$ through decomposition into the sub-graphs from all six combinations of assay data. (C) Comparison of the information content in the six sub-graphs, relative to the full graph, using graph-theoretical descriptors. The adjacency index is defined to be the sum of the lengths of minimal paths between all pairs of vertices. Since all edges are of equal length in these particular cases, this is equal to half the sum of all entries in the adjacency matrix: $W=[\Sigma\Sigma A_{n\times n}]/2$. The Zagreb M1 index is defined as the sum of the squares of the vertex connectivities: $Z=\Sigma c_n^2$, where $c_n$ is the number of edges from a particular vertex n. The Randic connectivity index, which encodes information about branching, is defined as $^1\chi_p=\Sigma (c_n c_m)^{-1/2}$, where $c_n$ and $c_m$ are the number of edges of adjacent vertices joined by each edge summed over all edges. For all three indices, a high value corresponds to a high percentage of the particular type of topological property in the graph being analyzed.

To visualize patterns and compute global properties of MDCG screening data, a general approach for analyzing networks of interactions would be useful. Accordingly, using principles from graph theory [1. Balaban, A. T. (1976). Chemical Applications of Graph Theory. (London: Academic Press); and 2. See vlado.fmf.uni-lj.si/pub/networks/pajek/] the screening data were used to construct a symmetric, square adjacency matrix ($A_{n \times n}$). Here, n equals the number of vertices/nodes (V), representing an assay or one of the 617 total active small molecules. In $A_{n \times n}$, each element $a_{ij}$=1 if the vertices $v_i$ and $V_j$ are connected by an edge (E), which indicates the activity of compound $v_i$ in assay $v_j$. Alternatively, $a_{ij}$=0, which indicates the inactivity of compound $v_i$ in assay $v_j$. From the information encoded in this adjacency matrix, the corresponding bipartite graph, $G_{deac}$=(V, E) was constructed (FIG. 30A). To aid in visualization of the graph, we applied the Fruchterman-Reingold algorithm [1. See vlado.fmf.uni-lj.si/pub/networks/pajek/; and 2. Fruchterman, T. M. G., and Reingold, E. (1991). Graph drawing by force-directed placement. Software-Practice and Experience 21, 1129–1164]. This algorithm is a 'spring-embedder' that considers the graph as a physical system composed of charged masses (vertices V) repelling each other, and connecting springs (edges E) pulling adjacent vertices together. The algorithm minimizes the 'energy' of the system when embedding the graph into a 2- or 3-dimensional space. Overall, using a 1.5-fold minimum normalized acetylation value as the criterion for 1,3-dioxane bioactivity, the resulting graph ($G_{deac}$) contains 620 nodes V (617 from chemicals; 3 from assays), 956 edges E, and has a bipolar, spindle-like structure (FIG. 30A). Here, edges on the ends of the graph generally represent small molecules selective for either the AcTubulin or AcLysine assays, as they radiate singly from their respective nodes. In the center of $G_{deac}$ are the most highly connected nodes of the chemical genetic network. These are the subset of small molecules that scored in both the AcTubulin and AcLysine assays, a portion of which also scored in the ITSA1+AcTubulin assay. Small molecules not suppressed in ITSA1+AcTubulin are either the most potent α-tubulin deacetylase inhibitors, or act mechanistically distinct from TSA. Thus, by further subdividing small molecules based upon interaction with ITSA1, five classes of deacetylase inhibitors with different patterns of bioactivity are observable in $G_{deac}$.

Figure 30B:
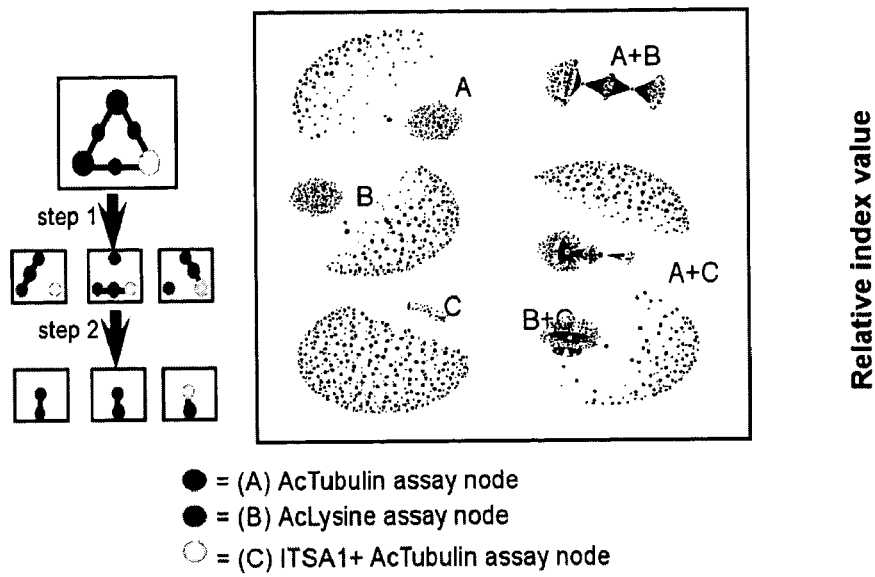
Figure 30C:
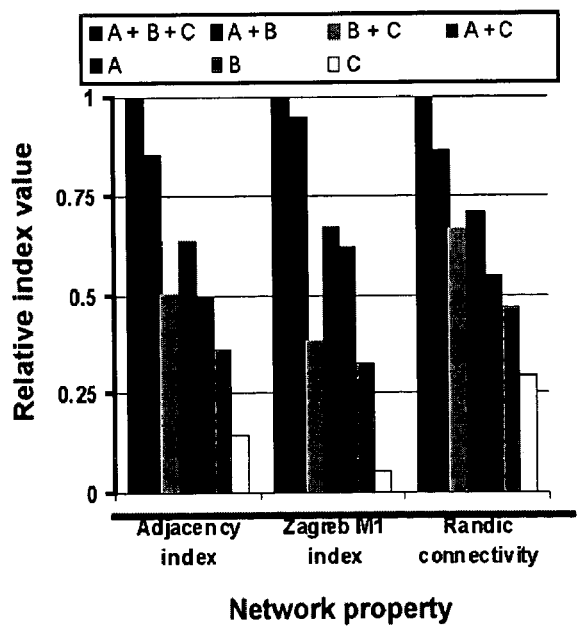

Small molecules are now routinely compared by decomposing their structures into components using molecular descriptors (e.g., cLogP, molecular weight, Chi connectivity indices). By analogy, in order to quantify the information obtained in each assay, and to compare the structure of the resulting networks, the adjacency matrix $A_{n \times n}$ was recursively decomposed into six sub-matrices. To quantitatively compare these six networks, we computed a set of three graph-theoretical descriptors for the corresponding networks (FIGS. 30B, C) [1. Balaban, A. T. (1976). Chemical Applications of Graph Theory. (London: Academic Press); and 2. See vlado.fmf.uni-lj.si/pub/networks/pajek/]. Based on the relative differences in these descriptors, the most complex subgraph was that of AcTubulin+AcLysine (A+B). Since the ITSA1+AcTubulin assay (C) did not contribute new nodes to the graph (compare A+B to complete graph A+B+C in FIG. 30A), all small molecules that scored in the ITSA1+AcTubulin assay (C) also scored in the AcTubulin assay (A). Overall, the A+C and B+C subgraphs were similar with respect to the adjacency and Randic connectivity indices, but B+C had a lower value for the Zagreb index, indicating lower vertex connectivity.

Global Analysis of Screening Data: Hierarchical Clustering and Principal Component Analysis One objective of this study was to determine the similarity/differences of chemicals based upon their biological interactions, or of biological assays based upon their chemical interactions. Toward this end, standardized covariance matrices were computed from the original chemical genetic data matrix using the Pearson correlation coefficient. Covariance matrices are square, symmetric matrices with off diagonal elements representing the correlation between descriptors. For all observed phenotypes, MDCG assigns an n-dimensional operator, $\Sigma_{bio}$, represented by a standardized covariance matrix that is computed globally across the set of n biological assays. Similarly, for all observed chemicals, MDCG assigns an m-dimensional operator $\Sigma_{chem}$ represented by a standardized covariance matrix that is computed globally across the set of m small molecules. This information can be further analyzed using clustering algorithms and other methods of pattern finding.

Figure 31:
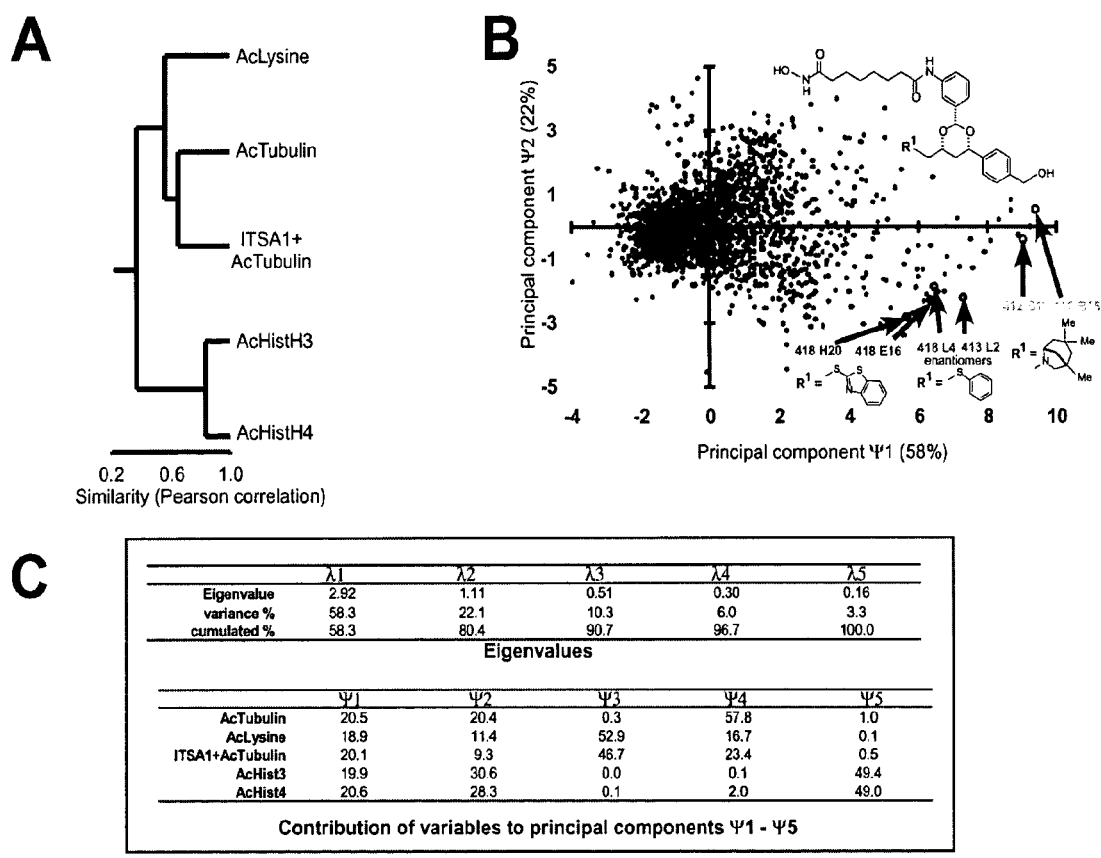
FIG. 31 depicts a hierarchical clustering and principal component analysis of 2,464 hydroxamic acids from a five-dimensional chemical genetic data matrix. (A) Dendrogram from clustering the standardized covariance matrix of chemical genetic assay data ($\Sigma_{bio}$) using the unweighted pair-group average method and Pearson correlation as the distance metric. (B) The principal components are obtained by solving the algebraic eigenvalue problem: $\Lambda=\Psi^T\Sigma_{bio}\Psi$, where $\Lambda$ is the eigenvalue matrix, $\Psi$ is the eigenvector matrix, $\Sigma_{bio}$ is the standardized covariance matrix of chemical genetic assay data, and T denotes a transpose of a matrix. $\Psi$ defines a coordinate transform (rotation) that best decorrelates the data into orthogonal linear subspaces. The chart shown plots the location of the hydroxamic acids (blue dots) on the reduced space formed by the first and second principal components. Position and structures of three of the decoded small molecules (colored) chosen for their overall activity are shown. (C) Summary of variance accounted for by each eigenvalue ($\lambda 1-\lambda 5$) and the contribution of each of the five original assay variables to the principal component ($\Psi_1-\Psi_5$).

Clustering was applied to data from the hydroxamic acid subset of the library across five different cell-based assays. This analysis indicated the greatest similarity between the AcTubulin and ITSA1+AcTubulin data sets, when compared to any of the assays measuring histone acetylation levels (FIG. 31A). Regarding the three acetyl-histone assays, the AcHisH3 and AcHisH4 assays are more correlated to each other than either is to the AcLysine assay. Overall, these results demonstrate that while there is redundancy between the assays, global differences exist in the window of biology described.

A principal component model was then computed [1. Legendre, P. and Legendre, L. (1998). Numerical Ecology-Developments in Environmental Modeling (New York: Elsevier); and 2. Hotelling, H. (1931). Analysis of a complex of statistical variables into principal components. J. Educ. Psychol. 24, 417–441; see Data analysis] from the standardized covariance matrix of the hydroxamic acid subset (FIG. 31B). The result is a global model that provides a visualizable representation of a chemical space that minimizes the information lost upon projection of the elements into a reduced space of 1–3-dimensions. Accordingly, principal components can be used to position chemicals, with respect to the new system of coordinate axes, in terms of a linear combination of the original assay variables. Using this method, principal component analysis (PCA) revealed that 58% of the information in the data set is accounted for in a one-dimensional space represented by the first principal component ($\Psi_1$). The second principal component ($\Psi_2$) represents a total of 22% of the information. Examination of the relative contribution of the different assays and small molecules to the information represented on $\Psi_1$ indicated that this component represents a composite measure of the activity of small molecules in all five assays (FIG. 31C) (see below for details of structures and use of this model in determining regions of selectivity).

Figure 32:
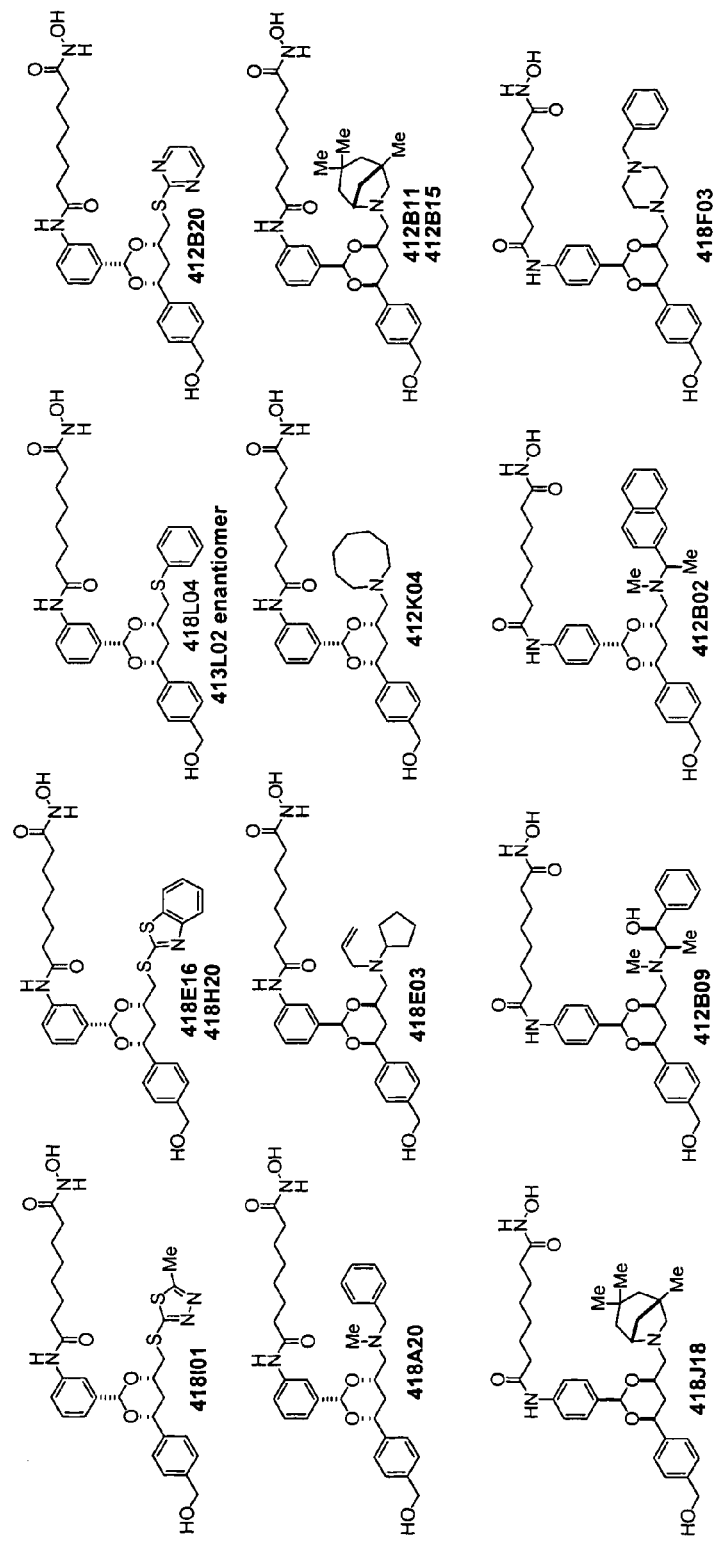
FIG. 32 depicts most potent 1,3-dioxane-based inhibitors of α-tubulin and histone deacetylation. Structures from decoded beads corresponding to wells that scored amongst the highest in the AcTubulin and AcLysine cytoblot assays. These compounds are like trichostatin in that they inhibit both α-tubulin deacetylation and histone deacetylation, but differ from trapoxin/HC toxin, which have no effect upon α-tubulin acetylation levels.

Correlating Chemical Structure with Activity: Hydroxamic Acids are the Most Bioactive Small Molecules Across Assays Seventeen small molecules exhibiting the highest levels of activity in both the AcTubulin and AcLysine assays were selected for bead-decoding and structure determination (see supplementary data FIG. 32) [See for example, Sternson, S. M., Wong, J. C., Grozinger, C. M., and Schreiber, S. L. (2001). Synthesis of 7200 small molecules based on a substructural analysis of the histone deacetylase inhibitors trichostatin and trapoxin. Org. Lett. 3, 4239–4242; and 2. Blackwell, H. E., Perez, L., Stavenger, R. A., Tallarico, J. A., Cope Eatough, E., Foley, M. A., and Schreiber, S. L. (2001). A one-bead, one-stock solution approach to chemical genetics: part 1. Chem. Biol. 8, 1167–1182]. Notably, of the 15 structures determined successfully, all are hydroxamic acids with six-carbon linkers. In addition, two molecules were present in duplicate within the set of 15, and both enantiomers of another molecule were identified. When the position of each decoded compound was plotted in the reduced space formed by principal components $\Psi_1$–$\Psi_2$, these identical or enantiomeric pairs were within very close proximity (FIG. 31B). Thus, the projection of a compound on $\Psi_1$ is positively correlated with a composite measure of bioactivity. Although we have not yet determined the structure of all small molecules within this "high activity neighborhood" across all five assays, we expect many of the other molecules in this region to share similar structural properties.

Figure 27B:
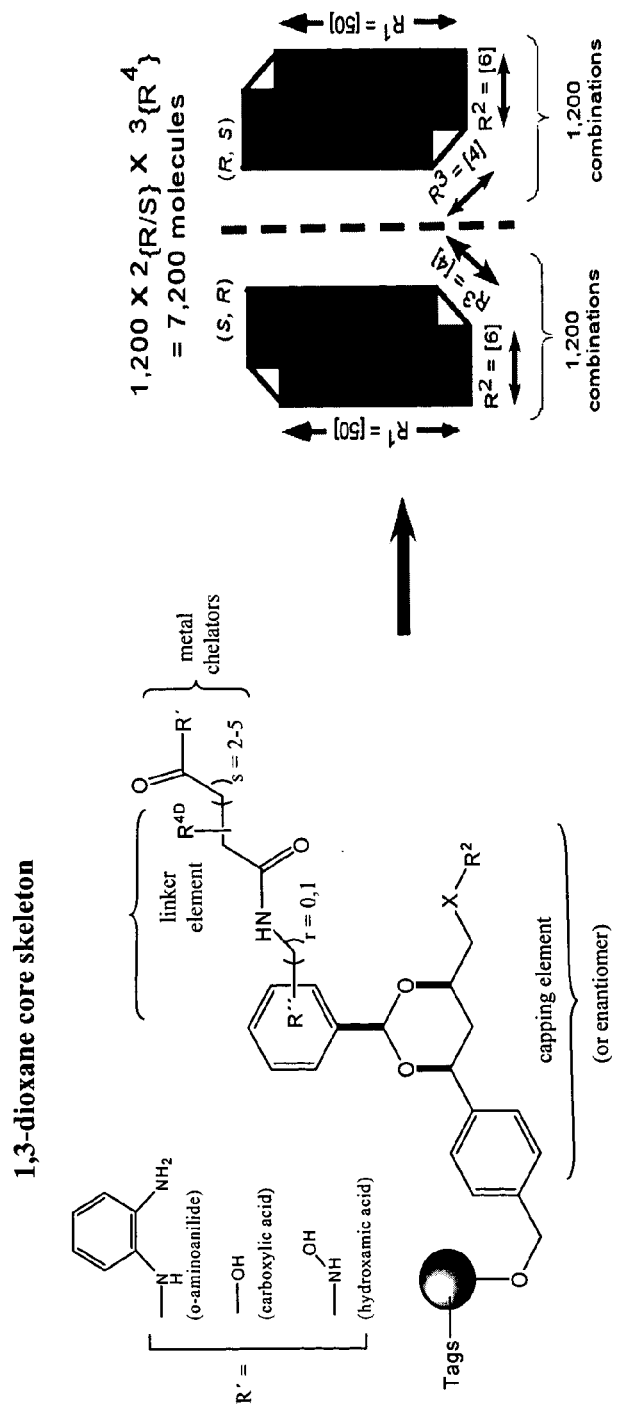
Figure 33A:
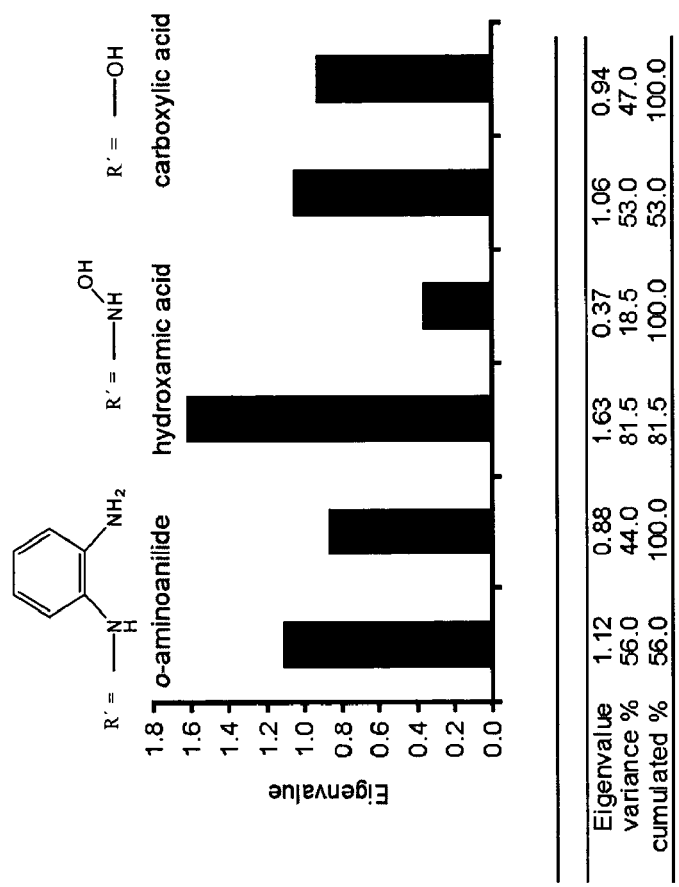
FIG. 33 depicts a principal component analysis of diversity position $R^4$. (A) Eigenvalue spectrum and variance associated with the three structural classes of deacetylase inhibitors. (B) Charts plotting a random sample of 10% of the small molecules (blue dots) of each structural class on the rotated space of $\Psi_1$ and $\Psi_2$. The location of histacin and tubacin, selective inhibitors of histone and α-tubulin deacetylation, respectively, are shown. (C) Relative position of decoded structures in a PCA model computed from five cell-based assay descriptors. AcTubulin-selective (red), AcLysine-selective (green), and most potent (blue).
Figure 34A:
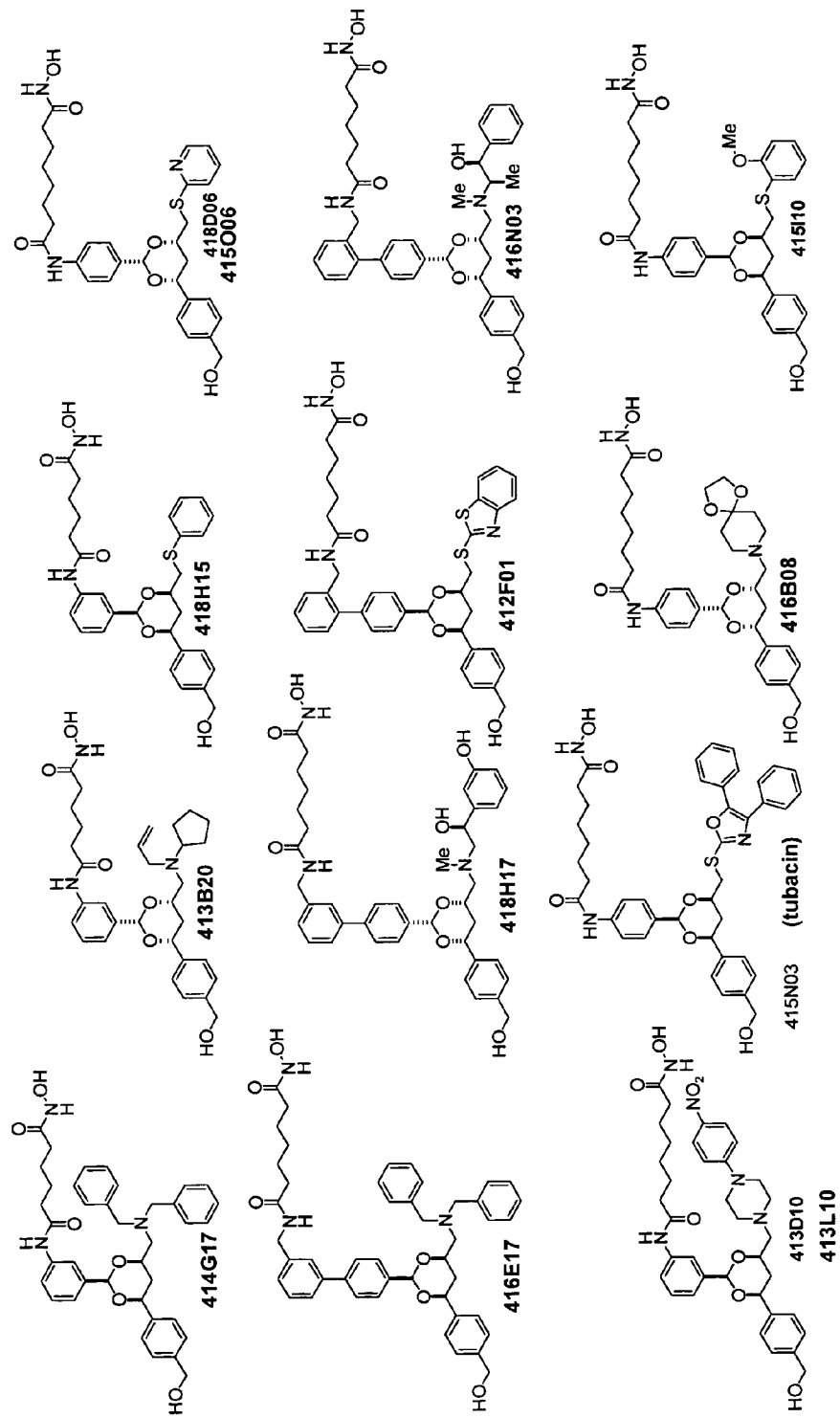
FIG. 34 depicts AcTubulin selective 1,3-dioxane-based inhibitors. Structures from decoded beads corresponding to wells that scored amongst the highest in the AcTubulin cytoblot but low in the AcLysine cytoblot. These compounds are selective inhibitors of α-tubulin deacetylation. 418 D6 when retested from the original stock solution using fluorescence microscopy also showed selectivity, but 413 D10 did not. See Haggarty, S. J., Koeller, K. M., Wong, J. C., Grozinger, C. M., and Schreiber. S. L. (2003). Domain-selective small molecule inhibitor of HDAC6-mediated tubulin deacetylation. Proc. Natl. Acad. Sci. USA. 100, 4389–4394 for further analysis of 415 N03 (tubacin).
Figure 34B:
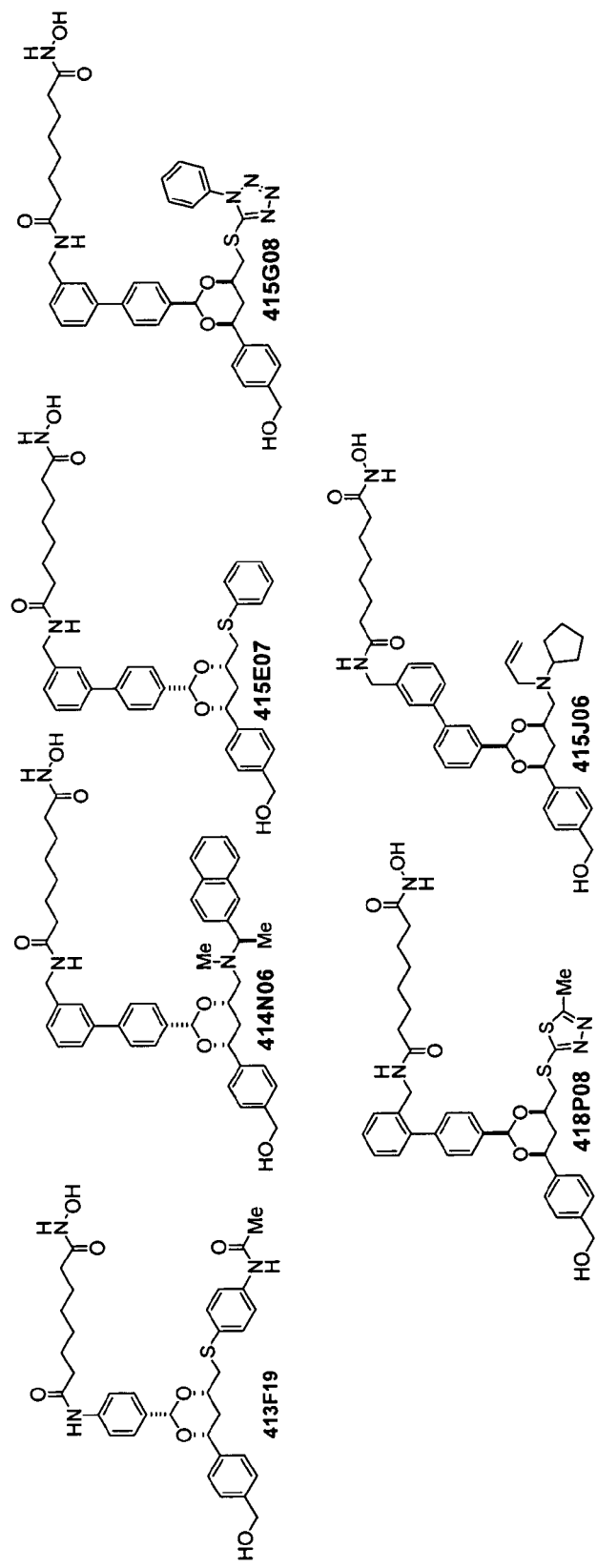
Figure 35A:
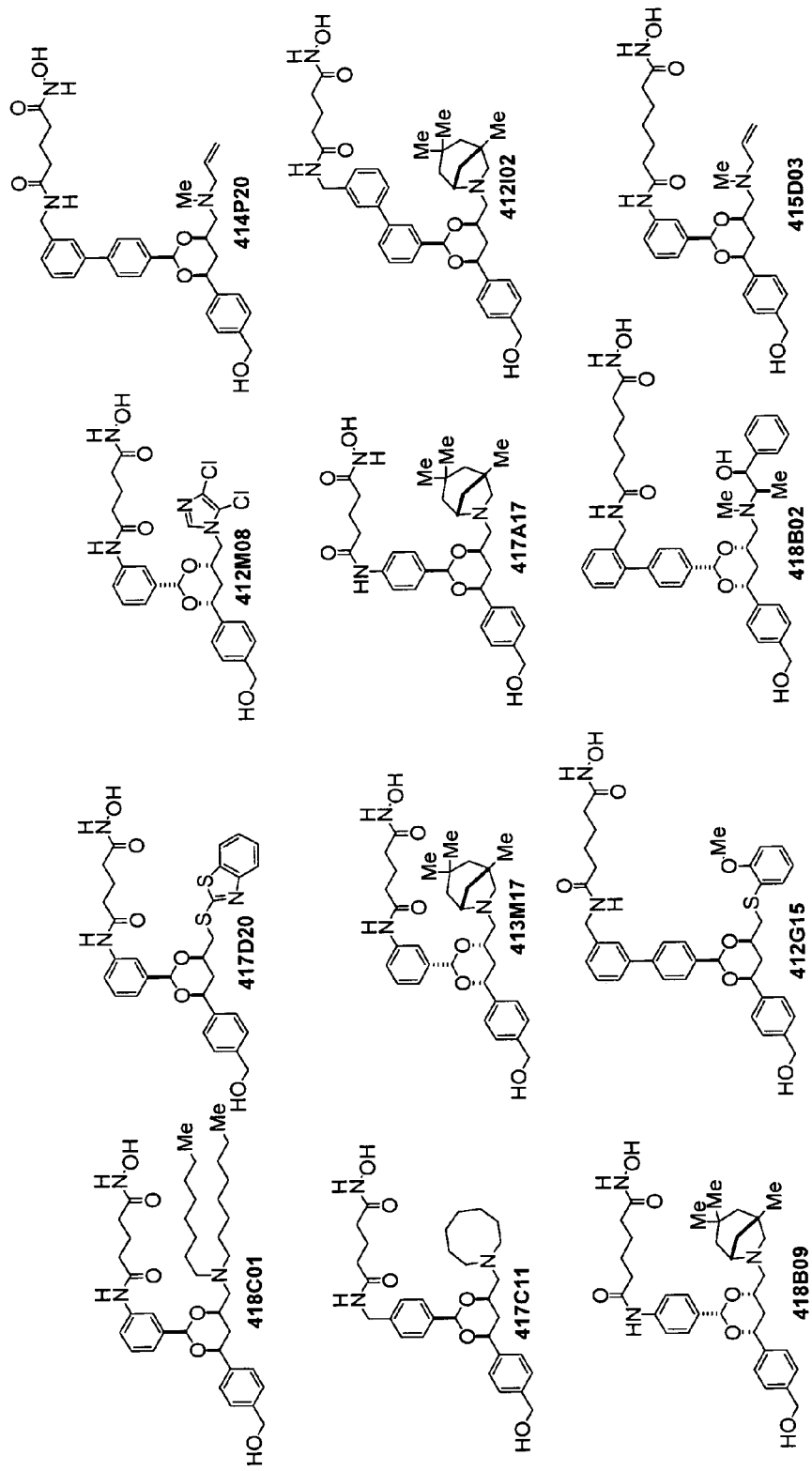
FIG. 35 depicts AcLysine selective 1,3-dioxanes-based inhibitors. Structures from decoded beads corresponding to wells that scored amongst the highest in the AcTubulin cytoblot, but low in the AcLysine cytoblot. These compounds are similar to trapoxin/HC toxin since they are selective inhibitors of histone deacetylation. 417 A20 when retested using fluorescence microscopy did not show selectivity. See Wong, J. C., Hong, R., and Schreiber, S. L. (2003). Structural biasing elements for in-cell histone deacetylase paralog selectivity. *J. Am. Chem. Soc.* 125(19): 5586–7] for further analysis of 410 F01 (histacin).
Figure 35B:
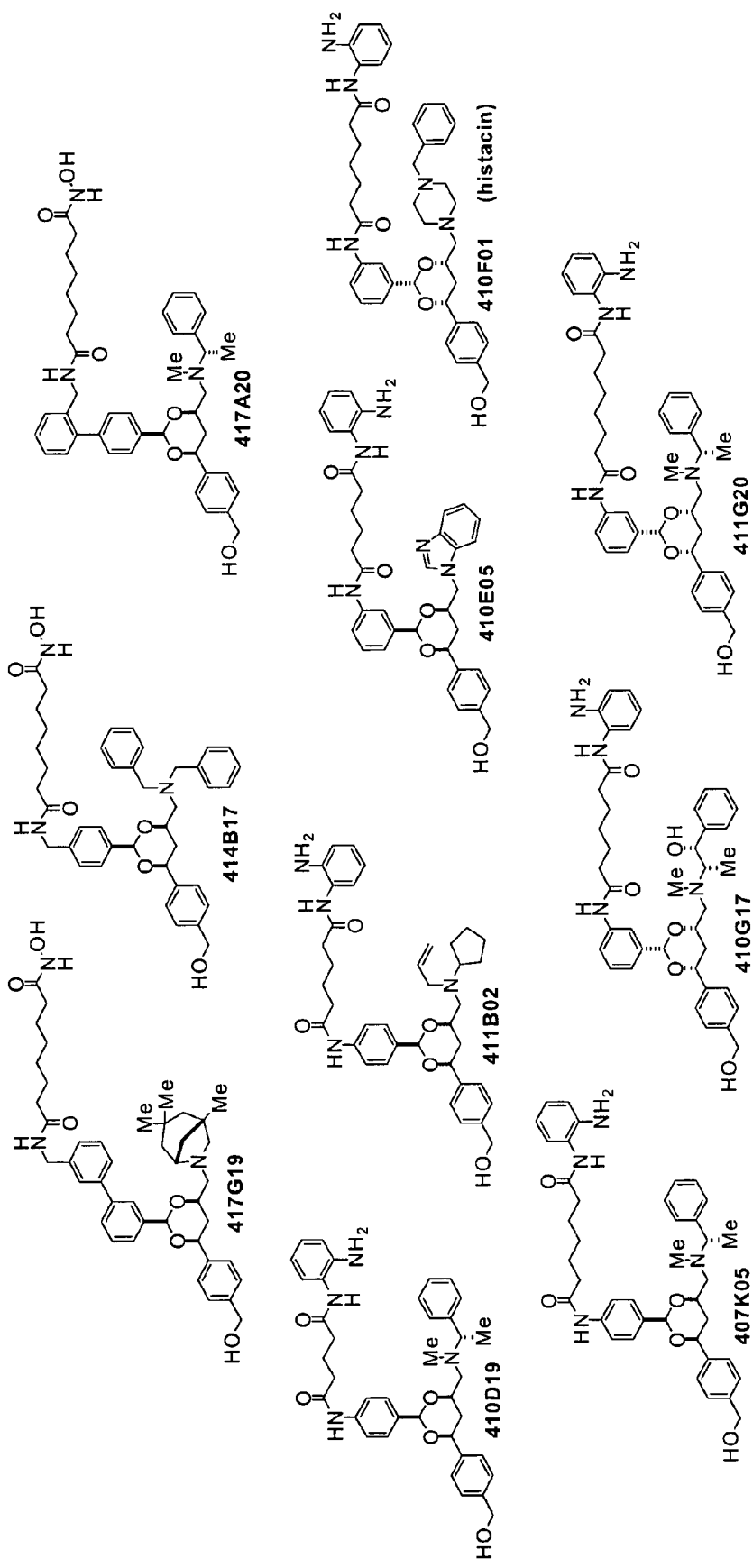

Correlating Chemical Structure with Selectivity: the Most Selective Class of Small Molecules Varies Between Assays In order to identify the most selective small molecules in both the AcTubulin and the AcLysine assays, PCA was performed on each structural class of 1,3-dioxanes defined by the three functionalities incorporated at position $R^4$ (FIG. 27B). As this analysis used data from the two assays in which the entire library was screened (AcTubulin and AcLysine), the input space was 2-dimensional. As such, PCA centered the data based on the distribution centroid, and rotated the original axes as specified by the eigenvectors, without any information loss. As shown (FIG. 33A), for both o-aminoanilides and carboxylic acids, the two eigenvalues ($\lambda 1$–$\lambda 2$) account for roughly equal amounts of the variance. This corresponds to low activity of these sets of small molecules and low correlation between bioactivity in one assay versus the other. Indeed, none of the 2,464 o-aminoanilides showed any activity toward inhibiting α-tubulin deacetylation, while 0.5% of these small molecules inhibited histone deacetylation (FIG. 28D). The o-aminoanilide functionality may therefore provide an effective means to target histone deacetylation without affecting α-tubulin acetylation levels (see Haggarty, S. J., Koeller, K. M., Wong, J. C., Grozinger, C. M., and Schreiber. S. L. (2003). Domain-selective small molecule inhibitor of HDAC6-mediated tubulin deacetylation. Proc. Natl. Acad. Sci. USA. 100, 4389–4394 for more information). In contrast, $\lambda 1$ accounted for more than 80% of the variance in the set of hydroxamic acids, which were on average more active than either the o-aminoanilides or carboxylic acids. This difference in eigenvalue magnitude corresponds to the high degree of bioactivity and strong correlation between the AcTubulin and AcLysine assays. Consequently, one principal component is capable of representing the majority of the information. The resulting bioactivity distributions on $\Psi_1$–$\Psi_2$ are shown in FIG. 33B. Based upon the average activity of the class of small molecules, and position within the rotated space of the principal components, a set of small molecules was chosen for bead decoding and structure determination (FIGS. 34 and 35) [See for example, Hubbert, C., Guardiola, A., Shao, R., Kawaguchi, Y., Ito, A., Nixon, A., Yoshida, M., Wang, X. F., and Yao, T. P. (2002). HDAC6 is a microtubule-associated deacetylase. Nature 417, 455–458; and Pipemo, G., LeDizet, M., and Chang, X. J. (1987). Microtubules containing acetylated alpha-tubulin in mammalian cells in culture. J. Cell Biol. 104, 289–302]. Twenty-four of these were selective for the AcTubulin assay and 22 selective for the AcLysine assay. Calculated masses of the inferred chemical structures matched those determined by liquid-chromatographic mass spectrometric analysis of the corresponding stock solutions (data not shown).

However, because chemical-encoding strategies record chemical history only, these structural assignments should be considered tentative.

Following decoding, it was noted that one structure, from two different plate positions, was common to both the AcLysine (418 B2) and AcTubulin (416 N3) selective lists. This anomalous result may be due to statistical variation in the assay results, differences in stock solution concentration, impurities, or an insufficiently stringent measure of selectivity. Since the majority of the selective inhibitors in both the AcTubulin and AcLysine assays, and all of the most potent deacetylase inhibitors, were hydroxamic acids the relative position of most of these compounds could be obtained using the 3-dimensional PCA model derived above using five assay descriptors (FIG. 33C). In this model, which accounts for 90.7% of the variance in the data, the AcTubulin-selective (red) and AcLysine-selective (green) sets clustered together and contributed less to the variation described by $\Psi_1$ then did either the full set of 2,464 small molecules (inset; black spheres) or the most potent inhibitors (blue; not all depicted).

Tubacin, a Selective Inducer of α-tubulin Acetylation

Figure 36A:
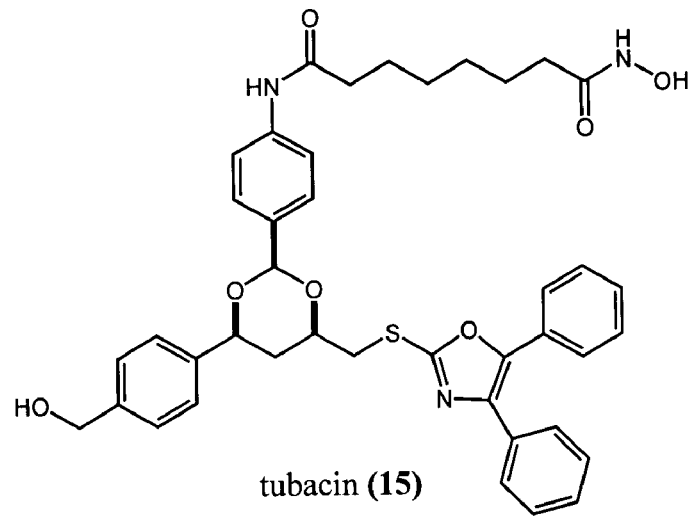
FIG. 36 depicts selective inhibitors of α-tubulin and histone deacetylation. (A) Chemical structure of tubacin (compound 415 N03). (B) Effect of tubacin (2 μM) and trichostatin (2 μM) treatment (19 h) on the acetylation level of α-tubulin (red) in A549 cells measured by immunofluorescence. Western blot analysis of acetylated α-tubulin and acetylated histone H3 (K9, K14) in A549 cells pre-treated (2 hours) with tubacin (2 μM) followed by ITSA1 (50 μM) for an additional 2 h. See reference [Haggarty, S. J., Koeller, K. M., Wong, J. C., Grozinger, C. M., and Schreiber. S. L. (2003). Domain-selective small molecule inhibitor of HDAC6-mediated tubulin deacetylation. Proc. Natl. Acad. Sci. USA. 100, 4389–4394] for further analysis of tubacin and its inhibition of HDAC6. (C) Chemical structure of histacin (compound 410 F1). (D) Effect of histacin (20 μM) and trichostatin (300 nM) treatment (5 h) on the acetylation level of histone H3 (yellow/green) in A549 cells measured by immunofluorescence. Western blot analysis of acetylated α-tubulin and acetylated histone H3 (K9, K14) in histacin (20 μM) treated (5 h) A549 cells. See reference [Wong, J. C., Hong, R., and Schreiber, S. L. (2003). Structural biasing elements for in-cell histone deacetylase paralog selectivity. *J. Am. Chem. Soc.* 125(19):5586–7] for further analysis of 410 F01 (histacin). (E) Network of genetic and chemical genetic interactions amongst 1,3-dioxane-based deacetylase inhibitors.
Figure 36B:
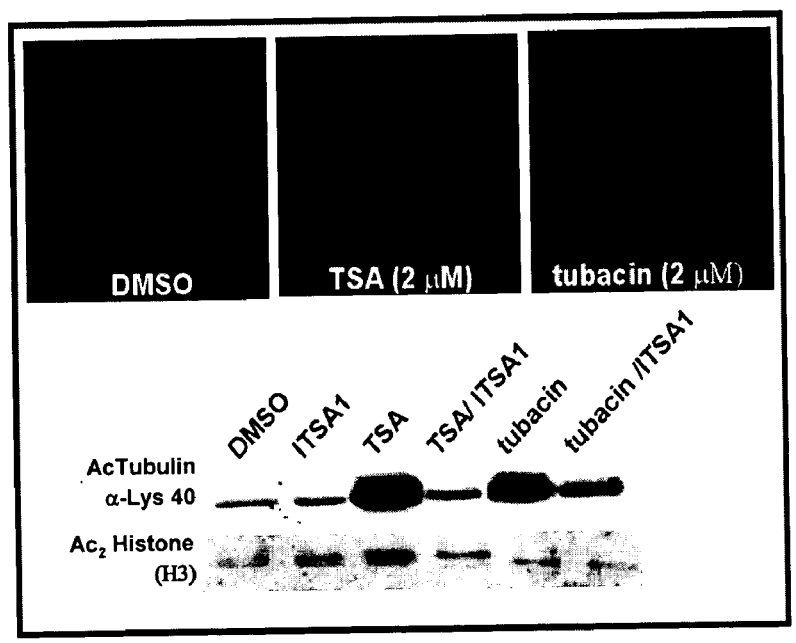

Two small molecules were chosen as selective inducers of α-tubulin acetylation, based upon their position in the rotated space of $\Psi_1$–$\Psi_2$. No apparent selectivity was observed for one of these molecules (413 D10) when a sample was tested in the secondary fluorescence microscopy assays for acetylated α-tubulin and acetylated lysine. This discrepancy might arise from higher compound concentrations in the secondary assay of (~10 µM versus a ~2–5 µM screening concentration), or increased sensitivity in the fluorescence microscopy assay. However, the second compound 415 N3 (FIG. 36A), here named tubacin (15) (tubulin acetylation inducer) strongly increased α-tubulin acetylation with no effect on lysine acetylation. This small molecule was re-synthesized to allow a systematic assessment of the effect on α-tubulin and histone acetylation. Treatment of A549 cells with tubacin (19 h) strongly increased α-tubulin acetylation levels (FIG. 36B) at concentrations as low as 125 nM (4 h, data not shown). Consistent with the original screening data, tubacin did not affect histone acetylation and was partially suppressed by ITSA1 (FIG. 36B). Thus, tubacin is the first known selective inhibitor of α-tubulin deacetylation.

In the 3-dimensional PCA model (FIG. 33C), the most proximal compound to tubacin (415 N3) was 415 O6. This compound had the identical structure as another decoded compound, 418 D6, which was also amongst the closest in proximity to tubacin in the 3-dimensional PCA model (FIG. 33C). Notably, 415 O6/418 D6 is one of the ~1.4% of the total library members (not considering stereochemistry) that share the same building blocks at three of the four diversity positions ($R^{4D}$, $R'$ and $R^{41}$) as tubacin. Furthermore, at the position that is different from tubacin ($R^2$) the 2-mercaptopyridine group shares some structural similarity to the core of the 4,5-diphenyl-2-oxazolethiol building blockpresent in tubacin. In agreement with these structural similarities, retesting of the original stock solution of 418 D6, using fluorescence microscopy, confirmed its selective inhibition of α-tubulin deacetylation (data not shown).

Histacin, a Selective Inducer of Histone Acetylation

Figure 36C:
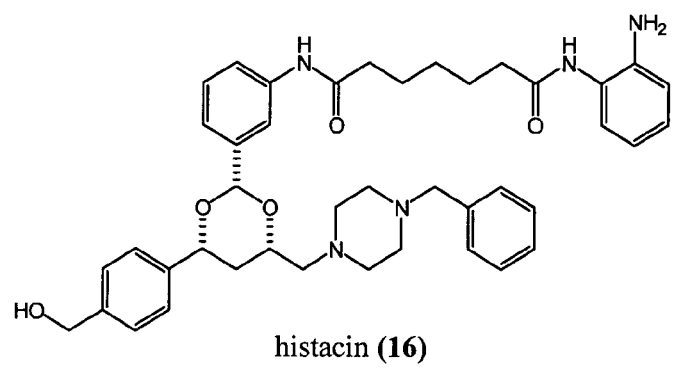
Figure 36D:
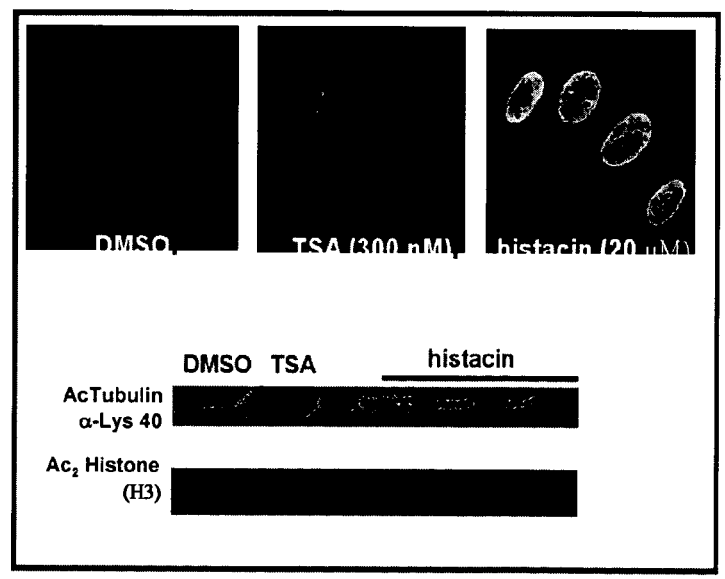
Figure 36E:
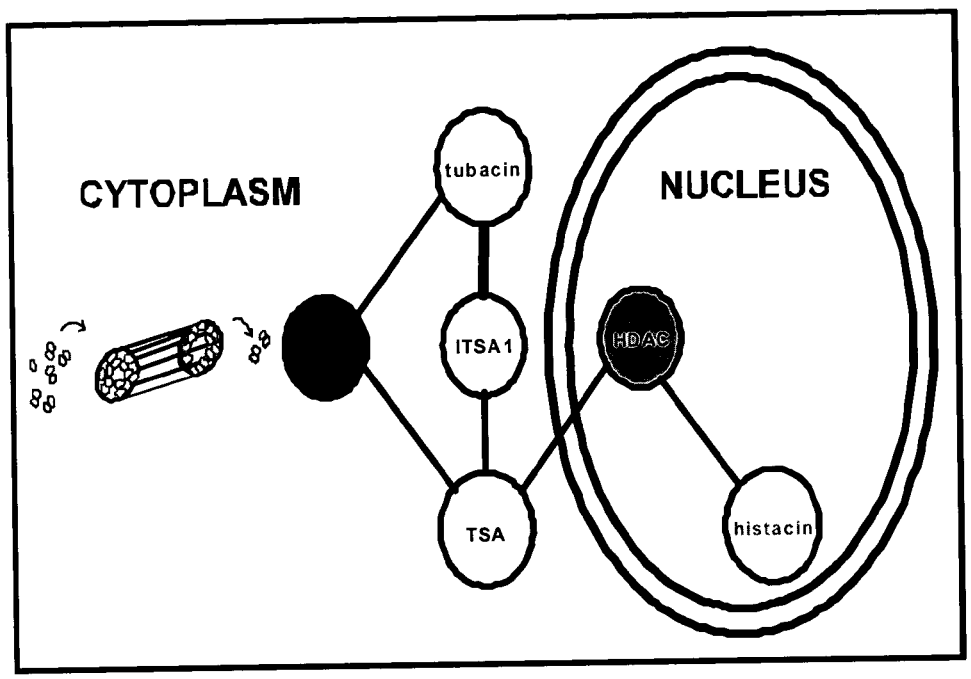

Two small molecules were chosen as selective inducers of histone acetylation based upon their position in the rotated space of $\Psi_1$–$\Psi_2$. Again, no selectivity was observed for one of these small molecules (417 A20) when tested in the secondary fluorescence microscopy assays for acetylated α-tubulin and acetylated lysine. However, the second compound 410 F1 (FIG. 36C), here named histacin (16) (histone acetylation inducer) strongly increased lysine acetylation with no effect on α-tubulin acetylation (FIG. 36D). After re-synthesis, treatment (14 h) of cells with histacin (20 µM) increased acetylated histone levels without affecting α-tubulin acetylation levels. Thus, histacin, like the epoxy ketone-containing HDAC inhibitors trapoxin and HC toxin, is a selective inhibitor of histone deacetylation. Furthermore, like trapoxin/HC toxin, histacin's effects on histone acetylation cannot be suppressed by ITSA1 (data not shown).

Annotation of a Chemical Space Derived from Molecular Descriptors Using Observed Biological Activites.

Figure 38:
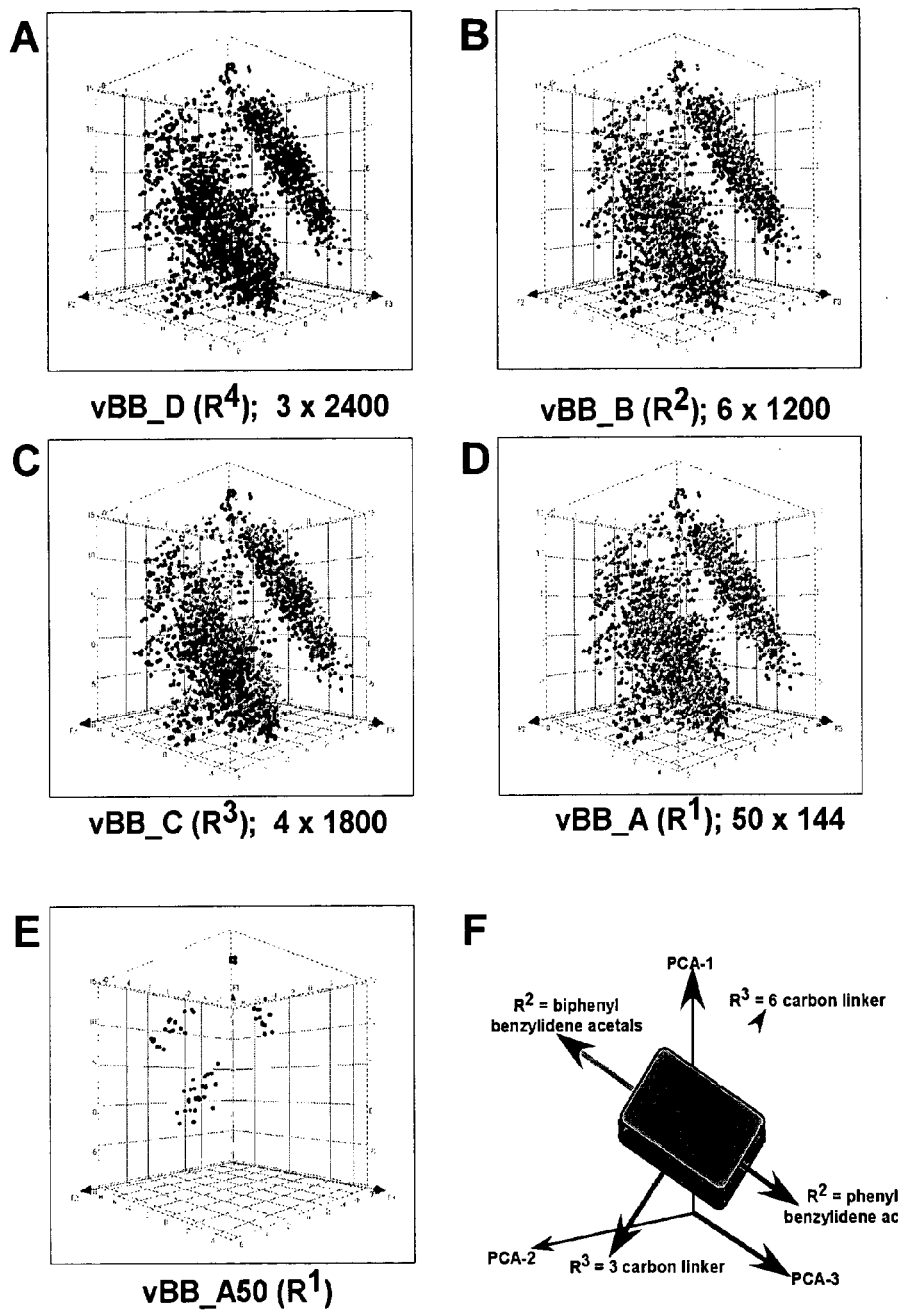
FIG. 38 depicts mapping of diversity positions $R^1$–$R^4$ from the 7,200 1,3-dioxanes onto the chemical space derived from principal component analysis (PCA) of the corresponding molecular descriptors. Images are of the positions of small molecules in the space formed by the first three PCA axes. Enantiomeris are located within the same position. Each of the different building blocks ($R^1$=50; $R^2$=6; $R^3$=4; $R^4$=3) at the different positions was colored separately (see FIG. 27B for more details). For example, in the top left, green corresponds to the o-aminoanilides, red corresponds to hydroxamic acids, and blue corresponds to carboxylic acids. Different building blocks cause different degrees of distribution in space. For example, in the bottom left, red balls depict the position of all 144 small molecules with the same building block as tubacin at $R^1$. Bottom right corner provides a summary of major trends in the space.
Figure 39:
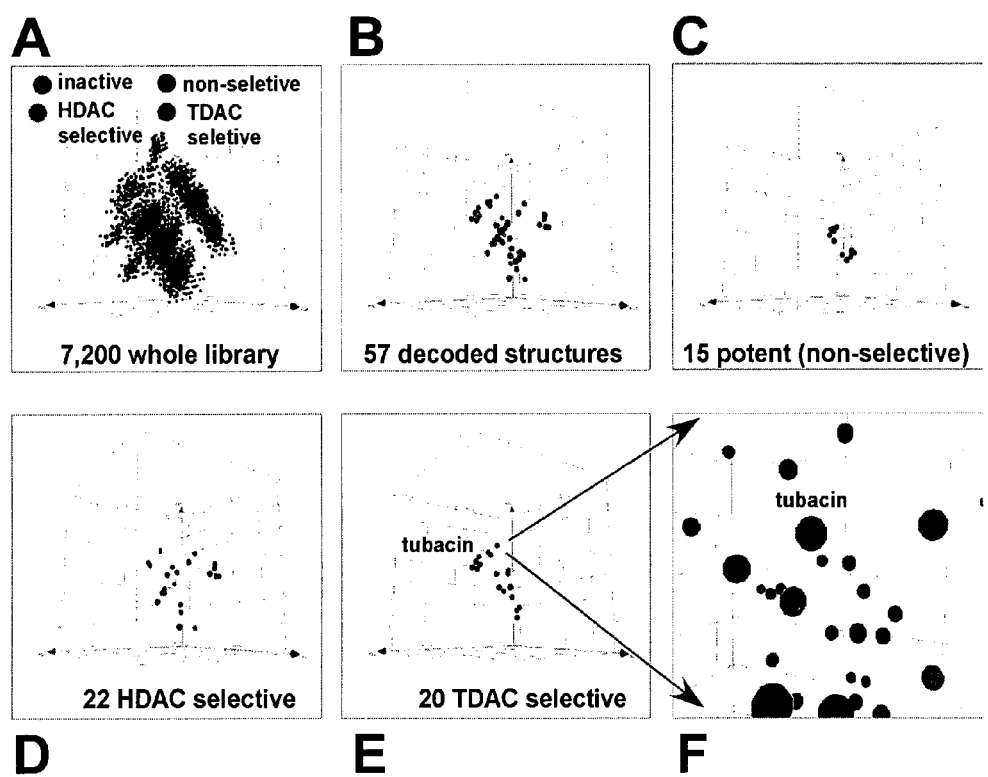
FIG. 39 depicts a mapping of functional classes of biologically active deacetylase inhibitors onto the chemical space derived from principal component analysis (PCA) of the molecular descriptors from the 7,200 1,3-dioxanes. Images are of the positions of the 57 small molecules whose structures were determined from decoding (FIGS. 32, 34 and 35) in the space formed by the first three PCA axes. Enantiomeris are located within the same position. AcLysine selective inhibitors (green), AcTubulin selective inhibitors (red), most potent inhibitors (blue), and inactive inhibitors (black). Location of tubacin is highlited (turquoise).
Figure 40:
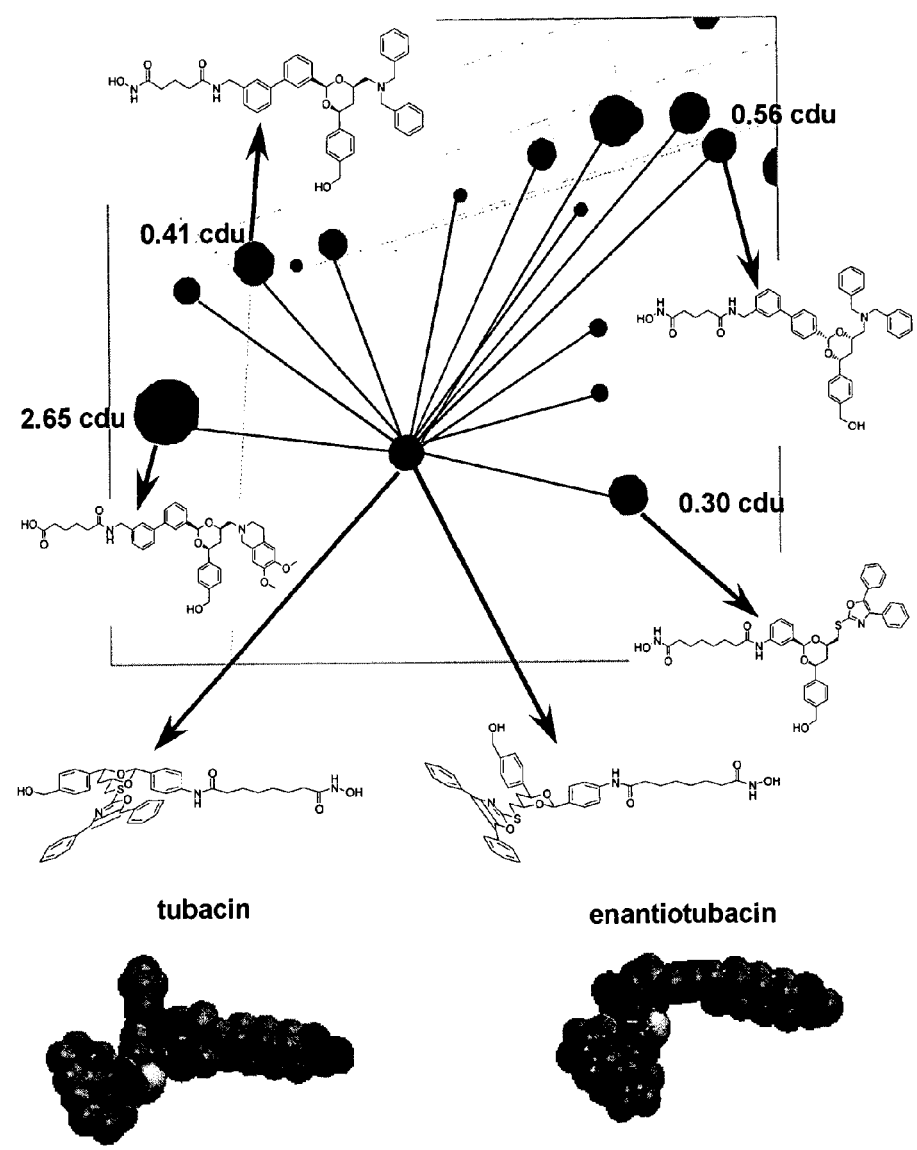
FIG. 40 depicts a nearest-neighbor analysis of tubacin (red/black center ball). Chemical structures of small molecules and their distance in chemical space measured in Euclidean units (cdu) in the chemical space derived from principal component analysis of the molecular descriptors from the 7,200 1,3-dioxanes. Increased proximity space results from more globally similar molecular descriptors. The enantiomer of tubacin is located within the same position as tubacin. Molecules shown here, other than tubacin and enatiotubacin, are virtual members of the 1,3-dioxane library. Upon re-synthesis and retesting enantiotubacin was equally as potent as tubacin in the AcTubulin cytoblot assay, but was ~5-fold less selective (S. J. H., J. C. W., and S. L. S., unpublished data).

The knowledge of the structures of 617 deacetylase inhibitors along with the knowledge of the structure of the full library screened will enable determination of global structure-activity relationships of the 1,3-dioxane deacetylase inhibitors based upon cellular screening data (S. J. H, Paul A. Clemons, J. C. W., Lucy Perez, and S. L. S, mansucript in preparation) (FIGS. 37 and 38). These maps of chemical space differ from those shown in FIG. 33 as they are derived based upon PCA analysis of calculated molecular descriptors. Although the decoding of the full set of deacetylase inhibitors is ongoing, preliminary results using the 57 known structures shown unequal distribution of functional classes of the inhibitors is amongst the 'pods' presence in the whole library (FIG. 39). Such visual properties will aid in understanding structure-activity relationships and guide future efforts of re-synthesis. For example, the 'nearest-neighbors' of tubacain can readily be identified and tested for biological activity (FIG. 40). Here, upon re-synthesis and retesting, enantiotubacin was equally as potent as tubacin in the AcTubulin cytoblot assay, but was ~5-fold less selective of a TDAC inhibitor (S. J. H., J. C. W., unpublished data).

Discussion

Classical genetics began annotating genetic factors by observing heritability and determining the linkage of simple phenotypic traits. Using these observations and the frequency of recombination during the first meiotic division as a metric, the relative distance between genes encoding for phenotypes was experimentally defined, one map unit being equal to 1% recombination (measured in centiMorgans) [See for example Morgan, T. H., Sturtevant, A. H., Muller, H. J., and Bridges, C. B. (1915). The Mechanism of Mendelian Heredity. (New York: Henry Holt and Company)]. Accordingly, a mutant gene could be 'mapped' as a point in a one-dimensional space. Through overlapping distance measurements, a genetic map could be constructed. Although not obvious at the onset, it is now well known that such maps represent the physical arrangement of genes within a linear and continuous sequence of deoxyribonucleic acids.

By analogy to the logic of classical genetics, we are interested in creating "chemical genetic maps" that position chemicals and biological systems in a multidimensional space. Such maps will facilitate systematic analysis of the factors determining interactions between small molecules and biological systems. At the core of such efforts is the relationship between information present in chemical genetic observations, and mathematical quantities that make up the geometric properties of vector spaces. While chemical space is often considered a vector space with dimensions represented by calculated molecular descriptors, we instead focused on measuring the similarity/differences of small molecules using phenotypic properties from cell-based assays. Pioneering work by the group of Dr. John Weinstein demonstrated that datasets representing interactions of small molecules with tumor cell lines were rich in 'information'

[See for example, Van Osdol, W. W., Myers, T. G., Paull, K. D., Kohn, K. W., and Weinstein, J. N. (1994). Use of the Kohonen self-organizing map to study the mechanisms of action of chemotherapeutic agents. J. Natl. Cancer Inst. 86, 1853–1859; and Weinstein, J. N., Myers, T. G., O'Connor, P. M., Friend, S. H., Fornace, A. J., Kohn, K. W., Fojo, T., Bates, S. E., Rubinstein, L. V., Anderson, N. L., Buolamwini, J. K., van Osdol, W. W., Monks, A. P., Scudiero, D. A., Sausville, E. A., Zaharevitz, D. W., Bunow, B., Viswanadhan, V. N., Johnson, G. S., Wittes, R. E., and Paull, K. D. (1997). An information-intensive approach to the molecular pharmacology of cancer. Science 275, 343–349]. Although limited to a single phenotype (cellular growth as measured by protein production), this analysis was able to classify small molecules into similar patterns of activity and tumor cell lines into similar groups. Here, the logic of this type of analysis is applied to a set of biochemical phenotypes, specifically acetylation levels of α-tubulin and histones in cells. In addition, the small molecules screened derive from a biased library rather than a 'random' collection. Our initial our analyses were limited to one genotype (that of a human lung cancer cell line), and thus could be expanded to include varying cell types and/or genotypes.

Genes can have multiple functions, as observed by multiple phenotypic effects resulting from their mutation. Similarly, small molecules can have multiple functions, as observed by multiple phenotypic effects resulting from their interaction with cellular components. The distribution of activities in a given assay, correlation across assays, and the relationships of the assays themselves, renders the number of comparisons required to find certain patterns of activity intractable. Accordingly, modeling and visualizing multidimensional data requires the use of dimensionality reduction and pattern finding algorithms. This allows higher-level representation of the information inherent in lower-level relational data.

For this purpose, the concept of a chemical genetic network for the analysis of screening data was introduced. If two small molecules score in the same phenotypic assay, then there is some probability that they are hitting the same target. However, if the same two small molecules exhibit different patterns of biological activity in other phenotypic assays, the probability that they are targeting the same gene product is reduced. Thus, the connectivity of a chemical node can be used to constrain the set of possible targets and to provide a discrete measure of a small molecule's selectivity. Similarly, the connectivity of an assay node can be used to compare the aspects of a biological system being queried and as to provide a discrete measure of an assay's sensitivity. Although the network constructed here was based upon an empirically defined threshold, similar networks could be formed at different levels of bioactivity. Furthermore, rather than using a binary edge length (=0 or 1), the lengths could be made proportional to the bioactivity of a compound or a likelihood score. As the annotation and subdivision of a chemical genetic network increases, predictions of whether a new member of a class will have additional targets within a cell, or will interact with a specific chemical genetic modifier may be possible.

As another form of multidimensional data analysis, a computational method, called principal component analysis was used [See for example, Legendre, P. and Legendre, L. (1998). Numerical Ecology—Developments in Environmental Modeling (New York: Elsevier); and Hotelling, H. (1931)]. Analysis of a complex of statistical variables into principal components. J. Educ. Psychol. 24, 417–441]. This eigenvalue/eigenvector approach takes into account the global properties of the space spanned by the variables under study. In doing so, it reduced the probability of selecting a compound as selective only due to a technical error, or the compound having an undesired cellular effect. Although we considered only a 2-dimensional space spanned by $\Psi_1$ and $\Psi_2$, the logic of this analysis holds upon the addition of more dimensions. Thus, PCA is well suited for the discovery of molecules with complex phenotypic effects, and not just activity in one particular assay. In the global analysis of the hydroxamic acids in the five assays, the first eigenvalue ($\lambda 1$) accounted for most of the information in the dataset and correlated with the bioactivity of the small molecules. In the discovery of selective inhibitors of α-tubulin deacetylation or histone deacetylation, the 2- and 3-dimensional PCA models delineated regions of chemical space with different patterns of bioactivity (FIGS. 33B, C). Besides allowing for a more informative visualization of multidimensional data, PCA has a practical application for data analysis, as the reduced number of dimensions simplifies subsequent computations that may be memory and time intensive.

The possibility exists that both tubacin and histacin affect the acetylation levels of proteins other than α-tubulin and histones, respectively. Future work with the small molecules discovered here will be directed toward determining their potency and testing for differential phenotypes on gene expression, stem cell differentiation, and zebrafish embryogenesis. With the remaining amount from each stock solution, additional screens of the 1,3-dioxane library will be aimed at determining the extent to which the small molecules affect other histone modifications, metalloenzymes (i.e., deubiquitinases and proteases), and other biological processes.

An outstanding question in the field of chemical biology is how best to quantify molecular diversity in a way that informs biological discovery. Although molecular descriptors based upon a chemical graph (structure) are generally trivial to compute, structure-activity relationships are often complex. As an alternative, the effectiveness of diversity-oriented syntheses can be quantified by the dimensionality of the biological space required to effectively describe the observed phenotype. For example, had the 1,3-dioxane library been composed of o-aminoanilides alone, all molecules could have been positioned on a one-dimensional space, since none of them scored in the AcTubulin assay. In contrast, a 1,3-dioxane library composed solely of hydroxamic acids would require two-dimensions, one for AcLysine and AcTubulin. Thus, through systematic screens of small molecule libraries in minimally redundant, maximally informative cell-based assays, maps of chemical space can be derived from biologically-based descriptors. Such maps may have more distinct geometric and topological properties than those derived from calculated descriptors.

The utility of antibodies to detect specific post-translational modifications in high-throughput phenotypic assays provides a powerful approach to identifying novel biologically active small molecules [See for example, Haggarty, S. J, Mayer, T. U., Miyamoto, D. T., Fathi, R., King, R. W., Mitchison, T. J., and Schreiber, S. L. (2000). Dissecting cellular processes using small molecules: identification of colchicine-like, taxol-like and other small molecules that perturb mitosis. Chem. Biol. 7, 275–286; Stockwell, B. R., Haggarty, S. J., and Schreiber, S. L. (1999). High-throughput screening of small molecules in miniaturized mammalian cell-based assays involving post-translational modifications. Chem. Biol. 6, 71–83; Koeller, K. M., Haggarty, S. J., Perkins, B. D., Leykin, I., Wong, J. C., Kao, M. C., and Schreiber. S. L. (2003). Chemical Genetic Modifier Screens:

small molecule trichostatin suppressors as probes of intracellular histone and tubulin acetylation. *Chem. Biol.* 10(5): 397–410]; and Roberge, M., Cinel, B., Anderson, H. J., Lim, L., Jiang, X., Xu, L., Bigg, C. M., Kelly, M. T., Andersen, R. J. (2000). Cell-based screen for antimitotic agents and identification of analogues of rhizoxin, eleutherobin, and paclitaxel in natural extracts. Cancer Res. 60, 5052–5058]. This complete screen consumed less than 20% (~20 nmoles) of the compound released from one synthesis bead, leaving the majority of compound for retesting, analytical analysis, or subsequent additional screening. The overall high level of observed activity (~8% of library small molecules active) at a concentration of 2–5 µM reflects prior knowledge guiding library synthesis, as well as apparent sensitivity of HDACs to small molecule modulation. While a number of small molecules (~80) have previously been reported to inhibit HDAC activity in vitro, only a limited set of these appear to be effective inhibitors of 14DAC activity within the context of living cells [See for example Remiszewski, S. W. (2002). Recent advances in the discovery of small molecule histone deacetylase, inhibitors. Curr. Opin. Drug Discov. Devel. 5, 487–499; and Johnstone, R. W. (2002). Histone-deacetylase inhibitors: novel drugs for the treatment of cancer. Nat. Rev. Drug Discov. 1, 287–299]. Since the cell-based screening methodology described in this paper is scalable, and can be generalized to other post-translational modifications, the development of additional assays coupled to important biological processes is possible. In particular, iterative cycles of chemical genetic modifier screens, using newly discovered bioactive small molecules, should facilitate the construction of chemical genetic networks for use in "chemical genomic profiling" experiments. An important direction in such studies will be the development of novel screening methodologies with increased efficiency, information content, and accuracy. Here, the combination of small molecules and RNAi-based perturbations promises to be an illuminating direction of research. In parallel, along with increasing the diversity of small molecule modulators, deconvolution of synthetic variables, such as efficiency and purity, will continue to be required. In the limit, beyond traditional functional characterization, one can imagine annotating proteins encoded within an entire genome using a set of small molecule modulators of their biochemical activities [See for example, Schreiber, S. L. and Bernstein, B. E. (2002). Signaling network model of chromatin. Cell, 111, 771–8; and Schreiber, S. L. (2003). Chemical Genetics. C&E News, 81, 51–61].

The identification of 617 small molecule inhibitors of intracellular deacetylation highlights multidimensional chemical genetics and diversity-oriented organic synthesis as tools for the discovery of probes of complex biological networks. New small molecules with diametrically opposed inhibitory activities (tubacin/tubulin deacetylase inhibitor vs. histacin/histone deacetylase inhibitor) provide a means to dissect the role of acetylation in microtubule dynamics and chromatin remodeling [See, for example, Schreiber, S. L. (2003). Chemical Genetics. C&E News, 81, 51–61; Haggarty, S. J., Koeller, K. M., Wong, J. C., Grozinger, C. M., and Schreiber. S. L. (2003). Domain-selective small molecule inhibitor of HDAC6-mediated tubulin deacetylation. Proc. Natl. Acad. Sci. USA. 100, 4389–4394; and Wong, J. C., Hong, R., and Schreiber, S. L. (2003). Structural biasing elements for in-cell histone deacetylase paralog selectivity. *J. Am. Chem. Soc.* 125(19):5586–7]. The discovery of potent, and especially selective, deacetylase inhibitors was possible through computational methods, most notably principal component analysis and consideration of proximity in multidimensional descriptor spaces. Using the principles of graph theory, a discrete model of the screening data was derived in the form of a 'chemical genetic network' and analyzed using topological invariants. By systematically mapping the structure-activity relationships of this particular "deacetylase" region of chemical space, the results of this study should assist in the discovery of selective HDAC inhibitors that may be more effective research tools and therapeutic agents.

Materials and Methods

Trichostatin A (TSA) and anti-acetylated α-tubulin (6-11B-1) antibody were purchased from Sigma. ITSA1 (5253409) was purchased from Chembridge. Anti-acetylated lysine antibody was purchased from Cell Signaling. Anti-acetyl histone H3 (K9, K14) and anti-acetyl histone H4 (K4, K7, K11, K15) antibodies were purchased from Upstate Biotechnology. Anti-mouse IgG horseradish peroxidsae (HRP) conjugated, anti-rabbit IgG-HRP conjugated secondary antibodies, and enhanced chemiluminescent mixture (luminol) were purchased from Amersham Pharmacia. Alexa 594 and Alexa 488-conjugated anti-mouse IgG antibody, anti-rabbit IgG antibody, and Hoechst 33342 were purchased from Molecular Probes.

Cell Culture

A549 human lung carcinoma cells (American Tissue Culture Collection) were cultured at 37° C. with 5% carbon dioxide in Dulbecco's modified eagle medium (DMEM) supplemented with 10% v/v fetal bovine serum (Gibco BRL), 100 units/mL penicillin G sodium (Gibco BRL), 100 µg/mL streptomycin sulfate (Gibco BRL), and 2 mM L-glutamine (Gibco BRL) (DMEM+).

1,3-dioxane Library Screen and Cytoblot Assays

A549 cells were seeded at a density of 4,000 cells/50 µl in DMEM+ in white tissue culture-treated 384-well plates (Nalge Nunc) using a Multidrop 384 liquid dispenser (Labsystems). Library small molecules were pinned twice (100–150 nl/pin) from ~1 mM stock solutions (DMSO) and incubated for 18 hours. For the ITSA1+AcTubulin assay, ITSA1 (50 µM) was added four hours after pin-transfer of library molecules. Media was aspirated with a 16-channel wand. For the acetylated α-tubulin cytoblot (AcTubulin), 40 µl/well of fixation solution (3.7% formaldehyde (1:10 from 37% stock) in Tris-buffered saline (TBS, 0.15 M NaCl, 0.02 M Tris-Cl, pH 7.4) was added and plates incubated for twenty minutes at room temperature. After aspiration, 30 µl 100% methanol (−20° C.) was added and incubated for five minutes at room temperature. After aspirating and washing three times with 90 µl of antibody dilution buffer (ADB, TBS/2% bovine serum albumin, 0.1% TritonX-100) the wells were blocked for twenty minutes in ADB. After aspirating, 20 µl/well of ADB containing anti-acetylated α-tubulin antibody (mouse; 1:1000) and anti-mouse IgG horseradish peroxidase (HRP)-conjugated antibody (1:750) was added and incubated overnight (4° C.). For the anti-acetyl lysine cytoblot (AcLysine), 40 µl/well of fixation solution (95% ethanol/ 5% acetic acid, −20° C.) was added and plates incubated for five minutes at room temperature. Wells were aspirated, washed, and blocked in ADB as for the AcTubulin protocol. After aspirating, 20 µl/well of ADB containing anti-acetylated lysine (rabbit; 1:375) and anti-rabbit IgG-HRP conjugated antibody (1:750) was added and incubated overnight (4° C.). For the anti-acetylated histone H3 (AcHistH3) and anti-acetylated histone H4 (AcHistH4) cytoblots, cells were fixed, washed, and blocked in ADB as for the AcLysine cytoblot. After aspirating, 20 µl/well of ADB containing anti-acetylated histone H3 antibody (rabbit, 1:500) or anti-acetylated histone H4 antibody (rabbit, 1:500)

was added and incubated for two hours at room temperature. Wells were aspirated and washed twice with 80 μl of ADB. After aspirating, 20 μl/well of ADB containing anti-rabbit IgG-HRP conjugated antibody (1:1000) was added and incubated for two hours (room temperature). For the AcTubulin and AcLysine assays, plates were washed three times with TBS before adding 20 μl/well of enhanced chemiluminescent (ECL) mixture. For the AcHistH3 and AcHistH4 assays, plates were washed three times with 80 μl TBS with 1% Triton X-100 and once with 80 μl TBS before adding 20 μl/well of ECL mixture. Plates were read on an Analyst plate reader (LJL Biosystems) with an integration time of 0.1 seconds.

Chemical Library and Retesting of Positives 1,3-dioxanes from single polystyrene macrobeads were prepared as 1–2 mM stock solutions in DMSO as described [Hubbert, C., Guardiola, A., Shao, R., Kawaguchi, Y., Ito, A., Nixon, A., Yoshida, M., Wang, X. F., and Yao, T. P. (2002). HDAC6 is a microtubule-associated deacetylase. Nature 417, 455–458]. Bead decoding and structure determination were as described [See for example, Hubbert, C., Guardiola, A., Shao, R., Kawaguchi, Y., Ito, A., Nixon, A., Yoshida, M., Wang, X. F., and Yao, T. P. (2002). HDAC6 is a microtubule-associated deacetylase. Nature 417, 455–458; and Piperno, G., LeDizet, M., and Chang, X. J. (1987). Microtubules containing acetylated alpha-tubulin in mammalian cells in culture. J. Cell Biol. 104, 289–302]. Small molecules (~2–5 μM) of interest were retested using a sample from the plate of stock solutions by fluorescence microscopy and comparison to the effects of trichostatin (300 nM to 1 μM).

Immunofluorescence

A549 cells were seeded at a density of 50,000/200 μl in DMEM+ on the surface of glass coverslips on top of Parafilm in a 10 cm dish and allowed to attach overnight. For detection of acetylated α-tubulin, cells were permeabilized and fixed with 100 mM K-PIPES, pH 6.8, 10 mM EGTA, 1 mM MgCl$_2$, 0.2% triton X-100, 0.2% glutaraldehyde for fifteen minutes. Coverslips were aspirated and excess glutaraldehyde quenched with sodium borohydride (10 mg/ml) for ten min. After washing twice with ADB, coverslips were blocked for ten minutes before adding anti-acetylated α-tubulin antibody (6-11B-1, mouse; 1:500) in ADB for 1–2 h. For detection of acetylated lysine, cells were fixed in 200 μl of fixation solution (95% ethanol/5% acetic acid, −20° C.) for five min at room temperature. Coverslips were washed for three times with ADB and blocked ten min in ADB. After aspirating, 50 μl/coverslip of ADB containing anti-acetylated lysine (rabbit; 1:375) in ADB was added and incubated for 1–2 h at room temperature. For detecting both acetylated α-tubulin and acetylated lysine, the coverslips were washed three times with ADB and incubated with Alexa 594 and Alexa 488-conjugated anti-mouse IgG (1:500) and anti-rabbit IgG (1:500) antibodies, along with a nuclear counter stain of Hoechst 33342 (1 μg/ml) for 1–2 h at room temperature. Coverslips were washed three times in TBS-Triton X-100 (0.1%) and mounted in 20 mM Tris, pH 8.8, 90% glycerol containing 0.5% p-phenylenediamine and mounted. Images were collected on a Zeiss LSM510 confocal scanning laser microscope at the appropriate wavelengths using the accompanying software and processed with Adobe Photoshop.

Data Analysis

Raw data files from the Analyst were imported into Excel (Microsoft). Plate values were first standardized by dividing by the mean (n=16) of the DMSO control on each plate. An average value from both replicates was used as the measure of a small molecule's activity. Testing of various transforms indicated that a Log$_2$-transformation reduced the skewness and kurtosis of the data. After Log$_2$-transformation, the data were each fit to a normal distribution to create a normalized acetylation value. All statistical tests, distribution properties, hierarchical clustering, and principal component analysis were performed using XLSTAT-PRO (v5.2). Principal component analysis (PCA) consists of a linear transformation of the original system of axes formed by the n-dimensions of the chemical genetic data matrix [See, for example, 1. Legendre, P. and Legendre, L. (1998). Numerical Ecology-Developments in Environmental Modeling (New York: Elsevier); and 2. Hotelling, H. (1931). Analysis of a complex of statistical variables into principal components. J. Educ. Psychol. 24, 417–441]. This transformation is in the form of a rotation, which preserves Euclidean distances. The directions of rotation are determined by considering the standardized covariance matrix $\Sigma_{bio}$ as a linear operator and computing a set of eigenvectors and corresponding eigenvalues that satisfy the eigenvalue equation: $\Sigma_{bio}\Psi=\Lambda\Psi$. The resulting eigenvectors ($\Psi_n$) of the matrix $\Psi$ form a set of new, linearly independent, orthogonal axes, called principal components, each of which accounts for successive directions in the n-dimensional ellipsoid spanning the multi-variate distribution of the original data. The corresponding eigenvalues ($\lambda 1$–$\lambda 5$) of matrix $\Lambda$ account for progressively smaller fractions of the total variance in the original data (FIG. 31C). Adjacency matrices were constructed using Notepad (Microsoft) and graphs drawn and analyzed using Pajek (v0.72) [See vlado.fmf.uni-lj.si/pub/networks/pajek/].

Molecular Descriptor Analysis

A structure descriptor file containing each small molecule was imported into QSARIS (SciVision, Inc.) for enumeration of a set of 221 graph and information theoretic and physiochemical descriptors. 3-dimensional descriptors were computed using an energy-minimized conformation. Descriptors with zero variance were removed before importing data into Microsoft excel and performing PCA (XL-STAT-Pro v5.2). Visualization of 3-dimensional PCA models was performed by importing the coordinates of compounds after PCA into Spotfire Descision Site software (v7.0).

IX. EXAMPLE 7

Domain-Selective Small Molecule Inhibitor Uncouples Tubulin Acetylation from Histone Acetylation and Cell Cycle Progression As discussed above, a multi-dimensional, forward chemical genetic screen of 7,392 small molecules was used to discover "tubacin", which inhibits intracellular deacetylation of α-tubulin in mammalian cells. It was recently reported that tubacin does not affect the level of histone acetylation, gene expression patterns, or cell cycle progression [See, Haggarty et al., "Domain-selective small-molecule inhibitor of histone deacetylase 6 (HDAC6)-mediated tubulin deacetylation", *Proc. Natl. Acad. Sci. USA*, 100(8): 4389–4394, 2003; which is incorporated herein by reference in its entirety]. It was suggested that the class II histone deacetylase HDAC6 is the intracellular target of tubacin. Only one of the two catalytic domains of HDAC6 possesses tubulin deacetylase activity, and only this domain is bound by tubacin. In addition, tubacin treatment did not affect the stability of microtubules to cold-, calcium-, or nocodazole-induced depolymerization, but did decrease cell motility. It was also shown that HDAC6 overexpression disrupted the localization of p58, a protein that mediates binding of Golgi elements to microtubules. The results of the study are detailed in Haggarty et al., "Domain-selective small-molecule inhibitor of histone deacetylase 6 (HDAC6)-mediated tubulin deacetylation", *Proc. Natl. Acad. Sci. USA*, 100(8): 4389–4394, 2003, and highlight the role of α-tubulin acetylation in mediating the localization of microtubule-associated proteins. Thus, compounds of the invention may selectively inhibit HDAC6-mediated α-tubulin deacetylation (e.g., tubacin). Such compounds may be useful as antimetastatic and antiangiogenic agents.

Figure 41A:
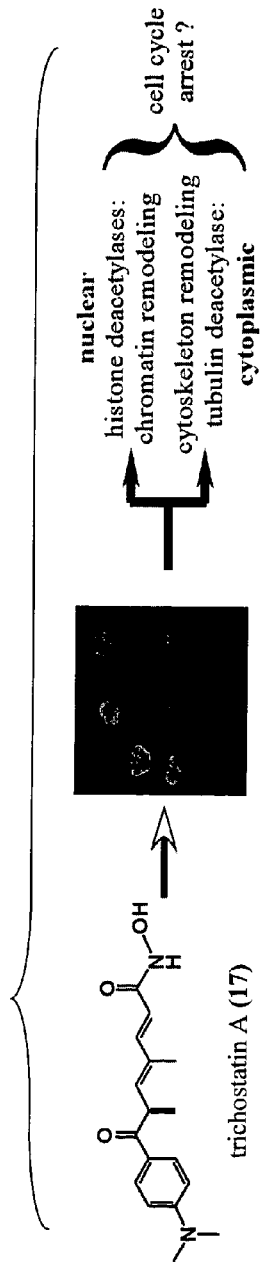
FIG. 41 depicts: (A) Chemical structure of TSA (17), an inhibitor of both α-tubulin and histone deacetylation, and immunofluorescence of BSC-1 cells treated with TSA (100 nM; 14 h) using anti-acetylated α-tubulin (pseudocolored red) and anti-acetylated lysine (pseudocolored green) primary antibodies. (B) Summary of multi-dimensional, cell-based screen of 7,392 small molecules having 1,3-dioxane diversity elements and deacetylase-biasing elements. (C) Image from six wells of a 384-well plate showing selectivity of tubacin (yellow box) in cytoblot assays measuring acetylated α-tubulin (AcTubulin) and acetylated lysine (AcLysine) in A549 cells. (D) Chemical structure of tubacin (15), an inactive analog niltubacin (18), and a polyethylene glycol (PEG)-linked, biotinylated analog, biotubacin (19). (E) Increased acetylated α-tubulin induced by tubacin in A549 cells detected by immunofluorescence using an anti-acetylated α-tubulin primary antibody (pseudocolored red) and nuclear staining with Hoechst 3342 (pseudocolored blue). (F) Selectivity of tubacin for inhibiting the TDAC versus HDACs, and inactivity of a control compound niltubacin (18), determined by western blot analysis of acetylated α-tubulin and histone H3 (K9, K14), and total α-tubulin levels in A549 cells treated (4 h) with DMSO, TSA (300 nM), tubacin (2 μM), and niltubacin (2 μM).
Figure 41B:
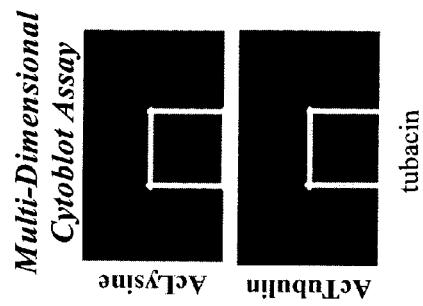
Figure 41C:
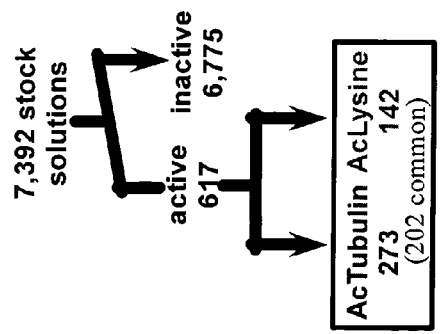
Figure 41D:
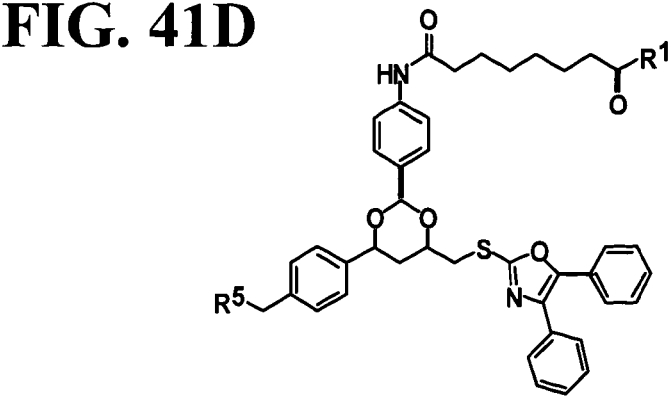
Figure 41D:
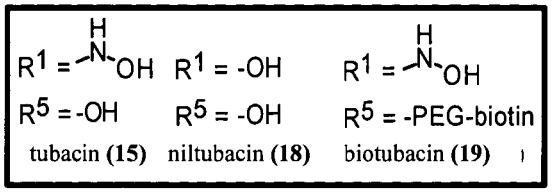
Figure 41E:
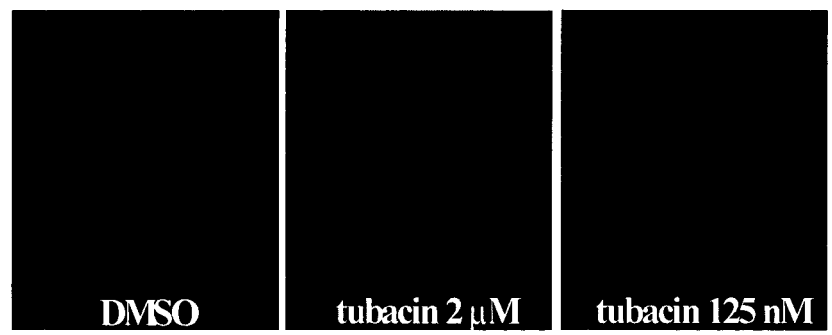
Figure 41F:
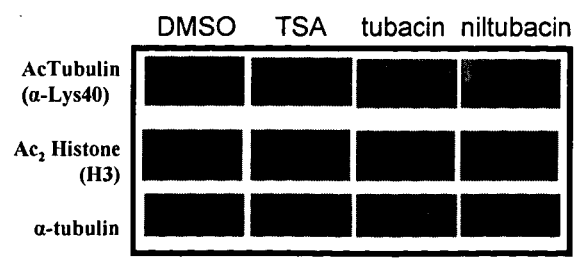
Figure 46:
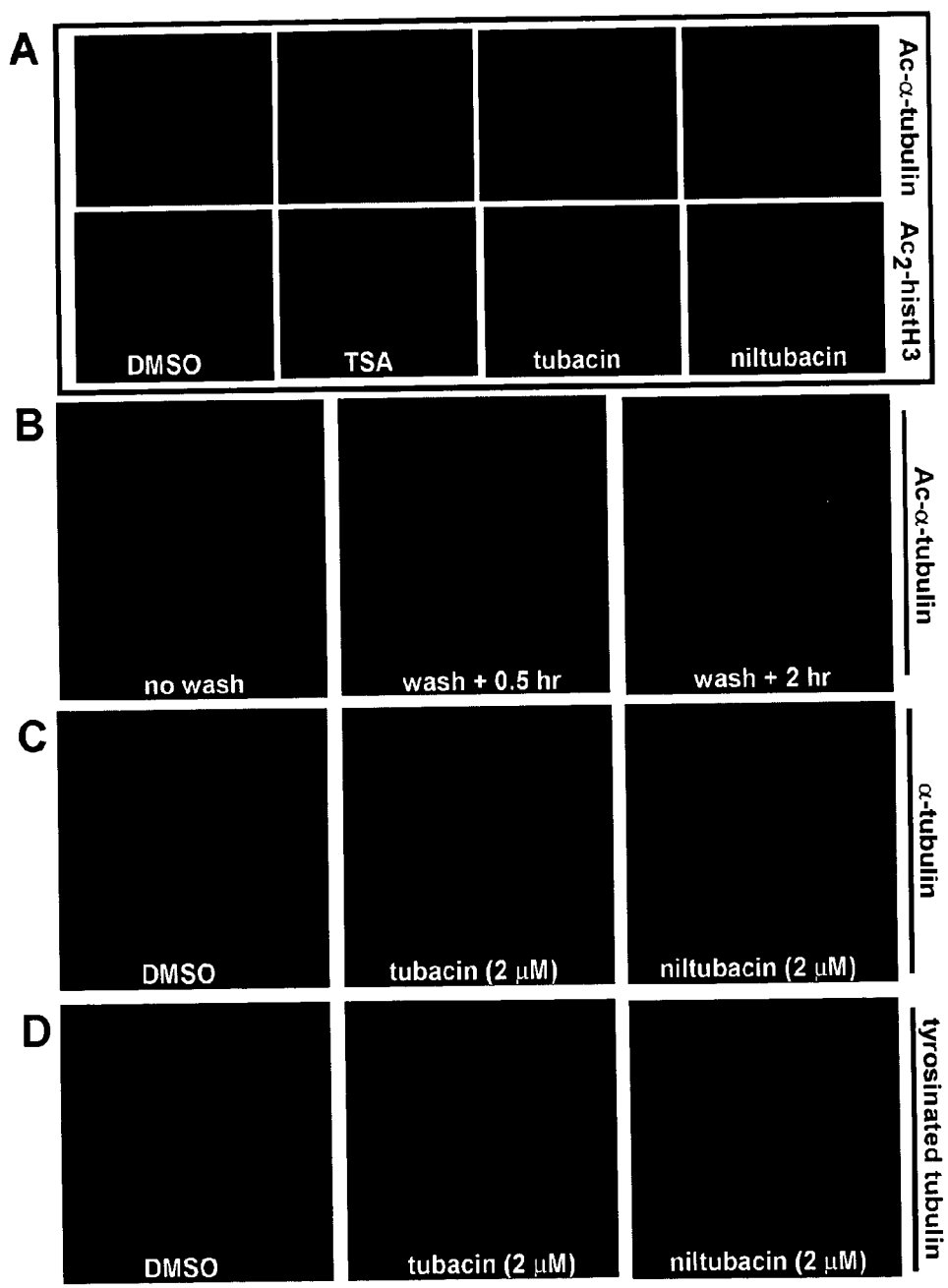
FIG. 46 illustrates the selectivity and reversibility of tubacin. (A) Effect of TSA (1 µM), tubacin (2 µM), and niltubacin (2 µM) treatment (14 h) on the level of acetylated α-tubulin and histone H3 detected by immunofluorescence using anti-acetylated α-tubulin (pseudocolored red) and anti-acetylated histone H3 (K9, K14) (pseudocolored green) primary antibodies. (B) Reversibility of tubacin-induced (2 µM; 5 h) α-tubulin acetylation detected by immunofluorescence using an anti-acetylated α-tubulin primary antibody (pseudocolored red) and nuclear staining with Hoechst 3342 (pseudocolored blue). (C) No effect of tubacin (2 µM) treatment (4 h) on the levels of α-tubulin detected by immunofluorescence using an anti-acetylated α-tubulin primary antibody (pseudocolored red). (D) No effect of tubacin (2 µM) treatment (4 h) on the levels of tyrosinated tubulin detected by immunofluorescence using an anti-tyrosine α-tubulin primary antibody (pseudocolored red).
Figures 47A, 47B:
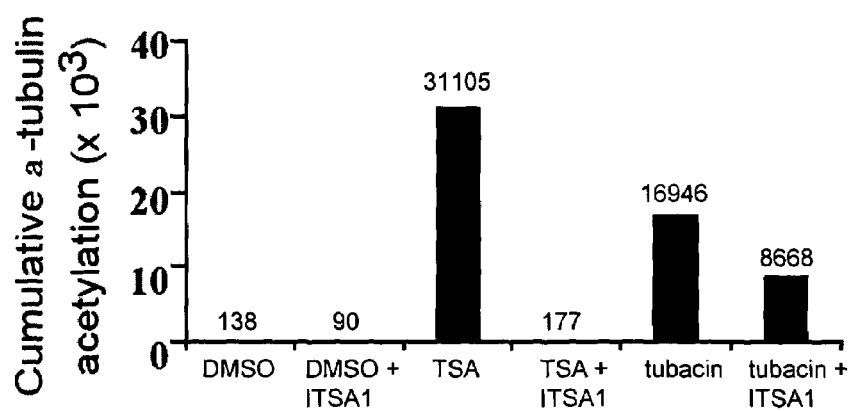
FIG. 47 depicts: (A) Mean (n=10,000) α-tubulin acetylation levels measured by FACS analysis of A549 cells pre-treated (4 h) with TSA (1 µM), or tubacin (2 µM), followed by the addition of ITSA1 (50 µM) for 14 h and staining for acetylated α-tubulin. (B) Cumulative α-tubulin acetylation level in a population of 10,000 cells treated as for (A). (C–F) Cytoplasmic localization of HDAC6 in BSC-1 cells untreated (C and D), treated (4 h) with TSA (250 nM) (E) or nocodazole (830 nM) (F) detected by immunofluorescence using anti-acetylated α-tubulin (pseudocolored red) and anti-HDAC6 (pseudocolored green) primary antibodies, and nuclear staining with Hoechst 3342 (pseudocolored blue). (G) Western blot analysis of HDAC6 purified from bovine brain after two rounds of polymerization-depolymerization of microtubules followed by elution of MAPs by phosphocellulose chromatography [See http://mitchison.med.harvard.edu/protocols/tubprep.html]. HDAC6 is abundantly expressed in whole brain and eluted with MAP fractions. (H) Western blot showing the levels of acetylated α-tubulin and total α-tubulin after incubation of MAP-stabilized or pure tubulin with immunoprecipitants from transfected TAg Jurkat cells. Whereas TSA (1 µM) and tubacin (1 µM) inhibited α-tubulin deacetylation, niltubacin (1 µM) or trapoxin B (TPX) (1 µM) did not. In contrast to Hubbert et al., [C. Hubbert et al., Nature 417, 455 (2002)], HDAC6 showed partial α-tubulin deacetylase activity in the absence of MAPs or additional stabilizing factors.
Figure 47:
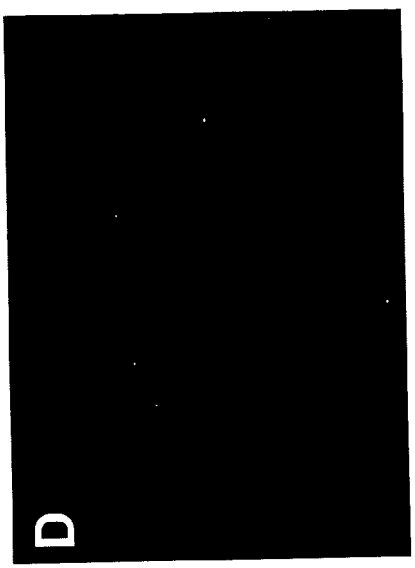
Figure 47:
Figure 47:
Figure 47:

At a threshold-level of a 1.5-fold increase in acetylation levels relative to untreated cells, 8.3% (n=617) of the deacetylase-biased 1,3-dioxane library (~5–10 μM) showed activity in either of the AcTubulin or AcLysine cytoblot assays (FIG. 41B; See also Example 6 above). To identify TDAC-selective inhibitors, stock solutions from wells corresponding to compounds with activity only in the AcTubulin and/or ITSA1+AcTubulin, but not the AcLysine assay, were retested for induction of α-tubulin or histone acetylation using fluorescence microscopy. Following retesting, promising precursor beads from the corresponding wells were subjected to gas chromatographic decoding, leading to structure determination and subsequent resynthesis. One hydroxamic acid-containing compound, here named tubacin (15) (FIGS. 41 C, D), was determined to be a potent (FIG. 41E), selective (FIG. 41F; FIG. 46A), and reversible (FIG. 46B) inhibitor of α-tubulin deacetylation. A close analog of tubacin containing a carboxylic acid at position R', here named niltubacin (18) (FIG. 41D), had no effect on α-tubulin or histone acetylation and was therefore used as a negative control (FIG. 41F). Without wishing to be bound to any particular theory, it is proposed that, due to the observed dependence of tubacin's activity on the presence of the hydroxamic acid, tubacin most likely targets a metal-dependent hydrolase. Tubacin did not affect the level of total α-tubulin or the level of α-tubulin containing a carboxy-terminal tyrosine (which is decreased in stabilized microtubules) (FIGS. 46C, D). In addition, unlike taxol, which increases α-tubulin acetylation due to direct stabilization of microtubules and which is not suppressed by ITSA1, tubacin had no overall effect on the morphology of A549 cells (FIG. 41E) and was partially suppressed by ITSA1 (FIGS. 47A, B). Together, these results suggest that tubacin causes an increase in α-tubulin acetylation without direct stabilization of microtubules.

Figure 42A:
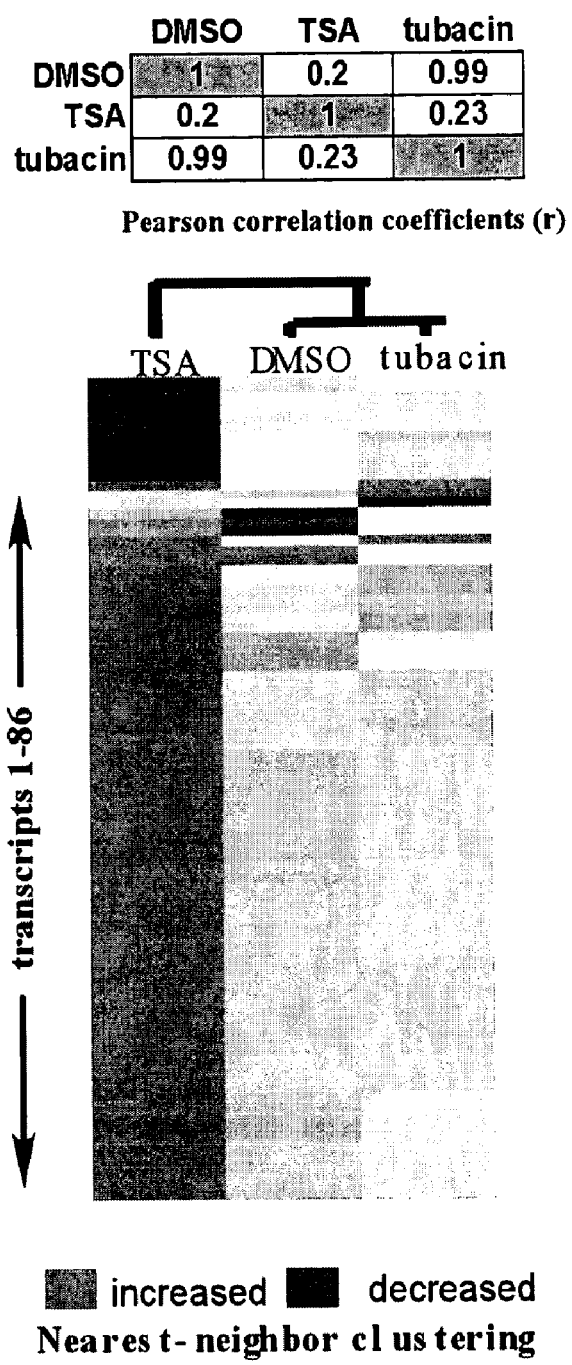
FIG. 42 depicts: (A) Pearson correlation matrix and nearest-neighbor clustering of a subset (86 of the most TSA-sensitive genes) of the average (n=2) gene expression data obtained from transcriptional profiling (U74Av2 gene chip; dChip software) of mouse embryonic stem cells treated with TSA (300 nM) and tubacin (2 μM). (B) No effect of tubacin on DNA synthesis or cell cycle distribution as determined by FACS analysis of BrdU-labeled and propidium iodide stained A549 cells after treatment (4 h) with TSA (300 nM) and tubacin (2 μM). (C) Mitotic abnormalities in A549 cells induced by TSA (10 μM) treatment (24 h) detected by immunofluorescence using an anti-acetylated α-tubulin primary antibody (pseudocolored red) and nuclear staining with Hoechst 3342 (pseudocolored blue). (D) Unlike TSA and HC Toxin, tubacin did not increase the frequency of mitotic abnormalities as calculated from the average (+/− one std. dev.) of two treatments (24 h; ~100 mitotic cells/treatment).
Figure 42B:
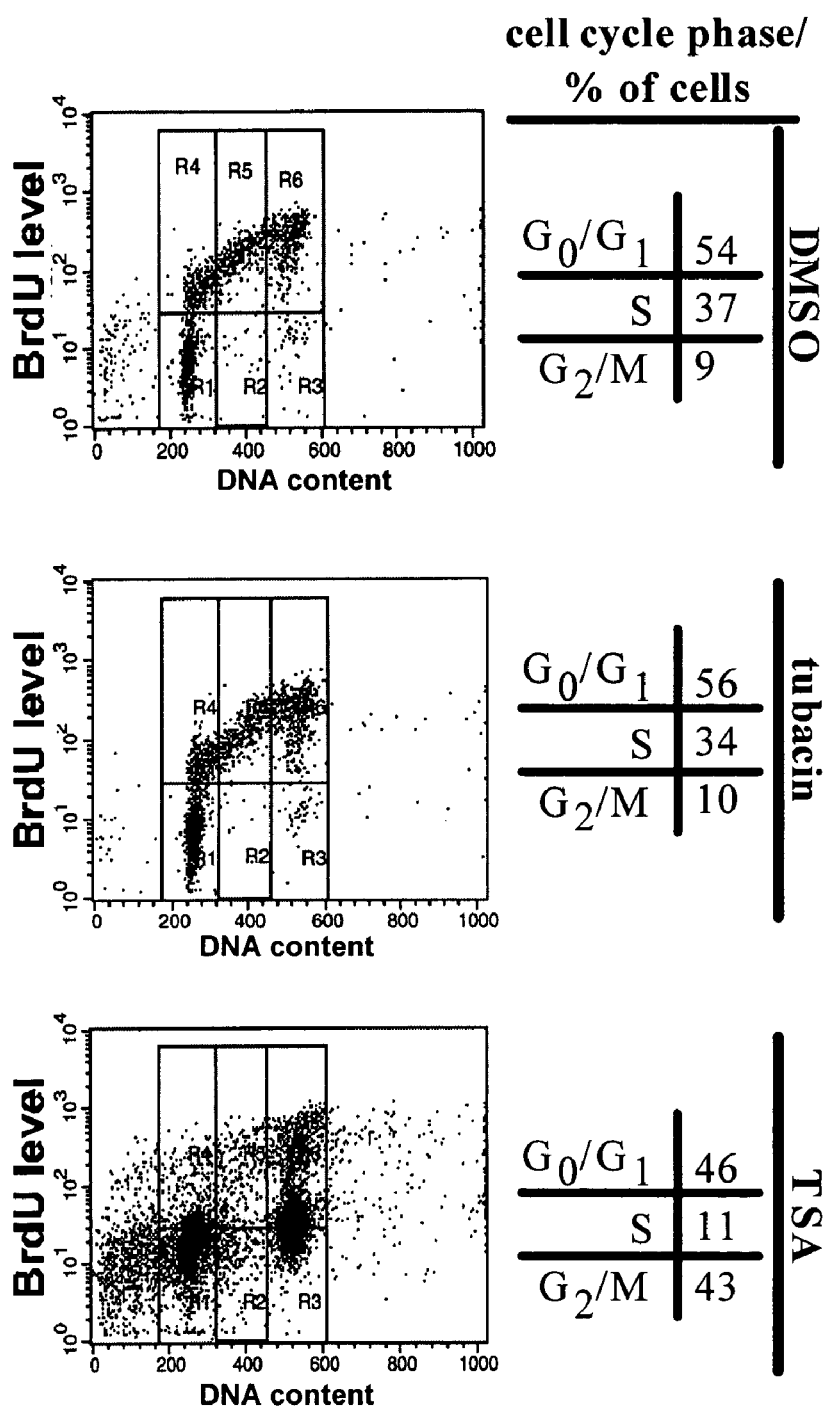
Figure 42C:
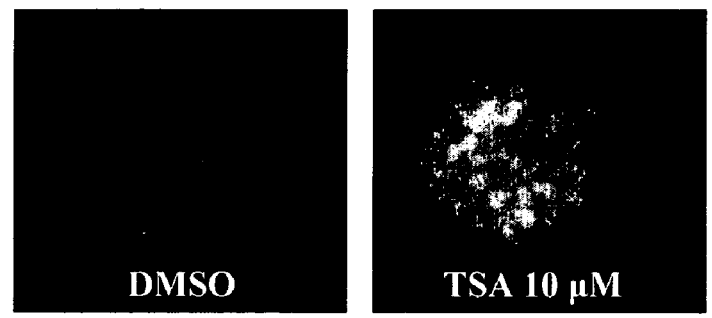
Figure 42D:
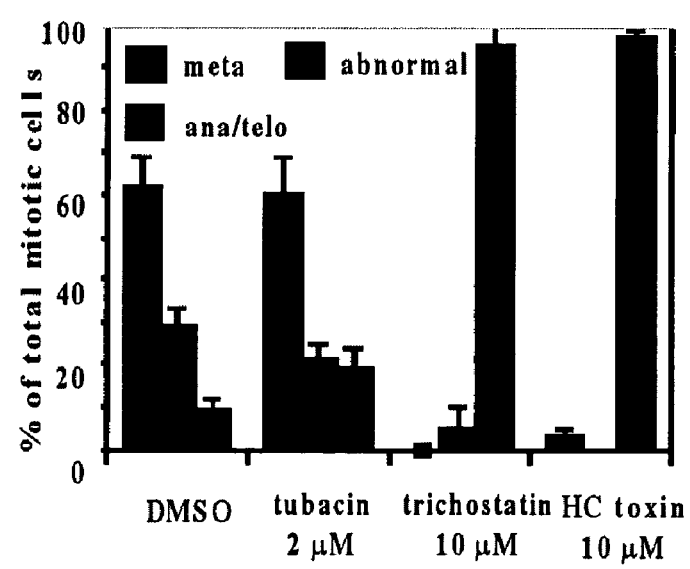
Figure 45B:
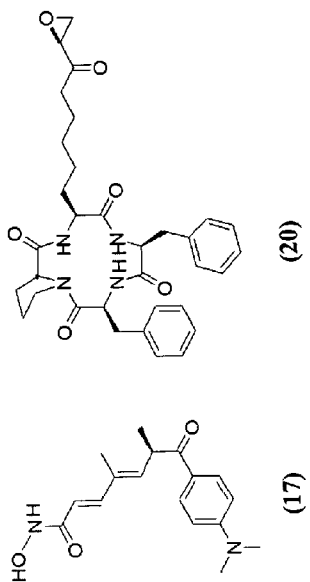
FIG. 45 depicts: (A) Effect of hydroxamic acid-containing trichostatin A (TSA (17); 300 nM) and the epoxy ketone-containing trapoxin B (TPX (20); 100 nM) treatment (4 h) on the acetylation of α-tubulin and histone H3 (K9, K14) in A549 cells determined by western blotting; ITSA1 (50 µM) was added 2 hours after TSA or TPX. (B) Chemical structures of TSA (17) and TPX (20). (C) Increased α-tubulin acetylation upon TSA (4 µM) treatment (24 h) of A549 cells detected by immunofluorescence using an anti-acetylated α-tubulin primary antibody. (D) Combinatorics of the 7,392-membered 1,3-dioxane library showing the three main functional classes (R') of biasing elements used to direct the compounds to the HDAC family of zinc hydrolases. The library was designed based upon the crystal structure of an HDAC homolog [M. S. Finnin et al., Nature 401, 188 (1999)] and substructural analysis of hydroxamic acid-, epoxy ketone-, and o-aminoanilide-based deacetylase inhibitors [S. M. Sternson et al., Org. Lett. 27, 4239 (2001)].
Figure 45A:
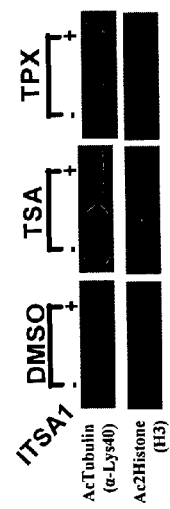
Figure 45C:
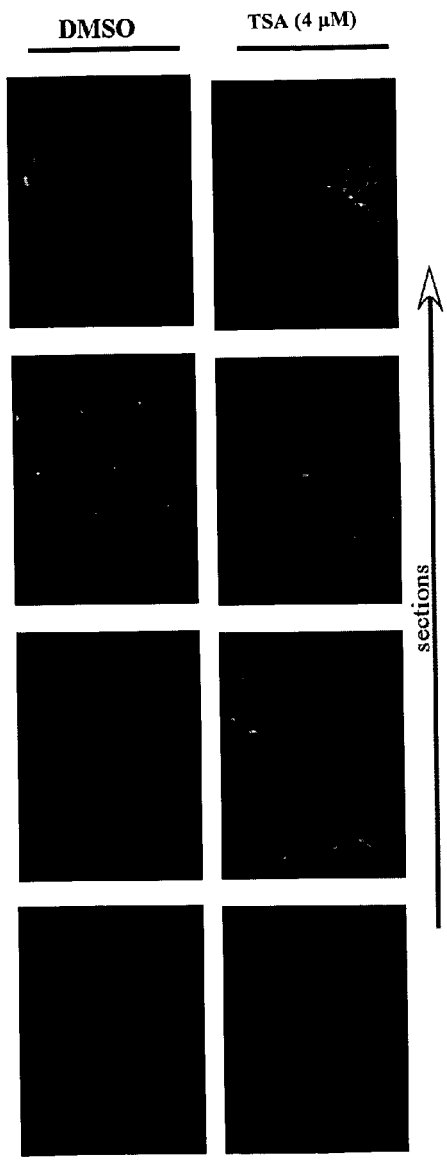
Figure 45D:
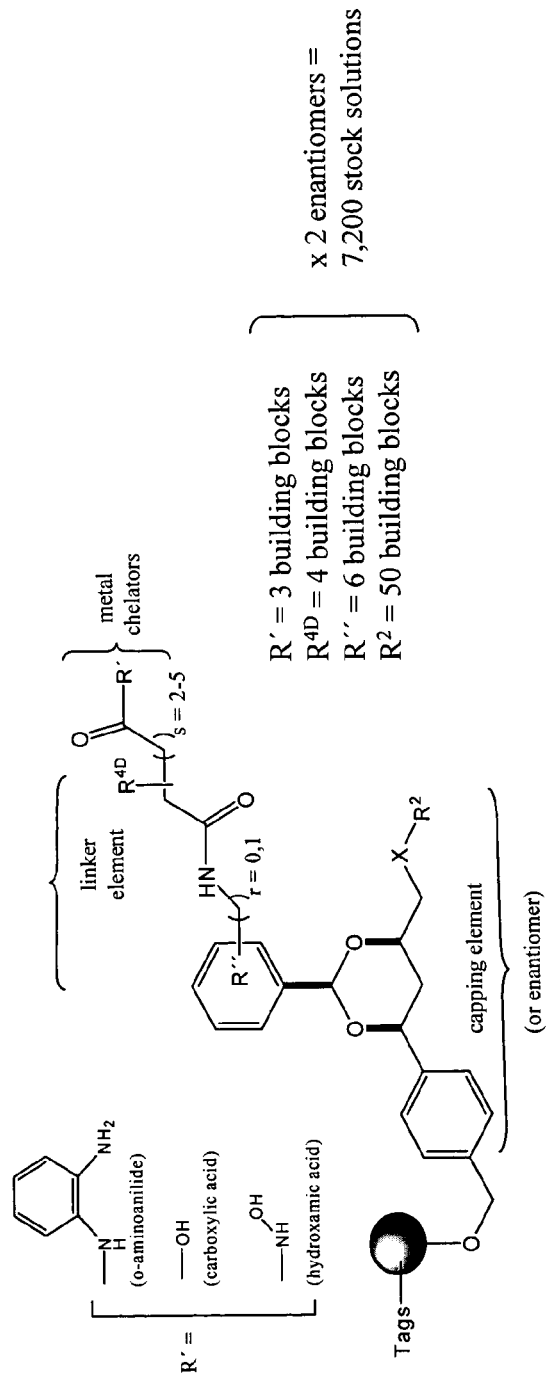

To test the intracellular selectivity of tubacin toward α-tubulin versus histone deacetylation, genome-wide transcriptional profiles of mouse embryonic stem cells treated with TSA and tubacin were compared. Using conditions sufficient for TSA and tubacin to increase α-tubulin acetylation (data not shown), TSA altered expression of 232 genes above a 1.3-fold threshold value. In contrast, in the presence of tubacin no genes showed a significant alteration in expression using the same statistical criteria (FIG. 42A). Globally, nearest-neighbor clustering indicated that tubacin treatment was more similar to the dimethylsulphoxide (DMSO)-treated control than to the TSA treatment (FIG. 42A). Thus, TDAC inhibition appears to have no or minimal effect on gene expression. As such, if cell cycle arrest induced by TSA-like compounds is linked to gene expression, then tubacin should also have no effect upon cycle progression. Indeed, as measured by fluorescence-activated cell sorting and bromodeoxyuridine labeling (BrdU), whereas TSA treatment led to a marked loss of a BrdU-positive S-phase population, and a concomitant increase in a sub-$G_1$ and $G_2$ population, tubacin treatment had no such effects (FIG. 42B). Besides the $G_1$ and $G_2$ cell cycle arrest, defects in mitotic spindle formation and chromosome orientation are also induced by TSA (FIG. 42C). To determine whether these defects are due to inhibiting tubulin deacetylation, we quantified abnormal mitotic cells following treatment (18 h) with TSA, tubacin, or HC toxin (an HDAC inhibitor with no effect on tubulin acetylation; FIG. 45A). Whereas tubacin had neither an effect on the number of mitotic cells nor spindle morphology, both TSA and HC toxin caused a significant number of abnormal mitotic cells, reminiscent of the effects of the Eg5-kinesin inhibitor monastrol (See, for example, T. U. Mayer et al., Science 286, 971, (1999)) (FIG. 42D). Because of the tubacin-insensitivity and HC toxin-sensitivity, we conclude that inhibition of α-tubulin deacetylation is not responsible for the mitotic defects caused by HDAC inhibitors. Instead, a deacetylase involved in chromatin remodeling is likely necessary for mitotic gene expression and/or proper kinetochore formation (See, for example, A. Taddei et al., Nat. Cell Biol. 3, 114 (2001)). Thus, through a chemical genetic approach we successfully uncoupled the effects of TSA on the TDAC from its effects on cell cycle progression.

Figure 47G:
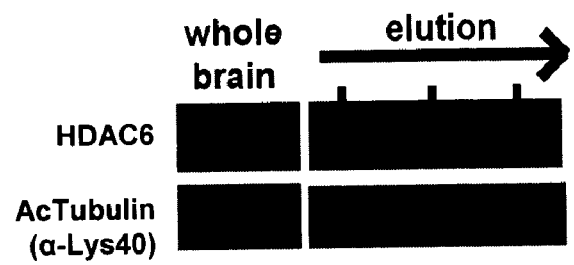
Figure 47H:
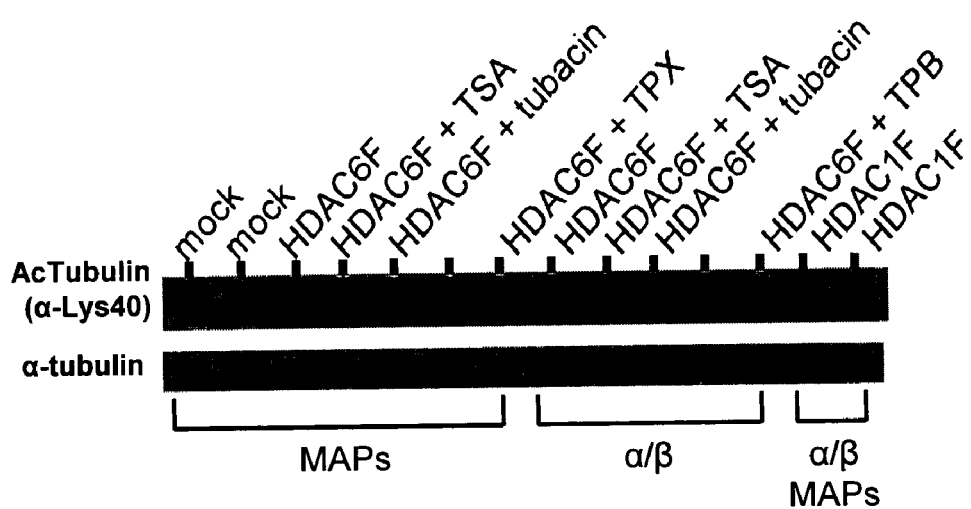

Unique features of the class II histone deacetylase HDAC6 lead us to speculate that it might be the intracellular target of tubacin. HDAC6 contains an internal pair of highly similar catalytic domains, shows cytoplasmic localization in certain cell types (FIGS. 47C–F), is resistant to trapoxin/HC toxin, shows few associations with other HDACs/transcription factors (See, for example, C. M. Grozinger, C. A. Hassig and S. L. Schreiber, Proc. Natl. Acad. Sci. U.S.A., 27, 4868 (1999)), and fractionates with microtubule-associated proteins (MAPs) from bovine brain (FIG. 47G). In agreement, while this work was in progress Hubbert et al. (C. Hubbert et al., Nature 417, 455 (2002)) described the identification of HDAC6 as a tubulin-associated deacetylase with in vitro TDAC activity. To test the notion that HDAC6 is the TDAC targeted by tubacin, TAg Jurkat cells were transiently transfected with wild-type, FLAG-tagged HDAC6F or HDAC1F expression vectors, and immunoprecipitants tested for TDAC activity using MAP-stabilized tubulin as substrate. As shown (FIG. 43A), the TDAC activity of HDAC6F was inhibited by the addition of TSA or tubacin, but not inhibited by the addition of niltubacin or trapoxin (FIG. 47H).

Although both catalytic domains of HDAC6 possess histone deacetylase activity, their activities toward tubulin deacetylation, as well as sensitivity to tubacin, remained to be determined. To this end, TAg Jurkat cells were transiently transfected with HDAC6F, catalytic subsite mutants (H216A or H611A), or a double mutant (H216A H611A), HDACs1F, 4F, or 5F, and the immunoprecipitants were subjected to in vitro deacetylase assays using [$^3$H]-histones as substrate (FIG. 43B). All immunoprecipitants, with the exception of the HDAC6 double mutant, possessed HDAC activity as expected. The HDAC6F H216A mutant, possessing residual HDAC activity from the H611 domain, was inhibited by tubacin or TSA. In contrast, the HDAC6F H611A mutant, possessing residual activity from the H216 domain, was not inhibited by tubacin or TSA. With acetylated tubulin as substrate, HDAC1F, HDAC4F, HDAC5F, and the HDAC6F H611A mutant all lacked deacetylase activity. In contrast, the HDAC6F H216A mutant exhibited TDAC activity that was inhibited by tubacin and TSA. Thus, we conclude that the H611 domain is the only domain having tubulin deacetylase enzymatic activity, and that the enzymatic activity of the H611 domain is a target of both tubacin and TSA. We speculate that the H216 domain serves as an α-tubulin K40-binding domain that facilitates recruitment and the generation of feedback loops in tubulin function. This two-domain feature is an important element to histone-modifying enzymes that impart processivity and switch-like behavior.

Figure 43D:
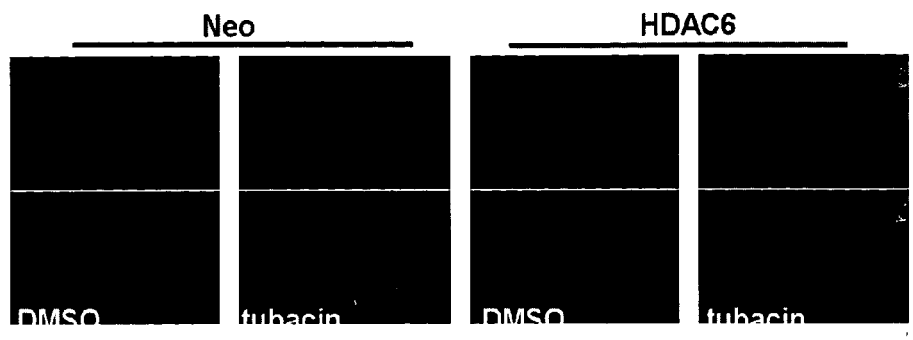
FIG. 43 depicts: (A) Western blot showing the levels of acetylated α-tubulin and total α-tubulin after incubation of MAP-stabilized tubulin with wild-type HDAC6F and wild-type HDAC1F immunoprecipitated from transfected TAg Jurkat cells. While HDAC1 showed no TDAC activity, the TDAC activity of HDAC6 was inhibited by TSA (300 nM) or tubacin (1 μM). (B) Effect of TSA and tubacin on the HDAC activity of immunoprecipitants from transfected TAg Jurkat cells. Activities (n=3; +/− mean absolute dev.) were measured by scintillation counting of [$^3$H]-labeled acetic acid released from [$^3$H]-labeled histones. Wild-type HDAC6F and the HDAC6F H216A mutant were only partial inhibited by TSA or tubacin, and the HDAC6F H611A mutant was not inhibited by either TSA or tubacin. (C) Western blot showing the levels of acetylated α-tubulin and total α-tubulin after incubation of MAP-stabilized tubulin with immunoprecipitants from transfected TAg Jurkat cells. Mutation of histidine 611 to alanine (H611A), but not histidine 216 to alanine (H216A), was sufficient to abolish the TDAC activity of HDAC6. (D) Decreased α-tubulin acetylation upon tubacin (2 µM) treatment (4 h) of HDAC6 overexpressing compared to control (Neo) NIH-3T3 cells detected by immunofluorescence using anti-acetylated α-tubulin (pseudocolored red) and anti-HDAC6 (pseudocolored green) primary antibodies, and nuclear staining with Hoechst 3342 (pseudocolored blue). (E) Increased co-localization of HDAC6 with acetylated α-tubulin in NIH-3T3 cells (Neo) upon tubacin (2 µM) treatment (4 h) detected by immunofluorescence using anti-acetylated α-tubulin (pseudocolored red) and anti-HDAC6 (pseudocolored green) primary antibodies, and nuclear staining with Hoechst 3342 (pseudocolored blue). Arrowhead indicates region of higher magnification. (F) Co-localization (yellow) of biotubacin (pseudocolored red) (19), a biotinylated analog of tubacin, with HDAC6 (pseudocolored green), and exclusion from nuclear regions, detected using fluorescence microscopy after incubation of biotubacin (50 µM) treated (4 h), formaldehyde-fixed cells with a streptavidin-TR conjugate, an anti-HDAC6 primary antibody, and nuclear staining with Hoechst 3342 (pseudocolored blue).
Figure 43E:
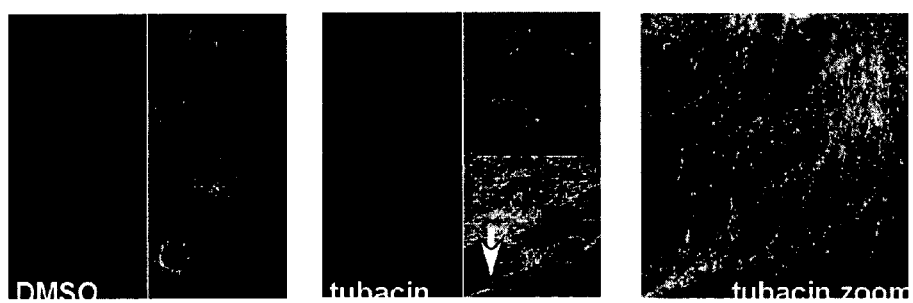
Figure 43F:
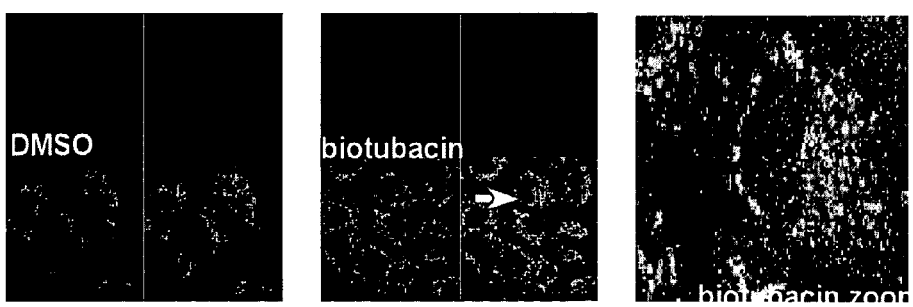
Figure 48A:
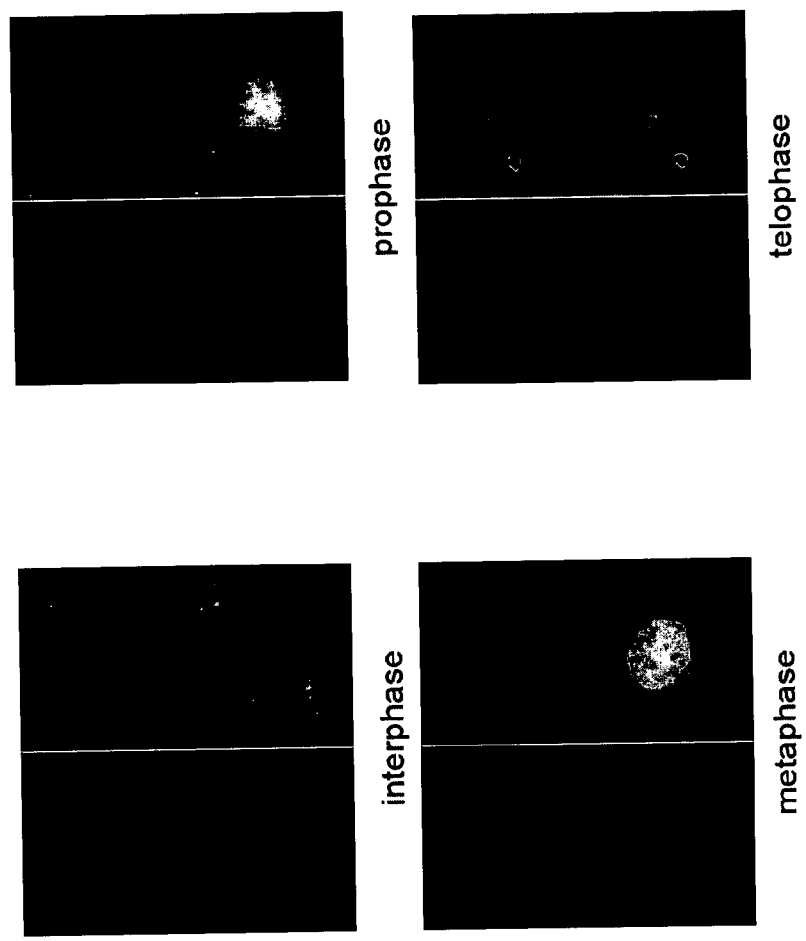
FIG. 48 depicts: (A) Restricted pattern of association of HDAC6 with acetylated microtubules composing the spindle and spindle pole body detected by immunofluorescence using anti-acetylated α-tubulin (pseudocolored red) and anti-HDAC6 (pseudocolored green) primary antibodies, and nuclear staining with Hoechst 3342 (pseudocolored blue) of A549 cells. (B) Microtubule depolymerization by nocodazole (332 nM; 5 h) is dominant to the effects of tubacin (2 µM) (S1–S4), and neither tubacin nor ITSA1 (50 µM; 30 minutes) prevents the repolymerization of microtubules following removal of nocodazole (S5–S8).

To test whether HDAC6 and tubacin interact in cells, we compared the staining pattern of acetylated α-tubulin in tubacin-treated fibroblasts stably expressing a control vector (Neo), HDAC6, or the HDAC6 double mutant. In control cells, tubacin induced an increase in α-tubulin acetylation. However, overexpression of HDAC6, but not the HDAC6 double mutant (data not shown), resulted in decreased tubucin-induced α-tubulin acetylation (FIG. 43D). In separate experiments, tubacin treatment caused an increase in the co-localization of HDAC6 along acetylated microtubules in interphase cells (FIG. 43E). In addition, HDAC6 was found to co-localize with the highly acetylated array of spindle microtubules and the spindle pole body in mitotic cells (FIG. 48A). These observations indicate that HDAC6 can associate with dynamic microtubule populations. Without wishing to be bound to any particular theory, since increased localization with microtubules was also observed upon serum starvation (C. Hubbert et al., Nature 417, 455 (2002)), we suggest that, besides acting as a substrate, acetylated α-tubulin may function to recruit HDAC6, and associated proteins, to its substrates. Such a signaling mechanism would be analogous to the recruitment of bromodomain-containing complexes to acetylated histones in chromatin (L. Zeng and M. M. Zhou, FEBS Lett. 513, 124 (2002)). As an additional test of the intracellular interaction of tubacin and HDAC6, a biotinylated analog of tubacin, here named biotubacin (19), was synthesized which retained the ability to induce α-tubulin acetylation (although approximately ten-fold less potently), and its subcellular localization using fluorescently-labeled streptavidin was determined. Control cells treated with a compound containing a biotinylated carboxylic acid, inactive analog (data not shown), showed steptavidin staining similar to untreated cells (FIG. 43F). In contrast, cells treated with biotubacin showed extensive co-localization of biotubacin and HDAC6 in the juxta-nuclear region, with a punctate staining pattern reminiscent of the Golgi apparatus, as well as exclusion from the nucleus (FIG. 43F). Collectively, these results suggest HDAC6 is indeed a TDAC and an intracellular target of tubacin.

Figure 44A:
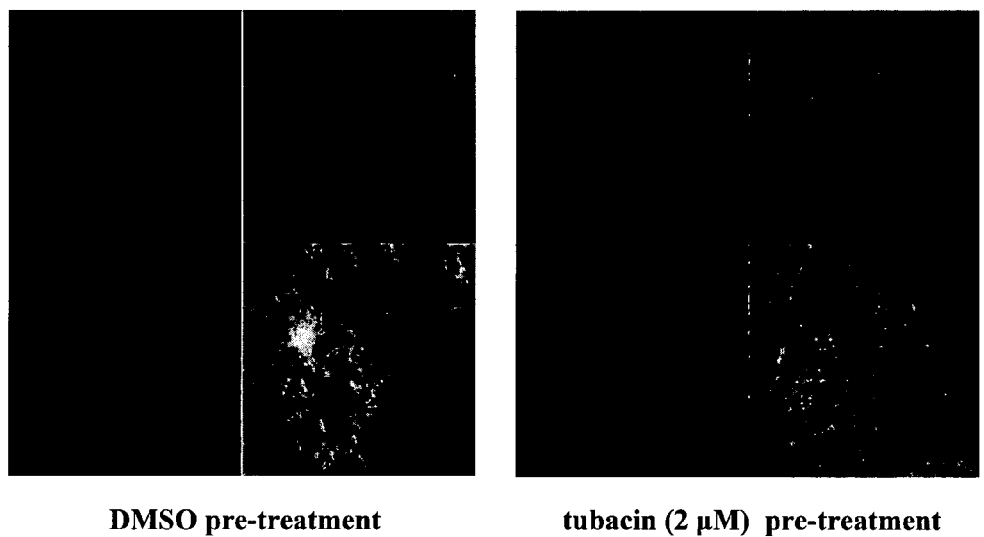
FIG. 44 depicts: (A) No effect of tubacin (2 µM) pre-treatment (4 h) on the stability of microtubules to nocodazole (332 nM; 2 h) induced depolymerization determined by immunofluorescence using anti-acetylated α-tubulin (pseudocolored red) and anti-α-tubulin (pseudocolored green) primary antibodies, and nuclear staining with Hoechst 3342 (pseudocolored blue). (B) In Transwell assays, tubacin (20–2 µM), but not niltubacin (20 µM), inhibited the migration of wild-type (Neo) NIH-3T3 cells (pseudocolored blue), as detected using a hematoxilyn stain. (C) Inhibition of control (Neo) and HDAC6-overexpressing NIH-3T3 cells measured by counting the number of hematoxilyn stained cells in Transwell assays. Data are presented as the mean (n=3; +/− one std. dev.) relative to untreated wild-type (Neo) cells. (D) Increased α-tubulin acetylation and decreased synaptotagmin staining of tubacin (1 µM), but not niltubacin (5 µM), treated (96 h) 8-day old rat hippocampal neuronal cultures detected by immunofluorescence using anti-acetylated α-tubulin and anti-synaptotagmin primary antibodies.
Figure 44B:
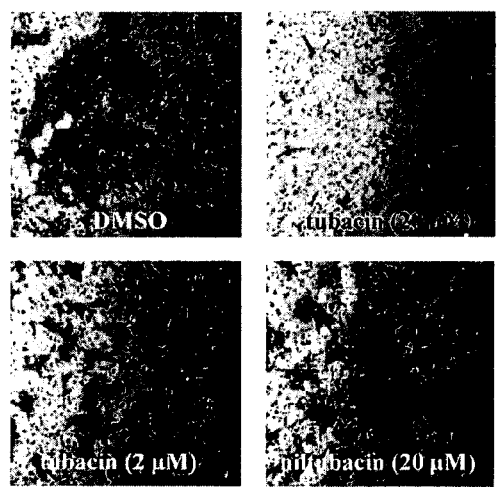
Figure 44C:
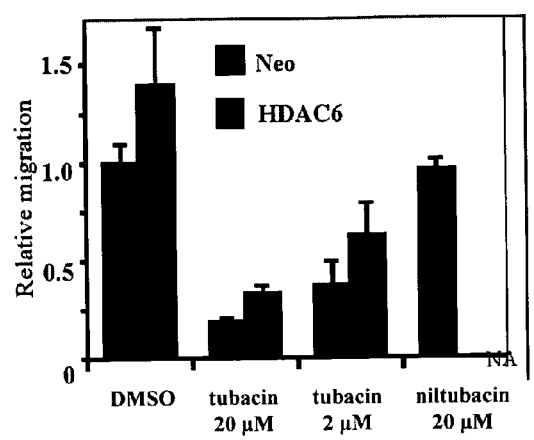
Figure 44D:
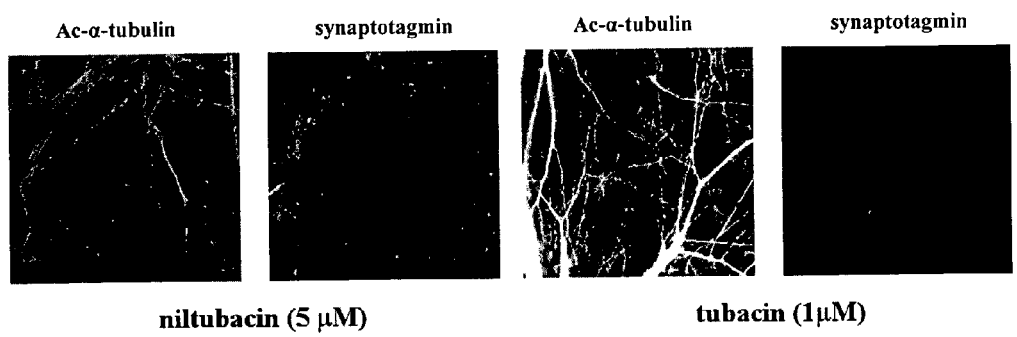
Figure 48B:
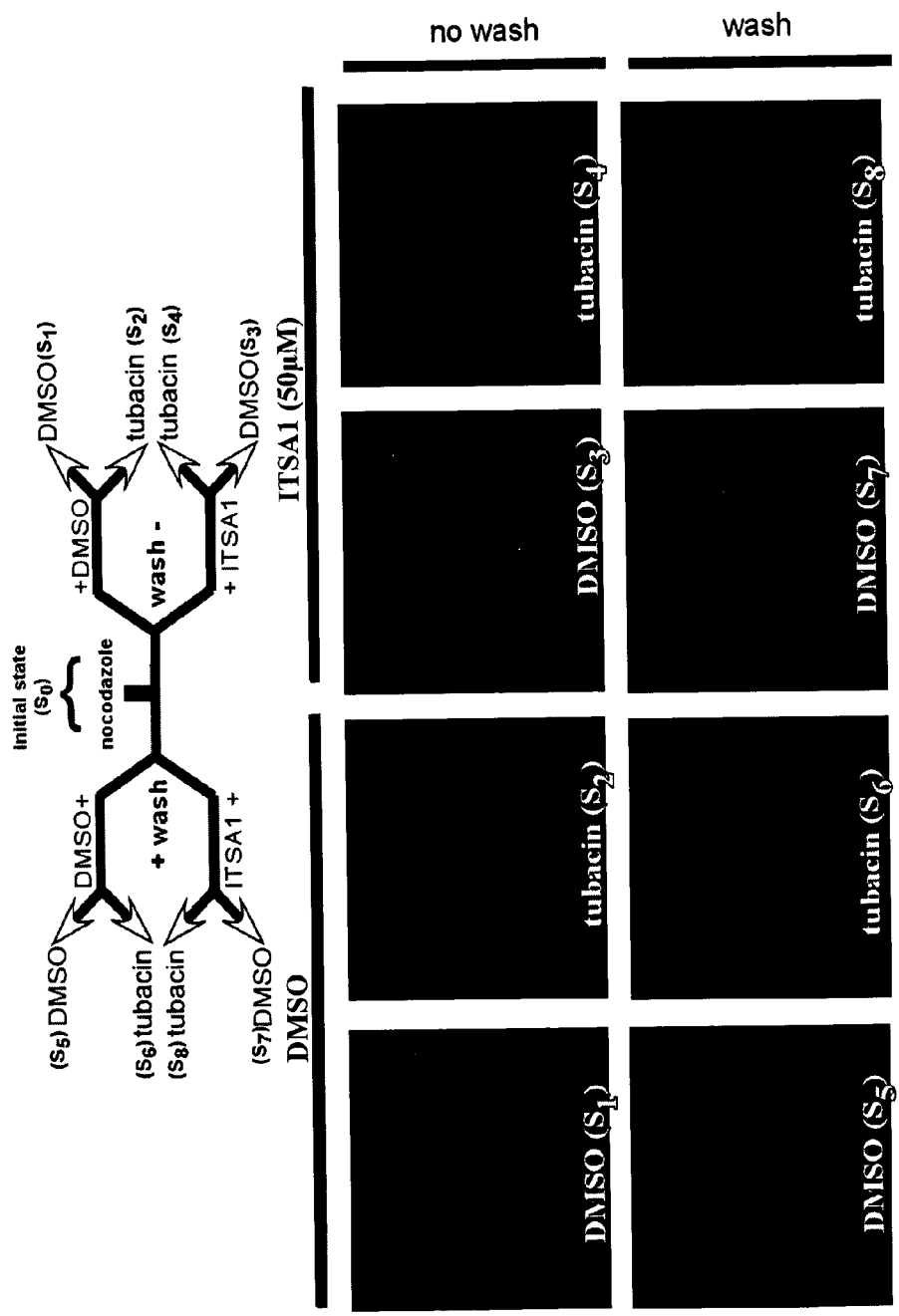
Figure 49A:
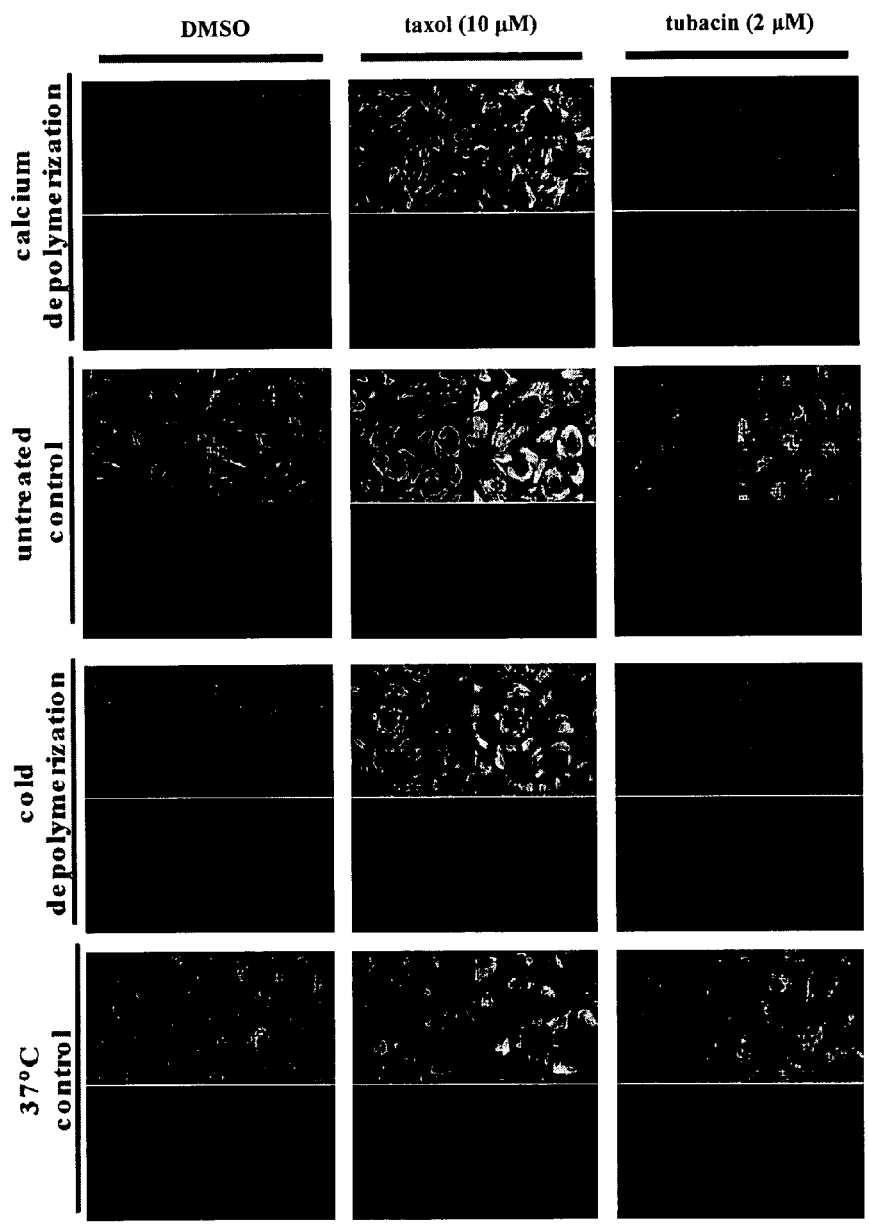
FIG. 49 depicts: (A) No effect of tubacin on the stability of microtubules to cold-depolymerization (90 minutes, 4° C.; left panel) or calcium-depolymerization (2 mM $CaCl_2$; 37° C.; right panel) in A549 cells. (B) Tubacin (20 µM), but not niltubacin (20 µM), treatment (39 h) increases F-actin microfilaments detected by fluorescence microscopy using TR-conjugated phalloidin (pseudocolored red), FITC-conjugated deoxyribonuclease (pseudocolored green), and nuclear staining with Hoechst 3342 (pseudocolored blue) in HT-1080 cells. (C) Overexpression of HDAC6, but not catalytic-inactive HDAC6, in NIH-3T3 cells causes mislocalization of p58, a Golgi-associated membrane protein, detected by immunofluorescence using anti-p58 (pseudocolored red) and anti-HDAC6 (pseudocolored green) primary antibodies.

Since α-tubulin acetylation is observed in non-mitotic cells within stable microtubule populations [G. Piperno, M. LeDizet, X. J. Chang, J. Cell. Biol. 104, 289 (1987); and M. Black, P. W. Baas and S. Humphries, J. Neurosci. 1, 358 (1989)], the theory as to whether increasing microtubule acetylation was sufficient to alter microtubule dynamics was tested. A549 cells were pre-treated with tubacin, and then treated with nocodazole, a microtubule destabilizer, or treated in the reciprocal order. In separate experiments, cells were pre-treated with either tubacin or taxol, and then calcium was added or the cells were placed on ice. Although tubacin treatment always increased α-tubulin acetylation levels, we observed no stabilization of microtubules to any of the depolymerizing conditions tested (FIG. 44A; FIGS. 48B and 49A). In addition, neither tubacin nor ITSA1 prevented the polymerization of microtubules after nocodazole was washed out (FIG. 48lB). The data suggests that increasing α-tubulin acetylation alone is not sufficient to stabilize microtubules or to prevent microtubule polymerization. Furthermore, although deacetylation may be coupled to depolymerization, deacetylation is not necessary for this process to occur [M. Black, P. W. Baas and S. Humphries, J. Neurosci. 1, 358 (1989)]. However, it is possible that acetylation-based stabilization of microtubules is beyond the resolution of our assay or is present within other physiological contexts. In support of this latter notion, and to extend the observation that overexpression of wild-type HDAC6 increases motility of serum-starved NIH-3T3 cells [C. Hubbert et al., Nature 417, 455 (2002)], it was determined whether tubacin treatment could block cell motility. In our hands, only a modest increase in the migration of HDAC6 overexpressing cells relative to wild-type cells was observable under normal culture conditions (i.e., not serum-starved cells). Regardless, tubacin (2 μM), but not niltubacin (20 μM), inhibited the migration of both wild-type- and HDAC6-overexpressing cells (FIGS. 44B,C). Tubacin, but not niltubacin, also caused an increase in the abundance of actin stress fibers in human fibrosarcoma cells, consistent with the notion that HDAC6 mediates signaling between the actin and tubulin cytoskeletal networks (FIG. 49B). In addition, overexpression of HDAC6, but not a catalytic inactive mutant disrupted the localization of p58, a Golgi membrane protein that mediates the binding of the Golgi to microtubules (FIG. 49C). These results support the idea that α-tubulin acetylation may be an important regulator of a variety of cellular processes.

Figure 50A:
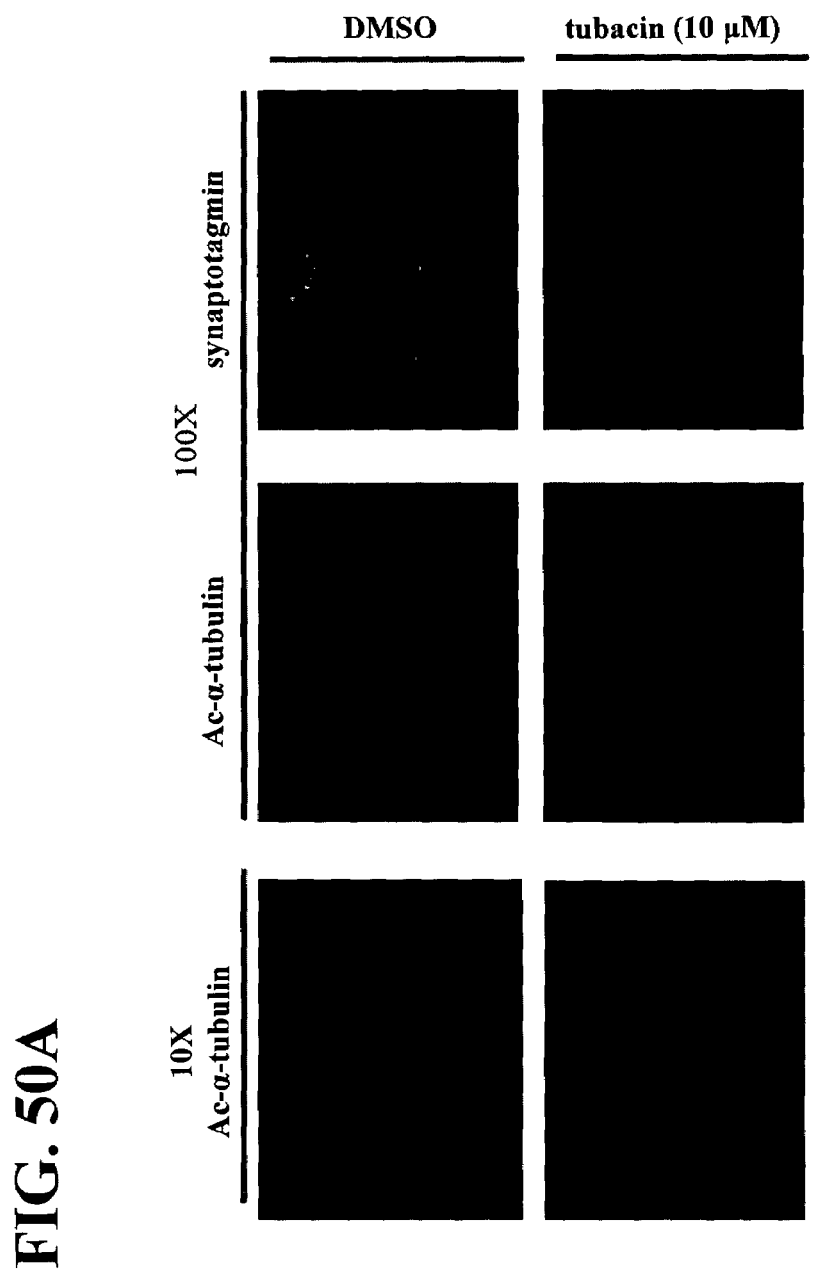
FIG. 50 depicts: (A) High concentrations of tubacin (10 µM; 48 hours), but not niltubacin (data not shown) increased the acetylation of α-tubulin (red) and decreased the viability and staining with synaptotagmin, a synaptic vesicle protein, of 7-day old cultured rat hippocampal neurons and astrocytes. (B) Low concentrations of tubacin had no affect on the viability of 10-day old neurons and astrocytes determined by the average (n=3) number of actin-EGFP positive transfected cells (C) after a 96-hour treatement (2 μM). No significant difference by the Student's T-test (two-tailed) for equality of means or the Fisher's F-test (one-tailed) for equality of variance was observed between the numbers of neurons (p=0.202/p=0.243) or astrocytes (p=0.156/p=0.167) upon tubacin treatment. Data are presented as the mean (n=3; +/− one standard dev.). (D) Effect of butyrate (10 mM) treatment (24 h) on the acetylation of α-tubulin and general acetylated lysine detected by immunofluorescence using anti-acetylated α-tubulin (pseudocolored red), anti-acetyl lysine (pseudocolored green) primary antibodies, and nuclear staining with Hoechst 3342 (pseudocolored blue) of A549 cells.
Figure 50B:
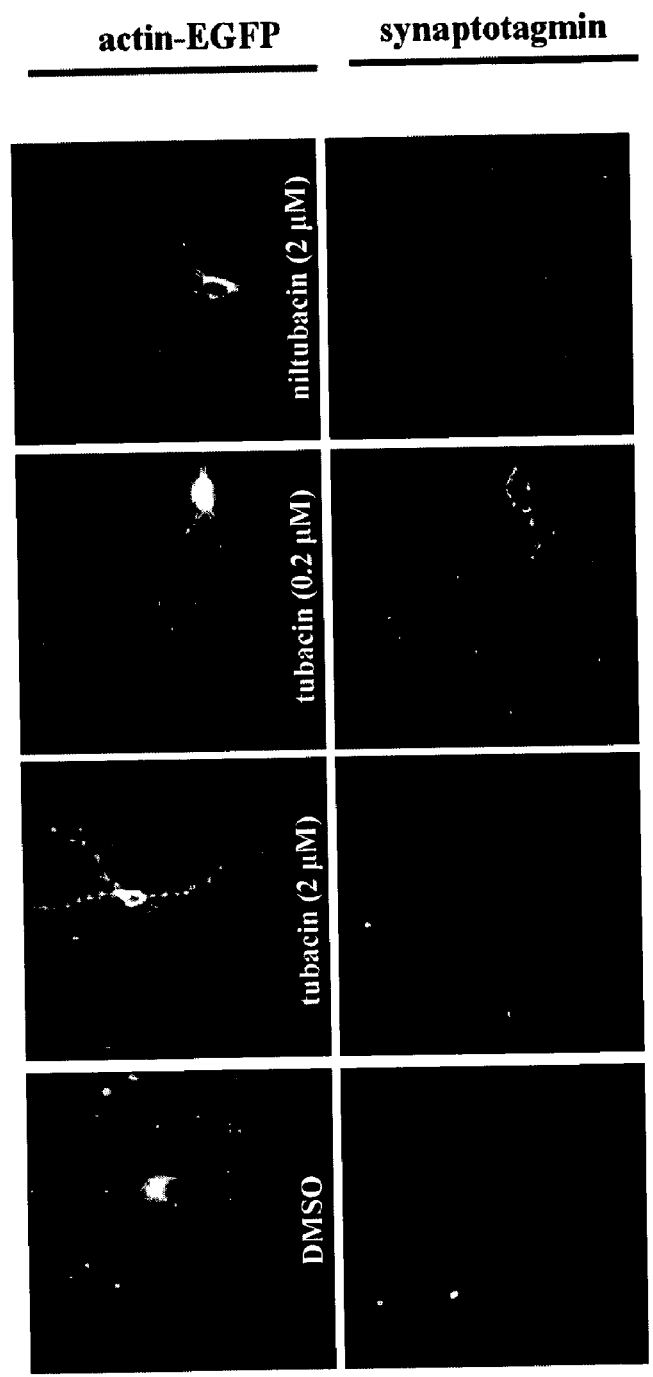
Figure 50C:
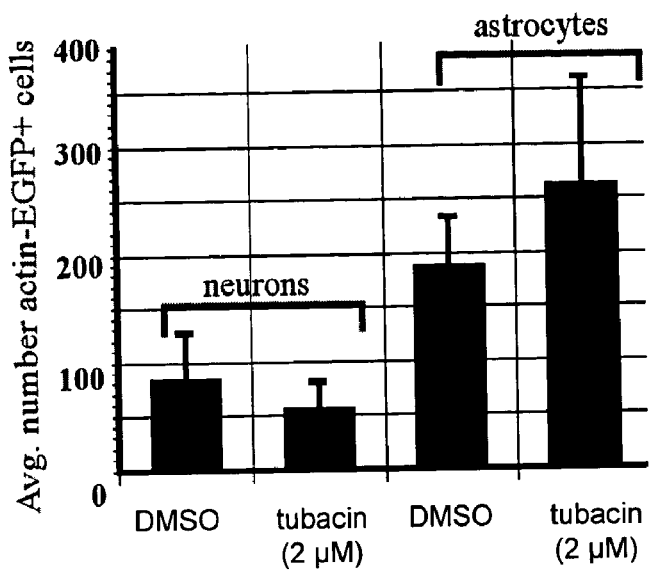
Figure 50D:
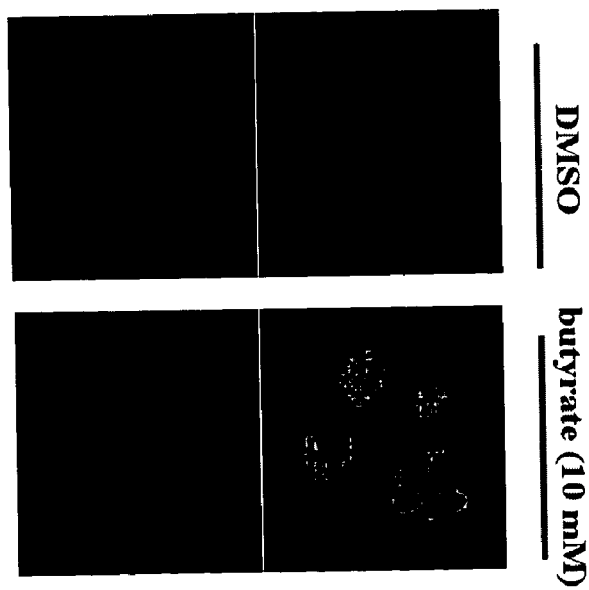

In contrast to the results obtained with tumor cell lines used in this study, tubacin (greater than 5 μM), but not niltubacin (greater than 5 μM) caused morphological changes and cell death in 7-day old cultured rat hippocampal neurons and astrocytes (FIG. 50A). However, 1 μM tubacin, which did not cause a significant decrease in the number of 10-day old rat hippocampal neurons or astrocytes (FIGS. 50B, C), increased α-tubulin acetylation in both cell types (FIG. 44E). Consistent with these results, HDAC6 was abundantly expressed within both rat hippocampal neurons and astrocytes (data not shown). The peak period for synaptogenesis in cultured hippocampal neurons is 7–9 days [T. L. Fletcher, P. Cameron, P. De Camilli, G. Banker, J. Neurosci. 11, 1617 (1991)]. We investigated the effect of adding tubacin to the neurons during this critical period. Immunostaining for synaptotagmin, a synaptic vesicle protein, showed that neurons treated with at least 1 μM tubacin for four days had fewer synapses when compared to control cells (FIG. 44E; FIG. 50B). These results suggest that a tubacin-sensitive, metal-dependent deacetylase, most likely HDAC6, is important for both neuronal survival and the establishment of the synapse. In this regard, we note that reduced α-tubulin acetylation levels have been reported in microtubules within neurons upon treatment with compounds that disrupt the Golgi apparatus [W. Elyaman, C. Yardin and J. Hugon, J. Neurochem. 81, 870 (2002)], and in certain neurodegenerative disorders, such as Alzheimer's disease [B. Hempen and J. P. Brion, J. Neuropathol. Exp. Neurol. 55, 964 (1996)]. In addition, both suberoylanilide hydroxamic acid [K. M. Koeller et al., *Chemistry & Biology*, 10 (5) (2003) pp. 397–410] and butyrate (FIG. 50D), the HDAC inhibitors used to suppress the neurotoxicity in poly-glutamine-repeat disorders (9), also inhibit HDAC6. Besides altering the expression levels of genes important for neuronal survival, the therapeutic effect of HDAC inhibitors may involve the inhibition of HDAC6 and concomitant acetylation of α-tubulin. Alternatively, given the presence of a carboxy-terminal poly-ubiquitin binding zinc finger domain (ZF-UBP; FIG. 43B) and co-purification of HDAC6 with deubiquitinating enzymes [S. S. Hook et al., Proc. Natl. Acad. Sci. USA 99, 13425 (2002)], modulating HDAC6's function may affect the trafficking and proteasomal degradation of proteins important for synaptic plasticity and development [A. N. Hegde and A. DiAntonio, Nat. Rev. Neurosci. 11, 854 (2002)].

In summary, by combining chemical and genetic perturbations, we have demonstrated an example of 'mapping' a point (tubacin) in a multi-dimensional space of chemical genetic observations to interactions with a specific gene product (HDAC6). Since tubacin did not cause gene expression changes, cell cycle arrest, or mitotic abnormalities, it is possible to uncouple α-tubulin acetylation from histone acetylation in the design of therapeutically relevant HDAC inhibitors. In this regard, targeting HDAC6, now shown to be possible, may provide a means to inhibit cell migration involved in tumor metastasis, as well as prevent the loss of α-tubulin acetylation observed in certain neurodegenerative disorders.

Materials and Methods

Trichostatin A, nocodazole, Paclitaxel (taxol), 5-bromo-2' deoxyuridine 5' triphosphate, α-FLAG M2 agarose affinity gel beads, anti-acetylated tubulin antibody (mouse, 6-11B-1, IgG), anti-synaptotagmin (rabbit, IgG) antibody, anti-p58 (mouse, IgG) antibody and anti-FLAG M2 antibody, ribonuclease A, and Harris hematoxilyn stain were purchased from Sigma. ITSA1 was purchased from Chembridge. Anti-acetylated lysine antibody (rabbit) was purchased from Cell Signaling. Anti-acetyl-histone (K9, K14) H3 antibody (rabbit) was purchased from Upstate Biotechnology. Anti-mouse IgG horseradish peroxidsae (HRP)-conjugated and anti-rabbitt IgG HRP-conjugated secondary antibodies and enhanced chemiluminescent mixture (luminol) were purchased from Amersham Pharmacia. Alexa 594 and Alexa 488-conjugated anti-mouse IgG and anti-rabbit IgG antibodies, Hoechst 33342, propidium iodide, Texas Red (TR)-conjugated phalloidin, and fluorescein isothiocyanate (FITC)-conjugated deoxyribonuclease were purchased from Molecular probes. FITC-conjugated anti-mouse IgG (goat) antibody was purchased from Santa Cruz. Streptavidin-Texas Red (TR) was purchased from Calbiochem. MAP-rich tubulin and purified tubulin were purchased from Cytoskeleton. Phosphate buffered saline, fetal bovine serum, penicillin G sodium, streptomycin sulfate, and L-glutamine were purchased from Gibco BRL. The EGFP expression vector was obtained from Clontech.

Cell Culture

All cells were cultured at 37° C. in a humidified incubator supplemented with 5% carbon dioxide. Human A549 lung carcinoma cells, Human HT-1080 fibrosarcoma cells, BSC-1 African green monkey kidney epithelial cells (all from American Tissue Culture Collection) were cultured in Dulbecco's modified eagle medium (DMEM) supplemented with 10% fetal bovine serum, 100 units/mL penicillin G sodium, 100 μg/mL streptomycin sulfate, and 2 mM L-glutamine (DMEM+). Human TAg Jurkat cells and mouse ROSA26 embryonic stem cells (gift of E. Roberston, Harvard University) were cultured as described (12). Mouse NIH-3T3 wild-type (Neo), HDAC6, HDAC6 double mutant, and HDAC1 overexpressing cells (gift from C. Hubbert, Duke University) were cultured as described (C. Hubbert et al., Nature 417, 455 (2002)1). Hippocampal neurons were dissociated from 1-day old rats and grown in culture using methods as described (E. N. Star, D. J. Kwiatkowski and V. N. Murthy, *Nat. Neurosci.* 5, 239 (2002)). All animal experiments were approved by Harvard University's standing committee on the use of animals in research and training.

1,3-dioxane Library Screen and Cytoblot Assays 1,3-dioxanes from a single, polystyrene macrobead were prepared as 1–2 mM stock solutions as described (15). Compounds (2–5 μM) were screened in duplicate in acetylated α-tubulin and acetylated lysine cytoblot assays in A549 cells as described in Example 6 above. Statistical analyses were performed using XLSTAT-PRO (v5.2). A full description of statistical methods and screen analysis is given in Example 6 above. Bead decoding and structure determination were as described [S. M. Sternson et al., Org. Lett. 27, 4239 (2001); and H. E. Blackwell et al., Chem. Biol. 8, 1167 (2001)]. Tubacin and niltubacin were synthesized as described (S. M. Sternson et al., Org. Lett. 27, 4239 (2001)). Biotubacin, and the control biotinylated carboxylic acid were synthesized using similar methods, except for the incorporation of a poly-ethylene glycol linker connecting to a biotin moiety (unpublished data).

Immunocytochemistry and Fluorescence Microscopy

Detection of acetylated α-tubulin and acetylated hi stones by immunofluorescence was performed as described in Example 6 above. For determining microtubule stability, A549 cells were treated as indicated, fixed in glutaraldehyde, and stained for acetylated α-tubulin and total α-tubulin in antibody dilution buffer (ADB, Tris-buffered saline (TBS), 0.15 M NaCl, 0.02 M Tris-Cl, pH 7.4, with 2% bovine serum albumin and 0.1% Triton-X 100). For cold-depolymerization, cells were incubated at 4° C. or 37° C. for an additional 90 minutes before fixation. For calcium depolymerization, cells were incubated at 37° C. for 10 minutes in a microtubule-stabilizing buffer (0.2% NP-40, 5 mM $MgCl_2$, 2 mM EGTA, 2 M glycerol, 100 mM PIPES, pH 6.8) with and without the addition of $CaCl_2$ (2 mM) before glutaraldehyde fixation. For co-localization experiments, biotubacin (50 μM) treated A549 cells were fixed in 3.7% formaldehyde in TBS and processed as for detecting acetylated α-tubulin (See Example 6 above) with biotubacin detected using streptavidin-TR (1:500). HDAC6 was detected using a rabbit polyclonal antibody (1:250–1:750; C. M. G., unpublished data) under the conditions used to detect acetylated α-tubulin (See Example 6 above). Filamentous actin in HT-1080 cells was detected using TR-conjugated phalloidin (1 μg/mL), and depolymerized actin using FITC-conjugated deoxyribonuclease (10 μg/mL), following fixation in 3.7% formaldehyde in TBS. p58 (1:100) in NIH-3T3 cells was detected after fixation in 3.7% formaldehyde in TBS. Images for these experiments were collected on a Zeiss LSM510 confocal scanning laser microscope at the appropriate wavelengths using the accompanying software and processed with Adobe Photoshop. Deconvoluted serial images of TSA and DMSO treated A549 cells were obtained by taking sections (8μ) on a Zeiss Axioskop 2 microscope using an AxioCam camera and the accompanying software. Rat hippocampal neuronal cultures were fixed at room temperature for 15 min in phosphate-buffered saline (PBS) containing 4% paraformaldehyde. Cells were permeabilized in 0.1% Triton X-100 and incubated with 10% BSA in PBS. Synaptotagmin (1:1000) and acetylated tubulin (1:500) primary antibodies were incubated at 4° C. overnight with 1% BSA in PBS. Anti-mouse and anti-rabbit IgGs coupled to Alexa488 or Alexa594 were used as secondary antibodies. Images (typically 1280×1024 pixels) were acquired using a cooled charge-coupled-device (CCD) camera (PCO Sensicam on an Olympus inverted microscope (IX-70) with a 60×, 1.35 NA oil lens or using an AxioCam camera with a 63×, 1.4 NA oil or 40×, 0.75 NA lens.

Cell Cycle Analysis and FACS Analysis

Bromodeoxyuridine labeling and fluorescence-activated cell sorting (FACS) were performed as described (K. M. Koeller et al., *Chemistry & Biology*, 10 (5) (2003) pp. 397–410). For FACS analysis of acetylated α-tubulin levels, A549 cells (~75% confluent) in 10 cm dishes were treated with DMSO (0.1%), TSA (500 nM), or tubacin (2 µM) for 4.5 hours and then either DMSO (0.1%) or ITSA1 (50 µM) added for an additional 17.5 hours. Samples were rinsed in PBS, trypsinized, and fixed for two hours in 70% ethanol/30% PBS (4° C.). Cells were then washed once in PBS and stored overnight in PBS (4° C.). To measure acetylated tubulin levels, samples were blocked for 45 minutes in ADB, aspirated, and incubated in ADB with anti-acetylated tubulin (1:500) overnight (4° C.). Samples were washed twice in ADB and incubated in ADB with FITC-conjugated anti-mouse IgG (goat; 1:200) for one hour (room temperature). After washing twice in TBS, cells were resuspended in 100 µL of ribonuclease A (100 µg/mL) and incubated for five minutes (37° C.). To measure the DNA content, 400 µL of propidium iodide (50 µg/mL) was added to the samples and incubated for one hour (room temperature). Samples were analyzed using a FACScanII flow cytometer (Becton-Dickinson), at the Dana Farber Cancer Institute, exciting at 488 nm and measuring the acetylated tubulin-linked FITC fluorescence through a 514 nm bandpass filter and the PI fluorescence through a 600 nm wave-length filter. Cell cycle distributions were calculated from 10,000 cells and modeled using ModFit LT (V2.0) software.

Cell Migration Assays

For Transwell migration assays, wild-type or HDAC6 overexpressing NIH-3T3 cells were seeded (150,000 cells/well) in the upper chamber (uncoated polycarbonate membrane, 6.5 mm, 8 µm) in DMEM+ media with compounds added as indicated. After incubation (22 hours), non-migrated cells were removed using cotton swabs and remaining cells stained in Harris Hematoxylin solution. For each treatment, cells within a region (spanning the maximum diameter) of three separate membranes were counted under low magnification on a Leitz Laborlux microscope. For DMSO treatments the average count was ~600 cells/region. Images were obtained using a Hitachi HV-C12 CCD camera.

Gene Expression Analysis

Gene expression analysis of tubacin, TSA, and DMSO-treated mouse embryonic stem cells were performed according to the Affymetrix protocol using an U74A v2 chip as described in full (K. M. Koeller et al., *Chemistry & Biology*, 10 (5) (2003) pp. 397–410). Present calls were determined by accompanying software and data analysis, including array normalization and clustering, performed using dChip software [C. Li and W. H. Wong, Genome Biol. 2, 32 (2001); and E. E. Schadt, C. Li, B. Ellis and W. H. Wong, J. Cell Biochem. Suppl. 37, 120 (2001)].

Transfections, Immunoprecipitations and Western Blotting

FLAG-tagged HDAC pBJ5 constructs were transiently transfected by electroporation with 5 µg DNA for expression of recombinant proteins (C. M. Grozinger, C. A. Hassig and S. L. Schreiber, Proc. Natl. Acad. Sci. USA, 27, 4868 (1999); and C. A. Hassig et al., Proc. Natl. Acad. Sci. USA 95, 3519 (1998)]. Cells were mock transfected without DNA or with a non-FLAG-tagged pCMV-LacZ construct as a negative control. Forty-eight hours after transfection recombinant proteins were immunoprecipitated using anti-FLAG M2 agarose affinity gel beads as described [C. A. Hassig et al., Proc. Natl. Acad. Sci. USA 95, 3519 (1998)]. Western blotting using anti-acetylated α-tubulin (1:1000) anti-tubulin (1:1000), and anti-acetylated (K9, K14) histone H3 (1:1000) antibodies was performed using standard methods (K. M. Koeller et al., *Chemistry & Biology*, 10 (5) (2003) pp. 397–410). Tubulin and MAPs were isolated from bovine brain as described [See http://mitchison.med.harvard.edu/protocols/tubprep.html]. Whole brain and fractions from phosphocellulose chromatography were blotted for HDAC6 and acetylated α-tubulin. Cultured hippocampal neurons from dissociated 1-day old rat brains were transfected with an enhanced green fluorescent protein (EGFP)-actin construct at 4–5 days using the calcium phosphate method [E. N. Star, D. J. Kwiatkowski and V. N. Murthy, Nat. Neurosci. 5, 239 (2002); and Z. Xia, H. Dudek, C. K. Miranti and M. E. Greenberg, J. Neurosci. 16, 5425 (1996)]. Transfected cultures were allowed to grow for at least 48 h before the addition of experimental compounds.

In Vitro Histone and Tubulin Deacetylase Assays

[$^3$H]Acetate-incorporated histones were isolated from butyrate-treated HeLa cells as described [J. Taunton, C. A Hassig and S. L. Schreiber, Science 272, 408 (1996)]. Immunoprecipitates were incubated with acetylated histones and HDAC activity determined by scintillation counting as described [J. Taunton, C. A Hassig and S. L. Schreiber, Science 272, 408 (1996)]. TDAC assays were performed with immunoprecipitates using MAP-stabilized microtubules polymerized from MAP-rich tubulin fraction as described [C. Hubbert et al., Nature 417, 455 (2002)], or using microtubules polymerized in the absence of MAPs. Reactions were incubated (2 h) at 37° C., then incubated on ice (15 min). After centrifugation, the supernatant (diluted to 0.4 µg tubulin) and α-FLAG M2 agarose affinity gel beads were analyzed by western blotting with an anti-FLAG M2 antibody (1:1750) to ensure equal protein levels.

The invention claimed is:

1. A compound having the structure (I):

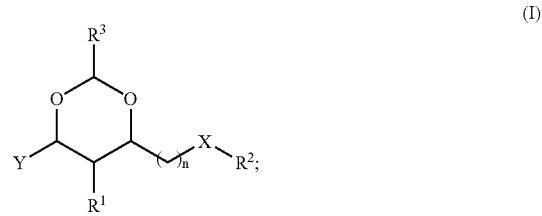

(I)

and pharmaceutically acceptable derivatives thereof;

wherein $R^1$ is hydrogen, or an aliphatic, alicyclic, heteroaliphatic, heterocyclic, aromatic or heteroaromatic moiety;

n is 1–5;

$R^2$ is hydrogen, a protecting group, or an aliphatic, alicyclic, heteroaliphatic, heterocyclic, aromatic or heteroaromatic moiety;

X is —O—, —C($R^{2A}$)$_2$—, —S—, or —NR$^{2A}$—, wherein $R^{2A}$ is hydrogen, a protecting group, or an aliphatic, alicyclic, heteroaliphatic, heterocyclic, aromatic or heteroaromatic moiety;

or wherein two or more occurrences of $R^2$ and $R^{2A}$, taken together, form an alicyclic or heterocyclic moiety, or an aryl or heteroaryl moiety;

$R^3$ is an aryl or heteroaryl moiety substituted with a moiety having the structure —L-$R^{4A}$, wherein L is a linker, and $R^{4A}$ comprises a metal chelator; and Y is aromatic moiety.

2. The compound of claim 1, wherein:

$R^1$ is hydrogen, or an aliphatic, alicyclic, heteroaliphatic, heterocyclic, aryl, heteroaryl, -(aliphatic)aryl, -(aliphatic)heteroaryl, -(heteroaliphatic)aryl, or -(heteroaliphatic)heteroaryl moiety;

$R^2$ is hydrogen, a protecting group, or an aliphatic, alicyclic, heteroaliphatic, heterocyclic, aryl, heteroaryl, -(aliphatic)aryl, -(aliphatic)heteroaryl, -(heteroaliphatic)aryl, or -(heteroaliphatic)heteroaryl moiety;

X is —O—, —C(R$^{2A}$)$_2$—, —S—, or —NR$^{2A}$—, wherein R$^{2A}$ is hydrogen, a protecting group, or an aliphatic, alicyclic, heteroaliphatic, heterocyclic, aryl, heteroaryl, -(aliphatic)aryl, -(aliphatic)heteroaryl, -(heteroaliphatic)aryl, or -(heteroaliphatic)heteroaryl moiety;

or wherein two or more occurrences of R$^2$ and R$^{2A}$, taken together, form an alicyclic or heterocyclic moiety, or an aryl or heteroaryl moiety;

R$^3$ is an aliphatic, alicyclic, heteroaliphatic, heterocyclic, aryl, heteroaryl, -(aliphatic)aryl, -(aliphatic)heteroaryl, -(heteroaliphatic)aryl, or -(heteroaliphatic)heteroaryl moiety; and Y is aryl, -(aliphatic)aryl, or -(heteroaliphatic)aryl moiety.

3. The compound of claim 1, wherein the compound has the structure as shown in formula (Ia):

(Ia)
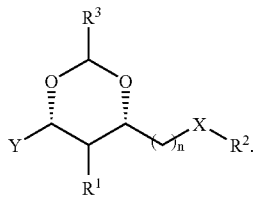

4. The compound of claim 1, wherein the compound has the structure as shown in formula (Ib):

(Ib)
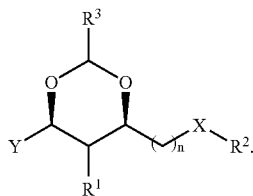

5. The compound of claim 1, wherein when R$^3$ represents a phenyl group substituted with a moiety having the structure —P-Q, the following groups do not occur simultaneously as defined:

P is selected from the group consisting of substituted or unsubstituted C$_4$–C$_8$ alkylene, C$_4$–C$_8$ alkenylene, C$_4$–C$_8$ alkynylene, and —R-T-U-, wherein R and U are independently absent or represent a C$_2$–C$_7$ alkylene, a C$_2$–C$_7$ alkenylene, or a C$_2$–C$_7$ alkynylene, and T represents O, S or NR$^T$, wherein R$^T$ represents hydrogen, lower alkyl, lower alkenyl, lower alkynyl, aralkyl, aryl or heterocyclyl; and Q is selected from the group consisting of:

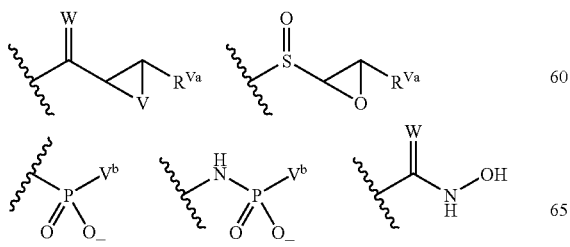

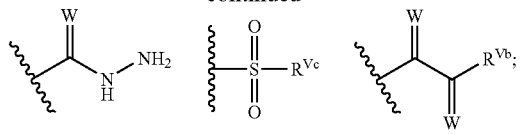

and a boronic acid moiety; wherein W is O or S; V is O, S or —NR$^{Vd}$, wherein R$^{Vd}$ is hydrogen, alkyl, alkoxycarbonyl, aryloxycarbonyl, alkylsulfonyl, arylsulfonyl, or aryl; R$^{Va}$ is hydrogen, alkyl, alkenyl, alkynyl, or aryl; R$^{Vb}$ is hydrogen, alkyl, aryl, alkoxy, aryloxy, amino, hydroxylamino, alkoxylamino or halogen; and R$^{Vc}$ is hydrogen, alkyl, aryl, hydroxyl, alkoxy, aryloxy or amino.

6. The compound of claim 1, wherein when R$^3$ represents a phenyl group substituted with a moiety having the structure —P-Q, the following groups do not occur simultaneously as defined:

P is selected from the group consisting of:

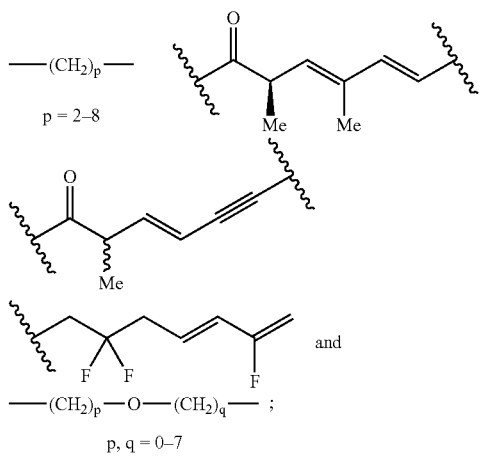

and Q is selected from the group consisting of:

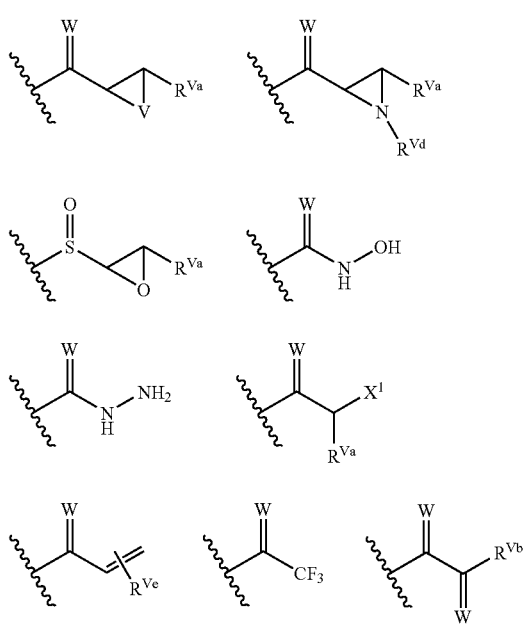

-continued

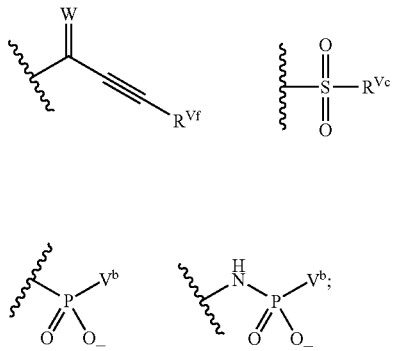

wherein W and $R^{Va-d}$ are as defined above; $X^1$ is a good leaving group (e.g., diazo, halogen, a sulfate or sulfonate ester such as a tosylate or mesylate); $R^{Ve}$ is hydrogen, alkyl, aryl, alkoxy, aryloxy, halogen; and $R^{Vf}$ is hydrogen, alkyl or halogen.

7. The compound of claim 1, wherein Y is an aryl or heteroaryl moiety substituted with Z, wherein Z is hydrogen, —$(CH_2)_qOR^Z$, —$(CH_2)_qSR^Z$, —$(CH_2)_qN(R^Z)_2$, —$C(=O)R^Z$, —$C(=O)N(R^Z)_2$, or an aliphatic, alycyclic, heteroaliphatic, heterocyclic, aryl, heteroaryl, -(aliphatic)aryl, -(aliphatic)heteroaryl, -(heteroaliphatic)aryl, or -(heteroaliphatic)heteroaryl moiety, wherein q is 0–4, and wherein each occurrence of $R^Z$ is independently hydrogen, a protecting group, a solid support unit, or an aliphatic, alycyclic, heteroaliphatic, heterocyclic, aryl, heteroaryl, -(aliphatic)aryl, -(aliphatic)heteroaryl, -(heteroaliphatic)aryl, or -(heteroaliphatic)heteroaryl moiety.

8. The compound of claim 1, wherein Y is a substituted phenyl moiety and the compound has the structure (II):

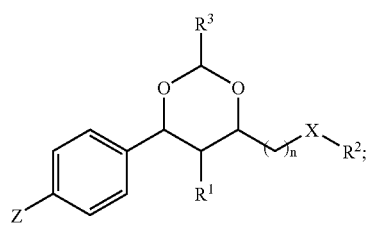

(II)

wherein Z is hydrogen, —$(CH_2)_qOR^Z$, —$(CH_2)_qSR^Z$, —$(CH_2)_qN(R^Z)_2$, —$C(=O)R^Z$, —$C(=O)N(R^Z)_2$, or an alkyl, heteroalkyl, aryl, heteroaryl, -(alkyl)aryl, -(alkyl)heteroaryl, -(heteroalkyl)aryl, or -(heteroalkyl)heteroaryl moiety, wherein q is 0–4, and wherein each occurrence of $R^Z$ is independently hydrogen, a protecting group, a solid support unit, or an alkyl, cycloalkyl, heteroalkyl, heterocyclic, aryl, heteroaryl, -(alkyl)aryl, -(alkyl)heteroaryl, -(heteroalkyl)aryl, or -(heteroalkyl)heteroaryl moiety.

9. The compound of claim 1, wherein Y is a substituted phenyl moiety and the compound has the structure (III):

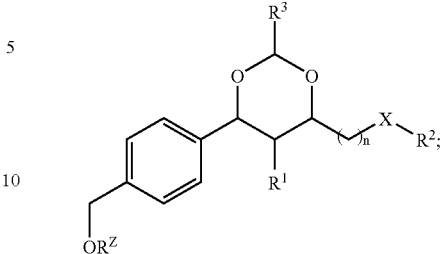

(III)

wherein $R^Z$ is hydrogen, a protecting group, a solid support unit, or an alkyl, cycloalkyl, heteroalkyl, heterocyclic, aryl, heteroaryl, -(alkyl)aryl, -(alkyl)heteroaryl, -(heteroalkyl)aryl, or -(heteroalkyl)heteroaryl moiety.

10. The compound of claim 1, wherein Y is a substituted phenyl moiety and X is S and the compound has the structure (IV):

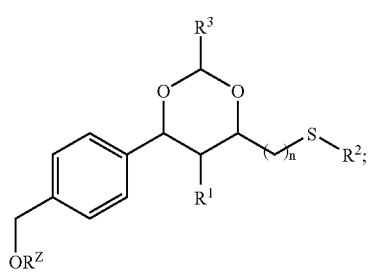

(IV)

wherein $R^Z$ is hydrogen, a protecting group, a solid support unit, or an alkyl, cycloalkyl, heteroalkyl, heterocyclic, aryl, heteroaryl, -(alkyl)aryl, -(alkyl)heteroaryl, -(heteroalkyl)aryl, or -(heteroalkyl)heteroaryl moiety.

11. The compound of claim 1, wherein Y is a substituted phenyl moiety and X is —$NR^{2A}$ and the compound has the structure (V):

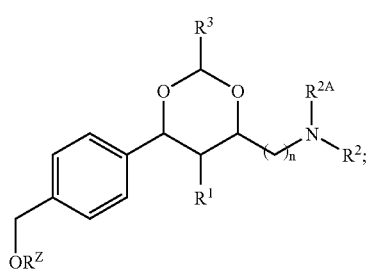

(V)

wherein $R^Z$ is hydrogen, a protecting group, a solid support unit, or an alkyl, cycloalkyl, heteroalkyl, heterocyclic, aryl, heteroaryl, -(alkyl)aryl, -(alkyl)heteroaryl, -(heteroalkyl)aryl, or -(heteroalkyl)heteroaryl moiety.

12. The compound of claim 1, wherein Y is a substituted phenyl moiety and X is —O— and the compound has the structure (VI):

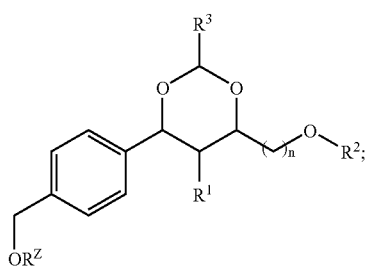

(VI)

wherein $R^Z$ is hydrogen, a protecting group, a solid support unit, or an alkyl, cycloalkyl, heteroalkyl, heterocyclic, aryl, heteroaryl, -(alkyl)aryl, -(alkyl)heteroaryl, -(heteroalkyl)aryl, or -(heteroalkyl)heteroaryl moiety.

13. The compound of claim 1, wherein Y is a substituted phenyl moiety and $R^3$ is a phenyl moiety substituted with $R^4$ and the compound has the structure (VII):

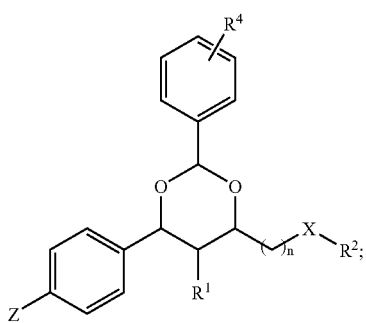

(VII)

wherein $R^4$ is —$(CH_2)_rN(R^{4A})_2$, —$(CH_2)_rSR^{4A}$, —$(CH_2)_r$ $OR^{4A}$, —$(CH_2)_rNR^{4A}C(=O)R^{4B}$, —$(CH_2)_r$ $C(=O)N(R^{4A})_2$, —$S(O)_2R^{4A}$, or is an aliphatic, alycyclic, heteroaliphatic, heterocyclic, aryl, heteroaryl, -(aliphatic)aryl, -(aliphatic)heteroaryl, -(heteroaliphatic)aryl, or -(heteroaliphatic)heteroaryl moiety, wherein each occurrence of $R^{4B}$ is independently hydrogen, an aliphatic, alycyclic, heteroaliphatic, heterocyclic, aryl, heteroaryl, -(aliphatic)aryl, -(aliphatic) heteroaryl, -(heteroaliphatic)aryl, or -(heteroaliphatic) heteroaryl moiety; and each occurrence of $R^{4A}$ is independently hydrogen, a protecting group, an aliphatic, alycyclic, heteroaliphatic, heterocyclic, aryl, heteroaryl, -(aliphatic)aryl, -(aliphatic)heteroaryl, -(heteroaliphatic)aryl, or -(heteroaliphatic)heteroaryl moiety, or is —$C(=O)CH(R^{4C})NH(SO_2)R^{4D}$, —$SO_2R^{4C}$, —$C(=O)R^{4C}$, —$C(=O)N(R^{4C})_2$, —$C(=S)N(R^{4C})_2$, or —$C(=O)(CH_2)_tC(=O)NHR^{4C}$, wherein each occurrence of $R^{4C}$ and $R^{4D}$ is independently hydrogen, a protecting group, hydroxyl, protected hydroxyl, or an aliphatic, alycyclic, heteroaliphatic, heterocyclic, aryl, heteroaryl, -(aliphatic) aryl, -(aliphatic)heteroaryl, -(heteroaliphatic)aryl, or -(heteroaliphatic)heteroaryl moiety, wherein r and t are each independently 0–5; and Z is hydrogen, —$(CH_2)_q$ $OR^Z$, —$(CH_2)_qSR^Z$, —$(CH_2)_qN(R^Z)_2$, —$C(=O)R^Z$, —$C(=O)N(R^Z)_2$, or an alkyl, heteroalkyl, aryl, heteroaryl, -(alkyl)aryl, (alkyl)heteroaryl, -(heteroalkyl) aryl, or (heteroalkyl)heteroaryl moiety, wherein q is 0–4, and wherein each occurrence of $R^Z$ is independently hydrogen, a protecting group, a solid support unit, or an alkyl, cycloalkyl, heteroalkyl, heterocyclic, aryl, heteroaryl, -(alkyl)aryl, -(alkyl)heteroaryl, -(heteroalkyl)aryl, or -(heteroalkyl)heteroaryl moiety.

14. The compound of claim 13, wherein Z is —$CH_2OR^Z$, and the compound has the structure (VIII):

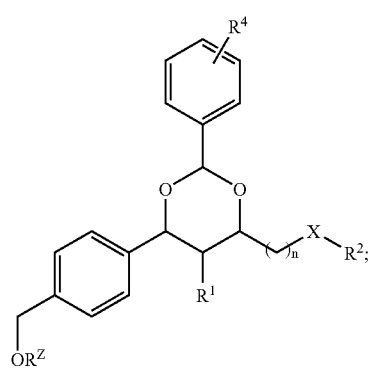

(VIII)

wherein $R^Z$ is hydrogen, a protecting group, a solid support unit, or an alkyl, cycloalkyl, heteroalkyl, heterocyclic, aryl, heteroaryl, -(alkyl)aryl, -(alkyl)heteroaryl, -(heteroalkyl)aryl, or -(heteroalkyl)heteroaryl moiety.

15. The compound of claim 1, wherein $R^1$ is hydrogen, methyl, or phenyl.

16. The compound of claim 1, wherein X—$R^2$ has one of the structures:

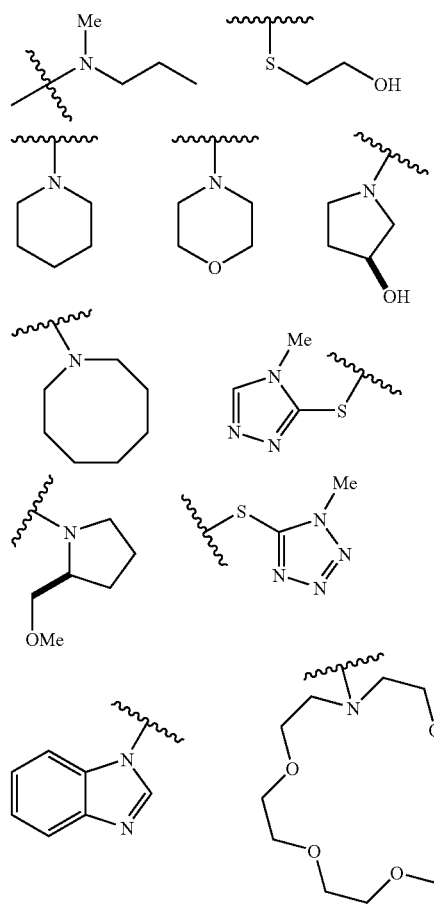

-continued
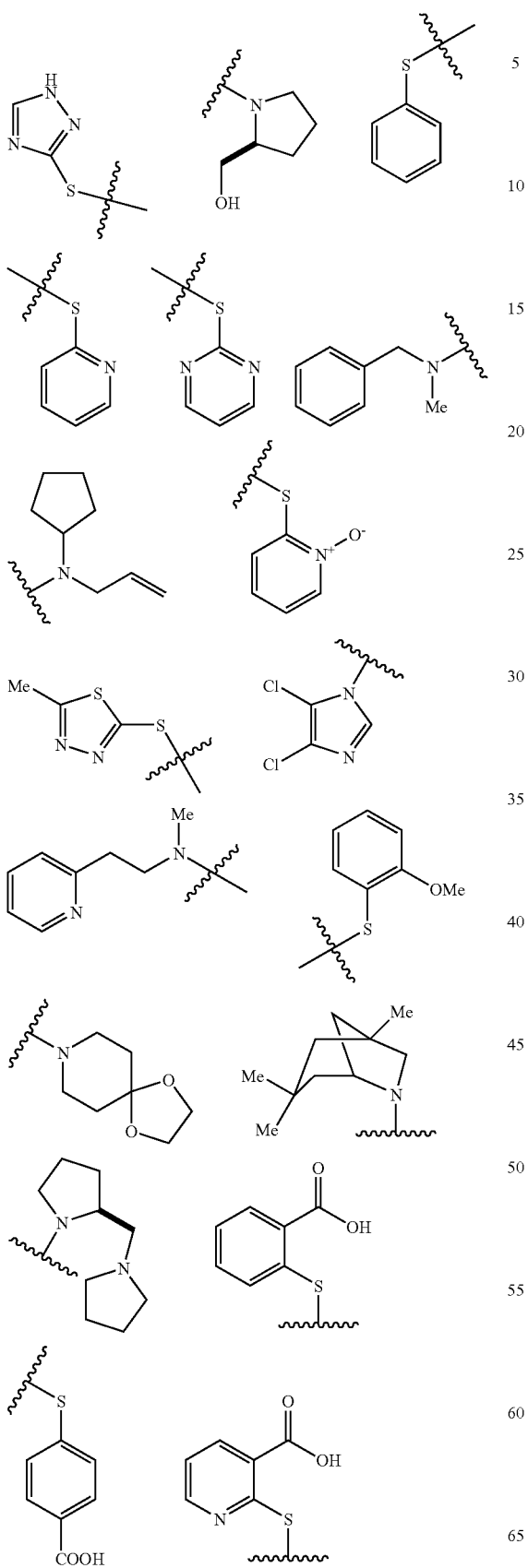
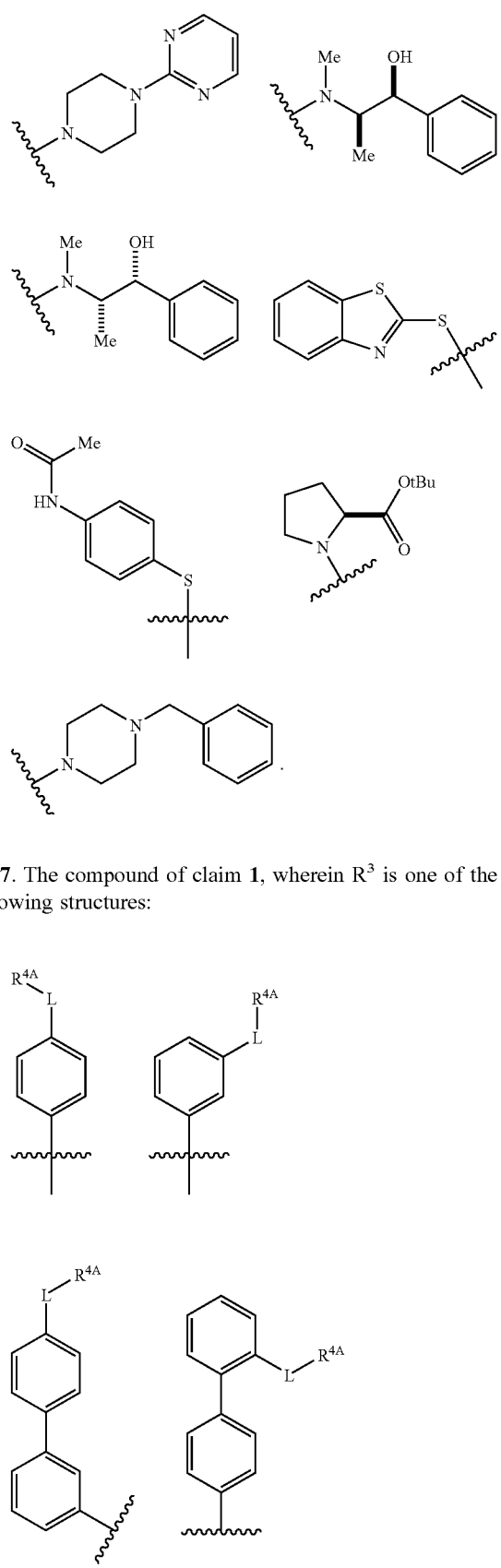
17. The compound of claim 1, wherein $R^3$ is one of the following structures:

-continued

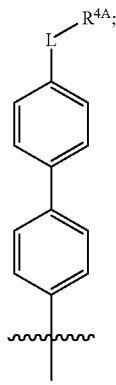

wherein L is a substituted or unsubstituted $C_{4-8}$alkylene or $C_{4-8}$alkenylene chain wherein up to two non-adjacent methylene units are independently optionally replaced by CO, $CO_2$, COCO, $CONR^{Z1}$, $OCONR^{Z1}$, $NR^{Z1}NR^{Z2}$, $NR^{Z1}NR^{Z2}CO$, $NR^{Z1}CO$, $NR^{Z1}CO_2$, $NR^{Z1}CONR^{Z2}$, SO, $SO_2$, $NR^{Z1}SO_2$, $SO_2NR^{Z1}$, $NR^{Z1}SO_2NR^{Z2}$, O, S, or $NR^{Z1}$; wherein each occurrence of $R^{Z1}$ and $R^{Z2}$ is independently hydrogen, alkyl, heteroalkyl, aryl, heteroaryl or acyl; and $R^{4A}$ comprises a metal chelator.

18. The compound of claim 17, wherein L is —$(CH_2)_rN(R^{4C})Alk^1$-, wherein r is 0 or 1; $R^{4C}$ is hydrogen, a nitrogen protecting group, alkyl, acyl, heteroalkyl, aryl or heteroaryl; and $Alk^1$ is a substituted or unsubstituted $C_{3-7}$alkylene or $C_{3-7}$alkenylene chain wherein up to two non-adjacent methylene units are independently optionally replaced by CO, $CO_2$, COCO, $CONR^{Z1}$, $OCON^{Z1}$, $NR^{Z1}NR^{Z2}$, $NR^{Z1}NR^{Z1}CO$, $NR^{Z2}CO$, $NR^{Z1}CO_2$, $NR^{Z1}CONR^{Z2}$, SO, $SO_2$, $NR^{Z1}SO_2$, $SO_2NR^{Z1}$, $NR^{Z1}SO_2NR^{Z2}$, O, S, or $NR^{Z1}$; wherein each occurrence of $R^{Z1}$ and $R^{Z2}$ is independently hydrogen, alkyl, heteroalkyl, aryl, heteroaryl or acyl.

19. The compound of claim 17, wherein L is —$(CH_2)_rN(R^{4C})C(=O)Alk^2$-, wherein r is 0 or 1; $R^{4C}$ is hydrogen, a nitrogen protecting group, alkyl, acyl, heteroalkyl, aryl or heteroaryl; and $Alk^2$ is a substituted or unsubstituted $C_{3-6}$alkylene or $C_{3-6}$alkenylene chain wherein up to two non-adjacent methylene units are independently optionally replaced by CO, $CO_2$, COCO, $CONR^{Z1}$ $OCONR^{Z1}$, $NR^{Z1}NR^{Z2}$, $NR^{Z1}NR^{Z2}$, CO, $NR^{Z1}CO$, $NR^{Z1}CO_2$, $NR^{Z1}CONR^{Z2}$, SO, $SO_2$, $NR^{Z1}SO_2$, $SO_2NR^{Z1}$, $NR^{Z1}SO_2NR^{Z2}$, O, S, or $NR^{Z1}$; wherein each occurrence of $R^{Z1}$ and $R^{Z2}$ is independently hydrogen, alkyl, heteroalkyl, aryl, heteroaryl or acyl.

20. The compound of claim 17, wherein L is —$(CH_2)_rNHC(=O)(CH_2)_t$—, wherein r is 0 or 1; and t is 3, 4, 5 or 6.

21. The compound of any one of claims 17–20, wherein $R^{4A}$ is —$C(=O)OR^{4B}$, —$C(=O)NHOR^{4B}$ or a moiety having the structure:

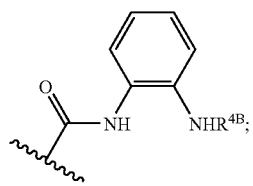

wherein each occurrence of $R^{4B}$ is independently hydrogen, alkyl, heteroalkyl, aryl, heteroaryl or acyl.

22. The compound of claim 1, wherein the compound has the structure:

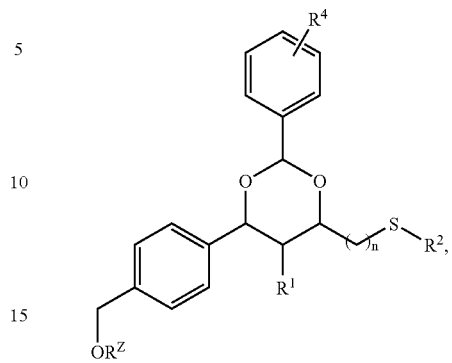

wherein $R^4$ is —$(CH_2)_rN(R^{4A})_2$, —$(CH_2)_rSR^{4A}$, —$(CH_2)_r OR^{4A}$, —$(CH_2)_rNR^{4A}C(=O)R^{4B}$, —$(CH_2)_r(=O)N(R^{4A})_2$, —$S(O)_2R^{4A}$, or is an aliphatic, alycyclic, heteroaliphatic, heterocyclic, aryl, heteroaryl, -(aliphatic)aryl, -(aliphatic)heteroaryl, -(heteroaliphatic)aryl, or -(heteroaliphatic)heteroaryl moiety, wherein each occurrence of $R^{4B}$ is independently hydrogen, an aliphatic, alycyclic, heteroaliphatic, heterocyclic, aryl, heteroaryl, -(aliphatic)aryl, -(aliphatic)heteroaryl, -(heteroaliphatic)aryl, or -(heteroaliphatic)heteroaryl moiety; and each occurrence of $R^{4A}$ is independently hydrogen, a protecting group, an aliphatic, alycyclic, heteroaliphatic, heterocyclic, aryl, heteroaryl, -(aliphatic)aryl, -(aliphatic)heteroaryl, -(heteroaliphatic)aryl, or -(heteroaliphatic)heteroaryl moiety, or is —$C(=O)CH(R^{4C})NH(SO_2)R^{4D}$, —$SO_2R^{4C}$, —$C(=O)R^{4C}$, —$C(=O)N(R^{4C})_2$, —$C(=S)N(R^{4C})_2$, or —$C(=O)(CH_2)_tC(=O)NHR^{4C}$, wherein each occurrence of $R^{4C}$ and $R^{4D}$ is independently hydrogen, a protecting group, hydroxyl, protected hydroxyl, or an aliphatic, alycyclic, heteroaliphatic, heterocyclic, aryl, heteroaryl, -(aliphatic)aryl, -(aliphatic)heteroaryl, -(heteroaliphatic)aryl, or -(heteroaliphatic)heteroaryl moiety, wherein r and t are each independently 0–5; and $R^Z$ is hydrogen, a protecting group, a solid support unit, or an alkyl, cycloalkyl, heteroalkyl, heterocyclic, aryl, heteroaryl, -(alkyl)aryl, -(alkyl)heteroaryl, -(heteroalkyl)aryl, or -(heteroalkyl)heteroaryl moiety.

23. The compound of claim 22, wherein $R^1$ is hydrogen, phenyl or methyl, $R^Z$ is hydrogen or a solid support unit; $R^2$ is a substituted or unsubstituted alkyl or heteroalkyl moiety, or a substituted or unsubstituted aryl or heteroaryl moiety; and $R^4$ is —$(CH_2)_rN(R^{4A})_2$, —$(CH_2)_rSR^{4A}$, —$(CH_2)_rOR^{4A}$, —$(CH_2)_rNR^{4A}C(=O)R^{4B}$, —$(CH_2)_rC(=O)N(R^{4A})_2$, —$S(O)_2R^{4A}$, or is an aliphatic, alycyclic, heteroaliphatic, heterocyclic, aryl, heteroaryl, -(aliphatic)aryl, -(aliphatic)heteroaryl, -(heteroaliphatic)aryl, or -(heteroaliphatic)heteroaryl moiety, wherein each occurrence of $R^{4B}$ is independently hydrogen, an aliphatic, alycyclic, heteroaliphatic, heterocyclic, aryl, heteroaryl, -(aliphatic)aryl, -(aliphatic)heteroaryl, -(heteroaliphatic)aryl, or -(heteroaliphatic)heteroaryl moiety; and each occurrence of $R^{4A}$ is independently hydrogen, a protecting group, an aliphatic, alycyclic, heteroaliphatic, heterocyclic, aryl, heteroaryl, -(aliphatic)aryl, -(aliphatic)heteroaryl, -(heteroaliphatic)aryl, or -(heteroaliphatic)heteroaryl moiety, or is —$C(=O)CH(R^{4C})NH(SO_2)R^{4D}$, —$SO_2R^{4C}$, —$C(=O)R^{4C}$, —$C(=O)N(R^{4C})_2$, —$C(=S)N(R^{4C})_2$, —$C(=O)(CH_2)_tC(=O)NHR^{4C}$, wherein each occurrence of $R^{4C}$ and $R^{4D}$ is independently hydrogen, a protecting group, hydroxyl, protected hydroxyl, or an aliphatic, alycyclic, heteroaliphatic, heterocyclic, aryl, heteroaryl, -(aliphatic)aryl, -(aliphatic)heteroaryl, -(heteroaliphatic)aryl, or -(heteroaliphatic)heteroaryl moiety, wherein r and t are each independently 0–5.

24. The compound of claim 22, wherein $R^4$ represents a moiety having the structure -L-$R^{4A}$ and the compound has the structure:

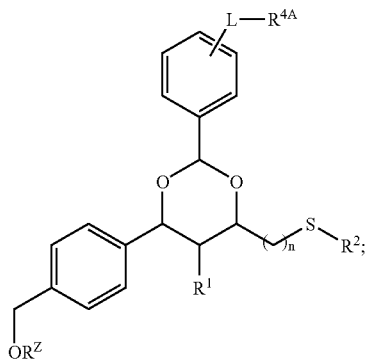

wherein L is a linker and $R^{4A}$ comprises a metal chelator.

25. The compound of claim 24, wherein L is a substituted or unsubstituted $C_{4-8}$alkylene or $C_{4-8}$alkenylene chain wherein up to two non-adjacent methylene units are independently optionally replaced by CO, $CO_2$, COCO, CONR$^{Z1}$, OCONR$^{Z1}$, NR$^{Z1}$NR$^{Z2}$, NR$^{Z1}$NR$^{Z2}$CO, NR$^{Z1}$CO, NR$^{Z1}$CO$_2$, NR$^{Z1}$CONR$^{Z2}$, SO, SO$_2$, NR$^{Z1}$SO$_2$, SO$_2$NR$^{Z1}$, NR$^{Z1}$SO$_2$NR$^{Z2}$, O, S, or NR$^{Z1}$; wherein each occurrence of $R^{Z1}$ and $R^{Z2}$ is independently hydrogen, alkyl, heteroalkyl, aryl, heteroaryl or acyl.

26. The compound of claim 25, wherein L is —(CH$_2$)$_r$NHC(=O)(CH$_2$)$_t$—, wherein r is 0 or 1; and t is 3, 4, 5 or 6.

27. The compound of claim 24, wherein $R^{4A}$ is —C(=O)OR$^{4B}$, —C(=O)NHOR$^{4B}$ or a moiety having the structure:

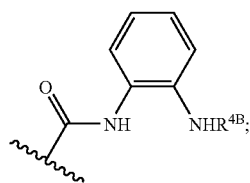

wherein each occurrence of $R^{4B}$ is independently hydrogen, alkyl, heteroalkyl, aryl, heteroaryl or acyl.

28. The compound of claim 24, wherein the compound has the structure:

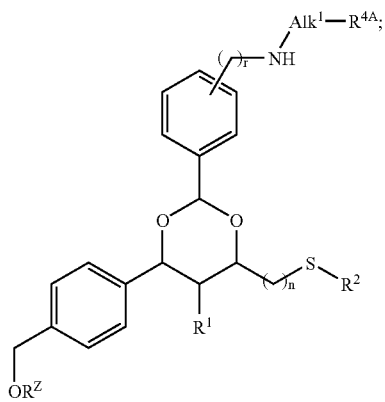

wherein r is 0 or 1; Alk$^1$ is a substituted or unsubstituted $C_{4-7}$alkylene or $C_{4-7}$alkenylene chain wherein up to two non-adjacent methylene units are independently optionally replaced by CO, $CO_2$, COCO, CONR$^{Z1}$, OCONR$^{Z1}$, NR$^{Z1}$NR$^{Z2}$, NR$^{Z1}$NR$^{Z2}$CO, NR$^{Z1}$CO, NR$^{Z1}$CO$_2$, NR$^{Z1}$CONR$^{Z2}$, SO, SO$_2$, NR$^{Z1}$SO$_2$, SO$_2$NR$^{Z1}$, NR$^{Z1}$SO$_2$NR$^{Z2}$, O, S, or NR$^{Z1}$; wherein each occurrence of $R^{Z1}$ and $R^{Z2}$ is independently hydrogen, alkyl, heteroalkyl, aryl, heteroaryl or acyl; $R^{4A}$ comprises a metal chelator; and $R^Z$ is hydrogen, a protecting group, a solid support unit, or an alkyl, cycloalkyl, heteroalkyl, heterocyclic, aryl, heteroaryl, -(alkyl)aryl, -(alkyl)heteroaryl, -(heteroalkyl)aryl, or -(heteroalkyl)heteroaryl moiety.

29. The compound of claim 28, wherein Alk$^1$ is a moiety having the structure —C(=O)-Alk$^2$- and the compound has the structure:

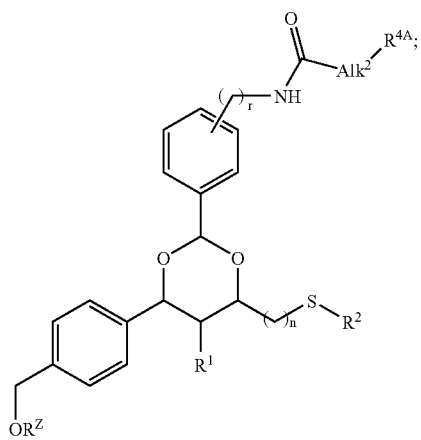

wherein Alk$^2$ is a substituted or unsubstituted $C_{3-6}$alkylene or $C_{3-6}$alkenylene chain wherein up to two non-adjacent methylene units are independently optionally replaced by CO, $CO_2$, COCO, CONR$^{Z1}$, OCONR$^{Z1}$, NR$^{Z1}$NR$^{Z2}$, NR$^{Z1}$NR$^{Z2}$CO, NR$^{Z1}$CO, NR$^{Z1}$CO$_2$, NR$^{Z1}$CONR$^{Z2}$, SO, SO$_2$, NR$^{Z1}$SO$_2$, SO$_2$NR$^{Z1}$, NR$^{Z1}$SO$_2$NR$^{Z2}$, O, S, or NR$^{Z1}$; wherein each occurrence of $R^{Z1}$ and $R^{Z2}$ is independently hydrogen, alkyl, heteroalkyl, aryl, heteroaryl or acyl.

30. The compound of claim 29, wherein Alk$^2$ is a substituted or unsubstituted $C_{3-6}$alkylene chain.

31. The compound of claim 29, wherein $R^{4A}$ is —C(=O)OR$^{4B}$, —C(=O)NHOR$^{4B}$ or a moiety having the structure:

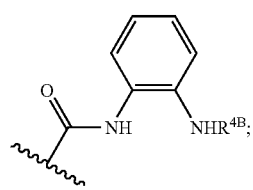

wherein each occurrence of $R^{4B}$ is independently hydrogen, alkyl, heteroalkyl, aryl, heteroaryl or acyl.

32. The compound of claim 28 having the structure:

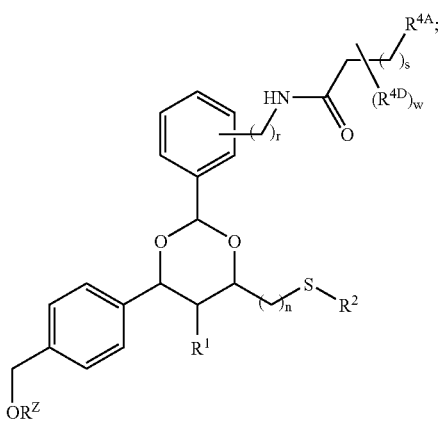

wherein s is an integer from 2–5; w is an integer from 0–4; $R^{4A}$ comprises a metal chelator and each occurrence of $R^{4D}$ is independently hydrogen, alkyl, heteroalkyl, cycloalkyl, heterocyclic, alkenyl, alkynyl, aryl, heteroaryl, halogen, CN, NO$_2$, or WR$^{W1}$ wherein W is O, S, NR$^{W2}$, —C(=O), —S(=O), —SO$_2$, —C(=O)O—, —OC(=O), —C(=O)NR$^{W2}$, —NR$^{W2}$C(=O); wherein each occurrence of R$^{W1}$ and R$^{W2}$ is independently hydrogen, a protecting group, a prodrug moiety or an alkyl, cycloalkyl, heteroalkyl, heterocyclic, aryl or heteroaryl moiety, or, when W is NR$^{W2}$, R$^{W1}$ and R$^{W2}$, taken together with the nitrogen atom to which they are attached, form a heterocyclic or heteroaryl moiety; or any two adjacent occurrences of R$^{2B}$, taken together with the atoms to which they are attached, form a substituted or unsubstituted, saturated or unsaturated alicyclic or heterocyclic moiety, or a substituted or unsubstituted aryl or heteroaryl moiety.

33. The compound of claim 32, wherein $R^{4A}$ is —C(=O)OR$^{4B}$, —C(=O)NHOR$^{4B}$ or a moiety having the structure:

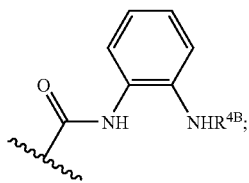

wherein each occurrence of $R^{4B}$ is independently hydrogen, alkyl, heteroalkyl, aryl, heteroaryl or acyl.

34. The compound of claim 1, wherein the compound has the structure:

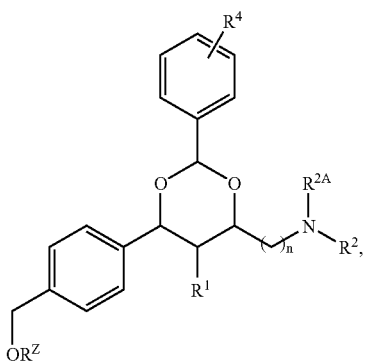

wherein R$^4$ is —(CH$_2$)$_r$N(R$^{4A}$)$_2$, —(CH$_2$)$_r$SR$^{4A}$, —(CH$_2$)$_r$OR$^{4A}$, —(CH$_2$)$_r$NR$^{4A}$C(=O)R$^{4B}$, —(CH$_2$)$_r$C(=O)N(R$^{4A}$)$_2$, —S(O)$_2$R$^{4A}$, or is an aliphatic, alycyclic, heteroaliphatic, heterocyclic, aryl, heteroaryl, -(aliphatic)aryl, -(aliphatic)heteroaryl, -(heteroaliphatic)aryl, or -(heteroaliphatic)heteroaryl moiety, wherein each occurrence of R$^{4B}$ is independently hydrogen, an aliphatic, alycyclic, heteroaliphatic, heterocyclic, aryl, heteroaryl, -(aliphatic)aryl, -(aliphatic)heteroaryl, -(heteroaliphatic)aryl, or -(heteroaliphatic)heteroaryl moiety; and each occurrence of R$^{4A}$ is independently hydrogen, a protecting group, an aliphatic, alycyclic, heteroaliphatic, heterocyclic, aryl, heteroaryl, -(aliphatic)aryl, -(aliphatic)heteroaryl, -(heteroaliphatic)aryl, or -(heteroaliphatic)heteroaryl moiety, or is —C(=O)CH(R$^{4C}$)NH(SO$_2$)R$^{4C}$, —SO$_2$R$^{4C}$, —C(=O)R$^{4C}$, —C(=O)N(R$^{4C}$)$_2$, —C(=S)N(R$^{4C}$)$_2$, or —C(=O)(CH$_2$)$_t$C(=O)NHR$^{4C}$, wherein each occurrence of R$^{4C}$ and R$^{4D}$ is independently hydrogen, a protecting group, hydroxyl, protected hydroxyl, or an aliphatic, alycyclic, heteroaliphatic, heterocyclic, aryl, heteroaryl, -(aliphatic)aryl, -(aliphatic)heteroaryl, -(heteroaliphatic)aryl, or -(heteroaliphatic)heteroaryl moiety, wherein r and t are each independently 0–5; R$^{2A}$ is hydrogen, a protecting group, or an aliphatic, alicyclic, heteroaliphatic, heterocyclic, aryl or heteroaryl moiety; and R$^Z$ is hydrogen, a protecting group, a solid support unit, or an alkyl, cycloalkyl, heteroalkyl, heterocyclic, aryl, heteroaryl, -(alkyl)aryl, -(alkyl)heteroaryl, -(heteroalkyl)aryl, or -(heteroalkyl)heteroaryl moiety.

35. The compound of claim 34, wherein R$^1$ is hydrogen, phenyl or methyl, R$^Z$ is hydrogen or a solid support unit; R$^2$ is a substituted or unsubstituted alkyl or heteroalkyl moiety, or a substituted or unsubstituted aryl or heteroaryl moiety; either or both of R$^2$ and R$^{2A}$, or R$^2$ and R$^{2A}$ taken together with the nitrogen atom to which they are attached, forms a substituted or unsubstituted cycloalkyl or heterocyclic moiety, or a substituted or unsubstituted aryl or heteroaryl moiety; and R$^4$ is —(CH$_2$)$_r$N(R$^{4A}$)$_2$, —(CH$_2$)$_r$SR$^{4A}$, —(CH$_2$)$_r$OR$^{4A}$, —(CH$_2$)$_r$NR$^{4A}$C(=O)R$^{4B}$, —(CH$_2$)$_r$C(=O)N(R$^{4A}$)$_2$, —S(O)$_2$R$^{4A}$, or is an aliphatic, alycyclic, heteroaliphatic, heterocyclic, aryl, heteroaryl, -(aliphatic)aryl, -(aliphatic)heteroaryl, -(heteroaliphatic)aryl, or -(heteroaliphatic)heteroaryl moiety, wherein each occurrence of R$^{4B}$ is independently hydrogen, an aliphatic, alycyclic, heteroaliphatic, heterocyclic, aryl, heteroaryl, -(aliphatic)aryl, -(aliphatic)heteroaryl, -(heteroaliphatic)aryl, or -(heteroaliphatic)heteroaryl moiety; and each occurrence of R$^{4A}$ is independently hydrogen, a protecting group, an aliphatic, alycyclic, heteroaliphatic, heterocyclic, aryl, heteroaryl, -(aliphatic)aryl, -(aliphatic)heteroaryl, -(heteroaliphatic) aryl, or -(heteroaliphatic)heteroaryl moiety, or is —C(=O)CH(R$^{4C}$)NH(SO$_2$)R$^{4D}$, —SO$_2$R$^{4C}$, —C(=O)R$^{4C}$, —C(=O)N(R$^{4C}$)$_2$, —C(=S)N(R$^{4C}$)$_2$, or —C(=O)(CH$_2$)$_t$C(=O)NHR$^{4C}$, wherein each occurrence of R$^{4C}$ and R$^{4D}$ is independently hydrogen, a protecting group, hydroxyl, protected hydroxyl, or an aliphatic, alycyclic, heteroaliphatic, heterocyclic, aryl, heteroaryl, -(aliphatic)aryl, -(aliphatic) heteroaryl, -(heteroaliphatic)aryl, or -(heteroaliphatic)heteroaryl moiety, wherein r and t are each independently 0–5.

36. The compound of claim 34, wherein $R^4$ represents a moiety having the structure -L-$R^{4A}$ and the compound has the structure:

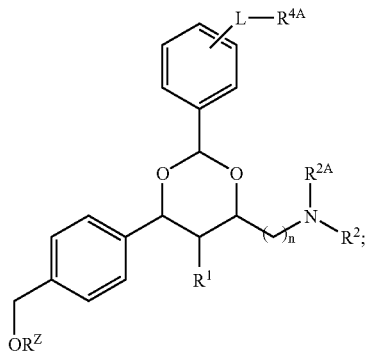

wherein L is a linker and $R^{4A}$ comprises a metal chelator.

37. The compound of claim 36, wherein L is a substituted or unsubstituted $C_{4-8}$alkylene or $C_{4-8}$alkenylene chain wherein up to two non-adjacent methylene units are independently optionally replaced by CO, $CO_2$, COCO, $CONR^{Z1}$, $OCONR^{Z1}$, $NR^{Z1}NR^{Z2}$, $NR^{Z1}NR^{Z2}CO$, $NR^{Z1}CO$, $NR^{Z1}CO_2$, $NR^{Z1}CONR^{Z2}$, SO, $SO_2$, $NR^{Z1}SO_2$, $SO_2NR^{Z1}$, $NR^{Z1}SO_2NR^{Z2}$, O, S, or $NR^{Z1}$; wherein each occurrence of $R^{Z1}$ and $R^{Z2}$ is independently hydrogen, alkyl, heteroalkyl, aryl, heteroaryl or acyl.

38. The compound of claim 37, wherein L is —$(CH_2)_r$HC(=O)$(CH_2)_t$—, wherein r is 0 or 1; and t is 3, 4, 5 or 6.

39. The compound of claim 36, wherein $R^{4A}$ is —C(=O)$OR^{4B}$, —C(=O)$NHOR^{4B}$ or a moiety having the structure:

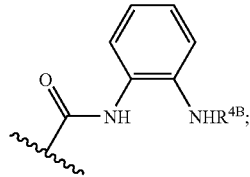

wherein each occurrence of $R^{4B}$ is independently hydrogen, alkyl, heteroalkyl, aryl, heteroaryl or acyl.

40. The compound of claim 34, wherein the compound has the structure:

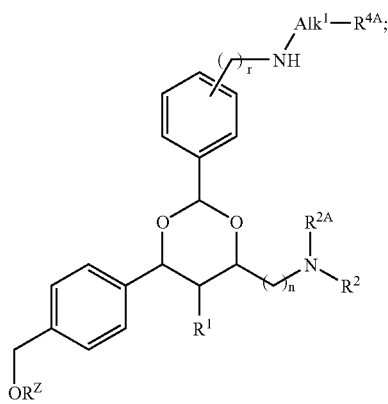

wherein r is 0 or 1; $Alk^1$ is a substituted or unsubstituted $C_{4-7}$alkylene or $C_{4-7}$-alkenylene chain wherein up to two non-adjacent methylene units are independently optionally replaced by CO, $CO_2$, COCO, $CONR^{Z1}$, $OCONR^{Z1}$, $NR^{Z1}NR^{Z2}$, $NR^{Z1}NR^{Z2}CO$, $NR^{Z1}CO$, $NR^{Z1}CO_2$, $NR^{Z1}CONR^{Z2}$, SO, $SO_2$, $NR^{Z1}SO_2$, $SO_2NR^{Z1}$, $NR^{Z1}SO_2NR^{Z2}$, O, S, or $NR^{Z1}$; wherein each occurrence of $R^{Z1}$ and $R^{Z2}$ is independently hydrogen, alkyl, heteroalkyl, aryl, heteroaryl or acyl; $R^{4A}$ comprises a metal chelator; and $R^Z$ is hydrogen, a protecting group, a solid support unit, or an alkyl, cycloalkyl, heteroalkyl, heterocyclic, aryl, heteroaryl, -(alkyl)aryl, -(alkyl)heteroaryl, -(heteroalkyl)aryl, or -(heteroalkyl)heteroaryl moiety.

41. The compound of claim 40, wherein $Alk^1$ is a moiety having the structure —C(=O)-$Alk^2$- and the compound has the structure:

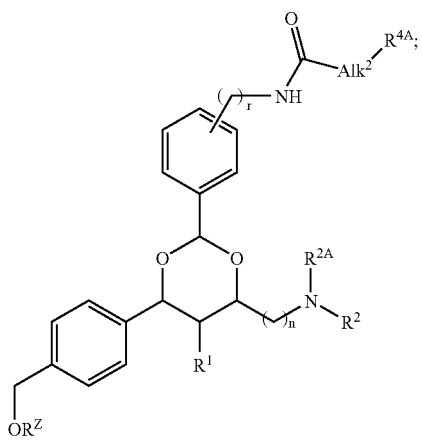

wherein $Alk^2$ is a substituted or unsubstituted $C_{3-6}$alkylene or $C_{3-6}$alkenylene chain wherein up to two non-adjacent methylene units are independently optionally replaced by CO, $CO_2$, COCO, $CONR^{Z1}$, $OCONR^{Z1}$, $NR^{Z1}NR^{Z2}$, $NR^{Z1}NR^{Z2}CO$, $NR^{Z1}CO$, $NR^{Z1}CO_2$, $NR^{Z1}CONR^{Z2}$, SO, $SO_2$, $NR^{Z1}SO_2$, $SO_2NR^{Z1}$, $NR^{Z1}SO_2NR^{Z2}$, O, S, or $NR^{Z1}$; wherein each occurrence of $R^{Z1}$ and $R^{Z2}$ is independently hydrogen, alkyl, heteroalkyl, aryl, heteroaryl or acyl.

42. The compound of claim 41, wherein $Alk^2$ is a substituted or unsubstituted $C_{3-6}$alkylene chain.

43. The compound of claim 41, wherein $R^{4A}$ is —C(=O)$OR^{4B}$, —C(=O)$NHOR^{4B}$ or a moiety having the structure:

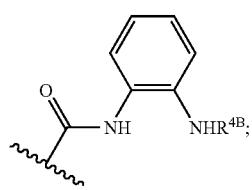

wherein each occurrence of $R^{4B}$ is independently hydrogen, alkyl, heteroalkyl, aryl, heteroaryl or acyl.

44. The compound of claim 34 having the structure:

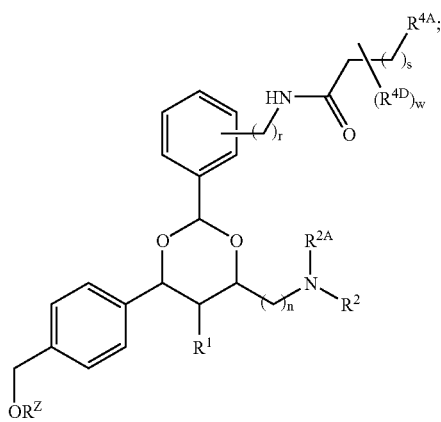

wherein s is an integer from 2–5; w is an integer from 0–4; $R^{4A}$ comprises a metal chelator and each occurrence of $R^{4D}$ is independently hydrogen, alkyl, heteroalkyl, cycloalkyl, heterocyclic, alkenyl, alkynyl, aryl, heteroaryl, halogen, CN, $NO_2$, or $WR^{W1}$ wherein W is O, S, $NR^{W2}$, —C(=O), —S(=O), —$SO_2$, —C(=O)O—, —OC(=O), —C(=O)$NR^{W2}$, —$NR^{W2}$C(=O); wherein each occurrence of $R^{W1}$ and $R^{W2}$ is independently hydrogen, a protecting group, a prodrug moiety or an alkyl, cycloalkyl, heteroalkyl, heterocyclic, aryl or heteroaryl moiety, or, when W is $NR^{W2}$, $R^{W1}$ and $R^{W2}$, taken together with the nitrogen atom to which they are attached, form a heterocyclic or heteroaryl moiety; or any two adjacent occurrences of $R^{2B}$, taken together with the atoms to which they are attached, form a substituted or unsubstituted, saturated or unsaturated alicyclic or heterocyclic moiety, or a substituted or unsubstituted aryl or heteroaryl moiety.

45. The compound of claim 44, wherein $R^{4A}$ is —C(=O)$OR^{4B}$, —C(=O)$NHOR^{4B}$ or a moiety having the structure:

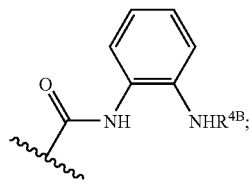

wherein each occurrence of $R^{4B}$ is independently hydrogen, alkyl, heteroalkyl, aryl, heteroaryl or acyl.

46. The compound of claim 1, 22, 32, 34 or 44, wherein $R^2$ is one of the following structures:

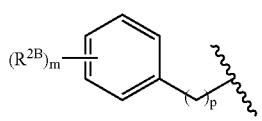

a

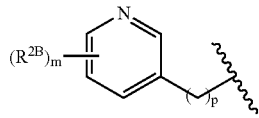

b

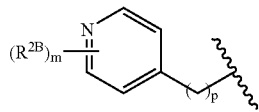

c

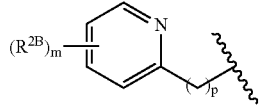

d

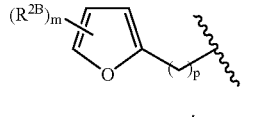

e

f

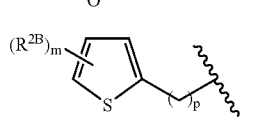

g

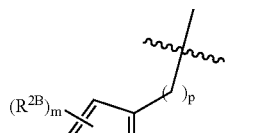

h

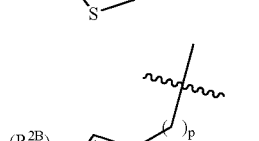

i

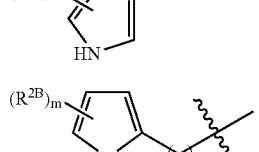

j

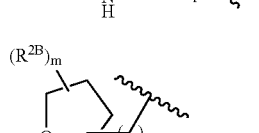

k

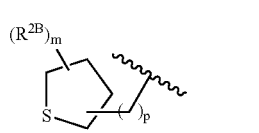

l

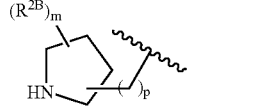

m

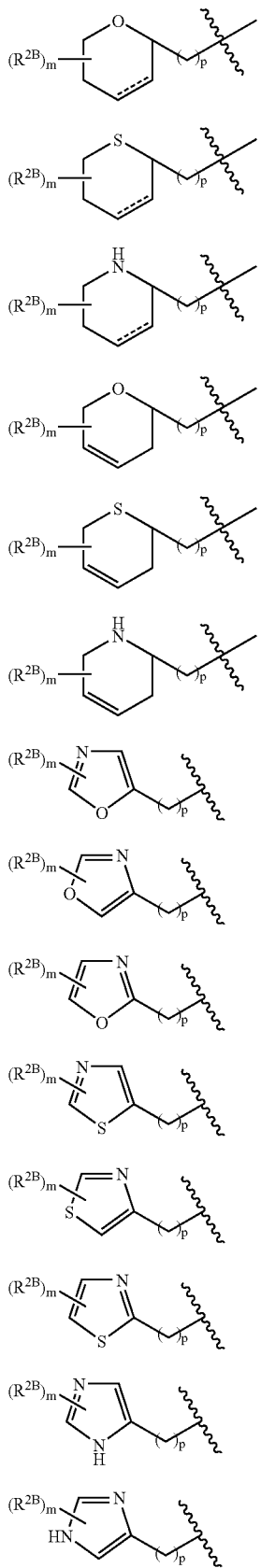
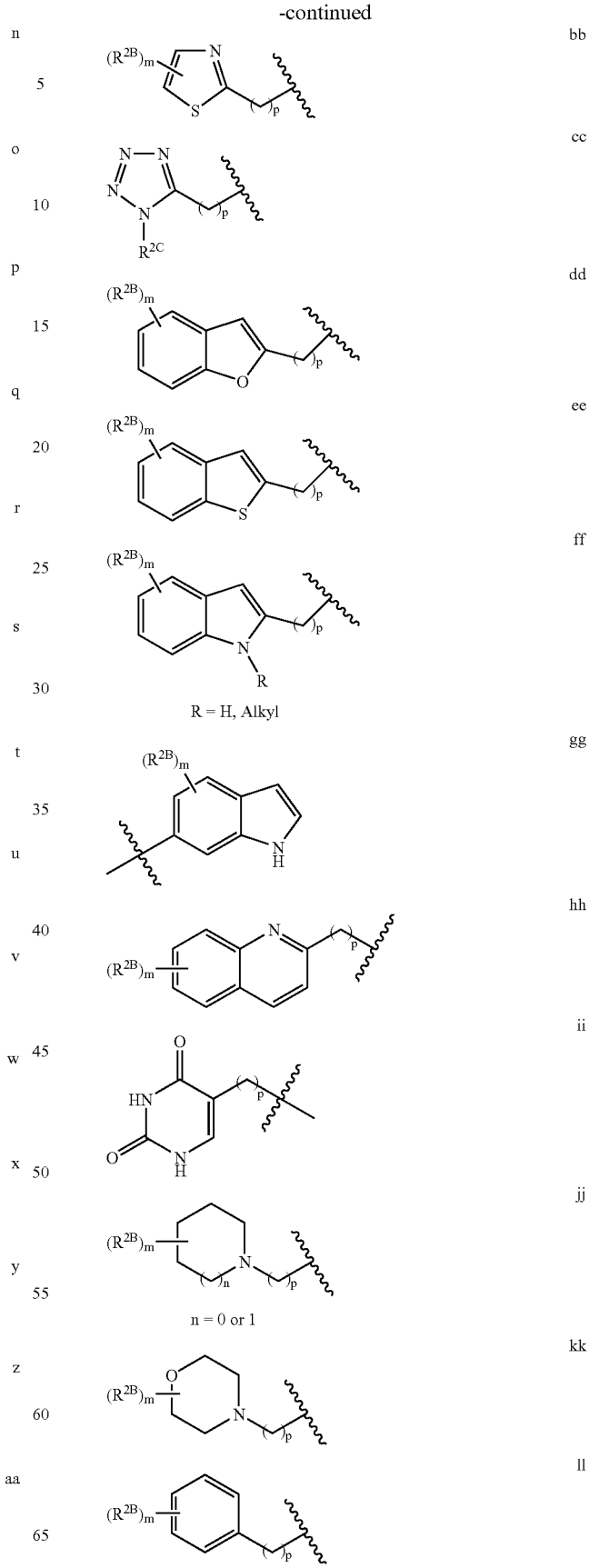

-continued

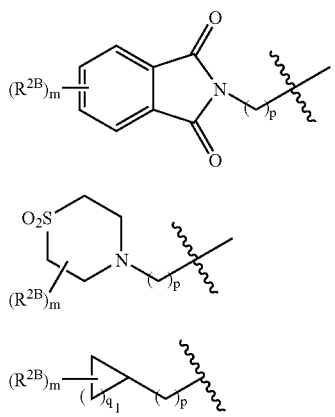

mm nn oo wherein m and p are each independently integers from 0 to 3; $q_1$ is an integer from 1 to 6; $R^{2C}$ is hydrogen, lower alkyl or a nitrogen protecting group; $R^{2D}$ is hydrogen or lower alkyl; and each occurrence of $R^{2B}$ is independently hydrogen, halogen, —CN, —COOH, NO$_2$, alkyl, heteroalkyl, aryl, heteroaryl, or WR$^{W1}$ wherein W is O, S, NR$^{W2}$, —C(=O), —S(=O), —SO$_2$, —C(=O)O—, —OC(=O), —C(=O)NR$^{W2}$, —NR$^{W2}$C(=O); wherein each occurrence of R$^{W1}$ and R$^{W2}$ is independently hydrogen, a protecting group, a prodrug moiety or an alkyl, cycloalkyl, heteroalkyl, heterocyclic, aryl or heteroaryl moiety, or, when W is NR$^{W2}$, R$^{W1}$ and R$^{W2}$, taken together with the nitrogen atom to which they are attached, form a heterocyclic or heteroaryl moiety; or any two adjacent occurrences of $R^{2B}$, taken together with the atoms to which they are attached, form a substituted or unsubstituted, saturated or unsaturated alicyclic or heterocyclic moiety, or a substituted or unsubstituted aryl or heteroaryl moiety.

47. The compound of claim 34 or 44, wherein either or both of $R^2$, $R^{2A}$, or $R^2$ and $R^{2A}$, taken together with the nitrogen atom to which they are attached comprise

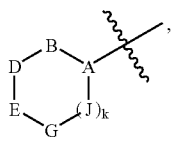

wherein k is an integer from 0–3; A-B, B-D, D-E, E-G, G-J, two or more occurrences of J, and J-A are each connected by a single or double bond; A is CH, C, or N; B is CR$^B$, C(R$^B$)$_2$, C(=O), NR$^B$, N, O or S; D is CR$^D$, C(R$^D$)$_2$, C(=O), NR$^D$, N, O or S; E is CR$^E$, C(R$^E$)$_2$, C(=O), NR$^E$, N, O or S; G is CR$^G$, C(R$^G$)$_2$, C(=O), NR$^G$, N, O or S; and each occurrence of J is independently CR$^J$, C(R$^J$)$_2$, C(=O), NR$^J$, N, O or S; wherein each occurrence of R$^B$, R$^D$, R$^E$, R$^G$ and R$^J$ is independently hydrogen, halogen, hydroxyl, protected hydroxyl, thiol, protected thiol, amino, protected amino, —COOH, —CONH$_2$, —NHCOOH, —NHCOO(alkyl), —NHCO(alkyl), or a substituted or unsubstituted, cyclic or acyclic, linear or branched alkyl or heteroalkyl moiety, or a substituted or unsubstituted aryl or heteroaryl moiety, or any two or R$^B$, R$^D$, R$^E$, R$^G$ or R$^J$ taken together comprises a substituted or unsubstituted alicyclic or heterocyclic, moiety or a substituted or unsubstituted aryl or heteroaryl moiety.

48. The compound of claim 34 or 44, wherein one or both of $R^2$ and $R^{2A}$ is an aryl or heteroaryl moiety substituted with —COOH, halogen, alkyl, heteroalkyl, aryl, heteroaryl, OH, SH, NO$_2$, NH$_2$, or —NHC(=O)alkyl.

49. The compound of claim 32 or 44, wherein $R^{4A}$ is —C(=O)OH, —C(=O)NHOH or a moiety having the structure:

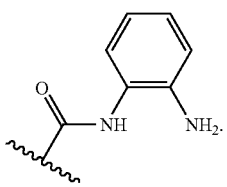

50. The compound of claim 32 or 44, wherein $R^{4A}$ is —C(=O)NHOH.

51. The compound of claim 1 having the structure:

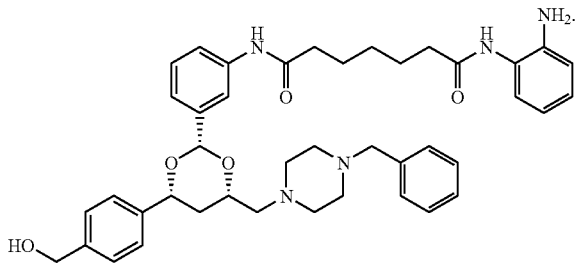

52. The compound of claim 1 having the structure:

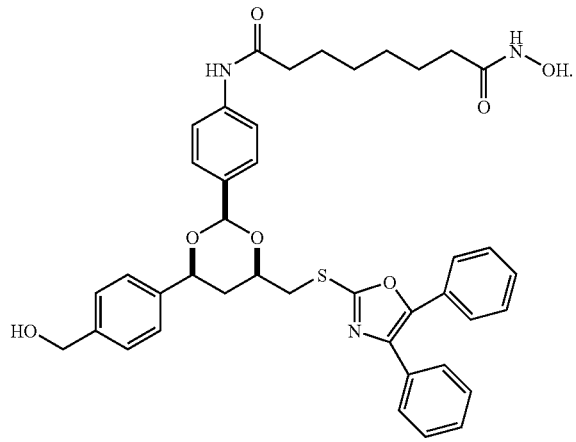

53. A pharmaceutical composition comprising:
a compound of any one of claims 1, 22, 32, 34 or 44; and
a pharmaceutically acceptable carrier or diluent, optionally further comprising an additional therapeutic agent.

54. The pharmaceutical composition of claim 53, wherein the compound is present in an amount effective to inhibit histone deacetylase activity.

* * * * *